(12) United States Patent  
Machida et al.

(10) Patent No.: US 8,008,049 B2  
(45) Date of Patent: Aug. 30, 2011

(54) DNA CODING FOR POLYPEPTIDE PARTICIPATING IN BIOSYNTHESIS OF PLADIENOLIDE

(75) Inventors: Kazuhiro Machida, Shizuoka (JP); Akira Arisawa, Shizuoka (JP); Susumu Takeda, Kumamoto (JP); Masashi Yoshida, Shizuoka (JP); Toshio Tsuchida, Shizuoka (JP)

(73) Assignee: EISAI R&D Management Co., Ltd., Tokyo (JP)

( * ) Notice: Subject to any disclaimer, the term of this patent is extended or adjusted under 35 U.S.C. 154(b) by 1023 days.

(21) Appl. No.: 11/630,689

(22) PCT Filed: Jul. 19, 2005

(86) PCT No.: PCT/JP2005/013541  
§ 371 (c)(1),  
(2), (4) Date: Dec. 27, 2006

(87) PCT Pub. No.: WO2006/009276  
PCT Pub. Date: Jan. 26, 2006

(65) Prior Publication Data  
US 2009/0269820 A1    Oct. 29, 2009

(30) Foreign Application Priority Data  
Jul. 20, 2004  (JP) .................................. 2004-211279

(51) Int. Cl.  
| C12P 17/16 | (2006.01) |
| C07H 21/04 | (2006.01) |
| C07K 2/00 | (2006.01) |
| C12N 9/00 | (2006.01) |
| C12N 15/63 | (2006.01) |
| C12N 1/00 | (2006.01) |

(52) U.S. Cl. ........ 435/118; 536/237; 536/232; 530/300; 435/320.1; 435/243; 435/183

(58) Field of Classification Search ........................ None  
See application file for complete search history.

(56) References Cited

U.S. PATENT DOCUMENTS

| 5,824,513 | A | 10/1998 | Katz et al. |
| 6,004,787 | A | 12/1999 | Katz et al. |
| 6,503,737 | B1 | 1/2003 | Reeves et al. |
| 7,026,352 | B1 | 4/2006 | Mizui et al. |
| 7,375,088 | B2 * | 5/2008 | Bachmann et al. ............ 514/25 |
| 2004/0266008 | A1 | 12/2004 | Bachmann et al. |
| 2005/0084859 | A1 | 4/2005 | Nakajima et al. |
| 2005/0245514 | A1 | 11/2005 | Kotake et al. |
| 2006/0141589 | A1 | 6/2006 | Okuda et al. |
| 2006/0234337 | A1 | 10/2006 | Arisawa et al. |
| 2006/0235002 | A1 | 10/2006 | Nagai et al. |
| 2009/0215134 | A1 | 8/2009 | Machida et al. |
| 2010/0313300 | A1 | 12/2010 | Nakajima et al. |

FOREIGN PATENT DOCUMENTS

| CA | 2463855 A1 | 5/2003 |
| CA | 2494536 A1 | 2/2004 |
| CA | 2507641 A1 | 6/2004 |
| CN | 1489583 A | 4/2004 |
| EP | 1 380 579 A1 | 1/2004 |
| EP | 1457558 A1 | 9/2004 |
| EP | 1500704 A1 | 1/2005 |
| EP | 1508570 A1 | 2/2005 |
| EP | 1 541 570 A1 | 6/2005 |
| EP | 1 705 247 A1 | 9/2006 |
| WO | WO 93/12236 A1 | 6/1993 |
| WO | WO-93/13663 A1 | 7/1993 |
| WO | WO02/060890 * | 8/2002 |
| WO | WO-02/060890 A1 | 8/2002 |
| WO | WO 02/092801 A2 | 11/2002 |
| WO | WO-03/008738 A1 | 1/2003 |
| WO | WO 03/040370 A1 | 5/2003 |
| WO | WO-03/087381 A1 | 10/2003 |
| WO | WO 03/099813 A1 | 12/2003 |
| WO | WO-2004/011459 A1 | 2/2004 |
| WO | WO-2004/011661 A1 | 2/2004 |
| WO | WO 2004/050890 A1 | 6/2004 |
| WO | WO 2004/061116 A2 | 7/2004 |
| WO | WO 2004/065401 A1 | 8/2004 |
| WO | WO 2005/052152 A1 | 6/2005 |
| WO | WO 2006/009276 A1 | 1/2006 |

OTHER PUBLICATIONS

Lamb et al (Journal of Biological Chemistry. 2002; 277(27): 24000-24006).*  
Machida et al. (Journal of Bioscience and Bioengineering. 2008; 105(6): 649-654).*  
Guilhot et al. (Journal of Bacteriology. Jan. 1994; 176(2): 535-539).*  
Sakai, Takashi et al. "Pladienolides, New Substances from Culture of Streptomyces platenesis Mer-11107 1. Taxonomy, Fermentation, Isolation and Screening" The Journal of Antibiotics vol. 57 No. 3, Mar. 2004. pp. 173-179. XP-002462515.  
Schwecke, Torsten et al. "The biosynthetic gene cluster for the polyketide immunosuppressant rapamycin" Proc Natl. Acad. Sci. USA vol. 92. pp. 7839-7843, Aug. 1995. XP-000652288.

(Continued)

Primary Examiner — Scott Long  
(74) Attorney, Agent, or Firm — Birch, Stewart, Kolasch & Birch, LLP

(57) ABSTRACT

The present invention provides polypeptides that participate in the biosynthesis of the pladienolide macrolide compounds, DNA that encodes these polypeptides and variants of this DNA, transformants that maintain all or a portion of this DNA or variant thereof, and a method of producing the pladienolide macrolide compounds using these transformants. More particularly, it provides an isolated pure DNA that contains at least one region encoding a polypeptide that participates in pladienolide biosynthesis; polypeptide encoded by this DNA; a self-replicating or integrated-replicating recombinant plasmid carrying this DNA; a transformant maintaining this DNA; and a method of producing a pladienolide, characterized by culturing this transformant on culture medium and collecting pladienolide from this culture medium.

15 Claims, 3 Drawing Sheets

OTHER PUBLICATIONS

Seki-Asano, Mitsuko et al. "Isolation and characterization of a new 12-membered macrolide FD-895" The Journal of Antibiotics vol. 47 No. 12 pp. 1395-1401, Dec. 1, 1994. XP-002951021.

Ikeda et al., "Biosynthesis, Regulation, and Genetics of Macrolide Production," *Macrolide Antibiotics: Chemistry, Biology, and Practice, Second Edition*, edited by Satoshi Omura, Academic Press. 2002, pp. 285-326.

Robert McDaniel et al., Proc. Natl. Acad. Sci. USA, vol. 96, pp. 1846-1851 and Corrections, PNAS Apr. 25, 2000 vol. 97, p. 5011, 5890.

J. M. Weber, et al., Science, vol. 252, (1991) pp. 114-117.

Blaine A. Pfeifer, Science, vol. 291, (Mar. 2, 2001) pp. 1790-1792.

Xue et al., Proc. Natl. Acad. Sci. USA, 1998, 95(21), pp. 12111-12116.

Donadio et al., Proc. Natl. Acad. Sci. USA, 1993, 90(15), pp. 7119-7123.

Hopwood et al., Annu. Rev. Genet., 1990, 24, pp. 37-66.

Katz et al., Annu. Rev. Microbiol., 1993, 47, pp. 875-912.

"Cell Technology," vol. 14, No. 5, pp. 591-593, 1995.

Beck et al., "Nucleotide sequence of bacteriophage fd DNA," Nucleic Acids Research, vol. 5, No. 12, pp. 4495-4503, Dec. 1978.

Bibb et al., "Genetic Studies of the Fertility Plasmid SCP2* Variants in Streptomyces coelicolor A3(2)," Journal of General Microbiology, vol. 126, pp. 427-442, 1981.

Bibb et al., "Nucleotide sequences encoding and promoting expression of three antibiotic resistance genes indigenous to Streptomyces," Mol. Gen. Genet., vol. 199, pp. 26-36, 1985.

Bibb et al., "The mRNA for the 23S rRNA methylase encoded by the ermE gene of *Saccharopolyspora erythraea* is translated in the absence of a conventional ribosome-binding site," Molecular Microbiology, vol. 14, No. 3, pp. 533-545, 1994.

Chater, "Streptomyces Phages and Their Applications to Streptomyces Genetics," The Bacteria, vol. IX, Chapter 5, pp. 119-158, 1986.

Chinese Office Action, dated Feb. 5, 2010, for Chinese Application No. 2006800182893.

Decker et al., "Cloning and Characterization of a Polyketide Synthase Gene from *Streptomyces fradiae* Tü 2717, Which Carries the Genes for Biosynthesis of the Angucycline Antibiotic Urdamycin A . . . ," Journal of Bacteriology, vol. 177, No. 21, pp. 6126-6136, Nov. 1995.

European Office Action, dated Dec. 21, 2009, for European Application No. 04799902.4.

Hyun et al., "An Efficient Approach for Cloning P450 Hydroxylase Genes from Actinomycetes,"Journal of Microbiology and Biotechnology, vol. 8. No. 3, pp. 295-299, XP008076424, 1998.

International Preliminary Report on Patentability, dated Jul. 24, 2006, for Application No. PCT/JP2004/17906.

International Search Report, dated Jul. 4, 2006 for PCT/JP2006/310835.

International Search Report, dated Mar. 8, 2005, for Application No. PCT/JP2004/017906.

Kendall et al., "Complete Nucleotide Sequence of the Streptomyces lividans Plasmid pIJI01 and Correlation of the Sequence with Genetic Properties," Journal of Bacteriology, vol. 170, No. 10, pp. 4634-4651, Oct. 1988.

Kojima et al., "The rpoZ Gene, Encoding the RNA Polymerase Omega Subunit, Is Required for Antibiotic Production and Morphological Differentiation in *Streptomyces kasugaensis*," Journal of Bacteriology, vol. 184, No. 23, pp. 6417-6423, Dec. 2002.

Lampel et al., "Cloning and Sequencing of a Gene Encoding a Novel Extracellular Neutral Proteinase from Streptomyces sp. Strain C5 and Expression of the Gene in *Streptomyces lividans* 1326," Journal of Bacteriology, vol. 174, No. 9, pp. 2797-2808, May 1992.

Machida et al., "Increase in Pladienolide D Production Rate Using a Streptomyces Strain Overexpressing a Cytochrome P450 Gene," Journal of Bioscience and Bioengineering, 2008, vol. 105, No. 6, pp. 649-654.

McAlpine et al., "Microbial Genomics as a Guide to Drug Discovery and Structural Elucidation: ECO-02301, a Novel Antifungal Agent, as an Example," J. Natl. Prod., vol. 68, pp. 493-496, 2005.

Neal et al., "Nucleotide sequence analysis reveals similarities between proteins determining methylenomycin A resistance in Streptomyces and tetracycline resistance in eubacteria," Gene, vol. 58, pp. 229-241, 1987.

Schmid et al., "AUD4, a new amplifiable element from *Streptomyces lividans*," Microbiology, vol. 145, pp. 3331-3341, 1999.

Shah et al., "Cloning, Characterization and Heterologous Expression of a Polyketide Synthase and P-450 Oxidase Involved in the Biosynthesis of the Antibiotic Oleandomycin," The Journal of Antibiotics, vol. 53, No. 5, pp. 502-508, May 2000.

Takano et al., "Construction of thiostrepton-inducible, high-copy-number expression vectors for use in *Streptomyces spp*," Gene, vol. 166, Issue 1, pp. 133-137, Dec. 1, 1995.

Triglia et al., "A procedure for in vitro amplification of DNA segments that lie outside the boundaries of known sequences," Nucleic Acids Research, vol. 16, p. 8186, 1988.

US Office Action dated Dec. 9, 2010, for U.S. Appl. No. 11/919,579.

US Office Action, dated Apr. 15, 2010, for U.S. Appl. No. 10/577,655.

US Office Action, dated Aug. 21, 2009, for U.S. Appl. No. 10/577,655.

US Office Action, dated Aug. 24, 2010, for U.S. Appl. No. 11/919,579.

US Office Action, dated Dec. 18, 2009, for U.S. Appl. No. 10/577,655.

US Office Action, dated Jan. 8, 2009, for U.S. Appl. No. 10/577,655.

US Office Action, dated Jun. 4, 2008, for U.S. Appl. No. 10/577,655.

US Office Action, dated Sep. 15, 2010, for U.S. Appl. No. 10/577,655.

US Office Action, dated Sep. 22, 2008, for U.S. Appl. No. 10/577,655.

Yanisch-Perron et al., "Improved M13 phage cloning vectors and host strains: nucleotide sequences of the M13mp18 and pUC19 vectors," Gene, vol. 33, Issue 1, pp. 103-119, 1985.

Yiguang, "Application of Genetic Engineering Techniques in the Study of Macrolide Antibiotics," Institute of Medicinal Biotechnology, vol. 18, No. 2, pp. 92-98, Mar. 31, 1997 (w/ full English translation).

Zalacain et al., "Nucleotide sequence of the hygromycin B phosphotransferase gene from *Streptomyces hygroscopicus*," Nucleic Acids Research, vol. 14, No. 4, pp. 1565-1581, 1986.

US Office Action, dated May 26, 2011, for U.S. Appl. No. 11/919,579.

* cited by examiner

DNA CODING FOR POLYPEPTIDE PARTICIPATING IN BIOSYNTHESIS OF PLADIENOLIDE

TECHNICAL FIELD

The present invention relates to polypeptides that participate in the biosynthesis of the pladienolide macrolide compounds, to DNA that encodes these polypeptides, and to variants of this DNA. The present invention also relates to transformants that maintain all or a portion of this DNA or variants thereof and to a method of producing the pladienolide macrolide compounds using these transformants.

PRIOR ART

Important bioactive substances have been discovered among the various metabolites produced by the actinomycetes. In particular, many compounds have been found having a polyketide in the basic structure (hereunder called polyketide compounds). Compounds having various biological functions are known including for example the antibacterial agents erythromycin, josamycin, tylosin, midecamycin and mycinamicin, the antifungal agents nystatin and amphotericin, the insecticidal agents milbemycin and avermectin, the immune suppressors tacrolimus and rapamycin and the anti-tumor agents daunomycin, adriamycin, aclacinomycin and the like.

The compounds include a group of macrolide compounds with excellent anti-tumor activity called pladienolides. "Pladienolide" is a general term for a group of compounds discovered in culture of the *Streptomyces* sp. Mer-11107 strain, and more than 50 relatives are known, beginning with 11107B (also called pladienolide B), which is represented by the formula (I) below (See WO 2002/060890).

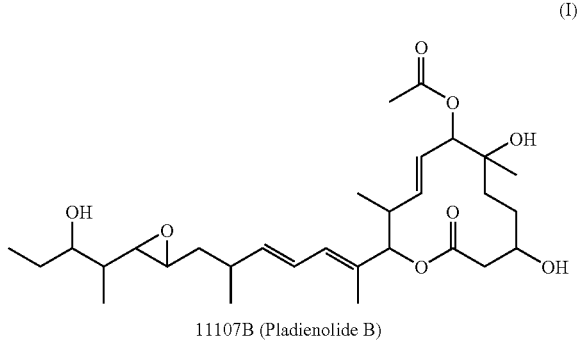

11107B (Pladienolide B)

Much is also known with regard to the mechanism of polyketide compound biosynthesis. It has been reported that the diverse polyketide compounds cited above share a common biosynthetic mechanism that very closely resembles fatty acid biosynthesis. Thus, polyketide compound biosynthesis proceeds by a process in which lower fatty acid, such as acetic acid or propionic acid, is successively condensed and the β-carbonyl group in the elongated acyl group is then variously subjected to ketone reduction, dehydration, or enoyl reduction by the same processes as in fatty acid synthesis. It has been reported that for many of these polyketide compounds the various repetitive synthesis steps are mediated by a high molecular weight multifunctional enzyme complex that has separate active sites (domains) required for the respective catalytic reaction activities. The general reaction scheme of polyketide biosynthesis is outlined in, for example, *Ann. Rev. Gen.*, 24 (1990) 37-66 and *Ann. Rev. Microbiol.*, 47 (1993) 874-912.

It has been demonstrated that the DNA sequence encoding a polyketide synthase generally encodes all the activity required for synthesis of the polyketide skeleton and is organized in repeat units, i.e., modules, that include the condensation step and post-condensation modification steps. Different domains participate with regard to the individual catalytic activities: these domains participate in the specificity for the specific carboxylic acid structural units present in the individual condensation steps or prescribe the particular post-condensation modification function that will be implemented. For example, the gene encoding the polyketide synthase for pikromycin biosynthesis by *Streptomyces venezuelae* ATCC15439 is described in *Proc. Natl. Acad. Sci. USA*, 95 (1998) 12111-12116. In addition, WO 93/13663 describes the structure of a gene that encodes the erythromycin polyketide synthase of *Saccharopolyspora erythraea*. This gene is constituted of 6 modules wherein each module carries out one condensation step. In other words, the exact sequence of acyl chain elongation and modification of the elongated chain are governed by the genetic information present in each module.

For a wide variety of polyketide compounds, synthesis of the polyketide skeleton by the polyketide synthase is frequently followed by modification by enzymes (hereafter also referred to as modification enzymes) that catalyze modification reactions such as hydroxylation, epoxidation, and methylation to give the final metabolite. It has been shown that the gene group that participates in the production of these compounds, that is, the enzymes necessary for the biosynthesis of the final metabolite, and genes that encode, for example, regulatory factors required to regulate production, are generally arranged in the form of a cluster in a DNA region on the genome or a plasmid of the producing microorganism (the gene group that participates in the biosynthesis of these compounds is also generally referred to hereafter simply as the "biosynthetic gene").

Determination of the nucleotide sequence information of the gene encoding a polyketide synthase raises the possibility, through domain modification based on this information, of changing the size of the carbon chain and the functional group on the β-carbon from the condensation step. For example, *Proc. Natl. Acad. Sci. USA*, 90 (1993) 7119-7123 reports that novel derivatives of erythromycin can be produced by the selective deactivation of particular domains within the polyketide synthase gene for erythrmoycin. Furthermore, the predictable production of novel compounds is made possible by the recombination of the domains of individual modules with other domains. For example, *Proc. Natl. Acad. Sci. USA*, 96 (1999) 1846-1851 reports that a variety of novel compounds can be become accessible through the recombination of some of the domains within the polyketide synthase gene for erythromycin.

In addition, determination of the nucleotide sequence of a biosynthetic gene cluster that includes the genes that encode modification enzymes (hereafter also referred to as modification enzyme genes) raises the possibility of the predictable production of novel compounds through the selective alteration of modification enzyme genes based on this information. For example, *Science* 252 (1991) 114-116 reports that the novel derivative, 6-deoxyerythronolide B, can be produced by disruption of the hydroxylase gene eryF present in the region of the polyketide synthase gene for erythromycin.

It may also be possible, by activation of the expression of a modification enzyme gene, to reduced unwanted by-products and produce solely a desired component. Methods generally known for the activation of gene expression include transcriptional activation based on promoter replacement, increasing the gene copy number using a multicopy vector, and increasing the enzyme activity by gene mutagenesis. It may also be possible to raise the productivity by activating a regulatory gene by the same methods, or conversely by deactivating a regulatory gene.

A desired polyketide compound can also be produced by a heterologous strain by acquiring the genes encoding the biosynthetic gene cluster and introducing them into a heterologous strain by an appropriate method. The heterologous strain used for this purpose is advantageously a microorganism and particularly E. coli with its capacity for rapid culture. For example, it is reported in Science, 291 (2001) 1790-1792 that, by incorporating a polyketide synthase gene into E. coli, the target 6-deoxyerythronolide B, a precursor for erythromycin, can be produced at good efficiencies.

DISCLOSURE OF THE INVENTION

An object of the present invention is to provide polypeptides that participate in the biosynthesis of pladienolide macrolide compounds, DNA that encodes these polypeptides, and variants of this DNA. An additional object of the present invention is to provide transformants that maintain all or a portion of this DNA or variants thereof and a method of producing pladienolide macrolide compounds using these transformants.

In order to achieve these objects, the present inventors attempted to obtain the target DNA from the strain *Streptomyces* sp. Mer-11107 (hereafter also referred to as strain Mer-11107), which is a strain that produces pladienolide macrolide compounds, by the colony hybridization procedure using a probe produced based on a sequence reported to be generally conserved in the ketosynthase domains of polyketide synthases; however, a large number of cosmids were selected and the target DNA could not be directly identified.

The present inventors therefore focused on the strong possibility that a modification enzyme gene would be present in the region of the polyketide synthase gene, and, using PCR, obtained gene fragments of a hydroxylase (cytochrome P450 enzyme), which is one of the modification enzymes, from publicly known actinomycetes. Using these as probes, several cosmids containing the target DNA were selected from the large number of cosmids obtained based on the sequence of the polyketide synthase region.

The Mer-11107 strain presumably contains a large number of modification enzymes based on the fact that it has the capacity to produce a variety of pladienolide analogues. The present inventors discovered that, among these numerous modification enzymes, the hydroxylase enzyme present in the selected cosmids was a 6-hydroxylase. Furthermore, the present inventors succeeded in obtaining and identifying the target DNA for the first time by overcoming characteristics inherent to the Mer-11107 strain that are unfavorable to the application of genetic engineering technology, such as resistance to conversion to the protoplast and resistance to the generally used drug markers.

That is, the present invention relates to the following (1) to (20).
(1) A DNA that is isolated and pure, and that contains at least one region encoding a polypeptide that participates in pladienolide biosynthesis.

(2) The DNA described in (1), characterized by containing the complete region encoding the polypeptide that participates in pladienolide biosynthesis.
(3) The DNA described in (1) or (2), characterized in that the polypeptide participating in pladienolide biosynthesis is at least one type selected from polyketide synthases, 6-hydroxylases, 7-acylation enzymes, 18,19-epoxidases and transcription regulator factors.
(4) The DNA described in any of (1) to (3), characterized by originating in a microorganism belonging to the genus *Streptomyces*.
(5) The DNA described in (1), comprising at least one nucleotide sequence selected from the nucleotide sequences defined in any of the following 1) to 5):
1) nucleotide sequences defined in any of the following (a) to (i):
(a) the continuous nucleotide sequence from the base 8340 to base 27935 of SEQ ID NO.: 1
(b) the continuous nucleotide sequence from the base 28021 to base 49098 of SEQ ID NO.: 1
(c) the continuous nucleotide sequence from the base 49134 to base 60269 of SEQ ID NO.: 1
(d) the continuous nucleotide sequence from the base 60269 to base 65692 of SEQ ID NO.: 1
(e) the continuous nucleotide sequence from the base 65707 to base 66903 of the SEQ ID NO.: 1
(f) the continuous nucleotide sequence from the base 68160 to base 66970 of SEQ ID NO.: 1
(g) the continuous nucleotide sequence from the base 69568 to base 68270 of SEQ ID NO.: 1
(h) the continuous nucleotide sequence from the base 72725 to base 70020 of SEQ ID NO.: 1
(i) the continuous nucleotide sequence from the base 1 to base 74342 of SEQ ID NO.: 1
2) a nucleotide sequence of a DNA that hybridizes under stringent conditions with a DNA comprising any of the nucleotide sequences defined in 1)
3) a nucleotide sequence having at least 70% homology with any of the nucleotide sequences defined in 1)
4) a nucleotide sequence complementary to any of the nucleotide sequences defined in any of 1) to 3)
5) a nucleotide sequence that, due to the degeneracy of the genetic code, does not hybridize under stringent conditions with a DNA comprising a nucleotide sequence defined in 1), but which codes for the same amino acid sequence as a nucleotide sequence defined in any of 1) to 3).
(6) The DNA described in (1), comprising at least one nucleotide sequence selected from the nucleotide sequences defined in any of the following (a) to (i):
(a) the continuous nucleotide sequence from the base 8340 to base 27935 of SEQ ID NO.: 1
(b) the continuous nucleotide sequence from the base 28021 to base 49098 of SEQ ID NO.: 1
(c) the continuous nucleotide sequence from the base 49134 to base 60269 of SEQ ID NO.: 1
(d) the continuous nucleotide sequence from the base 60269 to base 65692 of SEQ ID NO.: 1
(e) the continuous nucleotide sequence from the base 65707 to base 66903 of SEQ ID NO.: 1
(f) the continuous nucleotide sequence from the base 68160 to base 66970 of SEQ ID NO.: 1
(g) the continuous nucleotide sequence from the base 69568 to base 68270 of SEQ ID NO.: 1
(h) the continuous nucleotide sequence from the base 72725 to base 70020 of SEQ ID NO.: 1
(i) the continuous nucleotide sequence from the base 1 to base 74342 of SEQ ID NO.: 1.

(7) A polypeptide encoded by the DNA described in any of (1) to (6).

(8) The polypeptide described in (7), characterized by having a polyketide synthase activity.

(9) The polypeptide described in (8), characterized by having the amino acid sequence described by SEQ ID NOS.: 2, 3, 4 or 5, or having a partial sequence thereof.

(10) The polypeptide described in (7), characterized by having a 6-hydroxylase activity.

(11) The polypeptide described in (10), characterized by having the amino acid sequence described by SEQ ID NO.: 6 or having a partial sequence thereof.

(12) The polypeptide described in (7), characterized by having an 18,19-epoxidase activity.

(13) The polypeptide described in (12), characterized by having the amino acid sequence described by SEQ ID NO.: 8 or having a partial sequence thereof.

(14) The polypeptide described in (7), characterized by having a transcription regulator factor activity.

(15) The polypeptide described in (14), characterized by having the amino acid sequence described by SEQ ID NO.: 9 or having a partial sequence thereof.

(16) The polypeptide described in (7), characterized by having a 7-acylation enzyme activity.

(17) The polypeptide described in (16), characterized by having the amino acid sequence described by SEQ ID NO.: 7 or having a partial sequence thereof.

(18) A self-replicating or integrated-replicating recombinant plasmid carrying the DNA described in any of (1) to (6).

(19) A transformant maintaining the DNA described in any of (1) to (6).

(20) A method of producing a pladienolide, characterized by culturing the transformant described in (19) on culture medium; and collecting pladienolide from the culture broth.

(21) The method of production described in (20), wherein the pladienolide is pladienolide B.

(22) A method of producing a pladienolide D derivative represented by the formula (VI):

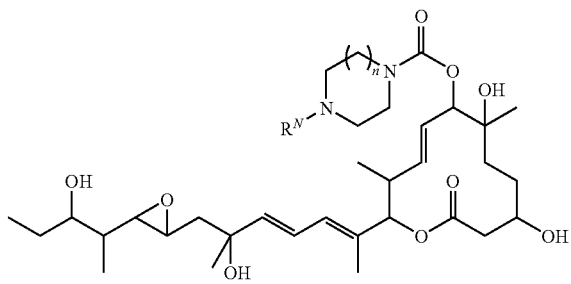

(wherein $R^N$ represents a lower alkyl group or a cyclic lower alkyl group; and n represents 1 or 2), comprising the steps of:

1) introducing a hydroxyl group at position 16 of the compound of the formula (I):

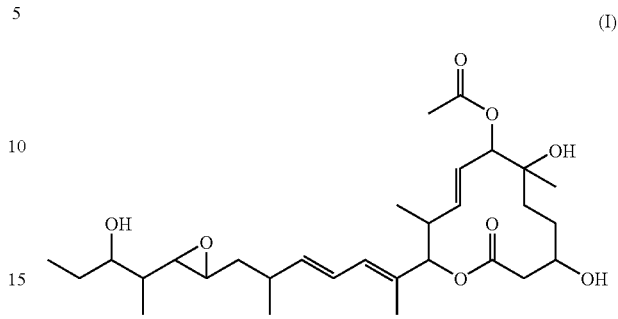

(pladienolide B) obtained by the method of production described in (20) or (21), thereby converting the compound of the formula (I) into a compound of the formula (II) (pladienolide D):

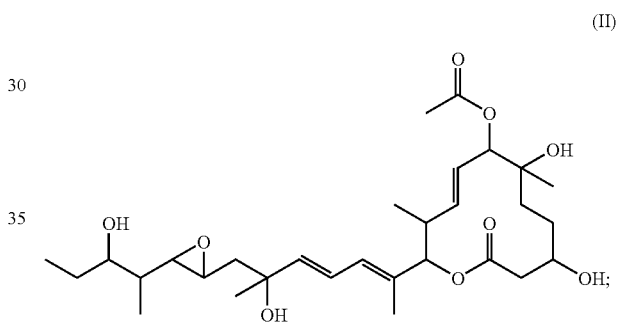

2) introducing a suitable protective group onto the hydroxyl groups at position 3, 6, 16 and/or 21 of the compound of the formula (II), thereby converting the compound of the formula (II) into a compound of the formula (III):

(III)

(wherein $R^{3A}$, $R^{6A}$, $R^{16A}$ and $R^{21A}$ represent a hydrogen atom or a protecting group of the hydroxyl group, provided that $R^{3A}$, $R^{6A}$, $R^{16A}$ and $R^{21A}$ do not all represent the hydrogen atom simultaneously);

3) eliminating the acetyl group at position 7 of the compound of the formula (III), thereby converting the compound of the formula (III) into a compound of the formula (IV):

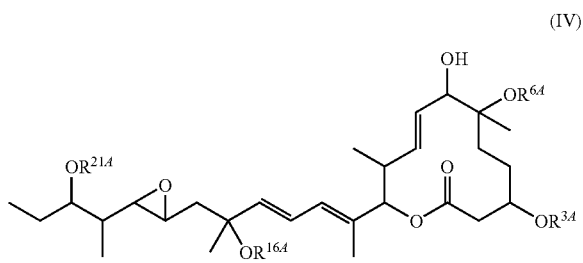

(wherein $R^{3A}$, $R^{6A}$, $R^{16A}$ and $R^{21A}$ are defined as above);
4) introducing a substituent at position 7 of the compound of the formula (IV), thereby converting the compound of the formula (IV) into a compound of the formula (V):

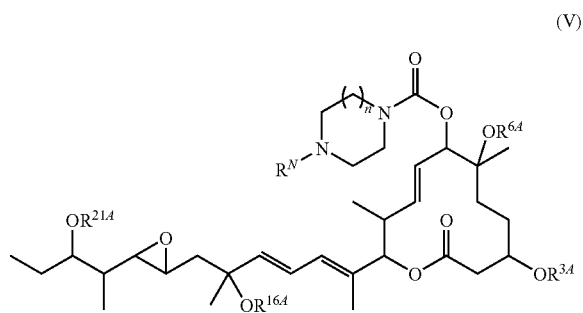

(wherein $R^N$, $R^{3A}$, $R^{6A}$, $R^{16A}$ and $R^{21A}$ are defined as above); and
5) eliminating the protective group from the compound of the formula (V).

DETAILED DESCRIPTION OF THE INVENTION

Embodiments of the present invention are described in detail in the following.

In the present specification, "lower alkyl group" denotes an alkyl group having 1 to 6 carbons and can be specifically exemplified by methyl, ethyl, propyl, isopropyl, butyl and so forth, wherein methyl, ethyl and isopropyl are particularly preferred.

"Cyclic lower alkyl group" denotes an alkyl group having 3 to 6 carbons and can be specifically exemplified by cyclopropyl, cyclobutyl, cyclohexyl and so forth, wherein cyclopropyl and cyclobutyl are particularly preferred.

"DNA that hybridizes under stringent conditions" denotes, for example, DNA obtained using a colony hybridization procedure, plaque hybridization procedure, Southern hybridization procedure, or the like, employing DNA having a nucleotide sequence as defined in any of the aforementioned (a) to (i) as probe, and can be specifically exemplified by DNA that can be identified by carrying out hybridization at 65° C. in the presence of 0.7-1.0 M sodium chloride using a filter on which DNA of colony or plaque origin has been immobilized, followed by washing the filter at 65° C. using 0.1×-2×SSC solution (the composition of 1×SSC solution comprises 150 mM sodium chloride and 15 mM sodium citrate).

A "DNA variant" denotes DNA that has been modified by, for example, the deletion, exchange, addition or insertion of a constituent nucleotide or derivatives thereof.

"Homology" refers to the percentage of nucleotides that are identical between two sequences that have been optimally aligned. In specific terms, the homology can be calculated from homology=(number of identical positions/total number of positions)$_{\times 100}$, and can be calculated using commercially available algorithms. In addition, algorithms of this nature are incorporated in the NBLAST and XBLAST programs described in Altschul et al., *J. Mol. Biol.*, 215 (1990) 403-410.

"Analogue" refers to a compound that has the same basic skeleton characteristic of a chemical structure, but which differs with respect to, for example, the type of modification or the form of a side chain.

In the present invention, the DNA encoding all or a portion of a polypeptide that participates in pladienolide biosynthesis can be isolated from the cultured mycelia of a microorganism that has the capacity to produce a pladienolide macrolide compound and the nucleotide sequence of this DNA can be determined. Any microorganism that has the capacity to produce pladienolide can be used as this microorganism regardless of the strain or species, but a preferred microorganism is the strain *Streptomyces* sp. Mer-11107, which was isolated from soil. The strain was deposited as FERM P-18144 at the National Institute of Bioscience and Human-Technology Agency of Industrial Science and Technology (1-3, Higashi 1-chome Tsukuba-shi, Ibaraki-ken 305-8566 Japan), which was subsequently reorganized into the International Patent Organism Depository (IPOD), National Institute of Advanced Industrial Science and Technology (Tsukuba Central 6, 1-1, Higashi 1-chome, Tsukuba, Ibaraki-ken, 305-8566 Japan), as of Dec. 19, 2000, and then transferred to International Deposit FERM BP-7812 at International Patent Organism Depositary (IPOD) National Institute of Advanced Industrial Science and Technology (Tsukuba Central 6, 1-1, Higashi 1-Chome, Tsukuba-shi, Ibaraki-ken 305-8566 Japan) as of Nov. 27, 2001. The taxonomical properties of the strains are as follows.

(1) Morphology

Spiriles type aerial hyphae were extended from the vegetative hyphae. Spore chains consisting of about 10 to 20 cylindrical spores were formed at the end of the matured aerial hyphae. The size of the spores was about 0.7×1.0 µm, the surface of the spores was smooth, and specific organs such as sporangium, sclerotium and flagellum were not observed.

(2) Cultural Characteristics on Various Media

Cultural characteristics of the strain after incubation at 28° C. for two weeks on various media are shown as follows. The color tone is described by the color names and codes which are shown in the parentheses of Tresner's Color wheels.

1) Yeast Extract-Malt Extract Agar Medium

The strain grew well, the aerial hyphae grew up on the surface, and light gray spores (Light gray; d) were observed. The reverse side of colony was Light melon yellow (3ea). Soluble pigment was not produced.

2) Oatmeal Agar Medium

The strain grew moderately, the aerial hyphae grew slightly on the surface, and gray spores (Gray; g) were observed. The reverse side of colony was Nude tan(4gc) or Putty (1½ec). Soluble pigment was not produced.

3) Inorganic Salts-Starch Agar Medium

The strain grew well, the aerial hyphae grew up on the surface, and gray spores (Gray; e) were observed. The reverse side of colony was Fawn (4ig) or Gray (g). Soluble pigment was not produced.

4) Glycerol-Asparagine Agar Medium

The strain grew well, the aerial hyphae grew up on the surface, and white spores (White; a) were observed. The reverse side of colony was Pearl pink (3ca). Soluble pigment was not produced.

5) Peptone-Yeast Extract-Iron Agar Medium

The strain growth was bad, and the aerial hyphae did not grow on the surface. The reverse side of colony was Light melon yellow (3ea). Soluble pigment was not produced.

6) Tyrosine Agar Medium

The strain grew well, the aerial hyphae grew up on the surface, and white spores (White; a) were observed. The reverse side of colony was Pearl pink (3ca). Soluble pigment was not produced.

(3) Utilization of Various Carbon Sources

Various carbon sources were added to Pridham-Gottlieb agar and incubated 28° C. for 2 weeks. The growth of the strain is shown below.

1) L-arabinose ±
2) D-xylose ±
3) D-glucose +
4) D-fructose +
5) Sucrose +
6) Inositol +
7) L-rhamnose −
8) D-mannitol +
9) Raffinose +
(+ positive, ± slightly positive, − negative)

(4) Various Physiological Properties

Various physiological properties of the present strain are as follows.

1) Range of growth temperature (yeast extract-malt extract agar, incubation for 2 weeks): 12° C. to 37° C.
2) Range of optimum growth temperature (yeast extract-malt extract agar, incubation for 2 weeks): 21° C. to 33° C.
3) Liquefaction of gelatin (glucose-peptone-gelatin medium): negative
4) Coagulation of milk (skim milk medium): negative
5) Peptonization of milk (skim milk medium): negative
6) Hydrolysis of starch (inorganic salts-starch agar): positive
7) Formation of melanoid pigment (peptone-yeast extract-iron agar): negative
(tyrosine agar): negative
8) Production of hydrogen sulfide (peptone-yeast extract-iron agar): negative
9) Reduction of nitrate (broth containing 0.1% potassium nitrate): negative
10) Sodium chloride tolerance (yeast extract-malt extract agar, incubation for 2 weeks): grown at a salt content of 4% or less (5) Chemotaxonomy LL-diaminopimelic acid and glycin were detected from the cell wall of the present strain.

The present inventors attempted to obtain DNA according to the present invention from this microorganism using the colony hybridization procedure described in *Molecular Cloning*, 2nd Edition. First, genomic DNA from the Mer-11107 strain was partially digested with a suitable restriction enzyme (for example, Sau3AI); this partial digest was ligated with a restriction enzyme digest (for example, BamHI) of a cosmid vector capable of replicating in *E. coli* to give recombinant DNA; and this recombinant DNA was incorporated into *E. coli* to give transductants. On the other hand, using DNA recovered from the Mer-11107 strain as template, amplified DNA was obtained by PCR using primers designed with reference to sequence information reported to be generally conserved in the ketosynthase domain of polyketide synthase and sequence information for a ketosynthase region in a pikromycin-producing organism (*Proc. Natl. Acad. Sci. USA*, 95 (1998) 12111-12116). The initially prepared transductants were screened using the obtained DNA as probe; however, a large number of positive clones (cosmids) was obtained and it was not possible to directly identify transductants having the target DNA.

Attention was then turned to the strong possibility that a modification enzyme gene would be present in the region of the polyketide synthase gene, and fragments of two types of hydroxylase (cytochrome P450 enzyme) genes were obtained by PCR from two publicly known actinomycetes. Using these as probes, the large number of already obtained transductants was screened and a single type of transductant binding to the probes was selected. The hydroxylase gene-binding DNA present in the selected cosmid was recovered and its sequence was determined. It was transduced into *E. coli*, and it was discovered that the transformed *E. coli* had the capacity to convert ME-265, whose formula is given below and which is the 6-deoxy form of pladienolide B, into pladienolide B. This DNA was therefore confirmed to be DNA coding for a 6-hydroxylase.

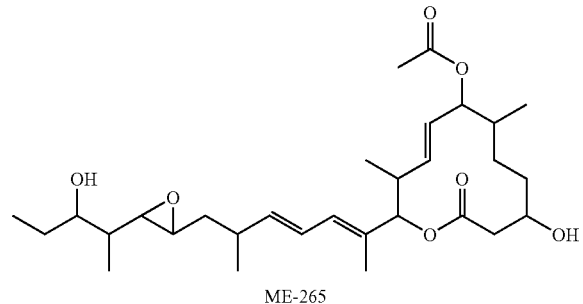

ME-265

Since this had resulted in the confirmation of a portion of the DNA participating in pladienolide biosynthesis, cosmids containing the pladienolide biosynthetic gene cluster adjacent to the cytochrome P450 gene were selected and aligned, using Southern hybridization and using the cytochrome P450 gene encoding this 6-hydroxylase in the probe, from the large number of positive clones (cosmids) that had already been obtained.

Among the several cosmids thus obtained, disrupted-gene strains were then prepared using cosmids thought to contain the polyketide synthesis region; it was confirmed that these disrupted strains had in fact lost the capacity to produce pladienolide, which thereby confirmed the functionality of the recovered DNA. The attempt was first made to obtain the disrupted-gene strain by constructing a cosmid having a partial deletion in the region thought to be the polyketide synthesis region and carrying out homologous recombination with the Mer-11107 strain using procedures in general use. However, several problems were encountered at this time. Thus, the Mer-11107 strain was not converted to the protoplast by the standardly used lysozyme treatment, which made it impossible to use the protoplast-PEG method in general use for the transformation of plasmids into actinomycetes.

The present inventors therefore attempted to replace the protoplast-PEG transformation procedure with a fusion method in which the DNA was delivered by mixing *E. coli* in the early logarithmic growth phase with a suitable amount of the actinomycetes spores. However, since a characteristic of the Mer-11107 strain is its refractoriness to spore formation, additional investigations were carried out, and transformation was finally accomplished through the use of mycelia cultured up to the early logarithmic growth phase instead of the actinomycetes in spore form.

Another problem stemmed from the fact that the Mer-11107 strain has a certain degree of natural resistance to thiostrepton, which as a consequence made it impossible to employ a thiostrepton resistance gene as a marker, although this is standardly used in the transformation of actinomycetes. The transformation procedure was therefore subjected to additional investigations, whereupon it was discovered that transformants from the Mer-11107 strain could be efficiently selected using an aminoglycoside phosphotransferase gene (aminoglycoside resistance gene) as the marker and using a ribostamycin-containing medium as the culture medium. Using this method, disrupted-gene strains were constructed in which the DNA thought to be the polyketide synthesis region was disrupted, and it was confirmed that these disrupted strains had in fact lost the capacity to produce pladienolide.

Since it had been confirmed that genes present in the previously obtained cosmids were related to pladienolide biosynthesis, the nucleotide sequences of the DNA fragments inserted in the individual cosmids were determined. First, after isolation of the individual cosmids by the cesium chloride method, shearing to about 1 kb and subcloning were carried out and the nucleotide sequences of the individual fragments were then determined for the obtained subclones, which resulted in the determination of an approximately 75 kb nucleotide sequence containing DNA related to pladienolide synthesis (refer to SEQ ID NO.: 1).

The DNA shown by SEQ ID NO.:1 contained 8 open reading frames (ORF): pldA I (bases 8340 to 27935), pldA II (bases 28021 to 49098), pldA III (bases 49134 to 60269), pldA IV (bases 60269 to 65692), pldB (bases 65707 to 66903), pldC (bases 68160 to 66970), pldD (bases 69568 to 68270), and pldR (bases 72725 to 70020). The amino acid sequences of the polypeptides encoded by these sequences are shown in SEQ ID NOS.: 2 to 9, respectively.

In the thusly obtained DNA related to pladienolide biosynthesis by the Mer-11107 strain, pldA I, pldA II, pldA III and pldA IV had several transcription reading frames, each containing one or more repeat units, known as modules, in the same manner as other already elucidated polyketide biosynthetic genes. As described below, each of the modules coded for some or all of the following domains: acyl carrier protein (ACP), β-ketoacyl ACP synthase (KS) and acyl transferase (AT), which participate in the condensation reaction in polyketide synthesis, and ketoacyl reductase (KR), dehydrogenase (DH), and enoyl reductase (ER), which participate in the β-carbonyl group modification reactions. The final module contained a thioesterase (TE) domain, which releases the polyketide chain from the polyketide synthase.

FIG. 1 shows the biosynthesis pathway of a pladienolide in the Mer-11107 strain. Unlike the other modules the loading module has the central cysteine replaced by glutamine, indicating that pldA I participates in the initial reaction. Module 10 includes a thioesterase (TE) domain, indicating that pldA IV participates in the final reaction of synthesizing the basic polyketide skeleton. After the basic skeleton of the polyketide has been formed in this way, it is thought that pladienolide biosynthesis proceeds through modifications by the enzyme group (PldB, PldC and PldD) coded by pldB, pldC and pldD. pldR, by virtue of its high homology with the aveR gene that encodes a transcription regulator factor in avermectin biosynthesis, is believed to code for a transcription regulator factor for the DNA participating in pladienolide biosynthesis.

The thusly elucidated modules and corresponding domains of the DNA participating in pladienolide biosynthesis are given below.

ORF pldA I (bases 8340 to 27935 of SEQ ID NO.: 1) encodes for the loading module, module 1, module 2 and module 3, and the corresponding polypeptide is shown by the amino acid sequence of SEQ ID NO.: 2.

Loading module (bases 8340 to 11384)
KSs: bases 8358 to 9620
ATs: bases 9702 to 10781
ACPs: bases 11148 to 11327
   Module 1 (bases 11385 to 16070)
KS1:s bases 11385 to 12650
AT1: bases 12747 to 13829
KR1: bases 14940 to 15803
ACP1: bases 15825 to 16007
   Module 2 (bases 16071 to 21431)
KS2: bases 16071 to 17336
AT2: bases 17445 to 18536
DH2: bases 18717 to 19418
KR2: bases 20298 to 21167
ACP2: bases 21189 to 21371
   Module 3 (bases 21432 to 27935)
KS3: bases 21432 to 22695
AT3: bases 22800 to 23880
DH3: bases 24066 to 24779
ER3: bases 25659 to 26588
KR3: bases 26610 to 27476
ACP3: bases 27498 to 27680

The amino acid sequence of the corresponding polypeptide is shown below.
KSs: amino acids 7 to 427
ATs: amino acids 455 to 814
ACPs: amino acids 937 to 996
KS1: amino acids 1016 to 1437
AT1: amino acids 1470 to 1830
KR1: amino acids 2201 to 2488
ACP1: amino acids 2496 to 2556
KS2: amino acids 2578 to 2999
AT2: amino acids 3036 to 3399
DH2: amino acids 3460 to 3693
KR2: amino acids 3987 to 4276
ACP2: amino acids 4284 to 4344
KS3: amino acids 4365 to 4786
AT3: amino acids 4821 to 5181
DH3: amino acids 5243 to 5480
ER3: amino acids 5774 to 6083
KR3: amino acids 6091 to 6379
ACP3: amino acids 6387 to 6447

ORF pldA II (bases 28021 to 49098 of SEQ ID NO.: 1) encodes for module 4, module 5, module 6 and module 7, and the corresponding polypeptide is shown by the amino acid sequence of SEQ ID NO.: 3.

Module 4 (bases 28021 to 33540)
KS4: bases 28132 to 29397
AT4: bases 29530 to 30627
DH4: bases 30865 to 31566
KR4: bases 32413 to 33276
ACP4: bases 33298 to 33480
   Module 5 (bases 33541 to 39003)
KS5: bases 33541 to 34806
AT5: bases 34912 to 35994
DH5: bases 36175 to 36876
KR5: bases 37755 to 38625
ACP5: bases 38647 to 38829
   Module 6 (bases 39004 to 43686)
KS6: bases 39004 to 40269

AT6: bases 40372 to 41454
KR6: bases 42550 to 43407
ACP6: bases 43429 to 43611
  Module 7 (bases 43687 to 49098)
KS7: bases 43687 to 44952
AT7: bases 45031 to 46128
DH7: bases 46303 to 47022
KR7: bases 47881 to 48744
ACP7: bases 48766 to 48948
  The amino acid sequence of the corresponding polypeptide is shown below.
KS4: amino acids 38 to 459
AT4: amino acids 504 to 869
DH4: amino acids 949 to 1182
KR4: amino acids 1465 to 1752
ACP4: amino acids 1760 to 1820
KS5: amino acids 1841 to 2262
AT5: amino acids 2298 to 2658
DH5: amino acids 2719 to 2952
KR5: amino acids 3246 to 3535
ACP5: amino acids 3543 to 3603
KS6: amino acids 3662 to 4083
AT6: amino acids 4118 to 4478
KR6: amino acids 4844 to 5129
ACP6: amino acids 5137 to 5197
KS7: amino acids 5223 to 5644
AT7: amino acids 5671 to 6036
DH7: amino acids 6095 to 6334
KR7: amino acids 6621 to 6908
ACP7: amino acids 6916 to 6976
  ORF pldA III (bases 49134 to 60269 of SEQ ID NO.: 1) encodes for module 8 and module 9, and the corresponding polypeptide is shown by the amino acid sequence of SEQ ID NO.: 4.
  Module 8 (bases 49134 to 53885)
KS8: bases 49235 to 50501
AT8: bases 50580 to 51656
KR8: bases 52752 to 53621
ACP8: bases 53642 to 53825
  Module 9 (bases 53886 to 60269)
KS9: bases 53886 to 55151
AT9: bases 55245 to 56342
DH9: bases 56514 to 57230
ER9: bases 58029 to 58925
KR9: bases 58947 to 59804
ACP9: bases 59826 to 60008
  The amino acid sequence of the corresponding polypeptide is shown below.
KS8: amino acids 35 to 456
AT8: amino acids 483 to 841
KR8: amino acids 1207 to 1496
ACP8: amino acids 1504 to 1564
KS9: amino acids 1585 to 2006
AT9: amino acids 2038 to 2403
DH9: amino acids 2461 to 2699
ER9: amino acids 2966 to 3264
KR9: amino acids 3272 to 3557
ACP9: amino acids 3565 to 3625
  ORF pldA IV (bases 60269 to 65692 of SEQ ID NO.: 1) encodes for module 10, and the corresponding polypeptide is shown by the amino acid sequence of SEQ ID NO.: 5.
  Module 10 (bases 60269 to 65692)
KS10: bases 60431 to 61696
AT10: bases 61781 to 62869
KR10: bases 63752 to 64609
ACP10: bases 64631 to 64813
TE10: bases 64832 to 65692

The amino acid sequence of the corresponding polypeptide is shown below.
KS10: amino acids 55 to 476
AT10: amino acids 505 to 867
KR10: amino acids 1162 to 1447
ACP10: amino acids 1455 to 1515
TE10: amino acids 1522 to 1808
  ORF pldB (bases 65707 to 66903 of SEQ ID NO.: 1) encodes for a pladienolide 6-hydroxylase, and the corresponding polypeptide is shown by the amino acid sequence in SEQ ID NO.: 6. ORF pldC (bases 68160 to 66970 of SEQ ID NO.: 1) encodes for a pladienolide 7-acylation enzyme, and the corresponding polypeptide is shown by the amino acid sequence in SEQ ID NO.: 7. ORF pldD (bases 69568 to 68270 in SEQ ID NO.: 1) encodes for a pladienolide 18,19-epoxidase, and the corresponding polypeptide is shown by the amino acid sequence in SEQ ID NO.: 8. ORF pldR (bases 72725 to 70020 in SEQ ID NO.: 1) encodes for a transcription regulator factor in pladienolide biosynthesis, and the corresponding polypeptide is shown by the amino acid sequence in SEQ ID NO.: 9.
  Furthermore, the DNA according to the present invention encompasses not only the aforementioned DNA, but also variants thereof as well as DNA that hybridizes with the aforementioned DNA under stringent conditions and participates in pladienolide biosynthesis. Such variants can be more specifically illustrated by sequences that exhibit at least 70% homology and preferably at least 80% homology and more preferably at least 90% homology with any of the following sequences: the nucleotide sequence continuously running from base 8340 to base 27935 of SEQ ID NO.: 1; the nucleotide sequence continuously running from base 28021 to base 49098 of SEQ ID NO.: 1; the nucleotide sequence continuously running from base 49134 to base 60269 of SEQ ID NO.: 1; the nucleotide sequence continuously running from base 60269 to base 65692 of SEQ ID NO.: 1; the nucleotide sequence continuously running from base 65707 to base 66903 of SEQ ID NO.: 1; the nucleotide sequence continuously running from base 68160 to base 66970 of SEQ ID NO.: 1; the nucleotide sequence continuously running from base 69568 to 68270 of SEQ ID NO.: 1; and the nucleotide sequence continuously running from base 72725 to base 70020 of SEQ ID NO.: 1.
  Thus, once it has been possible to establish a nucleotide sequence, DNA participating in pladienolide biosynthesis in accordance with the present invention can also be obtained by publicly known methods based on this information.
  For example, DNA with the nucleotide sequence shown in SEQ ID NO.: 1 is digested with a suitable restriction enzyme and the digested DNA is separated and recovered by a method described in *Molecular Cloning,* 2nd Edition to generate oligonucleotide for use as a probe or primer. In the case of use as a probe, the obtained DNA fragment is preferably labeled with, for example, digoxygenin. For example, a DIG Labeling & Detection Kit (Roche Diagnostics) is preferably used for digoxygenin labeling.
  A library is then constructed from a microorganism that exhibits the capacity to produce pladienolide, using a cDNA cloning procedure or a genomic cloning procedure as described in *Molecular Cloning,* 2nd Edition. Clones (colonies) that hybridize with the already prepared probe are selected from the resulting library; plasmid extraction is carried out on the selected clones according to the procedures described in *Molecular Cloning,* 2nd Edition; and target DNA that participates in pladienolide biosynthesis can be recovered from the plasmids thereby obtained.

When, in this case, only partial fragments of the DNA participating in pladienolide biosynthesis are present in the extracted plasmids, a restriction enzyme map of the plasmids is constructed by a standard method based on digestion of the extracted plasmids with suitable restriction enzymes, for example, BamHI. Restriction enzyme fragments present in common in several clones are then elucidated from this restriction enzyme map, and DNA containing the total DNA that participates in pladienolide biosynthesis can be obtained by stringing together the cloned fragments at their regions of overlap.

Or, the DNA participating in pladienolide biosynthesis can also be obtained using the aforementioned library and primers, by direct amplification of the target DNA by the direct PCR reaction.

The nucleotide sequence of the DNA encoding polypeptide that participates in pladienolide biosynthesis can be identified by analysis using the nucleotide sequence analysis procedures in general use, for example, using the dideoxy method (*Proc. Natl. Acad. Sci. USA,* 74, 5463 (1977)) or a nucleotide sequence analyzer, for example the 373A•DNA Sequencer (Perkin-Elmer). In specific terms, double-stranded plasmid DNA is used directly as the template in a cycle sequence reaction using various sequence-specific oligonucleotide primers. Or, the DNA fragments can be subdivided and randomly inserted into the bacteriophage M13, and, using a plasmid vector or library in which the individual fragments are partially overlapped, an overlap library can be constructed in which progressive deletion is introduced from the terminal region of the DNA fragments; the DNA sequence of the various recombinant DNA fragments can then be determined using a vector sequence-specific oligonucleotide primer.

In addition, based on the nucleotide sequence determined for the DNA, a target DNA can also be prepared by chemical synthesis using a DNA synthesizer, for example, a Model 8905 DNA Synthesizer (PerSeptive Biosystems). The processing, compilation, editing, and analysis of the obtained nucleotide sequence data can be carried out using existing software, for example, Genetyx™ from Software Development.

Polypeptide according to the present invention can be produced by inducing the expression of DNA according to the present invention in a host cell using, for example, the procedures described in *Molecular Cloning,* 2nd Edition, or *Current Protocols in Molecular Biology*. The site of incorporation of the DNA or variant thereof according to the present invention may be on either a plasmid or chromosome of the host microorganism. In addition to the subject DNA or variant thereof, such a plasmid may also contain, for example, a self-replicating sequence, promoter sequence, terminator sequence, and drug-resistance gene. In addition, the plasmid may be an integration plasmid that has a sequence homologous with a particular region of the genome of the anticipated host.

The host or plasmid-vector system for expression of polypeptide encoded by DNA according to the present invention may be any system in which this DNA can be stably maintained and expressed. However, when the host is an actinomycetes or related strain that has a native capacity to produce pladienolide, this enables the use of, for example, the self-replicating vector pIJ6021 (*Gene,* 166, 133-137 (1995)) or the chromosome-integrating vector KC515 (*The Bacteria,* Vol. 9, *Antibiotic-Producing Streptomyces* (ed: Queener, S. E. and Day, L. E.), pp. 119-158, Academic Press, Orlando, Fla.).

The procedures for isolating and purifying transformant-produced polypeptide according to the present invention can be those procedures in general use for the isolation and purification of enzymes. For example, when polypeptide according to the present invention is expressed in a soluble state within the cell, the cell is recovered by centrifugal separation after cultivation has been completed, and suspended in an aqueous buffer, and after disruption of the cell by, for example, an ultrasonic homogenizer, French press, Manton-Gaulin homogenizer, or Dynomill, a noncellular extract is obtained. A supernatant is prepared by centrifugal separation of the noncellular extract thus obtained, and a purified target product can be obtained from this supernatant by procedures in general use for the isolation and purification of enzymes.

Moreover, polypeptide according to the present invention can also be produced by chemical synthesis methods, such as the fluorenylmethyloxycarbonyl method (Fmoc method) or t-butoxycarbonyl method (t-Boc method), based on the data for the amino acid sequence of the previously obtained polypeptide.

In addition, pladienolide can be obtained by culturing, on a medium, a transformant containing a previously obtained pladienolide biosynthetic gene; allowing the pladienolide product to accumulate in the culture; and recovering the pladienolide from the culture. The culture conditions are not particularly limited, but are based on the general culture conditions for the host.

Based on the nucleotide sequence information of the DNA that participates in pladienolide biosynthesis, the size of the carbon chain in the basic polyketide skeleton and the functional group at the β-carbon from the condensation step can also be altered by modification of the modules. Moreover, by selectively inactivating a modification enzyme that acts after polyketide formation, it may be possible to preferentially produce a specific component of a predictable pladienolide. For example, it is possible to convert the Mer-11107 strain, which produces mainly pladienolide B, into a strain that produces mainly ME-265, the 6-deoxy form of pladienolide B, by deletion mutation of pldB. The procedure for effecting deletion mutation of pldB can be exemplified by conversion or substitution by homologous recombination by the general methods described in *Molecular Cloning,* 2nd Edition.

Using a thusly obtained strain endowed with the capacity to preferentially produce a specific pladienolide, it becomes possible to produce a specific pladienolide patterned on the method of producing pladienolide B.

The present invention enables the isolation of DNA that encodes polypeptide that participates in the biosynthesis of a pladienolide macrolide compound and enables the determination of its nucleotide sequence. In addition, a plasmid containing this DNA can be constructed; a transformant transformed by such a plasmid can be constructed; and pladienolide can be produced at good efficiencies using such a transformant. Moreover, by modifying or altering the sequence of the obtained DNA, it becomes possible to produce novel or specific pladienolides by altering the type of carboxylic acid that is incorporated, the post-condensation modification reactions, the modification reactions that occur after skeleton formation, and their numerous combinations.

EXAMPLES

Figure 1:
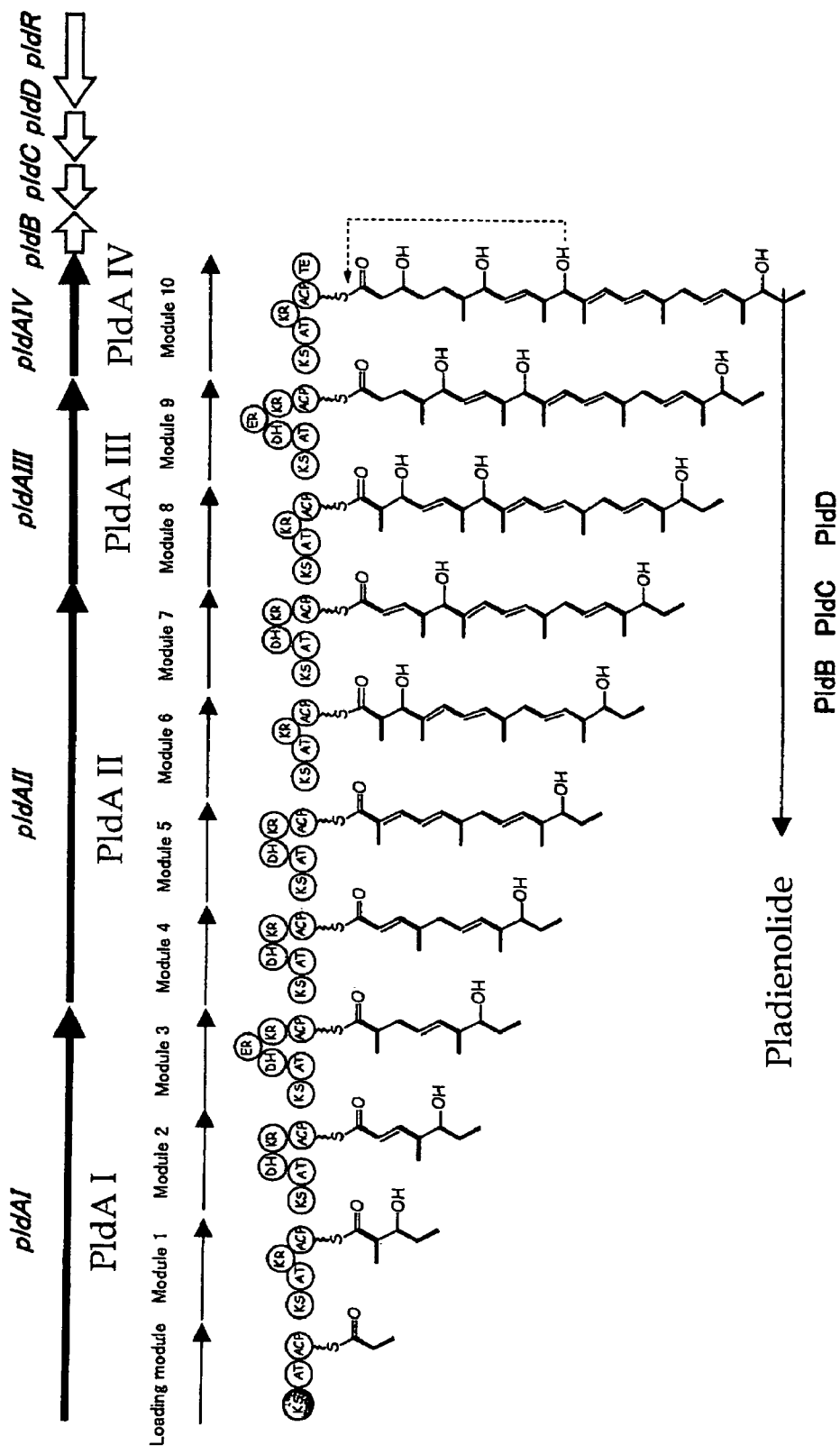
FIG. 1 shows the biosynthesis pathway of pladienolides in Mer-11107 strain.

The present invention is explained in detail below using examples, but the present invention is not limited by these examples. In the explanations below, concentrations are expressed as weight percentages unless otherwise specified.

Example 1

Cultivation of Mer-11107 and Isolation of Genomic DNA

Hyphae of *Streptomyces* sp. Mer-11107 were inoculated into 25 mL of Tryptic Soy Broth, and cultured with shaking at 28° C. for 3 days. Genomic DNA was prepared from the resulting culture broth according to the methods described under "Isolation genomic DNA" (pp. 162-170) in D. A. Hopwood et al's *Practical Streptomyces Genetics* (The John Innes Foundation, Norwich, England, 2000).

Example 2

Preparation of Mer-11107 Genomic Library

160 µL of sterile purified water, 200 µL of Mer-11107 genome DNA solution (1 mg/mL), 40 µL of 10× concentration M buffer solution (100 mM Tris-HCl (pH 7.5), 100 mM MgCl$_2$, 10 mM dithiothreitol, 500 mM NaCl) and 1 µL of restriction enzyme Sau3AI (1 unit/µL) were mixed and incubated at 37° C. for 3 minutes. 50 µL was then taken out and extracted with 50 µL of phenol-chloroform mixture (phenol: chloroform:isoamyl alcohol=25:24:1, volume ratio), the aqueous layer was collected and extracted again with 50 µL of chloroform, and the aqueous layer was again collected. 5 µL of 3 M sodium acetate (pH 6.0) and 150 µL of ethanol were added to the liquid, which was then left at −80° C. for 30 minutes and centrifuged to collect the precipitated DNA. After being washed in 70% ethanol, this DNA was dissolved in 90 µL of sterile purified water, and incubated at 37° C. for 3 hours after addition of 10 µL of 10 times concentration BAP buffer solution (500 mM Tris-HCl (pH 9.0), 10 mM MgCl$_2$) and 5 µL of bacterial alkaline phosphatase (0.5 unit/µL, Takara Shuzo Co., Ltd.). The reaction liquid was extracted with 100 µL of phenol-chloroform mixture (phenol:chloroform:isoamyl alcohol=25:24:1, volume ratio), the aqueous layer was collected and extracted again with 100 µL of chloroform, and the aqueous layer was again collected. 10 µL of 3 M sodium acetate (pH 6.0) and 300 µL of ethanol were added to this liquid, which was then left at −80° C. for 30 minutes and centrifuged to collect the precipitated DNA. After being washed in 70% ethanol, this DNA was dissolved in 20 µL of TE buffer solution (10 mM Tris-HCl (pH 8.0), 1 mM EDTA).

Meanwhile, 10 µg of SuperCos cosmid vector (Stratagene Co.) was digested with restriction enzyme XbaI in accordance with the Stratagene manual, the DNA terminals were de-phosphorylated with calf intestinal alkaline phosphatase (Takara Shuzo Co., Ltd.), and after being digested with restriction enzyme BamHI and purified, this was dissolved in 10 µL of TE buffer solution.

2.5 µL of the Sau3AI partial digest solution of Mer-11107 DNA described above was added to 1 µL of this cosmid DNA solution, and 1.5 µL of sterile purified water, 5 µL of DNA Ligation Kit (Takara Shuzo Co., Ltd.) Solution II and 10 µL of Solution I were added in that order and incubated at 23° C. for 10 minutes. 4 µL of the reaction liquid was packaged into a lambda-phage using Gigapack III XL Kit (Stratagene Co.). When the resulting packaged liquid (total 500 µL) was subjected to a transduction test, colony formation ability was tested at 380 cfu (colony forming units)/µL.

Example 3

Preparation of Various Probes (1) Preparation of Probes Comprising Keto Synthetase Coding Regions The following two primers, KS-3F and KS-4R, respectively comprising the nucleotide sequences in SEQ ID NOS.: 10 and 11 below, were synthesized based on sequences that are generally conserved in the ketosynthase domains of polyketide synthases.

(SEQ ID NO.: 10)
KS-3F: 5'-GACCGCGGCTGGGACGTGGAGGG-3'

(SEQ ID NO.: 11)
KS-4R: 5'-GTGCCCGATGTTGGACTTCAACGA-3'

These primers were used to carry out PCR under the following conditions.

(PCR Reaction Solution Composition)

| | |
|---|---|
| Sterile purified water | 31 µL |
| 2× GC buffer | 50 µL |
| dNTP mixed solution | 16 µL |
| (2.5 mM each dATP, dGTP, dTTP and dCTP) | |
| KS-3F (100 pmol/µL) | 0.5 µL |
| KS-4R (100 pmol/µL) | 0.5 µL |
| Mer-11107 total DNA (100 ng/µL) | 1 µL |
| LA Taq polymerase (5 U/µL, Takara Shuzo Co., Ltd.) | 1 µL |

(Reaction Temperature Conditions)
95° C. 3 minutes
(98° C. 20 sec, 63° C. 30 sec, 68° C. 2 minutes) 30 cycles
72° C. 5 minutes The 930 bp DNA fragments amplified as a result of this reaction were electrophoresed on 0.8% agarose gel, and the isolated 930 bp DNA fragments were excised and collected and purified using SUPREC-01 (Takara Shuzo Co., Ltd.). Using 10 ng of the resulting DNA fragments as the template, 930 bp DNA fragments comprising the keto synthetase coding region were amplified again under the same PCR conditions as above except that the number of reaction cycles was changed to 20. These DNA fragments were concentrated and purified using SUPREC-02 (Takara Shuzo Co., Ltd.), and 50 µL of the resulting TE solution was taken as the probe solution.

(2) Preparation of Probe Comprising Cytochrome P450 Gene Region

Two known cytochrome P450 genes were amplified from actinomycetes for purposes of preparing a cytochrome P450 gene probe. That is, the two primers CB-1F and CB-2R comprising the sequences shown in the following SEQ ID NOS.: 12 and 13 were synthesized for purposes of amplifying the ORF-A gene derived from *Streptomyces thermotolerans* ATCC11416 (*Biosci. Biotechnol. Biochem.* 59: 582-588, 1995).

(SEQ ID NO.: 12)
CB-1F: 5'-ATGACAGCTTTGAATCTGATGGATCCC-3'

(Sequence NO.: 13)
CB-2R: 5'-TCAGAGACGGACCGGCAGACTCTTCAGACG-3'

Meanwhile, the two primers PKC-1F and PKC-2R comprising the sequences shown in the following SEQ ID NOS. 14 and 15 were synthesized for purposes of amplifying the pik-C gene derived from *Streptomyces venezuelae* ATCC15439 (*Chem. Biol.* 5: 661-667, 1998).

```
                                         (SEQ ID NO.: 14)
PKC-1F: 5'-GTGCGCCGTACCCAGCAGGGAACGACC-3'

(SEQ ID NO.: 15)
PKC-2R: 5'-TCACGCGCTCTCCGCCCGCCCCTGCC-3'
```

These primers were used to carry out PCR under the following conditions.
(PCR Reaction Solution Composition)

| | |
|---|---|
| Sterile purified water | 31 μL |
| 2 × GC buffer | 50 μL |
| dNTP mixed solution | 16 μL |
| (2.5 mM each dATP, dGTP, dTTP, and dCTP) | |
| primer-F (100 pmol/μL) | 0.5 μL |
| primer-R (100 pmol/μL) | 0.5 μL |
| ATCC11416 or ATCC15439 genome DNA (100 ng/μL) | 1 μL |
| LA Taq polymerase (5 U/μL, Takara Shuzo Co., Ltd.) | 1 μL |

(Reaction Temperature Conditions)
95° C. 3 minutes
(98° C. 20 sec, 63° C. 30 sec, 68° C. 2 minutes) 30 cycles
72° C. 5 minutes The two 1.2 kb DNA fragments amplified as a result of this reaction were purified by QIAGEN PCR Purification Kit (QIAGEN Co.), and a mixed solution comprising 10 ng/μL of each DNA fragment was prepared and used as the probe.

Example 4

Screening Using Probe Comprising Keto Synthetase Coding Region

An *E. coli* XL-1Blue MR host (Stratagene Co.) was transduced with the Mer-11107 genome DNA library packaged solution prepared in the above (2) in accordance with the Stratagene manual. After transduction the bacterial suspension was dispensed and spread onto ten LB-50 μg/mL ampicillin-1.5% agar medium plates (inner diameter 90 mm, height 15 mm), and cultured for 18 hours at 37° C. The colonies growing on each plate were transferred to HybondoN+ filters (Amersham Biosciences), alkali and neutral treated under the conditions described in the manual for the HybondoN+ filters, and dried for 2 hours at 80° C. to fix DNA derived from the colonies onto the filters.

The genome DNA library was screened by colony hybridization using an AlkPhos Direct System (Amersham Biosciences) with 100 ng of the 930 bp DNA fragment comprising the keto synthetase region prepared in Example 3 (1) as the probe. Hybridization was performed for 2 hours at 65° C. at a salt concentration of 0.5 M NaCl. The conditions for hybridization and detection were those described in the manual attached to the AlkPhos Direct System. Of the roughly 7,600 colonies tested, 59 colonies which hybridized strongly with the alkali phosphatase-labeled probe were isolated. Cosmids were extracted and purified from *E. coli* clones derived from these colonies.

Example 5

Selection and Verification of Cosmid Clones Having Pladienolide Biosynthesis Gene Region Using Probe Comprising Cytochrome P450 Gene Region Two μL of each of the cosmid DNA solutions obtained in Example 4 was spotted onto a HybondoN+ filter, alkali and neutral treated under the conditions described in the attached manual, and dried for 2 hours at 80° C. to fix the DNA on the filter. Hybridization was performed with these filters under the same conditions as in Example 4 using the cytochrome P450 gene fragment described in Example 3 as the probe. One cosmid that hybridized strongly with the probe was selected as a result and named pKS58.

The pKS58 DNA was partially digested with Sau3AI restriction enzyme, ligated with the BamHI-CIAP treated phage vector Zap Express (Stratagene Co.), and packaged into a lambda phage using a Gigapack III XL Kit (Stratagene Co.). *E. coli* XL1-Blue MRF' was infected with this phage solution, and made to form a plaque. Plaque hybridization was performed using the cytochrome P450 gene probe prepared in Example 3 (2) to subclone an approximately 2 kb length DNA fragment containing cytochrome P450 gene.

This cytochrome P450 gene DNA fragment was sequenced, and two primers PDL58-1F and PDL58-2R having the sequences shown in the following SEQ ID NOS.: 16 and 17 were synthesized from the N- and C-terminals, which are considered to be the cytochrome P450 coding regions.

```
                                            (SEQ ID NO.: 16)
PDL58-1F: 5'-GCCCCGCATATGGATCTGGAAACCCAACTTCTC-3'

(SEQ ID NO.: 17)
PDL58-2R: 5'-GCACTAGTCAGCCGCGCTCGACGAGGAGGTG-3'
```

These primers were used to carry out PCR under the following conditions.
(PCR Reaction Solution Composition)

| | |
|---|---|
| Sterile purified water | 31 μL |
| 2 × GC buffer | 50 μL |
| dNTP mixed solution | 16 μL |
| (2.5 mM each dATP, dGTP, dTTP and dCTP) | |
| PDL58-1F (100 pmol/μL) | 0.5 μL |
| PDL58-2R (100 pmol/μL) | 0.5 μL |
| pKS58 DNA (100 ng/μL) | 1 μL |
| LA Taq polymerase (5 U/μL, Takara Shuzo Co., Ltd.) | 1 μL |

(Reaction Temperature Conditions)
95° C. 3 minutes
(98° C. 20 sec, 63° C. 30 sec, 68° C. 2 minutes) 20 cycles
72° C. 5 minutes The 1.2 kb DNA fragment amplified as a result of this reaction was purified with QIAGEN PCR Purification Kit (QIAGEN Co.), and digested with NdeI and SpeI restriction enzymes. After the reaction the DNA was electrophoresed on 0.8% agarose gel, the isolated 1.2 kb DNA fragment was excised and DNA was collected and purified using QIAGEN GelExtraction Kit (QIAGEN Co.). This DNA fragment was inserted into the NdeI and SpeI sites of the cytochrome P450 gene expression plasmid pT7NS-camAB (WO 03/087381-A1) to construct pPDL96.

*E. coli* BL21 (DE3) was transformed using this plasmid and cultured in M9CG medium (1.28% $NaHPO_4.7H_2O$, 0.3% $KH_2PO_4$, 0.05% NaCl, 0.1% $NH_4Cl$, 1% casamino acid, 0.4% glucose, 1 mM $MgCl_2$, 100 μM $CaCl_2$, 50 μg/mL ampicillin) to a density of 0.8 $OD_{600}$ (optical density at 600 nm). 5-Aminolevulinic acid was added to 80 μg/mL and IPTG to 0.1 mM, and cultivation was continued at 22° C. for 25 hours to induce the cytochrome P450 protein. After induction, the mycelia were collected and suspended in 5 mL of CV buffer solution (50 mM $NaPO_4$ (pH 7.3), 1 mM EDTA, 10% glycerol, 1 mM glucose). 1 mL of this suspension was taken in a test tube and 5 μL of a DMSO solution (50 mg/mL) of ME-265 (the 6-position deoxide of pladienolide B) was added and incubated at 28° C. for 15 hours. 1 mL of acetonitrile was added and mixed with this reaction solution, which was then centrifuged and supernatant analyzed by HPLC under the following conditions to confirm conversion to pladienolide B. These results lead the pladienolide biosynthesis gene region is involved in pKS58.

(HPLC Analysis Conditions)
Analyzer: Shimadzu HPLC 10 Avp
Column: Develosil ODS UG-3 (φ4.6 mm×50 mm 3 μm)
Mobile phase: 45% to 55% methanol (0 to 5 minutes)
  55% methanol (5 to 13 minutes)
  55% to 70% methanol (13 to 21 minutes)
  45% methanol (21 to 25 minutes)
Flow rate: 1.2 mL/min
Detection: UV 240 nm
Injection volume: 5 μL
Column temperature: 40° C.
Analysis time: 25 minutes
Retention time: ME-265: 20 minutes,
  Pladienolide B: 13 minutes Example 6

Selection of Cosmid Comprising Biosynthesis Gene Cluster Neighboring Cytochrome P450 Gene A cosmid comprising the biosynthesis gene cluster neighboring the cytochrome P450 gene obtained in Example 5 was selected from the 59 cosmid DNA samples obtained in Example 4.

The 59 cosmid DNA samples were digested with restriction enzymes EcoRI and BamHI, and the DNA obtained in each case was electrophoresed on agarose gel and subjected to Southern hybridization using as probes the KS domain DNA (aveA2 KS6 domain) and the AT domain DNA (aveA1 AT2 domain) of the avermectin aglycone biosynthesis gene (see *Proc. Natl. Acad. Sci. USA* 96 (1999) 9509-9514; JP-A 2000-245457; or WO 00/50605) and the cytochrome P450 gene obtained in Example 5.

Figure 2:
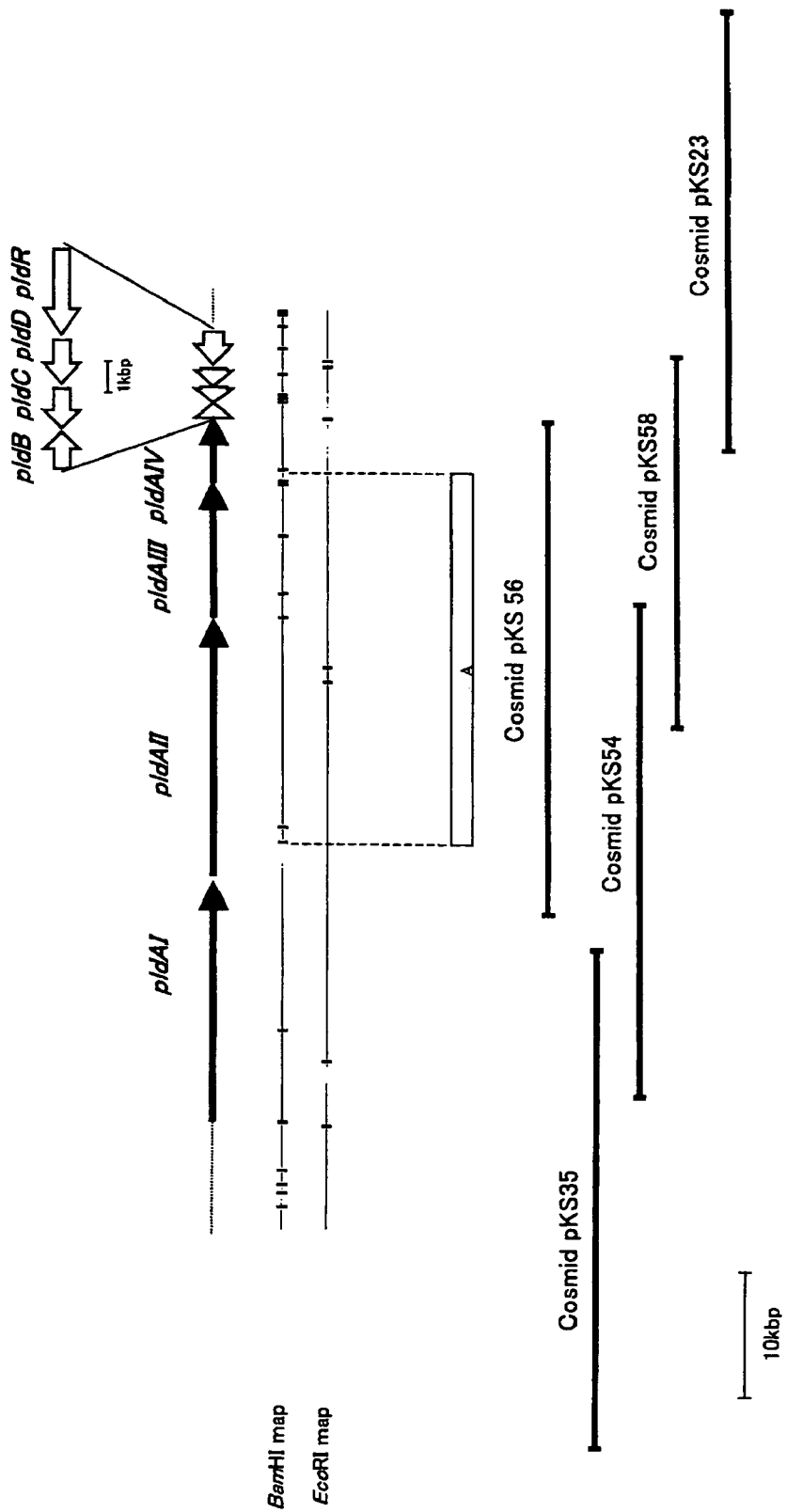
FIG. 2 shows the correspondence between cosmids and each of ORFs of DNA participating in biosynthesis of pladienolides in Mer-11107 strain.

Those cosmids having DNA fragments that hybridized at the same length were grouped on the basis of the electrophoresis patterns of DNA digested with restriction enzymes EcoRI and BamHI, and the hybridization band patterns using the various probes. Of these, all but one of the cosmids exhibiting similar patterns were deleted, and the remaining cosmids were organized according to partially matching band patterns. Beginning with the pKS58 cosmid comprising the cytochrome P450 gene obtained in Example 5, pKS56 and pKS54 were selected as cosmids neighboring the side comprising the polyketide synthetase gene from the cytochrome P450 gene side, and pKS35 was selected as a cosmid neighboring pKS54. pKS23 was also selected as a cosmid neighboring the cosmid pKS58 from cytochrome P450 gene side to the side not comprising the polyketide synthetase gene. As a result, as shown in FIG. 2, pKS23, pKS58, pKS56, pKS54 and pKS35 were selected as cosmid clones encompassing the pladienolide biosynthesis gene cluster.

Example 7

Production of Pladienolide Biosynthetic Gene Cluster-Deficient Strain

From among the cosmids selected in Example 6, a disrupted biosynthetic gene strain was produced using the DNA of pKS56, which was thought to contain the polyketide synthesis region.

The cosmid DNA from pKS56 was digested with the BamHI restriction enzyme and a 2 kb spectinomycin resistance gene (aminoglycoside 3"-adenyltransferase, abbreviated hereafter as aadA) was ligated with the BamHI digestion fragments using an NEB Quick Ligation Kit (New England Biolabs Inc.). This resulted in the BamHI-mediated deletion of 30 kb of the cosmid DNA from pKS56 (region A in FIG. 2: nucleotides 31194 to 61374 in SEQ ID NO.: 1), and cosmid p56aadA, which was recombined with the 2 kb spectinomycin resistance gene, was obtained. The aadA was prepared by digesting the plasmid pHP45omega (Gene 190, 315-317 (1997)) with the BamHI restriction enzyme.

Figure 3:
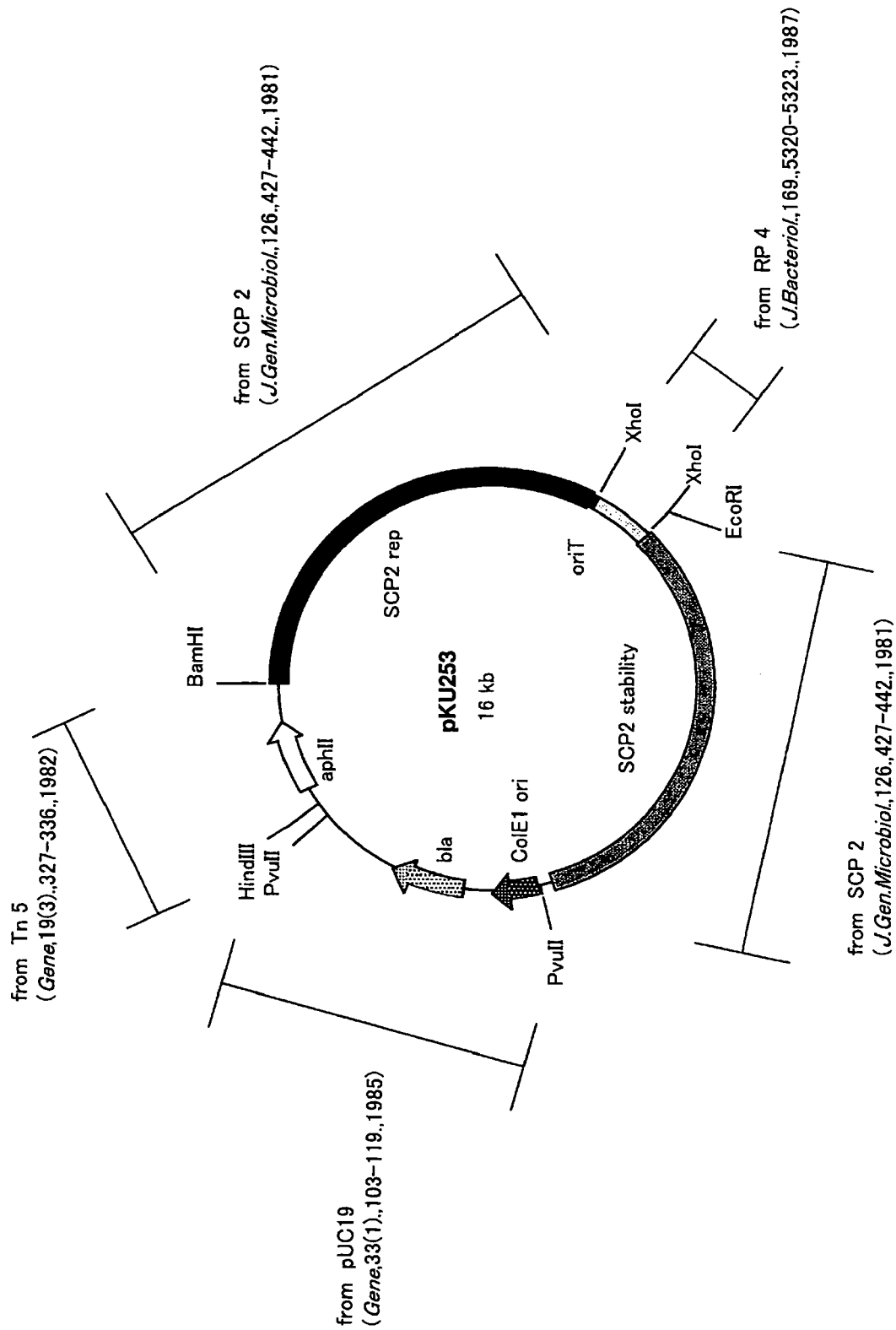
FIG. 3 shows the structure of plasmid pKU253.

The shuttle vector pKU253 was used to incorporate cosmid p56aadA into the Mer-11107 strain. p56aadA was digested with the EcoRI restriction enzyme, and 14 kb lacking any cosmid vector regions was separated by agarose gel electrophoresis and was purified using a Gene Clean II Kit (Bio101 Co.). The obtained 14 kb EcoRI fragment was ligated with the EcoRI digest of the shuttle vector pKU253 using an NEB Quick Ligation Kit, yielding pKU253-56aadA. As shown in FIG. 3, pKU253 was constructed by joining the *E. coli* plasmid pUC19 (*Gene*, 33(1), 103-119, 1985) to the base of the SCP2 plasmid originating from the actinomycetes *Streptomyces coelicolor* A3(2) (*J. Gen. Microbiol.*, 126, 427-442, 1981) and introducing the aminoglycoside resistance gene aphII (*Gene*, 19(3), 327-336, 1982) and the conjugation gene oriT (*J. Bacteriol.*, 169, 5320-5323, 1987).

The resulting pKU253-56aadA was transformed into conjugated *E. coli* S17-1 (ATCC47055) by electroporation to obtain S17-1/pKU253-56aadA. The resulting S17-1/pKU253-56aadA was inoculated into 10 mL of LB medium (1% bacto tryptone, 0.5% yeast extract, 0.5% NaCl) comprising 25 μg/mL of kanamycin and 200 μg/mL of spectinomycin and shaking cultured at 30° C. for 2 hours, and the mycelia were collected, washed twice with 10 mL of LB medium and suspended in 5 mL of LB medium. This was the donor suspension.

While the donor suspension was being prepared, Mer-11107 was inoculated into 10 mL of TSB medium (Trypto-Soya broth: Nissui Pharmaceutical Co., Ltd.) and shaking cultured at 30° C. for 5 hours, and the mycelia were collected, washed twice with 10 mL of sterile water and suspended in 1 mL of sterile water. This was the recipient suspension.

500 μL of the S17-1/pKU253-56aadA donor suspension was mixed with 10 μL of the Mer-11107 recipient suspension followed by plating on Actino Medium No. 4 agar medium (Nihon Pharmaceutical Co., Ltd.). After culture at 30° C. for 18 hours, 2.5 mL SNA (0.8% nutrient medium: Difco, 0.4% agar) containing 2 mg/mL ribostamycin was layered on. Incubation for at 30° C. 7 days then gave a ribostamycin-resistant pKU253-56aadA transformant strain.

The resulting pKU253-56aadA transformant was seeded to 10 mL TSB medium that did not contain ribostamycin and shaking cultured at 30° C. for 24 hours. The plasmid vector pKU253 has a poor replication efficiency in the Mer-11107 strain, and the Mer-11107 strain is unable to maintain pKU253 when cultured on medium lacking a drug resistance marker (ribostamycin).

The cells were collected from the pKU253-56aadA transformant culture medium and were washed twice with 10 mL sterile water and suspended in 10 mL sterile water. The suitably diluted suspension was plated on YMS agar medium (0.4% yeast extract, 1% malt extract, 0.4% soluble starch, 2% agar, 10 mM calcium chloride) containing 200 μg/mL spectinomycin and was cultured at 30° C. for 4 days. Single colonies that grew on the spectinomycin-containing YMS agar medium were reseeded to YMS agar medium containing 200 µg/mL spectinomycin and YMS agar medium containing 200 µg/mL ribostamycin followed by culture at 30° C. for 2 days.

After culture, the spectinomycin-resistant, ribostamycin-sensitive strain was selected, and it was confirmed by Southern hybridization that the spectinomycin resistance gene had been inserted in the region regarded as the targeted biosynthetic gene on the genomic DNA. The resulting strain was named Mer-11107-56::aadA.

Example 8

Pladienolide Productivity Test of Pladienolide Biosynthetic Gene Cluster-Deficient Strain The productivity test of pladienolide B was conducted in a total of three strains: the Mer-11107-56::aadA strain obtained in Example 7, the original Mer-11107 strain and its transformant, the Mer-11107/pKU253 strain as control.

200 µL each of frozen seed of Mer-11107-56::aadA strain prepared in Example 7, Mer-11107 strain and Mer-11107/pKU253 strain was inoculated into 20 mL of seed medium (soluble starch 2%, ESUSAN-MEAT 2%, yeast extract 0.5%, $K_2HPO_4$ 0.1%, $MgSO_4.7H_2O$ 0.25%, $CaCO_3$ 0.3%, pH not adjusted) and incubated at 25° C. for 2 days.

300 µL of the resulting seed culture broth was inoculated into 30 mL of seed culture medium (5% Stabilose, 1% glucose, 3% Pharmamedia, 2% β-cyclodextrin, 0.1% $CaCO_3$, pH 7.5) and cultured at 25° C. for 4 and 5 days. After the completion of the cultivation, the resulting culture liquid was extracted by addition of 9 times the amount of acetonitrile. The amounts of pladienolide B in the resulting extract was measured by HPLC. The measurement results are shown in Table 1.

The HPLC measurement conditions are shown below.
Analyzer: Shimadzu HPLC 10 Avp
Column: Develosil ODS UG-3 (4.6 mm×50 mm 3 µm)
Mobile phase (volume %): 45% to 55% methanol (0 to 5 min)
  55% methanol (5 to 13 min)
  55% to 70% methanol (13 to 21 min)
  45% methanol (21 to 25 min)
Flow rate: 1.2 mL/minute
Detection: UV 240 nm
Injection capacity: 5 µL
Column temperature: 40° C.
Analyzing time: 25 minutes
Retention time: pladienolide B: 13 min

TABLE 1

| | Pladienolide B (mg/L) | | |
|---|---|---|---|
| | Mer-11107 strain | Mer-11107/ pKU253 strain | Mer-11107- 56::aadA strain |
| culture for 4 days (96 hr) | 1117.5 | 992.0 | 0.0 |
| culture for 5 days (120 hr) | 1673.4 | 1481.5 | 0.0 |

These results confirmed that the Mer-11107-56::aadA strain, which had been subjected to deletion of the A region shown in FIG. 2, was completely unable to produce pladienolide B. This demonstrated that the gene at the A region is related to pladienolide biosynthesis.

Example 9

Determination of the Nucleotide Sequence of the Pladienolide Biosynthetic Gene Cluster The nucleotide sequence of a DNA group coding for the pladienolide biosynthesis gene was determined. The gene at the A region shown in FIG. 2 was confirmed to be related to pladienolide biosynthesis by the fact that the A site-deficient strain in Example 8 was unable to produce pladienolide B. The nucleotide sequence of the DNA fragment inserted into each of the 4 cosmids selected in Example 6, pKS35, pKS54, pKS58 and pKS23, was therefore determined.

Each cosmid, after isolation by the cesium chloride method, was then sheared to approximately 1 kb using a HydroShear (Genomic Solutions Inc.) and subcloned using a BKL Kit (Takara Shuzo Co., Ltd.).

The resulting subclones were subjected to a cycle sequence reaction (Amersham Biosciences Co.) using fluorescent-labeled primers and the nucleotide sequences of respective fragments were determined (MegaBACE 1000: Amersham Biosciences Co.), thus, an approximately 75 kb nucleotide sequence comprising DNA associated with pladienolide biosynthesis (see SEQ ID NO.: 1) was determined.

A search of the open reading frames (ORF) in this DNA showed it to contain the following 8 ORFs.
pldA I: bases 8340 to 27935
pldA II: bases 28021 to 49098
pldA III: bases 49134 to 60269
pldA IV: bases 60269 to 65692
pldB: bases 65707 to 66903
pldC: bases 68160 to 66970
pldD: bases 69568 to 68270
pldR: bases 72725 to 70020

The correlation between the ORFs and the cosmids is shown in FIG. 2.

Example 10

Preparation of Pladienolide 6-Hydroxylase Gene (pldB)-Deficient Strain

It has been demonstrated that pladienolide is biosynthesized by the biosynthetic pathway shown in FIG. 1 from the approximately 75 kb nucleotide sequence (see SEQ ID NO.: 1) comprising DNA associated with pladienolide biosynthesis which was sequenced in Example 9. A pldB-deficient strain was therefore prepared as described hereinbelow based on the idea that it would be possible to obtain a strain that produces only ME-265, the 6-deoxy form of pladienolide B, by disrupting only the cytochrome P450 gene pldB.

Four primers, pldB-L-Bgl2F, pldB-L-Hind3R, pldB-R-Hind3F and pldB-R-Bgl2R, comprising the nucleotide sequences shown in the following SEQ ID NOS.: 18, 19, 20 and 21, were synthesized based on the nucleotide sequence of SEQ ID NO.: 1.

pldB-L-Bgl2F:
(SEQ ID NO.: 18)
5'-GGGAGATCTAGAGGCCGGTTACCTCTACGAGTA-3' pldB-L-Hind3R:
(SEQ ID NO.: 19)
5'-GGGAAGCTTGCGATGAGCTGTGCCAGATAG-3'

-continued

```
pldB-R-Hind3F:
                                           (SEQ ID NO.: 20)
5'-GGGAAGCTTGAACTGGCGCGACAGTGTCTT-3' pldB-R-Bgl2R:
                                           (SEQ ID NO.: 21)
5'-GGGAGATCTGCAGCGGATCGTCTTCGAGACCCTT-3'
```

PCR was performed under the following conditions using these primers.

(PCR Reaction Solution Composition)

| | |
|---|---|
| Sterile purified water | 30 μL |
| 2× GC buffer | 50 μL |
| dNTP mixed solution | 16 μL |
| (2.5 mM each dATP, dGTP, dTTP and dCTP) | |
| pldB-L-Bgl2F or pldB-R-Hind3F (50 pmol/μL) | 1 μL |
| pldB-L-Hind3R or pldB-R-Bgl2R (50 pmol/μL) | 1 μL |
| Mer-11107 total DNA (100 ng/μL) | 1 μL |
| LA Taq polymerase (5 U/μL, Takara Shuzo Co., Ltd.) | 1 μL |

(Reaction Temperature Conditions)
95° C. 3 minutes
(98° C. 20 sec, 63° C. 30 sec, 68° C. 2 minutes) 30 cycles
72° C. 5 minutes As a result, a 1.57 kb DNA fragment (DNA fragment L1) comprising nucleotides 64756 to 66302 in SEQ ID NO.: 1 was amplified by the reaction using pldB-L-Bgl2F and pldB-L-Hind3R, while a 1.54 kb DNA fragment (DNA fragment R1) comprising nucleotides 66849 to 68368 in SEQ ID NO.: 1 was amplified from the reaction using pldB-R-Hind3F and pldB-R-Bgl2R. DNA fragments L1 and R1 were purified with a QIAGEN PCR purification Kit (QIAGEN Co.), and digested with restriction enzymes BglII and HindIII.

The DNA fragments L1 and R1 which had been digested with restriction enzymes BglII and HindIII, a 2.3 kb hygromycin B resistance gene (derived from pHP45omegahyg: Gene 190, 315-317, 1997, sometimes abbreviated hereunder as "hyg") which had been digested with restriction enzyme HindIII and the shuttle vector pKU253 (see FIG. 3) which had been digested with restriction enzyme BamHI were all four connected to DNA ligation kit Ver. 2.1 (Takara Shuzo Co., Ltd.). A roughly 5.4 kb DNA fragment having the hygromycin B resistance gene inserted between DNA fragments L1 and R1 was thus inserted into pKU253 to construct a roughly 21.4 kb plasmid called pKU253-L1-hyg-R1.

The resulting pKU253-L1-hyg-R1 was transformed into conjugative E. coli S17-1 by electroporation to obtain 517-1/pKU253-L1-hyg-R1. The resulting S17-1/pKU253-L1-hyg-R1 was inoculated into 10 mL of LB medium (1% bacto tryptone, 0.5% yeast extract, 0.5% NaCl) comprising 25 μg/mL of kanamycin and 100 μg/mL of hygromycin B and shaking cultured at 30° C. for 2 hours, and the mycelia were collected, washed twice with 10 mL of LB medium and suspended in 5 mL of LB medium. This was the donor suspension.

While the donor suspension was being prepared, Mer-11107 was inoculated into 10 mL of TSB medium (Trypto-Soya broth: Nissui Pharmaceutical Co., Ltd.) and shaking cultured at 30° C. for 5 hours, and the mycelia were collected, washed twice with 10 mL of sterile water and suspended in 1 mL of sterile water. This was the recipient suspension.

500 μL of the S17-1/pKU253-L1-hyg-R1 donor suspension was mixed with 10 μL of the Mer-11107 recipient suspension, and plated to Actino Medium No. 4 agar medium (Nihon Pharmaceutical Co., Ltd.). After incubated at 30° C. for 18 hours, this was covered with 2.5 mL of SNA (0.8% nutrient medium: Difco, 0.4% agar) comprising 2 mg/mL ribostamycin, and incubated at 30° C. for 7 days to obtain a ribostamycin-resistant pKU253-L1-hyg-R1 transformant strain.

The resulting pKU253-L1-hyg-R1 transformant strain was inoculated into 10 mL of TSB medium containing no ribostamycin, and shaking cultured at 30° C. for 24 hours. Mycelia were collected from the pKU253-L1-hyg-R1 transformant culture broth, washed twice with 10 mL of sterilized water and suspended in 10 mL of sterilized water. After being diluted appropriately, the suspension was plated to YMS agar medium (0.4% yeast extract, 1% wheat germ extract, 0.4% soluble starch, 2% agar, 10 mM calcium chloride) comprising 200 μg/mL hygromycin B, and incubated at 30° C. for 4 days. Single colonies growing on the YMS agar medium comprising hygromycin B were transplanted to YMS agar medium comprising 200 μg/mL of hygromycin B and YMS agar medium comprising 200 μg/mL of ribostamycin, and incubated at 30° C. for 2 days.

After incubated, a hygromycin B-resistant, ribostamycin-sensitive strain was selected. The resulting strain, called Mer-11107 pldB::hyg, was a pldB-deficient strain lacking 546 bp (nucleotides 66303 to 66848 in SEQ ID NO.: 1) of the pldB gene from the genome, with the hygromycin B resistance gene inserted in its place.

Example 11

Pladienolide Productivity Test of Pladienolide
6-Position Hydroxylase Gene (pldB)-Deficient Strain 200 μL of frozen seed of the Mer-11107 pldB::hyg strain obtained in Example 10 was inoculated into 20 mL of seed medium (soluble starch 2%, ESUSAN-MEAT 2%, yeast extract 0.5%, $K_2HPO_4$ 0.1%, $MgSO_4.7H_2O$ 0.25%, $CaCO_3$ 0.3%, pH not adjusted) and incubated at 25° C. for 2 days.

300 μL of the resulting seed culture broth was inoculated into 30 mL of seed culture medium (5% Stabilose, 1% glucose, 3% Pharmamedia, 2% β-cyclodextrin, 0.1% $CaCO_3$, pH 7.5) and cultured at 25° C. for 4 and 5 days.

After the completion of the cultivation, 20 mL of the resulting culture liquid was extracted by adding an equal amount of acetonitrile thereto. Part of this extract was taken and diluted with 5 times the amount of acetonitrile, and levels of pladienolide B and ME-265 were measured by HPLC under the following conditions. The measurement results are shown in Table 2.

(HPLC Analysis Conditions)
Analyzer: Shimadzu HPLC 10 Avp
Column: Develosil ODS UG-3 (4.6 mm×50 mm 3 μm)
Mobile phase (vol %): 45% to 55% methanol (0 to 5 minutes)
  55% methanol (5 to 13 minutes)
  55% to 70% methanol (13 to 17 minutes)
  70% methanol (17 to 35 minutes)
  45% methanol (35 to 40 minutes)
Flow rate: 1.2 mL/min
Detection: UV 240 nm
Injection volume: 10 μL
Column temperature: 40° C.
Analyzing time: 35 minutes
Retention time: ME-265: 22 minutes, pladienolide B: 16 minutes

TABLE 2

| Mer-11107 pldB::hyg strain | ME-265 (mg/L) | Pladienolide B (mg/L) |
|---|---|---|
| cultured for 4 days (96 hours) | 1247.7 | 0.0 |
| cultured for 5 days (120 hours) | 1316.6 | 0.0 |

Example 12

Isolation and Purification of Me-265 and its Structure Confirmation

The acetonitrile extraction solution obtained in Example 11 was filtered and the mycelia were washed with 10 mL water and 40 mL water. The filtrate and the washed solution were then combined and extracted with 100 mL ethyl acetate. To the aqueous layer was added 50 mL brine, which was then re-extracted with 50 mL ethyl acetate. The ethyl acetate layers were then combined and washed with 50 mL brine, dried over anhydrous sodium sulfate and then the solvent was removed. Then, the residue was purified by thin-layer chromatography (TLC, Merck Art. 5744, developing solvent: toluene:acetone=2:1), to give 20.3 mg ME-265.

$^1$H-NMR spectrum (CD$_3$OD, 500 MHz): δ ppm (integration, multiplicity, coupling constant J (Hz)): 0.87 (3H, d, J=7.0 Hz), 0.90 (3H, d, J=7.0 Hz), 0.94 (3H, d, J=7.3 Hz), 0.97 (3H, d, J=7.0 Hz), 1.08 (3H, d, J=7.0 Hz), 1.17-1.21 (1H, m), 1.24-1.36 (2H, m), 1.42-1.52 (3H, m), 1.61-1.66 (3H, m), 1.74 (3H, d, J=1.1 Hz), 1.89-1.96 (1H, m), 2.00 (3H,$), 2.41-2.47 (1H, m), 2.43 (1H, dd, J=5.5, 13.9 Hz), 2.51-2.58 (1H, m), 2.56 (1H, dd, J=3.7, 13.9 Hz), 2.65 (1H, dd, J=2.2, 8.1 Hz), 2.72 (1H, dt, J=2.2, 5.9 Hz), 3.51 (1H, dt, J=4.4, 8.4 Hz), 3.75-3.80 (1H, m), 4.91 (1H, dd, J=8.8, 10.6 Hz), 5.00 (1H, d, J=10.6 Hz), 5.42 (1H, dd, J=9.2 Hz, 15.0 Hz), 5.49 (1H, dd, J=9.2, 15.0 Hz), 5.65 (1H, dd, J=8.4, 15.0 Hz), 6.08 (1H, d, J=10.6 Hz), 6.32 (1H, dd, J=10.6, 15.0 Hz)

These results demonstrated that the pldB-deficient strain Mer-11107 pldB::hyg does not produce pladienolide B and does produce ME-265. That is, ME-265 could be produced and obtained by the method described above.

Example 13

Production of Pladienolide 7-Acylation Enzyme Gene (pldC)-Deficient Strain

It has been shown that a pladienolide is biosynthesized by the biosynthesis pathway shown in FIG. 1 from the roughly 75 kb nucleotide sequence comprising DNA participating in pladienolide biosynthesis which was sequenced Example 9 (see SEQ ID NO.: 1). A pldC-deficient strain was thus prepared by the following methods with the idea that a strain producing the 7-deacyl form of pladienolide (pladienolide B$_{12}$) could be obtained by disrupting only the 7-acylation enzyme gene, pldC.

Four primers, pldB-L-Bgl2F, pldC-L-Hind3R, pldC-R-Hind3F and pldC-R-Bgl2R, having the nucleotide sequences shown in the following SEQ ID NOS.: 18, 22, 23 and 24, were synthesized based on the nucleotide sequence of SEQ ID NO.: 1.

pldB-L-Bgl2F:
(SEQ ID NO.: 18)
5'-GGGAGATCTAGAGGCCGGTTACCTCTACGAGTA-3' pldC-L-Hind3R:
(SEQ ID NO.: 22)
5'-GGGAAGCTTCCAGTCTCGTGCTCACCAA-3' pldC-R-Hind3F:
(SEQ ID NO.: 23)
5'-GGGAAGCTTAGGCCCGTTGGAGAAGCTGTT-3' pldC-R-Bgl2R:
(SEQ ID NO.: 24)
5'-GGGAGATCTGCAGCCTCATCCTCACCGAGCTGAA-3'

PCR was performed under the following conditions using these primers.

(PCR Reaction Solution Composition)

| | |
|---|---|
| Sterile purified water | 30 μL |
| 2 × GC buffer | 50 μL |
| dNTP mixed solution (2.5 mM each dATP, dGTP, dTTP and dCTP) | 16 μL |
| pldB-L-Bgl2F or pldC-R-Hind3F (50 pmol/μL) | 1 μL |
| pldC-L-Hind3R or pldC-R-Bgl2R (50 pmol/μL) | 1 μL |
| Mer-11107 strain total DNA (100 ng/μL) | 1 μL |
| LA Taq polymerase (5 U/μL, TAKARA HOLDINGS INC.) | 1 μL |

(Reaction Temperature Conditions)
95° C. 3 minutes
(98° C. 20 sec, 63° C. 4 sec) 30 cycles
68° C. 5 minutes As a result of this reaction, an approximately 2.5 kb DNA fragment (DNA fragment L2) comprising bases 64756 to 67220 in SEQ ID NO.: 1 was amplified by the reaction using pldB-L-Bgl2F and pldC-L-Hind3R, while an approximately 3.0 kb DNA fragment (DNA fragment R2) comprising bases 68106 to 71112 in SEQ ID NO.: 1 was amplified by the reaction using pldC-R-Hind3F and pldC-R-Bgl2R. DNA fragments L2 and R2 were purified with a QIAGEN PCR Purification Kit (QIAGEN Co.) and were digested with restriction enzymes BglII and HindIII.

The DNA fragments L2 and R2 which had been digested with restriction enzymes BglII and HindIII, a 2.3 kb hygromycin B resistance gene (derived from pHP45omegahyg: Gene 190, 315-317, 1997, sometimes abbreviated hereunder as "hyg") which had been digested with restriction enzyme HindIII and the shuttle vector pKU253 (see FIG. 3) which had been digested with restriction enzyme BamHI were all four connected to DNA ligation kit Ver. 2.1 (Takara Shuzo Co., Ltd.). A roughly 7.8 kb DNA fragment having the hygromycin B resistance gene inserted between DNA fragments L2 and R2 was thus inserted into pKU253 to construct an approximately 23.8 kb plasmid called pKU253-L2-hyg-R2.

The resulting pKU253-L2-hyg-R2 was transformed into conjugative E. coli S17-1 by electroporation to obtain S17-1/pKU253-L2-hyg-R2. The resulting S17-1/pKU253-L2-hyg-R2 was inoculated into 10 mL of LB medium (1% bacto tryptone, 0.5% yeast extract, 0.5% NaCl) comprising 25 μg/mL of kanamycin and 100 μg/mL of hygromycin B and shaking cultured at 30° C. for 2 hours, and the mycelia were collected, washed twice with 10 mL of LB medium and suspended in 5 mL of LB medium. This was the donor suspension.

While the donor suspension was being prepared, Mer-11107 was inoculated into 10 mL of TSB medium (Trypto-Soya broth: Nissui Pharmaceutical Co., Ltd.) and shaking cultured at 30° C. for 5 hours, and the mycelia were collected, washed twice with 10 mL of sterile water and suspended in 1 mL of sterile water. This was the recipient suspension.

500 μL of the S17-1/pKU253-L2-hyg-R2 donor suspension was mixed with 10 μL of the Mer-11107 recipient suspension, and plated to Actino Medium No. 4 agar medium (Nihon Pharmaceutical Co., Ltd.). After incubated at 30° C. for 18 hours, this was covered with 2.5 mL of SNA (0.8% nutrient medium: Difco, 0.4% agar) comprising 2 mg/mL ribostamycin, and incubated at 30° C. for 7 days to obtain a ribostamycin-resistant pKU253-L2-hyg-R2 transformant strain.

The resulting pKU253-L2-hyg-R2 transformant strain was inoculated into 10 mL of TSB medium containing no ribostamycin, and shaking cultured at 30° C. for 24 hours. Mycelia were collected from the pKU253-L2-hyg-R2 transformant culture broth, washed twice with 10 mL of sterilized water and suspended in 10 mL of sterilized water. After being diluted appropriately, the suspension was plated to YMS agar medium (0.4% yeast extract, 1% wheat germ extract, 0.4% soluble starch, 2% agar, 10 mM calcium chloride) comprising 200 μg/mL hygromycin B, and incubated at 30° C. for 4 days. Single colonies growing on the YMS agar medium comprising hygromycin B were transplanted to YMS agar medium comprising 200 μg/mL of hygromycin B and YMS agar medium comprising 200 μg/mL of ribostamycin, and incubated at 30° C. for 2 days.

After incubated, a hygromycin B-resistant, ribostamycin-sensitive strain was selected. The resulting strain, called Mer-11107 pldC::hyg, was a pldC-deficient strain lacking 886 bp (bases 67221 to 68105 in SEQ ID NO.: 1) of the pldC gene from the genome, with the hygromycin B resistance gene inserted in its place.

Example 14

Pladienolide Production Test of Pladienolide 7-Acylation Enzyme Gene (pldC)-Deficient Strain 200 μL of frozen seed of the Mer-11107 pldC::hyg strain obtained in Example 13 was inoculated into 20 mL of seed medium (soluble starch 2%, ESUSAN-MEAT 2%, yeast extract 0.5%, $K_2HPO_4$ 0.1%, $MgSO_4 \cdot 7H_2O$ 0.25%, $CaCO_3$ 0.3%, pH not adjusted) and incubated at 25° C. for 2 days.

300 μL of the resulting seed culture broth was inoculated into 30 mL of seed culture medium (5% Stabilose, 1% glucose, 3% Pharmamedia, 2% β-cyclodextrin, 0.1% $CaCO_3$, pH 7.5) and cultured at 25° C. for 4 and 5 days.

After the completion of the cultivation, 25 mL of the resulting culture liquid was extracted by adding an equal amount of acetonitrile thereto. Part of this extract was taken and diluted with 5 times the amount of acetonitrile, and levels of pladienolide B and pladienolide $B_{12}$ were measured by HPLC under the following conditions. The measurement results are shown in Table 3.

(HPLC Analysis Conditions)
Analyzer: Shimadzu HPLC 10 Avp
Column: Develosil ODS UG-3 (4.6 mm×50 mm 3 μm)
Mobile phase (vol %): 45% to 55% methanol (0 to 5 minutes)
  55% methanol (5 to 13 minutes)
  55% to 70% methanol (13 to 17 minutes)
  70% methanol (17 to 35 minutes)
  45% methanol (35 to 40 minutes)
Flow rate: 1.2 mL/min
Detection: UV 240 nm
Injection volume: 10 μL
Column temperature: 40° C.
Analysis time: 35 minutes
Retention time: pladienolide $B_{12}$: 16 minutes, pladienolide B: 12 minutes

TABLE 3

| Mer-11107 pldC::hyg strain | Pladienolide $B_{12}$ (mg/L) | Pladienolide B (mg/L) |
|---|---|---|
| cultured for 4 days (96 hours) | 190.3 | 0.0 |
| cultured for 5 days (120 hours) | 252.9 | 0.0 |

Example 15

Isolation and Purification of Pladienolide $B_{12}$ and its Structure Confirmation The acetonitrile extraction solution obtained in Example 14 was filtered and further the mycelia were washed with 10 mL water and 10 mL acetonitrile. The filtrate and the washed solution were extracted with 40 mL ethyl acetate, and the organic layer was dried over sodium sulfate, filtered and evaporated. The resulting residue 91.4 mg was purified by thin-layer chromatography (TLC, Merck Art. 5744, developing solvent: hexane:ethyl acetate=10:50), to give pladienolide $B_{12}$ (Rf=0.46, 3.1 mg).

1. Molecular weight: 478, ESI-MS m/z 501 $(M+Na)^+$, 477 $(M-H)^-$
2. $^1$H-NMR spectrum ($CD_3OD$, 500 MHz): δ ppm (integration, multiplicity, coupling constant J (Hz)): 0.89 (3H, d, J=6.7 Hz), 0.90 (3H, d, J=7.1 Hz), 0.94 (3H, t, J=7.5 Hz), 1.07 (3H, d, J=6.8 Hz), 1.08 (3H, d, J=6.8 Hz), 1.16-1.26 (2H, m), 1.27-1.36 (1H, m), 1.41-1.67 (7H, m), 1.74 (3H, d, J=1.1 Hz), 2.42 (1H, dd, J=5.4, 14.2 Hz), 2.44-2.58 (2H, m), 2.56 (1H, dd, J=3.5, 14.1 Hz), 2.65 (1H, dd, J=2.3, 8.2 Hz), 2.72 (1H, dt, J=2.3, 6.0 Hz), 3.51 (1H, dt, J=4.4, 8.6 Hz), 3.57 (1H, dd, J=9.6, 9.6 Hz), 3.72-3.79 (1H, m), 5.00 (1H, d, J=10.7 Hz), 5.30 (1H, dd, J=9.7, 15.1 Hz), 5.46 (1H, dd, J=9.5, 15.0 Hz), 5.65 (1H, dd, J=8.4, 15.1 Hz), 6.07 (1H, d, J=10.9 Hz), 6.32 (1H, dd, J=10.9, 15.1 Hz)

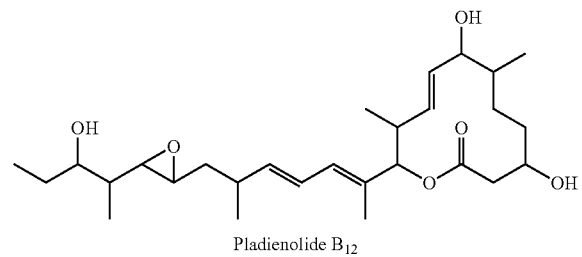

Pladienolide $B_{12}$

These results confirmed that the Mer-11107 pldC::hyg strain, which is a pldC-deficient strain, did not produce pladienolide B and did produce pladienolide $B_{12}$. In other words, pladienolide $B_{12}$ could be produced and obtained by the method described above.

Example 16

Production of Pladienolide 18,19-Epoxidase Gene (pldD)-Deficient Strain

It has been demonstrated that pladienolide is biosynthesized by the biosynthetic pathway shown in FIG. 1 from the approximately 75 kb nucleotide sequence (see SEQ ID NO.: 1) comprising DNA associated with pladienolide biosynthesis which was sequenced in Example 9. A pldD-deficient strain was therefore prepared as described hereinbelow based on the idea that it would be possible to obtain a strain that produces the 7-deacyl, 18,19-olefin form of pladienolide (pladienolide Z) by disrupting the 18,19-epoxidase gene (pldD) and inhibiting the expression of the downstream 7-acylation enzyme gene (pldC).

Four primers, pldD-L-Bgl2F, pldD-L-Hind3R, pldD-R-Hind3F and pldD-R-Bgl2R, comprising the nucleotide sequences shown in the following SEQ ID NOS.: 25, 26, 27 and 28, were synthesized based on the nucleotide sequence of SEQ ID NO.: 1.

```
pldD-L-Bgl2F:
                                     (SEQ ID NO.: 25)
5'-GGGAGATCTAGACCTGTCCATGGATCTGGAAAC-3' pldD-L-Hind3R:
                                     (SEQ ID NO.: 26)
5'-GGGAAGCTTCGGATCGTCTTCGAGACCCTT-3' pldD-R-Hind3F:
                                     (SEQ ID NO.: 27)
5'-GGGAAGCTTGTGGGGTGCCCTTTCTGACTT-3' pldD-R-Bgl2R:
                                     (SEQ ID NO.: 28)
5'-GGGAGATCTGCAGGAGGAGCTGCTCGGGCTGAA-3'
```

PCR was performed under the following conditions using these primers.
(PCR Reaction Solution Composition)

| | |
|---|---|
| Sterile purified water | 30 μL |
| 2 × GC buffer | 50 μL |
| dNTP mixed solution | 16 μL |
| (2.5 mM each dATP, dGTP, dTTP, and dCTP) | |
| pldD-L-Bgl2F or pldD-R-Hind3F (50 pmol/μL) | 1 μL |
| pldD-L-Hind3R or pldD-R-Bgl2R (50 pmol/μL) | 1 μL |
| Mer-11107 total DNA (100 ng/μL) | 1 μL |
| LA Taq polymerase (5 U/μL, Takara Shuzo Co., Ltd.) | 1 μL |

(Reaction Temperature Conditions)
95° C. 3 minutes
(98° C. 20 sec, 63° C. 4 minutes) 30 cycles
68° C. 5 minutes As a result, a 2.7 kb DNA fragment (DNA fragment L3) comprising bases 65700 to 68368 in SEQ ID NO.: 1 was amplified by the reaction using pldD-L-Bgl2F and pldD-L-Hind3R, while a 2.4 kb DNA fragment (DNA fragment R3) comprising bases 69514 to 71951 in SEQ ID NO.: 1 was amplified from the reaction using pldD-R-Hind3F and pldD-R-Bgl2R. DNA fragments L3 and R3 were purified with a QIAGEN PCR purification Kit (QIAGEN Co.), and digested with restriction enzymes BglII and HindIII.

The DNA fragments L3 and R3 which had been digested with restriction enzymes BglII and HindIII, a 2.3 kb hygromycin B resistance gene (derived from pHP45omegahyg: Gene 190, 315-317, 1997, sometimes abbreviated hereunder as "hyg") which had been digested with restriction enzyme HindIII and the shuttle vector pKU253 (see FIG. 3) which had been digested with restriction enzyme BamHI were all four connected to DNA ligation kit Ver. 2.1 (Takara Shuzo Co., Ltd.). A roughly 7.4 kb DNA fragment having the hygromycin B resistance gene inserted between DNA fragments L3 and R3 was thus inserted into pKU253 to construct an approximately 22.4 kb plasmid called pKU253-L3-hyg-R3.

The resulting pKU253-L3-hyg-R3 was transformed into conjugative E. coli S17-1 by electroporation to obtain S17-1/pKU253-L3-hyg-R3. The resulting S17-1/pKU253-L3-hyg-R3 was inoculated into 10 mL of LB medium (1% bacto tryptone, 0.5% yeast extract, 0.5% NaCl) comprising 25 μg/mL of kanamycin and 100 μg/mL of hygromycin B and shaking cultured at 30° C. for 2 hours, and the mycelia were collected, washed twice with 10 mL of LB medium and suspended in 5 mL of LB medium. This was the donor suspension.

While the donor suspension was being prepared, Mer-11107 was inoculated into 10 mL of TSB medium (Trypto-Soya broth: Nissui Pharmaceutical Co., Ltd.) and shaking cultured at 30° C. for 5 hours, and the mycelia were collected, washed twice with 10 mL of sterile water and suspended in 1 mL of sterile water. This was the recipient suspension.

500 μL of the S17-1/pKU253-L3-hyg-R3 donor suspension was mixed with 10 μL of the Mer-11107 recipient suspension, and plated to Actino Medium No. 4 agar medium (Nihon Pharmaceutical Co., Ltd.). After incubated at 30° C. for 18 hours, this was covered with 2.5 mL of SNA (0.8% nutrient medium: Difco, 0.4% agar) comprising 2 mg/mL ribostamycin, and incubated at 30° C. for 7 days to obtain a ribostamycin-resistant pKU253-L3-hyg-R3 transformant strain.

The resulting pKU253-L3-hyg-R3 transformant strain was inoculated into 10 mL of TSB medium containing no ribostamycin, and shaking cultured at 30° C. for 24 hours. Mycelia were collected from the pKU253-L3-hyg-R3 transformant culture broth, washed twice with 10 mL of sterilized water and suspended in 10 mL of sterilized water. After being diluted appropriately, the suspension was plated to YMS agar medium (0.4% yeast extract, 1% wheat germ extract, 0.4% soluble starch, 2% agar, 10 mM calcium chloride) comprising 200 μg/mL hygromycin B, and incubated at 30° C. for 4 days. Single colonies growing on the YMS agar medium comprising hygromycin B were transplanted to YMS agar medium comprising 200 μg/mL of hygromycin B and YMS agar medium comprising 200 μg/mL of ribostamycin, and incubated at 30° C. for 2 days.

After incubated, a hygromycin B-resistant, ribostamycin-sensitive strain was selected. The resulting strain, called Mer-11107 pldD::hyg, was a pldD-deficient strain lacking 1146 bp (nucleotides 68369 to 69513 in SEQ ID NO.: 1) of the pldD gene from the genome, with the hygromycin B resistance gene inserted in its place.

Example 17

Pladienolide Production Test of Pladienolide 18,19-Epoxidase Gene (pldD)-Deficient Strain 200 μL frozen seed of the Mer-11107 pldDC::hyg strain obtained in Example 16 was inoculated into 20 mL of seed medium (soluble starch 2%, ESUSAN-MEAT 2%, yeast extract 0.5%, $K_2HPO_4$ 0.1%, $MgSO_4.7H_2O$ 0.25%, $CaCO_3$ 0.3%, pH not adjusted) and incubated at 25° C. for 2 days.

300 μL of the resulting seed culture broth was inoculated into 30 mL of seed culture medium (5% Stabilose, 1% glucose, 3% Pharmamedia, 2% β-cyclodextrin, 0.1% $CaCO_3$, pH 7.5) and cultured at 25° C. for 4 and 5 days.

After the completion of the cultivation, 20 mL of the resulting culture liquid was extracted by adding an equal amount of acetonitrile thereto. Part of this extract was taken and diluted with 5 times the amount of acetonitrile, and levels of pladienolide B and pladienolide Z were measured by HPLC under the following conditions. The measurement results are shown in Table 4.

(HPLC Analysis Conditions)
Analyzer: Shimadzu HPLC 10 Avp
Column: Develosil ODS UG-3 (4.6 mm×50 mm 3 μm)
Mobile phase (vol %): 45% to 55% methanol (0 to 5 minutes)
　　55% methanol (5 to 13 minutes)
　　55% to 70% methanol (13 to 17 minutes)
　　70% methanol (17 to 35 minutes)
　　45% methanol (35 to 40 minutes)
Flow rate: 1.2 mL/min
Detection: UV 240 nm
Injection volume: 10 μL
Column temperature: 40° C.
Analysis time: 35 minutes
Retention time: pladienolide Z: 20 minutes, pladienolide B: 12 minutes

TABLE 4

| Mer-11107 pldDC::hyg strain | Pladienolide Z (mg/L) | Pladienolide B (mg/L) |
|---|---|---|
| cultured for 4 days (96 hours) | 676.9 | 0.0 |
| cultured for 5 days (120 hours) | 695.8 | 0.0 |

Example 18

Isolation and Purification of Pladienolide Z and its Structure Confirmation

The acetonitrile extraction solution obtained in Example 17 was filtered and further the mycelia were washed with 10 mL water and 10 mL ethyl acetate. To the filtrate and the washed solution were added 40 mL brine and 90 mL ethyl acetate, and the mixture extracted and the extract was washed with 50 mL brine. The organic layer was dried over sodium sulfate, filtered, and evaporated. The resulting residue was purified by thin-layer chromatography (TLC, Merck Art. 5744, developing solvent: hexane:ethyl acetate=10:50), to give pladienolide Z (Rf=0.59, 22.8 mg).

1. Molecular weight: 462, ESI-MS m/z 485 (M+Na)$^+$, 461 (M-H)$^-$
2. $^1$H-NMR spectrum (CD$_3$OD, 500 MHz): δ ppm (integration, multiplicity, coupling constant J (Hz)): 0.89 (3H, d, J=6.8 Hz), 0.92 (3H, t, J=7.5 Hz), 0.98 (3H, d, J=6.8 Hz), 1.01 (3H, d, J=6.8 Hz), 1.07 (3H, d, J=6.8 Hz), 1.17-1.37 (3H, m), 1.49-1.67 (4H, m), 1.73 (3H, d, J=1.0 Hz), 2.04 (2H, dd, J=6.8, 6.8 Hz), 2.07-2.15 (1H, m), 2.23-2.31 (1H, m), 2.42 (1H, dd, J=5.3, 14.1 Hz), 2.50-2.59 (1H, m), 2.55 (1H, dd, J=3.4, 14.1 Hz), 3.16-3.22 (1H, m), 3.57 (1H, dd, J=9.6, 9.6 Hz), 3.72-3.79 (1H, m), 5.00 (1H, d, J=10.7 Hz), 5.17-5.43 (3H, m), 5.46 (1H, dd, J=9.5, 15.0 Hz), 5.64 (1H, dd, J=7.8, 15.1 Hz), 6.05 (1H, d, J=10.8 Hz), 6.21 (1H, dd, J=10.8, 15.1 Hz)

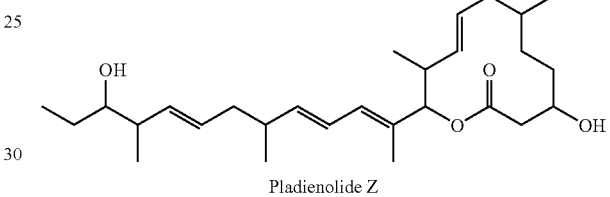

Pladienolide Z

These results confirmed that the Mer-11107 pldDC::hyg strain, which is a pldD-deficient strain, did not produce pladienolide B and did produce pladienolide Z. In other words, pladienolide Z could be produced and obtained by the method described above.

---

The invention claimed is:

1. A DNA that is isolated and pure, and that contains at least one region encoding a polypeptide that participates in pladienolide biosynthesis, said DNA comprising at least one nucleotide sequence selected from the nucleotide sequences defined in any of the following (1) to (3):
(1) nucleotide sequences defined in any of the following (a) to (g): (a) the continuous nucleotide sequence from the base 8340 to base 27935 of SEQ ID NO: 1; (b) the continuous nucleotide sequence from the base 28021 to base 49098 of SEQ ID NO: 1; (c) the continuous nucleotide sequence from the base 49134 to base 60269 of SEQ ID NO: 1; (d) the continuous nucleotide sequence from the base 60269 to base 65692 of SEQ ID NO: 1; (e) the continuous nucleotide sequence from the base 65707 to base 66903 of SEQ ID NO: 1; (f) the continuous nucleotide sequence from the base 68160 to base 66970 of SEQ ID NO: 1; (g) the continuous nucleotide sequence from the base 69568 to base 68270 of SEQ ID NO: 1;
(2) a nucleotide sequence having at least 90% identity over the full length sequence with any of the nucleotide sequences defined in (1);
(3) a DNA encoding SEQ ID NO:2-8.

2. The DNA according to claim 1, comprising at least one nucleotide sequence selected from the nucleotide sequences defined in any of the following (a) to (g): (a) the continuous nucleotide sequence from the base 8340 to base 27935 of SEQ ID NO: 1; (b) the continuous nucleotide sequence from the base 28021 to base 49098 of SEQ ID NO: 1; (c) the continuous nucleotide sequence from the base 49134 to base 60269 of SEQ ID NO: 1; (d) the continuous nucleotide sequence from the base 60269 to base 65692 of SEQ ID NO: 1; (e) the continuous nucleotide sequence from the base 65707 to base 66903 of SEQ ID NO: 1; (f) the continuous nucleotide sequence from the base 68160 to base 66970 of SEQ ID NO: 1; (g) the continuous nucleotide sequence from the base 69568 to base 68270 of SEQ ID NO: 1.

3. A polypeptide encoded by the DNA according to claim 1.

4. The polypeptide according to claim 3, characterized by having a polyketide synthase activity.

5. The polypeptide according to claim 4, characterized by having the amino acid sequence described by SEQ ID NOS: 2, 3, 4 or 5, or having a partial sequence thereof.

6. The polypeptide according to claim 3, characterized by having a 6-hydroxylase activity.

7. The polypeptide according to claim 6, characterized by having the amino acid sequence described by SEQ ID NO: 6 or having a partial sequence thereof.

8. The polypeptide according to claim 3, characterized by having an 18,19-epoxidase activity.

9. The polypeptide according to claim 8, characterized by having the amino acid sequence described by SEQ ID NO: 8 or having a partial sequence thereof.

10. The polypeptide according to claim 3, characterized by having a 7-acylation enzyme activity.

11. The polypeptide according to claim 10, characterized by having the amino acid sequence described by SEQ ID NO: 7 or having a partial sequence thereof.

12. A vector comprising the DNA according to claim 1.

13. A genetically modified cell comprising the vector according to claim 12.

14. A method of producing a pladienolide, comprising culturing the cell according to claim 13 on culture medium; and collecting pladienolide from the culture broth.

15. The method of production according to claim 14, wherein the pladienolide is pladienolide B.

* * * * *

SEQUENCE LISTING

```
<160> NUMBER OF SEQ ID NOS: 28

<210> SEQ ID NO 1
<211> LENGTH: 74342
<212> TYPE: DNA
<213> ORGANISM: Streptomyces sp.

<400> SEQUENCE: 1
cgattttgca ccttgtccat cgctggtggt gtgaggcatg ctcctattgg aacataaaac        60
ctctgaacct ttaagaggtt atggcggagg ctttcgacgc gacacgaggg agaagcggat       120
gagaatcgtg gggattcacc gggagggcgc aggcatagag gtggcccggc tgtcggacga       180
cgggcggcgg gcagtcgtgc tggccccgct cgaagtcttc tgggccgacg ccaccggcca       240
tctggcgcgc ggggacggtg gaccagtcgt cccggtgtcc gcggtggagc tggtaccgcc       300
ggttctgccg gacgcgcggg tgatctgcat cgggctcaac tacctcaagc atgtggccga       360
gggaacctac cgcgaccagg aagtccccga gcaccccacg ctgttcgccc gctggacacg       420
gtcgctgacc gtggacggag ccgaggtccc ggtgccctcg gacgaggccg ggctggactg       480
ggagggtgag gtggtggcct gggtgggcgc accactcgtg gacgccacgc cggaggaggc       540
gctgaccgcc gtcatcggct actccctctt caacgacctc acctcccggc gggctcagaa       600
```

```
gctcacctct cagtggaccc tgggcaagaa cggggacaac tccggcccgc tcgggccgat    660
ggtgccggct gccgaggtgg gcgacctgcg cgacgggctg cgggtacaga cccgggtcaa    720
cggggagacg atgcaggatg gcagcacgga cgagatggtc tacaccgtgg gtgacacgct    780
cgcgcacatc tcccgcacct tcatcctgcg tcccggcgac ctgctggcga cgggcacccc    840
gtccggagtc ggctacgccc ggaccccacc gcagctcctg cagccgggag acgtcgtcga    900 ggtgaggtc gaacgctcg gcgtgctgcg caaccccgtg gtgtccaacg acgcccggct    960
gcgcgcaccc aagtgaggac gcaagaggcc ccgcgcccgc ccgcggaacg cgggtgctcg   1020
ccctgcggca cacgccgcag gacacacctg gtcaccgtcc tgcgtcgccg ggtcctgcgg   1080
tggggcaccg ttgaccgtgg tcaaggacta caccgagaac cagaagcgcc cggactgagc   1140
gcggcccgat cgtgggagca ttccgaagcg aggcggcggc gctccgcgcc gccttgctca   1200
ggatgcgttt cctcccgggc gtgaacgccc ggggttcctc gcacggtcag gctgagactt   1260
ctctcacatg gggagtccag tcgtcggccg gatctgcggc cggagccggt accggcggcg   1320
agggctggaa cggcgaactc acgtactcct ccacgagcgg attacggtgc gggacacgaa   1380
aggtcggaga ccaggggggcg gctcggggccg gggattaggc gtaggggtgg ctgatggtgt   1440
gctggcgccg ggcggtggcc aggacgttgt cagggaagcg ggagccggcg acgtagtggc   1500
ggcccttggt ctgccccacc gccgtcagca gctccgcctt ggtcagggcc tgcaggtccc   1560
gtgtggcctg ctgggtgttg agggcctcgg ctcgctcata gcgcgagcgg cgaacccggc   1620
ccaccatcgc cacctcgtgc agcgcggtga tctgccgctc ggtgatcccg aggctgtcgg   1680
cggcgtccat gagctgcctc cagcagtcgt tggagcggtc gacgcggcgc tgcacccgct   1740
gggtctgctg gtggtaggcg agcaggttga agcggatcca cggcccggtg tcgcgcttcg   1800
gtgagtagac cgggccgccg acctcgcgca gcgctttgta gtactcccag gtgttgcccg   1860
gcatgcccag ccactcctcg atggaggaga actccggcgc cagcactccg ccccggggcga   1920 tgaccagcgt ctgcagggag cgggacatcc gcccgttccc gtccgaccac gggtggatct   1980
tcaccaggtt caggtgcgcc atcgccgccc gcaccaggac gtgggcgtcc aggtcgccgt   2040
cgttgagcca gtccaccagc tcgcccatca ggcccggcag caggtcggcg tccgggcctt   2100
cgtagtcggt ggccagctcg tcgccggggg cggtgatgcg gatcgcagtg cgacgccact   2160
ggccggccag ccgcagcgga tggtggtggc cctgcagcat ccagtgcagc gagttgagca   2220
actccttgct gtagctgaag tcgcctacgt cgtgcaggga ctggatgtag gccatcgcct   2280
gctggtaggc cagcgtctcg gccttgttct cctcgctggc atccacggca tcgcgttcgc   2340
cgtccatcag gtccgcgaca tccttcgcat cgacctggta accctcgatg gtgttggacg   2400
ccgcgatcgc gctggccgtc agcgccttgc gcagatcctg cgtccacttc gtcggcacct   2460
gctgcaccgc gtggcgcagc tgctcctgca gggaattgat ctcctccagg acccggcggt   2520
cgtcggtggt gaggtgaggc gtctgataca gcataagtga atgatacctg actcctatca   2580
ttccttcaac gctgcggctt catcaccgtc cgtccacgat gaacatgaac tcgcccagct   2640
cgacgagcag ggccaccggc ctgccgaccc acgctggtca ctgatcaaca caccaggtca   2700
acgagtacgt ctgcaggact ggatggagtg acaggcagcg cggggcagcc aagcaggcgg   2760
cgcgaccacg taacggaccg gcgaacccga gctgagcacc ggtgagctcc gcaccggct   2820 gactgccctc agctacaaca tcgagaacag ctggccgagc ttgcccggag ccggcggcgc   2880
ggatcacgtc cgccgtgtgt gcgaggggcg cgccgcttcc ggcggtgtcg tcgacgccag   2940
gcccgccaag ttgctgagcg acgcggcgtt ccggacgtcc gcacgtcgcg gatcccgaga   3000
```

```
cgaggggtga gccaagccgc cgggatcacg ccgccgcgca tgatgcctac cacggcttgc    3060
cgatgtggag gctgggcaga gatcccctca gcctccggta cgtcgacggg caggcacccg    3120
cctggccgga gctccgtgcg gggccgttgg agcggagtgt gccccgcac cggagacccg     3180 ccaggactcc gtgcgaccaa aagactcttc gtctcacctg gtctcacaca tctctcacaa    3240
acgagagcgc acgggagcac gcgagaacct ctgacctgga cattcgctgt cgccacggac    3300
cacggcggac caggtagaca ttacataggc taggactcga ttctagtgat caagtcaaat    3360
gcccaggtca gaggctgttt ttgctgttcg ccagggctg atatctcaca tatttattgc     3420
tggaactgcg gcacaaggtc gagatccatc ggatgaccgg gcgggtcgtc gagtgctcga    3480
tcgacgaggt ggaccgcccg cgggtatcca aggacgccgc cctgcggatc ccgccgaccg    3540
agctggaggt caggcgctgt tcatcggctg ggttggcgag ctggcgactt gccgcaagtt    3600
cgccctcacc gcgcggaact acaccgcatc gaaactgatg tcgtaggtcg ggctcggggt    3660
gagcgaggca tgcaaactcg acctggccga catcaagtgg gacctgggcc gcttcggcaa    3720
gctccatgtg cgtcacggcg agggcgcccg cggctcgggt ccgcgcgagc ggatggtgcc    3780
gctgatcaac ggcgccgacc gcatgctgcg gtggttcatc gaggacgtcc ggggccagtt    3840
cgacgacgac cgcacccgcc ccggtgcccc gctgttcccc tctgagcgca agaacgccgt    3900
cggctcctcg cgcctcgtcg gcgacgacgc gttgcgcaac ggtctggccg ccgcggcgga    3960
ggtcgcgtcc aaaaggtggt gtaaaaggcg acgagcgaaa gtttcgtact gaacagccaa    4020
gttcgtacga aaggacccac gctcgtgtag tcacgagtgt cacccatcga ggcgatccat    4080
gccgagatcg atgccgtctt cgcctagtac tgcaacggtt tttgccgtga cggttgggca    4140
ggctggtcgt tggtctgagc atgggtgggg accttgctga tgtcggggtg tgggccagtg    4200
aagtggacgc tgtgcacgag aggttcgtgc accggttttc cagggcggag ccgcgggagt    4260
cggcgcttgc ctatatgcgg ggactgaccg ctccgctgga gcggaagaac ggctggacac    4320
tggccgaaca ggccggtcat gtcgctccgg accgtattca tcgactgctg aaccggatcg    4380
agtgggaagc cgatgaggtc ctggccgatg tgcgcgacta cgtcatggag aacctcggcg    4440
accccgaggc cctcatcgtg gacgacaccg gcttcctgaa gaaggggacc cgttcggcag    4500
ggggccggcg tcagtactcc gggaccgcgg gggcctgtat ttcaattact gctcggtgaa    4560
cgggtgttgg cgggacaatg agatgtgact gcgcgcacgg ccgctcgggc ctcagttgtg    4620
gctttgaggg cgaagttcga tcagttcctt ccccatctcg atgagcggcg ccgtcggatc    4680
tacctggcca gcgaggccgc cgcgcttggc cacggcggga tcacgctggt ggccaccgct    4740
tccggcgcca gtgcggccac catcgcacgc gggatcgccg agctgtccgg gcacactctg    4800
ccggccgggc ggatccgggc tccggagccg ggccgcaagc cggtcacggt caccgacccc    4860
ggtctgctgc ccgcgcttga agctctgatc gagccgcaca cccggggcga tccggtctcg    4920
ccattgcgct ggaccacgct ctcgctgcgg tccctggcct cggcgctgac cactcagggc    4980
cacccggtca gcgcggcgac cgtcggacgc ctgctacatg ccctgggata cagcctgcag    5040
ggcaccgcca agaccacgga aggggccagt catcccgacc gggatgctca gttcacgcac    5100
atcaacgcca ccgccgcgga cttcctcgaa gacaaccagc cggtgatcag cgtcgacacc    5160
aaggccaagg agtggctcgg caaccgcgac cgacccggac gcacctggcg accgggcaag    5220
aaccctatcc gtgtggactg ccacacgttc accaccagtg accagccagt agccatcccc    5280
tacgggatct acgacatcgc tcgcaacacc ggctgggtca acgtcgggac cgaccacgac    5340
acgggcgagt tcgcggtgga atccatccgc cgctggtggt agcagcacgg acgcggcgac    5400
```

```
cacccggacg ccggccgact gctcatcacc gccgactgcg gtggttccaa cgaccccgc    5460
cgctggacat ggaagaagca tctcgccgcc ttcgccctgg aaagcggact cgagatcacg   5520
gtctgccact tcccacccgg aacatcgaag tggaacaaga tcgaacaccg gatgttctgc   5580
cacatcaccg cgaactggcg cggcaggccc ctgaccagct accaggtcgt catcgagacc   5640
atcgccgcca cgaccactcg caccgggctc agcatcggcg ccgaactcga caccggccga   5700
tacgacctgg gcaccacagt cccacccgcc gagttccaag ccctgccaat cacaccccac   5760
accttccacg gcgactggaa ctacaccctg gcaccactcg cacccggct gcccgagccg    5820
gcaccgagcc gacaacggat cgaccccgcc ctgaccacga tgctcaccga cccggccctg   5880
accggcatgt cacgctccgc cttcgaccac ctggtcgcca tctcggaacc gtactgggac   5940
gccctggccg aggcggcatt ccaacgacgc ttccaccgcc cacgcagcta cctccacccg   6000
cagaccagca gcctcgacca ctaccaccgc ctgctgaccg ccctgttacg ccgccgcaga   6060
gccgtcacca gcacactgct ggcccagctc ctgaacgtcg gccgcaccaa cctgtccaac   6120
cagttccaag acggccaccg cctcctggac ctgcaccgca tcgcggtcac tccgctatct   6180
ggagccccgg cccgcaccct cgcccaacta caagcccgcc taccgccaca cgacgacacc   6240
cgcacagatc aactctgaca gttattcaga cacaggcccc cggcggatc gagaactccc    6300
aggtcgccgt ctacctggtc taggcaggtg cccggggcca cgcggcggtg gacccgggaac  6360
tgtacgtgcc ccgttcctgg acctgtgacc agggccgctg cagggcggcg ggctcggcg    6420
aggacatcgt cttcgccacc aagcggagc tggcccgcac gatgatcgaa cggttcctgg    6480
acgccggaca ccacgtgggc tgggtcgctg gcgacgaggt ctacggcggc aacccgaagc   6540
tgcgatctgc gctggaggta cgcggcctcg gctatgtcct cgcggtggcc tgctcggccg   6600
aagtcaccac caaggcaggc aagttccgag ccgacacgct ggcggcgaag gtaccgaagc   6660
gggcctggca gaagctgtcg gcaggcgcgg gagccaaggg caaccgcttc tacgactggg   6720
ccgtcgtcga cctggccgag cccggccccg gccaccggca gctgctgatc cgccgcaacc   6780
gccgcaccgg tgaactggcc tactaccgat gccactccac ctcaccggtc ccgctcgcca   6840
ccctggtcag ggttgccgga tcacggtggc gggtggagga gacattccag accgagaagg   6900
gcctggccgg cctggacgag caccagctcc gccgctaccc ctcctgggcc cgctggggca   6960
ccctcgccat gctcgcccac gctttcctcg ccgtcgtccg cgccgacgaa cacacccgcc   7020
cgacccccga cgacctcatt ccgctgacct gcaacgagat ccagcacctg ttcctcgcgc   7080
tcgtcgtcca gccgctgtcc aacgtcgccc accgcctcgc ctggtccgag tggagacgac   7140
gtcatcaagc ccgatcacgc accagtcact accggcgaca agccgcaact cagacatgaa   7200
gatcacgatc tacagctgga gtattaggtc cccgaacaac aaccggggac agtcctaatg   7260
ggcgtcactt tcgtatcgaa ccagcaaaat ttggagggaa cgatattcga ctcgcatagc   7320
cttacggtcg gagcatatta cgaccaggtc aatgaattgc tccccgccat gcattctcag   7380
gcgggatgcc gtcgaggggg cgagggtctg tatgatgtcg ttgacatcgg ccgcagtggt   7440
gatggccttg agcggagtgc cgtgtccgtc acagatcagg tggtgtctgc tgccggtcct   7500
gcgccggtcg accggcgcag gaccggcgtc ggctccccc tttcgcgcgg acatgagagc    7560
cgtccacgca cgcgcgtgac cagtcgagtt cgccggccgc gttgagttcg cgagcgggga   7620
tgcggtgcga ccctggtctg ctgccatcgt tccagccgcc gcaccgctgc tctcgcagat   7680
ccgctcgata gtccggccgg gacgctcacc gcgacacctc ttcgagggcg agggctaccc   7740
gacgccgacc ggccagcggt actgcatcaa ctcgatctcc ctgcggctga ttcccgacga   7800
```

-continued

| | |
|---|---|
| gggctgagat ccgtatcgac acaccacgtc cgtggacgtg gcccacgggc gtccggtcaa | 7860 |
| gcgtgagtgt cgtggcatcg atctcctgcg cgctcagtga ccgcgcgagg cgggccggaa | 7920 |
| tcggcgagtt ggacggggtc ggggcgagcc tgcgtggctt tcttggccgt caactcgacg | 7980 |
| acgtggccgt gctgctggcc gtagccgtgt cctgcccgcc gggcgggtgg ctgtccgggg | 8040 |
| ctgcccgcct ccccgcggtc gttgccgcca ccaggccgca cgccactgag cagctgaccc | 8100 |
| ggcgcggact cgacgaggcc gccttcgtca ccgaactcgt cctgagggca ccgggtcacc | 8160 |
| aacgccttcc gttgctcccc agacctctct gggaagatca ataggggccc gtaaaggggg | 8220 |
| ggtgagggtt gaaaaagggg gggtattcaa aaataggctg agtccgctgc aaaaatcttg | 8280 |
| agaccggtcg gaacgggtgt agctgaatga ctgaatcgaa tgaattcacg tccgaagcgg | 8340 |
| tgctcagtgc ggctgatgat gcaatagcca tcatcggcat gtcttgccgg ctgccgcgag | 8400 |
| cagtcaatcc tcaggagttc tgggaactcc tgaggaatgg tgagagcggg attaccgagg | 8460 |
| tgccgcccca gcggtgggac gcgaactccc tcttcgatgc ggaacggtcc acgcccggga | 8520 |
| cgatgaatac acgctggggc gggttcatcg acggcgtgga ccagttcgac cccggcttct | 8580 |
| tcgggatctc ctcccgcgaa gcggtcgcca tggatccgca gcaacggctc gtactggagc | 8640 |
| tgagctggga ggccctggag gacgcgcgaa tcgtcccgga gcgccttcgc cacaccgcta | 8700 |
| ccggtgtctt cgtcggcgcg atctgggacg actacgcatc attgatgagc gcgcgaggcc | 8760 |
| gagaagcggt gacccatcac accgtgaccg gtacgcaccg cagcatcatt gccaaccggg | 8820 |
| tgtcgtacgc cctcggccta caggggccga gcatggcggt ggactccggg cagtcgtcgt | 8880 |
| cactggtctc cgtccatctg gcctgcgaga gcctgcgcag gggggagtcc acgctcgcgc | 8940 |
| tggccggcgg ggtgaatctc aaccttgtcc cggagagcac catcggcatg gcgaagttcg | 9000 |
| gcgggctctc ccccgatggc cgctgcttca ccttcgacac ccgcgccaac ggctacgtgc | 9060 |
| ggggtgaggg cggcggtgtg gtcgtcctca aaccgctggc ggacgcgatc gcggaccagg | 9120 |
| acccgatcta ctgcgtcatc cgtggcagcg ccgtcaacaa cgacggttcc ggtgagaacc | 9180 |
| tgaccacgcc gaactcccag gcgcaggcag ctgtgctgcg cgaggcctac cgccgcgccg | 9240 |
| gcgtggaccc ggcccaggtc cagtacgtgg aactgcacgg taccgggacc cctgtcggcg | 9300 |
| acccgattga agccgaggcc ctcggcgcgg tgatcggtgc cgcccggccg ccgggtgacc | 9360 |
| ccctgtgggt gggatcggcg aagaccaaca tcggccatct ggaggccgcc gccggcatcg | 9420 |
| ccggcctgct caaggtcgtg ctgtccatca gccaccggga gctcccggcc agtctcaact | 9480 |
| tcgccacggc caatccgcgg attccactgg actccctgaa cctgcgcgtg ggcgacgagc | 9540 |
| tcacatcgtg gccgtctgcc ggtcggccga tgctcgccgg tgtgagcgcg ttcggcatgg | 9600 |
| gcggtaccaa cgcccacgcc gtggtcgaac aatctcccgt agcagcgcgg cagattccgg | 9660 |
| ctcccggagg cacgccgacg gatcaggggg ggccggtgcc gtggttgttg tcgggtgggt | 9720 |
| cggtggcggc ggtgcgggt caggcggcgc ggttgttgtc gcatctggag ggtcggtcgg | 9780 |
| gtctgcgtgc ggtggatgtc ggctggtcgc tggccacgac tcgttccgtg ttccctcatc | 9840 |
| gtgctgttgt cgttgccgac gatggtggtt acgccagag tctcgccgcg ctggccgcg | 9900 |
| gttccgtgga tgccggggtg gttgagggcc ttgccgatgt gagtggcaag acggtgttcg | 9960 |
| tcttccccgg tcaggttcg cagtgggtgg gtatggccgt tgagctgctg gacggctcgg | 10020 |
| aggttttcgc cgagcatatg gccgcctgcg ccagggccct ggaaccgttt gtgggctggt | 10080 |
| ccctggagga tgtcctgcgt caggtggacg gtacgtggtc actggatcgt gtggatgtgg | 10140 |
| tccagcctgt gctgtgggcg gtcatggtct cgctcgcggg actgtggcag gcacatggcg | 10200 |

```
ttgagcctgc tgcggtgctg ggccactccc aaggtgagat cgctgcggct tgcgtggcgg    10260
gtgcgctgag tctggaagac ggagcccggg tggtggctct tcgcagccgc gccatcgccg    10320
aggcccttgc gggccatggc gggatgctgt cgatagccgc ccccgccacc gaagtcacgg    10380
ccctgatcac cccctggggc aggcagatca ccattgccac ggtcaacgga ccgcattcgg    10440
tggtggtcgc aggagaccct gacgcgctcg aggcactccg cggcgaactg agacccgtg     10500 gtctccgcaa tcgtcgcatc ccggtcgact acgcctcaca caccccctcac gtcgaggcga   10560 tccgtgaacg gctcctggcc gacctggcag tgatccagcc acgtgccgcg agcattcccg    10620
tgctgtccac cgtcaccggc gcatggctcg acaccaccgt gatggacgcc gagtactggt    10680
accgcaacct acgtcagacc gtggagttcg aagcagccac ccgcactctc ctcgaccagg    10740
accaccgcta cttcgtcgag atcagcccgc accccgtact caccaccgcg atccaggaaa    10800
ccctcgacgt cacagacacc gccgccgtcg ccaccggaac cctgcgacgc aacgaaggca    10860
gcctccggcg tttccagctc gcccttgccg aactcgtcac ccgtggcctc accccgcact    10920
ggcccgccct ctatcccgac gcccgccaca cggacctccc cacctatccc ttccaacgcg    10980
agcgctactg ggtcggcagc tcctcggtgc gggacgcggc gccggctccg caaccggacc    11040
cggcaactgg gcgagcggcc ggtccggctt cgggccgggc cgccgtcgat ggcggcgacg    11100
ggcccgcgga gctgctggct ctggtgcgtg cccacgtggc cgtggtgctc ggtgagacga    11160
cgccggacag tgtcgatccg aaactgacct tcaagcagct cggcttcgac tcggtcatgt    11220
ccgtcgagct ccggaaccgg ctgagctccg ccaccggatc gtctctgccg agcacagtgc    11280
tgttcaacca ccccacgccg gaccggctcg cccgccatct gtccgccgag gcgtccagcc    11340
aggtggaagg cgcgcacgac gcggcgccga cgggtgccgc cgacgagccg atcgcgatcg    11400
tgggtatggg atgcaggtac cccggaggag tcgcgtcgcc ggaggacttg tggcggctgg    11460
tgacatccgg gggcgatgcg atctccggct tccccacgga ccgtggctgg gacctcgagg    11520
tcatgtacga cccggaccat cggcggcccg gcaccagcag tacccgcgag ggcgggttcc    11580
tgtacgaggc cggtgacttc gacgccggtt tcttcggcat cagcccgcgc gaggcgtcgg    11640
ccatggaccc gcagcagcgc ctgctgctcg agacttcctg ggaggccgtg gaacgggcgg    11700
gcatcgaccc gctgtcgctg cacggtacgc gggccggggt tttcgtcggg gccatggccc    11760
aggagtacgg cccgcgtctg gacgagggcg cggacggcta tgagggcttc ctgctgaccg    11820
gtggcctgac gagcgtgttg tccgggcggc tggcctacag cctggggttg gagggacccg    11880
cggtcaccgt ggacaccgcg tgctcgtcgt cgctggtcgc cgtgcacatg gccgcccagg    11940
ctctccgtca ggggcagtgt tccctggcgc tggcaggcgg ggtcaccgtc atgtccggcc    12000
ccgggatatt cctggagttc agcaggcaga gcggactggc accggacggc cgctgcaagg    12060
cgttcgcggc cggagctgac ggcacgggct gggccgaagg cgtcggcgtg ctggtgctgg    12120
agcggctctc cgacgcccgg cgcaacggac atcggtgct ggcggtggta cggggtcgg     12180 cgatcaacca ggacggtgcc tcgaacggcc tgacggcacc gaacgggctc gcgcaggagc    12240
gggtgatccg tgaggccctg acggacgcag ggctgtctcc cgccgacgtc gacctggtcg    12300
aggcccacgg caccggcacc accttgggtg acccgatcga ggcgcaggcc ctgatcgcga    12360
cctacggaca gggccgtccg gcggaccggc cgctgcgact gggctcgctg aagtccaaca    12420
tcggccacgc ccaggcggca gccggagtgg gcggagtcat caagacggtg atggcggtgc    12480
ggcacgcaac catgcccag accctgcatt tcgacgcgcc gtcaccgcat gtggactggt   12540
cgtccggcca ggtccggctg ctgaccgagg cagtgccgtg gcccgagtcc gaccaccccc    12600
```

```
ggagggcggc ggtctcgtcc ttcgggatca gcggcaccaa cgctcacgtt gtcgttgagc    12660 agccccggc ggaggtgtcc gcggtcaccg ggccatcacc tatggcgccg gacgaggccg    12720
taccggcccc ggggcagccg gtgccctggc tgctgtcggg caagtcaccg gaagcggtgc    12780
gcgagcaagc ggcgcggctg cggtcgtacc tggccgaccg gcccggcgcc ggtctcgccg    12840
acatcggctg gtccctggcg tcgacccggt cggcgttcga gcaccgtacg gtggtggtcg    12900
cggcggacca tgggcagttc cgtgaggcgc tgggcgcggc cgcggcgggt tcggcggatg    12960
cccgggtcgt cgagggcgtg gccgacatcg acggcaagac cgtcttcgtc ttccccggcc    13020
agggcgcgca gtgggccggc atggccgggg aactcctgga ctcctccgag gtgttcgccg    13080
cccggatggc cgactgcgcg cgggctttgg ccccgttcgt cggctggtcg ttgcaggatg    13140
tcgtccggca ggccgagggc gccccgccgc tggaccgggt cgacgtcgtc cagccggtgc    13200
tgtgggcggt catggtgtcg ctggccgacc tatggcgtgc tcatggcgtt gagccctcgg    13260
ccgtggtggg ccactcgcag ggtgagatcg cggccgcctg cgtcgccggt gggctgacgc    13320
tggaagacgc cgcgcgggtg gtgtcgctgc ggagccgggc catcgccgaa gtactcgccg    13380
gacacggcgg catgctgtcg gtgaccgcgg cccgggaaca ggtcgaggag tggctgctcc    13440
cctgggaggg caggatttcg ctcgcaacca tcaacggaac cgaatccgtc gtggtcgccg    13500
gcgatcccga cgcgctggcg gaattccgcg cgtggttggg gaaccgacag atccgtagcc    13560
gcaccctgcc ggtcgattac gcctctcact cggcgcaggt cgaggctgtc caccagcgac    13620
tgctggacga cctggcgccg atccgccccc gtacgtgccg tacccgctg ctgtcctcgg    13680 tcaccggcca gtggctggac accgcctcga tggacgccga gtactggtac cagaacctgc    13740 gccgaccgt ggagttcgcc gcggcgaccc gcaccttggc cgacgggggg caccgcatct    13800
tcatcgaggt gagctcgcat ccggtgctgg tcggcgcgat acgggaaacc ctcgaagccg    13860
tcgaggtcca ggccgctgtc gccgggtcac tccggcgtga cgacgaggc ctgcggcgtt    13920 tccggctctc gcttgccgcg ctcgtcaccc gggggctggc ccccgactgg tccatgctct    13980
gccccggggt gagccgaacc gacctcccca cctacccttt ccagcgcagc cgttactgga    14040
tcaccgcctt ctcggggtcg cggagcgccg gtgaactcaa cgctgcggac tcacgcttct    14100
gggaggcggt cgacagcgag gaccccgggc ggctggccga ggtgctcagc ctcgacgacg    14160
acgcgtcgct cgaaccggtc ttcctggcac tgtcctcgtg gcggcgacgg caccgggtgc    14220
ggtccaccct ggacgactgg cgttatcggg tgacctggca gccgctgccc ggggccgccg    14280
tcccgttgac ggcggcaacc ctcggaggga cctggctggt ggccgtgccc cacgaggacg    14340
cctacgtctc ccaggtgctg cgcgggctgg gcgaccgcgg cgcgaccgtg atcaccctac    14400
gagccgacga cccgcgccac ggcccgctcg ccgagcgggt ccgggaggcg ctggccgag    14460 cgggcgagat caccggcgtg ctgtcgctgc tggcgttgga cgagcggccg caccggaac    14520 atccggtcct tccatgggc ctggcgctca acacggcgct ggtgcgggca ctggtggaca    14580
aggacgtccg ggctccgttg tggtgcgcca cgcggggcgc ggtgtcggtg gccgatccg    14640 accggctggg cagccctgcc caggcgatgg tgtgggggct cggcctggtg gcggccctgg    14700
aacacccgcg gcactggggc gggctggtgg atctgcccga aaccgtggac gagcgggtgc    14760
tgaaccggct ggtgaccgtg atctcgggcc aacgagtcca cggacaggga gccccgggcc    14820
aggacggcga aaacccgggc gatgaggacc agcttgcggt gcgggcgtcc ggagtgttcg    14880
cgcggcggct gtcgcacgcg cccgtgtcgg cagccgcaa ccgggagtgg acgccccggg    14940
gcaccgtgct ggtcaccgga ggcaccggtg gcgcgggcac ccaggtggct cgctggctgg    15000
```

```
cccgtaacgg cgccgaacac ctgctgctga ccagccgtcg tggcagggac gccgaggggg    15060
ccgccgagct ggcggccgaa ctcacggaag ccggcgtcag ggtcacggtc gccgcctgcg    15120
acgtagcgga ccgggacgcc ctggcccggc tgctcgccgg cgtaccggac gagctgccgc    15180
tgaccgccgt gattcatgcc gccggtgtgg tcaccaccgc cccgctggac agcaccggtc    15240
cggaggaact ggccgaggtg ctggcgggca aggtggccgg cgccgcccat ctggacgctc    15300
tgctcggcga ccggcagttg gacgccttcg tactgttctc ctccaacgcc ggcgtgtggg    15360
gcagcggcgg gcaggcggcc tacgccgcgg ccaacgccta cctggacgcc ctggcccagc    15420
agcggtcctc tatgggccag accgcgacct cagtggcctg gggtgcctgg ggcggggccg    15480
ggatggcggc cgaggaaggg ttcaaggagc ggctgcgccg gcgggcatc atcgaaatgg     15540 acccggagct ggccgtcacg gcgctcgtgc aggccgtcga gtccggagag cgtcgatag     15600 ccgttgccga cgtcgattgg gcacgcttcg tgcccggctt cacctcgaac cggcccagtc    15660
cgctgatcgg cgacctgcct gaggtgcggg acgcgctgcg ggaggccgac agccggcccg    15720
ccgtcgatca gggcgggtcg gcgctcgcca cgcggctggc cgggctgtcc gtgctcgaac    15780
gggagcgggt cctgctcaac ctggtgcgca ccgaggtggc ctcggtactc ggtcacacca    15840
cggccgacat ggtcgatgcc cgtcgcccct tccgtgaact cgggttcgac tcgctgatcg    15900
cggtggagtt ccgcggccgg ttgaacgccg cgaccgggct gcggctgcct acctcggtcg    15960
ccttcgacca ccccacccccg gccgagctcg ccggccatct gcgggagttg ttcgccggat    16020
cccgcggtga caccgccatg cccgtgtcgg tgaccaccgc cggggacgac gaaccgatcg    16080
ccatcgtagc gatgtcctgc cggtacccgg gcggtgtgcg cactccggag gacctgtggc    16140
ggctggtggc cgagggccgg gacgcgatca cggacttccc caccgaccgc ggctgggata    16200
tcgaaagcct gtatgacccc gacccggggcc ggtccggcac ctcctacacc cggcggggcg    16260
gcttcctcga cgacgcggcg gccttcgatc cggcgttctt ccggatctcc ccccgcgagg    16320
ccctggccat ggacccgcag cagcggctgc tcctcgaaat gacgtgggag accctcgaac    16380
gggcgctcat cgaccaaaca acgctgaagg gcagccaggc cggggtgttc atcggcaccg    16440 cacacccccgg ctacgcgag ggcatccacc acgagtcgca gggcgtcgag ggccagcagc    16500
tgttcggcgg ctcggccgcc gtggccgcag gccggatcgc ctacacgttc ggcctggaag    16560
ggccggcgat gacggtggac accatgtgct cgtcctcgct ggtggcactc catctggcct    16620
gccagtccct gcgcaccggc gagtcctcga tggcgctcgc cggcggggtc acggtaatgg    16680
cacggccgac cgctttcacc gagttcagcc ggcatcgggg actgtccccc gacggacggt    16740
gcaagtcctt ctccgacgcc gccgacggca ccggctgggc cgagggcgcc ggtgtgctcc    16800
ttctcgaacg gctctccgac gcccgtcgaa acggccaccc cgtgctggcc gtcatccgcg    16860
gcagcgccat caaccaggac ggcgccagca acggccttac cgcacccaac ggcccctccc    16920
agcaacgcgt catccagcag gccctggcga acgcgtccct gtcgccggcc gacgtcgccg    16980
ccgtcgaggc ccacggcacc ggtaccaccc tgggcgaccc gatcgaggcc caggccctga    17040
tcgccgccta cggacaggac cgcccgacgg accggccgct acggctgggc tgctgaagt    17100 ccaacatcgg ccacgcgcag tccgcagccg cagtcggcgg cgtgatcaag atggtccagg    17160
ccatccggca cggcctcctc ccgcgcacgc tgcacgcgga gcagccctcc cgccacgtgg    17220
actggtccgc cggctcggtg gaactgctca ccgaggcgat gccgtggccg acaacgacc    17280 aaccccggcg ggcgggtgtc tcggcgttcg gcggcagcgg caccaacgcc cacatgatca    17340
tcgagcaggc gcccgcgccg gacgagccgg agcacaccga cggcacgagc aggaccagcg    17400
```

```
gcgagagcgg cgccgaacag gccaggccgc tgccgatggt gccctgggtg ctgtccgcgc  17460
ggagtgacac cgcgctgcgg gcacaggccc ggcgcctgcg cgcctacgcg gccgccgccg  17520
aggcgggcag catctgcgac atcgggtggg cgctggcgac cacccgagcc acgctggacg  17580
accgggccgt ggtcgtggcc gcggaacggg aaggattcct caccgctctc gacgcgctgg  17640
ccgaggaccg gaccgccccc ggtctggtcc gggggcggc tggaacagga gtgcggtcgg  17700
cattcctgtt ctccggccag ggctcacaaa gactcggcat ggggcgcgag ctgtacgaca  17760
cgtccctcgt gttcgccgag gcgctggacg aggtgtgcgc ccagctcgac gggcacctgg  17820
accgcccct cctgcgggtg ctgttcgcgc cggagggttc cgacgacgcg tcgatgctgg  17880
accagaccgc cttcacccag gccgcgttgt tcgcggtcga ggtggcgctg ttccgcctcg  17940
tctggtcctg gggcctgcgg cccgatttcc tcatcgggca ttccgtgggc gaagtcgcgc  18000
ccgcccatgt ctcgggcgtg ctgtccctcg ccgacgccgc gacactggtg gtcgcccgcg  18060
gtcggctgat gcaggcgttg ccctccgcg gcgcgatggc ggccttgcaa gcgggtgagg  18120
aggaagtacg gctgtccctg gcgggactgg aggacgttgt cggcgtcgcc gccctcaacg  18180
gccccgcctc gaccgtgatc tctgcgacg aggaggccgt cctcccggtg gccgcgcact  18240
ggcgcgcgca gggccgcaag acgcgtcgcc tcaaggtgag ccacgccttc cactcacccc  18300
gtatggaacc catgttgcac cggttccacg ccgtgctcaa aacgctttcc ttcgccgagc  18360
cggccattcc cgtggtctcg aatgtgaccg gccgtcccgc cgagcggacc gaactgtgcg  18420
cggcggacta ctgggtgcgc catgtccggc atacggtgcg cttccatgac ggcatccgcg  18480
cgctggaggc cgaaggcgtc agcgcattcc tggagttggg gcccgacggc acactctcgg  18540
cgatggtccg cgactgcctg gacaccagcc gcccggtggt cacggcaccg gttttgcgac  18600
gtgaccgtac cgatgtgtct gccgcgttga cggcactggc cgaagcgcac gggcacgggg  18660
tgccggtgga ctgggcgtcg ctcttcgccg gctcgaccgc ccggggcggtc gagctgccga  18720
cgtacccgtt ccagcgggaa cacttctggc tggattccgt cacgggcagc agtgacatga  18780
gcacggccgg actggcgtcc cccgatcatc cgctgttggg agccgtgacg acggtggccg  18840
gcgaggacgg cctcctcttc accggcaacc tgtcggtacg gacgcaccca tggctggccg  18900
accacaggat caccggttcg gtcctgctgc ccggcacggc gttcctggaa ctggccgtcc  18960
aggccgggga ccaggccggc tgcgggcggg tcgaggacct gacgctgctg gctccgctcg  19020
tactgcccga agagggcagc gtcagggtcc agatgaaggt gggggagccc gacgccacgg  19080
gccgccgcac catcgaggtg tactcctcgg accagcaggc cccggccgg gaacgctggg  19140
tcctcaacgc gagcgggatg cttgccggcg aaccggtgga ggccccgccg agtctcacca  19200
cctggcccc ggaaggcgct gtccccgttc cgctggacgg cttccacgac cggctggcgg  19260
cacgcggcta cggctacggc ccgacattcc gcgggctgag cgccgcgtgg tcacgcggtg  19320
acgagatctt cgccgaagcg gcgctcccct cgggccatcg gcaggatgcc gcccgctatg  19380
gactccaccc cgccctactc gacgctgccc tgcacgccat ggaactccgg gaaccccgcc  19440
cggcggcgcga cggagtccgg cttccgttcg cctggaacgg cttctccctg cacgcgtcgg  19500
gtgccgaagc ggtacggctg cgcctcgcgc cgacgggcgc cgacgctctg tcggtgaccc  19560
tcgccgatgc catcggtcgc ccggttgcct cagcccgctc gctggccctg cgggagctct  19620
cgtccgacct gctgcgcccg gcgtccgtct cgtacgggga ctcgctgttc cgcaccgctt  19680
ggataccgc cctcgtcggc ccggaggcgg agtccgggcc ggtgcgaccg tccgccggct  19740
gggcggtgct gggccccgat ccgctcggcg cggccaacgc cctgaacctc acgggaacct  19800
```

```
cctgctcctg ctatccggac ctggcggcgc tgatcgcggc cgtcgacggc ggagccgcgg   19860
tgcccgaggc cgtactcgcg ccgtacgcgg cggagccagc cccggacgcg ggatctcccg   19920
cggacgccgt acgggcctcg accggccggg cgctgcaact gctgcaatcc tggctgtccg   19980
aggaccggtt ggagcgaagc cggctgatcg tgctcacccg gggggcggtg gccgtcggta   20040
cggacgaagg cgtcaccgac ctggtgagtg cgtcggtccg gggtctggtc cgttcggcgc   20100
aggccgagca ccctggcagg ttctccctgg tcgacatcga cgaccgggag gagtcctggg   20160
ccgtcctgag cgcggcggcg gtatccgatg agccacaact cgccctgcgc tgcggccaga   20220
tgaaggtgcc ccgcctcggc tccgtcgacg ttcccacgac cggtatgcct gagatgcccg   20280
acgtttgggg tgttgacggt accgtgttga tcactggcgg gaccggtgtg ctgggtgggc   20340
tcgtcgcccg tcatctggtc gccgggcatg gggtccgtcg tctgttgctc tgcagcaggc   20400
ggggccctga tgcgccgggt gcggtggagc tggtcgccga gctcaccgct ctgggtgcgg   20460
atgtcaccgt tgccgcctgc gacgcggccg accgggatgc gctggccgcg ctcttggaca   20520
ccgttcccgc cacgcaccct ctgactggtg tcgtgcatac cgctggtgtc atcgatgacg   20580
ccactgtcac caccctcact cccgagcgca tcgacgcggt cctacgcccc aaggtcgacg   20640
ccgcgctcaa cctccatcag ctgacggcgc atctcggctt gacccgcttt gtgctcttct   20700
cctccgccgc cgggctcttc ggcggcgcgg gccagggtaa ctacgcggcc gccaacgcct   20760
tcctcgacgc actggcccaa caccggcggg ccaacggcct caatgcccag tccctggcgt   20820
ggggactgtg ggcggaagcc agcgggatga ccgggcacct ggacgcggcc gacctcgccc   20880
gggtggcccg ttccggcctc accgcgatgc ccaccgggga cgggctggcg ctgctcgaca   20940
ccgctcagcg ggtggacgaa gccacccctgg tcacggccgc gctggacacc cgggccctgc   21000
atgcccgggc cgcagacggc acgctgccgg cgctgttcca cgcactcgtg cccgtaccgc   21060
gccgatccgc gacctccccg gcggcccagg ccgcggggcc ggatggactc cgccagcggt   21120
tgtcggggtt ggtcgagggg gagcgtcgag cggcgctgct ggatttggtg tgtggtcatg   21180
tcgcgagggt gctggggcac gcggacccga gcagcattga ggagacccgg cccttcaagg   21240
acaccggctt cgactcattg accgctgtgg agctgcgcaa tgtgctgcac ggtgcgaccg   21300
ggttgcggct gccggccacg ctggtcttcg actacccgac gcctgcagct ctcaccgatc   21360
acctctacga cgagcttctg ggttcccgcg aggacgccgt gctcgccccg atcaccaggg   21420
ccgcgtacga cgagccgatc gcgatcgtgg ggatggcctg ccgctatccg gcgggggtgg   21480
agtccccgga ggaccgtgtgg cagctggtcg ccgacgccg tgacgccatc tccgacttcc   21540
ccgccgaccg gggctggaac gtcgagagcc tctaccaccc cgaccccgac caccccggca   21600
ccagctacac ccgtgccgga ggcttcctgc acgacgcggc ggacttcgac ccggagttct   21660
tcgggatctc accgcgtgag gcactggcca ccgaccccca gcagcgactg ctgctggaga   21720
cgacgtggga ggccttcgaa cacgccgggg tcggcccggc gtcactgcgt ggcagccgga   21780
ccggcgtctt cgtcggcgtg atgtacaacg actacgcctc gcgtatccgg cacatcccag   21840
agagcgtcga gggcggtctg accaccaaca gcgcggggag tgtggcgtcg gcccgggtct   21900
cgtacacgtt cggtctggag ggaccggccg tcacggtgga taccgcgtgt cgtcgtcgc   21960 tggtggcgtt gcatctggcc gcgcaggcgt tgcgcaacgg tgagtgcact ctggctctgg   22020
cgggcggtgt tgcggtgatg tccactcctg ccacgtttgt cgagttcagc cggcagcggg   22080
ggctggcagc tgatgggcgg tgcaaagcct tcgcggacgc tgccgacggc accggctggg   22140
gcgaaggcgt cggtgtgctg ctggtggagc gtttgtcgga cgcgcgccgc aacgggcatc   22200
```

```
cggtgctggc ggtcgtttcg ggcagtgctg tcaaccagga cggggccagc aatggtctga   22260
cggcgcccaa tggtccttcg cagcaacggg tgatccaaca ggcgctggcc aatgcggggt   22320
tggcgggggc ggatgtcgat gccgtggagg cgcacggcac gggaacccgg ctgggcgacc   22380
cgatcgaggc gcaagcgttg atcgccacct acgacaggc ccggtcggcg gaccggccgt   22440
tgtggctggg ttcgctgaag tccaacatcg gtcacaccca ggccgccgcg ggcgtcgccg   22500
gcgtcatcaa aatggtgcag gcgatgcagc acgggactct gccgcccacc ctgcacatcg   22560
accagcccac gggccaggtc gactgggcta cgggtgcagt ggagctgctg accgaggccg   22620
tgccctggcc ggacagtgac cggccccgcc gggtggctgt ctcctcgttc ggtgtcagcg   22680
gtaccaacgc ccacgtcatc atcgaacaca ccccacacac cccacacacc cccgcacct   22740 cccaatcctc ccaatccccc caggcccgc agactgtgca ggccatcgg ccggtgccgt   22800 ggctgctgtc ggcgaagacc tcgcaggccc tggccgcgca ggcccggcgc ctgtcagctc   22860
acttgcgagc caaccccgat ctgcgttcgg ctgatgtggc gcattccctg ctcaccacgc   22920
ggtctgtcca cgccgagcgc gccgtcttca tcgccggtga ccgggatgag gctcttgccg   22980
ccctggacgc actggccgac ggcacccctg cccctcacct cgttcagggc cttgccgatg   23040
tgagtggcaa gacggtgttc gtcttccccg gtcagggttc gcagtgggtg ggtatggccg   23100
ttgagctgct ggacggctcg gaggttttcg ccgagcatat ggccgcctgc gccagggccc   23160
tggaaccgtt tgtggactgg tccctggagg acgtcctacg ccagacggac ggtacgtggc   23220
cactggaacg cgtcgaagtg gtccagcccg tgctgtgggc ggtcatggtc tcgctcgcgg   23280
gactgtggca ggcacatggc gttgagcctg ctgcggtgct gggccactcc caaggtgaga   23340
tcgctgcggc ttgcgtggcg ggagcccga gtctggaaga cggagcccgc gttgtcgcgc   23400
ttcgcagcca agccatcgcc gaaaccctcg caggacacgg cggaatgctc tcaatcgccg   23460
cccccgccac cgacatcgca cccctgatcg cccgctggaa cgagcggatc tccatcgcca   23520
cggtcaacgg accgcattcg gtggtggtcg caggagaccc tgacgcgctc gaggcactcc   23580
gcggcgaact ggagaccccgt ggtctccgca atcgtcgcat cccggtcgac tacgcctcac   23640
acacccctca cgtcgaggcg atccgtgaac ggctcctggc cgacctggca gtgatccagc   23700
cacgtgccgc gagcattccc gtgctgtcca ccgtcaccgg cgcatggctc gacaccaccg   23760
tgatggacgc cgagtactgg taccgcaacc tacgtcagac cgtggagttc gaagcagcca   23820
cccgcactct cctcgaccag gaccaccgct acttcgtcga gatcagcccg caccccgtac   23880
tcaccatcgg tctacagcag accatcgagg aaaccaccgc tccggccgg accctctcca   23940 ccctccgacg caacgaaggc accctccggc acctgttcac ttccctcgcc caggcccacg   24000
cccacggcct gaccatcgac tggacccccg ccttcaccca caccgagccc cgcaccaccc   24060
ccctgcccac ctaccccttc caacacgaac gctactggct ggaggacgga gctccgaagt   24120
ccggggacgt ggcttcggcc ggactcggct cggcggacca tccgctgctg ggcgccgctg   24180
tgccgctgcc cgattccggg ggcttcctgt tcaccggcca gttgtcgctg cggagtcacc   24240
cctggttcgc cgaccacgcg gtacacggca ccgtgctgct gccgggcacc gcgttcgtgg   24300
aactggcgct ccaggccggt ggccgtctcg gctgcgggct gctggaggaa ctcaccctgg   24360
aggcaccgct ggtgctgccg gaaaacagct ccgtccagtc ccaactcgtg gtgaacgccc   24420
cggacgccca ggacgactcg ggcggcagga ccttcagcgt gtactcgcgc ccgcaggacc   24480
gtactgcgga cgcgccctgg gtgcggcacg ccaccggagt ggtccggtcc ggaggcgcgc   24540
cggagccgga gggactgacc gtgtggccgc cgaccggagc ggtcgcggtg ccggtcgagg   24600
```

```
acttctacca ggtgctcggt gaccgtggct atgactacgg acctgcgttc cgtggggtaa    24660
gggccgcgtg gcgccacggt gacgtggtgt atgccgaggc cgcactggcc gaggagcagc    24720
agtcggacgc cgcgctgttc cacctccacc cggccctgct cgactcggcg ctgcacggga    24780
tgggactgat gccctcggcg agcgcggagc agacccggct gccgttcgcg tggcgcggtg    24840
tgacgctgca tgcggtgggg gcgtcggccc ttcgggtgag tcttaggccc gccgggcccg    24900
acacggtgga ggtcctactg gccgatggcg caggtcggcc ggtcgcttcg gccgacgcac    24960
tggtggtccg gccgctccga caggaggaac tggcggtctg gcaggacgcg taccgcgact    25020
ggctgtaccg ggtcgactgg cccgagttgc cggaggtccc cctggtggct ccggccgggc    25080
catgggccgt cctgggcggg aacgccggcg ggatactcgg caccgatggc tcggccgggt    25140
tgctggccgg ggtcccgatc gacgcctatc gggacctggc ggagctgcgc gaccggacgg    25200
gcccgagcag cgcgttcccg gccgtggtgg tcgcgccggt cgccacggga accggtgccg    25260
cgccggacgc ggtgcgggag gtgacgtacc aggtgctgga catgatccag tcatggctcg    25320
ccgacgatcg ttccgcctcg tcgacccttc tcctggtgac ccgcggcgcg gtgtccaccg    25380
gcttcgggga cgacctggtc gatctggggc aggcggcgg atggggttg gtgagggccg    25440
cgcagtcgga gaacccggac cgcttcgtcc tcctcgacct cgacgggagc gagccggtcg    25500
ggcctctccc gacggcggcg ctgctctccg gggagccgca actggcgttc cgggagggca    25560
aggtgctgac cgcccggctg gaccgggtgt cgtccgacgc gggaacgctg ctgccgcccg    25620
ccgggccgga cccgtggcga ctcgacgtca ccagccgggg cacgctcgac aacctcgcgc    25680
tcctcgcggc gccgcaggtg tcggcgccgc tcgccgaggg acaggtccgg gtcgcggtgc    25740
acgcggccgg cctgaacttc gcgcatgtgc tggtcgctct gggcatgtac ccgggtgagg    25800
gttcgatggg cagcgaaggc gccggcgtgg tgctggaggt cgggccccggc gttgagcggc    25860
tggccccggg cgaccgggtg atgggcatgc tcgcgggcgg cttcttcggg ccggtcgccg    25920
taaccgacca gcgcatggtg accaagcttc cggacggctg gtcgttcacc gagggcgcat    25980
cggtaccgat cgtcttcctc accgcgtact acggactggt cgacctgggc ggcctgcgcg    26040
ccggccagtc gctgctggtg catgcggcga ccggtggtgt gggaatggcg gctacgcagc    26100
tggcccggca cctcggcgct gaggtgttcg gcacggcgag ccccggcaag tgggaggcgc    26160
tgcgggggat gggattggac gaggagcaca tcgcctcgtc gcgggacctg gacttcgaga    26220
agaagttctc ggccgcgacc ggtggccgcg tgtcgacgt ggtgctgaac tcgctggccc    26280
gggagttcgt ggacgcgtcg ctgccggctgc tgccgcgcgg cggtcgattc gtggagatgg    26340
gcaagaccga catccgtgac gccgaggcgg ttgccgccgg gcatcccggc gtcgtctacc    26400
gggccttcga cctgctggac gccgcgggc cggaccgtat ccaggagatg ctggccgagt    26460
tgctcgcgct cttcgaggcg ggggtgatcg agccgctgcc gctgacgacc tgggacatcc    26520
ggcgtgcccc ggaggcgctg cggcacctga gccaggcacg gcacatcggc aagatggtct    26580
tcaccctgcc gccccgcccg gacccggacg gtacgttcct gatcacgggt gtgcccggag    26640
cgctgggcaa cctggtcgcc cgccatctgg tgaccgaggg tggcatacgg aacctgctgc    26700
tcgtcagccg ccgggggccg gcggcccccg gcgcggaggg gctggccacc gagctggccg    26760
ggctggggc gacggtgacc ctgccggcct gtgacgtggc cgaccgccag gccctggccg    26820
ggctgctcgc cgacatcccg gcggagcatc cgctgacggg tgtggtgcac gccgccggtg    26880
tgctggacga cgggatcgtg gcatccctga cccgcgaacg gctggacgcg gtctaccgcc    26940
ccaaggtgga cgccgcctgg aacctgcacg agctgaccaa ggacagcggc ctggccgcgt    27000
```

```
tcgtactgtt ctcctcggcc gccgcgacgc tcggcagcgc aggccagggc aactatgcag    27060
cggccaacgc cttcctcgac gccttggccc aattccgcca ggcccagggc ctggcggcca    27120
gctccctcgg ctggggattc tgggccgaga gcggtgagat gaccggtcac ctgggggcct    27180
ccgacctggc acggatggca cgttcggca tcgccgccct gacggtcgag cagggcctgg    27240
ccctgttcga ctccgcacgg tcgggtgtct gtgcgtcagt gctgccggta cggctggaac    27300
tcaccgggcc cggtgcgcgg gccgggtcgg aacggtgcc ggcgctgatg cggggctgg    27360 tgcgggcacc ggcccggcgg gtggtggaaa caaccacggg cggtgccgtc acaggcctgc    27420
gccaacggct ggcgccgctg tccggcgcgg accgcgaccg cgccctccaa gagctggtgt    27480
gctcgcatgc ggccaccgtg ctggggcaca gccgttccgg atcggtgccc gcgcagcggg    27540
cgttcaagga gctcggcttc gattcgctga cagccgtcga gttgcgcaac cggctcaacg    27600
tggcgaccgg cctccggctc cccgcgactc tggtgttcga ccacccgacc ccgctggcga    27660
tggcggaaca gctccggaag gagctgttcg cggacgagat cccggtggcg ccgcaggttt    27720
tggaggaact ggaccgtctg gaggcggcgt tcgccgtctc ctccgccggc gacctccagc    27780
agtcgggagc cgcggcacgg ctgagggcac tgctgaggcg gatcggcacc gtcactccgg    27840
cgggagggga cgctgccgac ggcctcgccg tagagctcga aacagccacc cacgacgaga    27900
tcttcgccct tatcgacgag gaggtagggg acgtgtgacc ggtcggtcgc tccccctca    27960 cccctacccc ccgcccggac tagcagcatg gatgagatca cgatgactga tgagaccgct    28020
gtgcccaaaa cagagaccac cgaggagaag ctcttctcct acctgaagaa ggccacctcc    28080
gaactccagc agagccgccg ccgggtggca gagctggagg cggcggaggc ggagcccatc    28140
gcgatcgtgg gcacggcctg ccggtacccg ggtggagtac gttccccgga ggacctgtgg    28200
cggttggtcg cggaggggca gcacgcgatc tccagcttcc cgacggaccg cggctgggat    28260
ctcgaagacc tctacgaccc ggaccccgac cggcccggca agtcctacgc ccgggacggc    28320
ggcttcctcg acggtgccgc ccagttcgac gcggcgttct tcgggatctc gccacgtgag    28380
gcgctggcca tggaccccgca gcagaggctg ctgctcgaga cgacgtggga ggtcttcgag    28440
cgcgccggga tcgacccgac atcgctccgt ggcagccgga ccggggtgtt cgccggcatc    28500
agccaccagg actacgctgc cggacagcgc ccgtcggccg aggtctccga ggggcacctg    28560
atgaccggca ccgcggtcag cgtggtgtcc gggcgggtcg cctatgcctt cggcctggaa    28620
gggccggcca tgacggtgga cacggcctgc tcctcgtcgc tggtggcgtt gcacctggcc    28680
gcgcaggcgt tgcgcaatgg tgagtgcacg ctggcggtgg ccggcggcgt caccgtcatg    28740
gccacgccgg gcgccttcac caggttcagc cgggagcggg gcctggcccc ggacgggcgc    28800
tgcaaggcct tcagctcgga cgccgacggc accggcttca gcgagggtgt gggtgtgctg    28860
ctggtggagc gtttgtcgga cgcgcgccgc aacgggcatc cggtgctggc ggtcgtttcg    28920
ggcagtgctg tcaaccagga cggggccagc aatggtctga cggcgcccaa tggtccttcg    28980
cagcaacggg tgatccaaca ggcgctggcc aatgcggggt tggcggggc ggatgtcgat    29040 gccgtggagg cgcacggcac gggaacccgg ctgggtgacc cgatcgaggc gcaggcgttg    29100
atcgcgacgt atggacaggc ccggtcggcg gaccggccgt tgtggctggg ttcgctgaag    29160
tccaacatcg gccacaccca ggccgccgcg ggcgtcgccg gcgtcatcaa gatgatccag    29220
gccatgggtc acgggacgct gccccgtacg ctgcatgtca accagccctc gccccaggtc    29280
gactgggcgg caggcgcggt ggagctactg accgaagcca tgcctggcc cgagggtgac    29340 cggccccgcc gggccggaat ctcctccttc ggaatcagcg gtaccaacgc ccacgtcatc    29400
```

| | |
|---|---|
| atcgaacagg gggccccgcc acggacagcg tccgaccccg gtgaaagtcg tgctgacgag | 29460 |
| cccggcgtac ggggcggcgc tcccgtccct gccaccacgg agtcggccac cgaaccgcag | 29520 |
| ccggttccct ggctgctgtc cgggcacagc gcgaccgcgc tgcgggcgca ggcggatcgc | 29580 |
| ttgaagtcgt acgcggccaa caacaccggc atccgtccgg ccgacatcgg cttctcgctg | 29640 |
| gtcaccaccc gggccgcgct ggaacaccgc gctgtcgtcg tggcagccga ccatgccggt | 29700 |
| ttcacggctg gtctcgacgc gctggccgag ggccggacag ctcccggagt ggtgagcgga | 29760 |
| acggtcgtcg ccggtgcccg gagcgcgttc ctcttctccg gtcagggctc gcagcgggtc | 29820 |
| ggcatggggc gcgagctcca gcaggcgttc ccggttttcg ccgaggcttt cgaagcagtc | 29880 |
| tgcgcccagg tcgacccgta cctggagcac ccacttctcg atgtcgtact cgccgcgccg | 29940 |
| gacagcgact tcggcgcgtt gctccatcag accgcctaca cgcagccggc actgttcgcc | 30000 |
| ctcgaagtgg ccctgttccg gctggtcgaa tcctggggtg tcaggccgga ttacgttgcc | 30060 |
| gggcattcgg tcggtgagat cgcggcgccc catgtggcgg gggtgttctc gctggaggat | 30120 |
| gcggctcgtc tggtggtggc gcgcggacag ttgatgcagg cgttgccggc tgaaggcgcg | 30180 |
| atggtggcgc tccaggtgtc cgaggacgag gtcctgccgt ccctgactcc ttggctggag | 30240 |
| caggaccggg tggatgtcgc ggcggtcaac ggcgcagcat ccacagtggt gtcggcgat | 30300 |
| gaggaggcgg tcctggcggt tgccgagcac tggcaggcgc ggggccgcaa ggttcgtcgg | 30360 |
| ctcactgtca gccatgcctt ccactcacct cgtatggacc cgatgctcga ccagttccgt | 30420 |
| gtggtcgtgg agggtatccg tttcgcggag ccggccatcc cggtcgtctc cagcgtcacc | 30480 |
| ggtcgtcttg ccgagcccgg gcagttgacc actgcggact actgggtgcg ccacgtccgt | 30540 |
| caaacggtcc gcttccacga cgccctccag accctccaga ccgagaatgt gaccgcgttt | 30600 |
| ctggagatcg gtcccgacgg gcaactctcg gcaatgaccc cgacttcct gaccgatacc | 30660 |
| ggggcccacg ccgccgtcgc acccctcctg cggcgcgaac gtcccgaggc acccagcgcg | 30720 |
| ctcaccgcaa tcgccgggct gcacacccac ggcgtctcga tcgactggcg cacgtacttc | 30780 |
| accagcacca gcaccagcac cagcaccagc accggtaccg gtaccggtac ggggcaggcc | 30840 |
| actgccgaca cgcccgtcca gctgcccacg tacgccttcc agcaccagtc cttctggctc | 30900 |
| ggccccacgg ccctgtcgg cgacgtcagc accgccgggc tcacctcgcc cgaccacccc | 30960 |
| ctgctcagcg cagccaccac caccgctgtc gacggcagcc tcctgctcac cggcaggctg | 31020 |
| tcgcagcggt cgcccgcgtg gatcggcgac caccgcatcg gcggtgtggt cctgctgcca | 31080 |
| ggcaccgctc tcgtggaact cgtcgtacgc gccgggacc aggccggttg cagccgcatc | 31140 |
| gacgaactca tcatgctcac gccgctgacg ctgcccgagc atggtgccgt gcggatccag | 31200 |
| gtcgccgtcg gcggcccggc ccacgacggc cgccgcccgg tgcacatcca ctccagcacc | 31260 |
| tcggacacga ccggcgacga acagtggacc ctcaacgcca gcggtctgct caccgtcgag | 31320 |
| atgaccgatc cgcccgccga tctcaccccc tggccgccgc agcacgccac ccgcataccg | 31380 |
| ctcgacggcc tctacgagcg gctcgccgaa agcggctacg gatacggccc ggtcttccag | 31440 |
| ggcctgcgcg ctgcctggac actcggcgac gacacctacg ccgaggtcga gatccccgcc | 31500 |
| ggcgaccaga ccgacaccga ccgctacgaa ctccaccccg cgctcctcga cgccgcgctg | 31560 |
| cacgcgtcct ccctccaggg cgacgaggcc ggggccgggc agctgctgcc gttcgcctgg | 31620 |
| accggggtgt cgctgtacgc ggccggcgcc tcggccctgc tcgtcaaggt gtcccgtacc | 31680 |
| ggtccggaca ccatggcgct gctcgtggcc gacaccgagg gccacccggt cgccaccgtc | 31740 |
| gactcactga ctgtccggcc gatggccatc gaccagaccg cccggagcac cagccaccct | 31800 |

```
gacgcgctgt tcaccgtggg gctggagtgg gcccaagccc gggagggcaa ccggaccatc    31860
cccctgtccg actgcgccat gctggctccg gacgaaccgg acctcacctc cgccccggcc    31920
tggcccgggt cctccgcgca gcggtacgcc ggcctcgcgg cgctcgctga gatctgcgga    31980
acggacgggc cggtacctgc cgtggtactg gcgcccttcc tccccggcga tgccgcgccc    32040
gccgacaccg ccgccgcgac gcacgcgacg acgcgccgcg ccgccgctct catcaagggc    32100
tggctgggcg acgaccgttt caccgactcg cgtctggtct tcgtcacccg tggcgcggtg    32160
gccaccagcg gccgggacga actgcacgac ctggaacact ccacggtctg gggtctggtc    32220
cggtcggccc agaccgagaa ccccggcagg ttcgcgctgc tcgatctcga cgacccggac    32280
accgtcaccg aactgccgga agccatcctg gccgatcagg cacagctggt cctgcgggac    32340
gggcggctgg gaaacctccg gctggccaag ggcgctgcga tacaggatcc cgacccgggt    32400
tggggtgttg acggtaccgt gttgatcact ggcgggaccg gtgtgctggg tgggctcgtc    32460
gcccgtcatc tggtcgccgg gcatggggtc cgtcgtctgt tgctctgcag caggcggggc    32520
cctgatgcgc cgggtgcggt ggagctggtc gccgagctca ccgctctggg tgcggatgtc    32580
accgttgccg cctgcgacgc ggctgaccgg gatgcgctgg ccgcgctctt ggacaccgtt    32640
cccgccacgc accctctgac tggtgtcgtg cataccgctg gtgtcatcga tgacgccact    32700
gtcaccaccc tcactcccga gcgcatcgac gcggtcctac gccccaaggt cgacgccgcg    32760
ctcaacctcc atcagctgac ggcgcatctc ggcttgaccc gctttgtgct cttctcctcc    32820
gccgccgggc tcttcggcgg cgcgggccag ggtaactacg cggccgccaa cgccttcctc    32880
gacgcactgg cgcagctgcg gaagcggcag ggactgccgg gcgtgtcgct ggcctggggt    32940
gcctgggtcc aggacggcgg aatgaccgca acgctggacg cgggcgacgt cgagcggatg    33000
gcgcgcggcg gtgtgctgcc gctcagccac gagcagggcc tgaacctgtt cgacctggca    33060
gtggcagggt ccgagccgct ggtggcaccg atgcggctgg acaccaccgc gctgcgcgag    33120
tccggtgcca ccgtgccgga gatgctgcgc gggttggtgc gtgagcggtc acgccgccgg    33180
gtcggaccct cgcacacgac gtccgccgcc atggcgctgg aacaacggtt gtcggggttg    33240
gtcgaggggg agcgtcgagc ggcgctgctg gatttggtgt gtggtcatgt cgcgagggtg    33300
ctggggcacg cggaccccga gcagcattga gagacccggc ccttcaagga caccggcttc    33360
gactcattga ccgctgtgga gctgcgcaat gtgctgcacg gtgcgaccgg gttgcggctg    33420
ccggccacgc tggtcttcga ctacccgacg cctgcagctc tcaccgatca cctctacgac    33480
gagcttctgg gttcccgcga ggacgccgtg ctcgccccga tcaccagggc cgcgtacgac    33540
gagccgatcg ccatcgtagc gatgtcctgc cggtacccgg gcggtgtctg cactccggag    33600
gacctgtggc ggctggtggc cgagggccgg gacacgatca cggacttccc ggacgaccgc    33660
ggctgggata tcgacgccct gtatgacccc gacccgggcc accccggcac ctcctacacc    33720
cggcggggcg gcttcctgtc cgacgcgcg ggtttcgatc cggcgttctt ccggatctcc    33780
ccccgcgagg cgctggccat ggacccgcag cagcggctgc tgctcgaaat gacgtgggag    33840
atgttcgaac gggcgctcat cgacccaaca acgctgaagg gcagccaggc cggggtgttc    33900
atcggcaccg ccggccccgg ctacggcggc cgcatccacc acgagtcgca gggcgtcgag    33960
ggccagcagc tgttcggcgg ctcggccgcc gtgacctcag gccggatctc gtacacgttc    34020
ggcctggaag ggccggcgat gacggtggac accatgtgct cgtcctcgct ggtggccctg    34080
cacctggccg tccagtccct gcgcaacgga gagtcctcga tggcgctcgc cggcggggtc    34140
acggtgatgt cccggccggc cgcgttcacc gagttcagcc ggcagcgggg gctgtcccc    34200
```

```
gacgggcggt gcaagtcgtt cgccgacgcg gccgacggca ccggctgggg cgagggcgcc    34260
ggcgtgctcc tcctcgagcg gctctccgac gcccgtcgca acggccaccc ggtgctggcc    34320
gtcatccgcg gcagcgccgt caaccaggac ggcgccagca acggcctcac ggcacccaac    34380
ggcccctcgc agcaacgcgt catccgccag gccctggcga acgcgtccct gtcgccggcc    34440
gacgtcgacg ccgtcgaggc ccacggcacc gggacccccc tgggcgaccc gatcgaggcg    34500
caggccctga tcgccaccta cggacaggac cgcccggcgg accggccgct gcggctgggc    34560
tcggtgaagt ccaacatcgc ccacgcgcag gccgcagccg cagtcggcgg cgtcatcaag    34620
atggtccagg cgatccggca cggcctcctc ccgaagaccc tgcacgtgga gcagccctcc    34680
cgccacgtcg actggtccgc cggctcggtg gagctgctca ccgaggcgat gccgtggccg    34740
gagaccgacc aaccccggcg ggccggtgtc tcggcgttcg gcggcagcgg caccaacgcc    34800
cacatgatca tcgagcaggc gcccgcgccg gacgaggagc acaccgacgg cacgagcagg    34860
accagcggcg agagcggcgc cgaacaggcc aggccgctgc cgatggtgcc ctggctgctg    34920
tcggcgaaga cctcgcaggc cctggccgcg caggcccggc gcctgtcagc tcacttgcga    34980
gccaaccccg atctgcgttc ggctgatgtg gcgcattccc tgctcaccac gcggtctgtc    35040
cacgccgagc gcgccgtctt catcgccggt gaccgggatg aggctcttgc cgccctggac    35100
gcactggccg acggcacccc tgcccctcac ctcgttcagg gccttgccga tgtgagtggc    35160
aagacggtgt tcgtcttccc cggtcagggt tgcagtgggg tgggtatggc cgttgagctg    35220
ctggacggct cggaggtttt cgccgagcat atggccgcct cgccagggc cctggaaccg    35280 tttgtggact ggtccctgga ggacgtccta cgccagacgg acggtacgtg gccactggaa    35340
cgcgtcgaag tggtccagcc cgtgctgtgg gcggtcatgg tctcgctcgc gggactgtgg    35400
caggcacatg gcgttgagcc tgctgcgctg ctgggccact cccaaggtga gatcgctgcg    35460
gcttgcgtgg cgggagccct gagtctggaa gacggagccc gcgttgtcgc gcttcgcagc    35520
caagccatcg ccgaaaccct cgcaggacac ggcggaatgc tctcaatcgc cgccccgcc    35580 accgacatcg caccctgat cgcccgctgg aacgagcgga tctccatcgc cacggtcaac    35640
ggaccgcatt cggtggtggt cgcaggagac cctgacgcgc tcgaggcact ccgcggcgaa    35700
ctggagaccc gtggtctccg caatcgtcgc atcccggtcg actacgcctc acacacccct    35760
cacgtcgagg cgatccgtga acggctcctg gccgacctgg cagtgatcca gccacgtgcc    35820
gcgagcattc ccgtgctgtc caccgtcacc ggcgcatggc tcgacaccac cgtgatggac    35880
gccgagtact ggtaccgcaa cctacgtcag accgtggagt tcgaagcagc cacccgcact    35940
ctcctcgacc aggaccaccg ctacttcgtc gagatcagcc cgcacccccgt actctcggcg    36000 atggtccgcg actgcctgga caccagccgc ccggtggtca cggcacccac cctccgacgt    36060
gaccgtaccg atgccactgc cgcgttgacg gcactggccg aagcgcacgg gcacggggtg    36120
ccggtcgact gggcgtcgct cttcgccggc tcgaccgccc gggcggtcca cctgccgacg    36180 tacccccttcc agcggcaaca ctactggctg gattccggta cgggcagcag tgacatgagc    36240
acggccggac tggcgtcccc cgatcatccg ctgttgggag ccgtgacgac ggtggccggc    36300
gaggacggcc acctcttcac cggccggctg tcggtacgga cgcacccatg gctggccgac    36360
caccagatca ccggttcggt cctgttgccg ggcacggcct tcgtcgaact ggccgtccgg    36420
gccggggacc aggccggctg cgggcgggtc gaggagctga cgctgctggc tccgctcgta    36480
ctgcccgaag agggcagcgt cagggtccag atgaaggtgg gggagcccga cgccacgggc    36540
cgccgcacca tcgaggtgta ctcctcggac cagcaggccc ccggccggga acgctgggtc    36600
```

```
ctcaacgcga gcgggatgct tgccggcgaa ccggtggagg ccccgccgag tctcaccacc   36660
tggcccccgg aaggcgctgt ccccgttccg ctggacggct tccacgaccg gctggcggca   36720
cgcggcttcg gctacggtcc gacattccgc gggctgagcg ccgcgtggtc acgcggtgac   36780
gagatcttcg ccgaagcggc gctcccctcg ggcatcggc aggatgccgc ccggttcgga   36840
ctccacccgg cgctactcga cgctgccctg cacgccatgg aactccggga accccgcccg   36900
gccggcgacg gagtccggct tccgttcgcc tggaacggct tctccctgca cgcgtcgggt   36960
gccgaagcgg tacggctgcg cctcgcgccg acgggcgccg acgtctgtc ggtgaccctc   37020 gccgatgcca tcgtcgccc ggttgcctca gcccgctcgc tggccctgcg ggagctctcg   37080
tccgacctgc tgcgcccggc gtccgtctcg tacggggact cgctgttccg caccgcttgg   37140
atacccgccc tcgtcggccc ggaggcggag tccgggccgg ggcgaccgtc cgccggctgg   37200
gcggtgctgg gccccgatcc gctcggcgcg gccaacgccc tgaacctcac gggaacctcc   37260
tgctcctgct atccggacct ggcggcgctg atcgcgccg tcgacggcgg agccgcggtg   37320
cccgaggccg tactcgcgcc gtacgcggcg gagccagccc cggacgcggg atctcccgcg   37380
gacgccgtac gggcctcgac cggccgggcg ctgcaactgc tgcaatcctg gctgtccgag   37440
gaccggttgg agcgaagccg gctgatcgtg ctcacccggg gggcggtggc cgtcggtacg   37500
gacgaaggcg tcaccgacct ggtgagtgcg tcggtccggg gtctggtccg ttcggcgcag   37560
gccgagcacc ctggcaggtt ctccctggtc gacatcgacg accgggagga gtcctgggcc   37620
gtcctgagcg cggcggcggt atccggtgag ccgcaggtcg ccctgcgctg cggccagatg   37680
aaggtgcccc gcctcggctc cgtcgacgtt cccacgaccg gtatgcctga gatgcccgac   37740
gtttggggtg ttgacggtac cgtgttgatc actggcggga ccgtgtgct gggtgggctc   37800 gtcgcccgtc atctggtcgc cgggcatggg gtccgtcggt tgttgctctg cagcaggcgg   37860
ggccctgatg cgccgggtgc ggtggagctg gtggccgagc tcaccgctct gggtgcggat   37920
gtcaccgttg ccgcctgtga tgcggccgac cgggatgcgc tggccgcgct cttggacacc   37980
gttcccgcca cgcaccctct gactggtgtc gtgcataccg ctggtgtcat cgatgacgcc   38040
actgtcacca ccctcactcc cgagcgcatc gacgcgtcc tacgcccaa ggtcgacgcc   38100 gcgctcaacc tccatcagct gacggcgcat ctcggcttga cccgctttgt gctcttctct   38160
tcggccgccg ggctcttcgg cggcgcgggg cagggcaact acgcggcggc caacgccttc   38220
ctcgacgcac tggcccaaca ccgccgggcc aacggcctca atgcccagtc cctggcgtgg   38280
ggactgtggg cggaagccag cgggatgacc gggcacctgg acgcggccga cctcgcccgg   38340
atgggccgtt ccggcctcac cgcgatgccc accggggacg ggctggcgct gctcgacacc   38400
gcccagcggg tggacgaagc cacccctggtc acggccgcgc tggacacccg ggccctgcat   38460
gcccgggccg cagacggcac gctgccggcg ctgttccacg cactcgtgcc cgtaccgcgc   38520
cgatccgcga cctccccggc ggcccaggcc gcgggccgg atggactccg ccagcggttg   38580
tcggggctgg tcgtggggga cgccgagcg gcgctgctgg atttggtgtg tggtcatgtc   38640
gcgagggtgc tggggcacgc ggacccgagc agcattgagg agaacaaggg cttcaaggac   38700
accggcttcg actccttgag cgcggtggag ttccgcaacc ggctgcacgg tgcgaccggg   38760
ttgcggctgc cggccacgct ggtcttcgac tacccgacgc ctgcagctct caccgatcac   38820
ctctacgacg agcttctggg ttcccgcgag gacgccgtgc tcgcccgat caccagggcc   38880 gcgtacgacc cggtggactt cgactacccg acgcctgcag ctctcaccga tcacctctac   38940
gacgagcttc tgggttcccg cgaggacgcc gtgctcgccc cgatcaccag ggccgcgtac   39000
```

```
gacgagccga tcgcgatcgt ggggatggcc tgccgctatc cgggcggggt ggagtccccg   39060
gaggacctgt ggcagctggt cgccgacggc cgtgacgcca tctccgactt ccccgccgac   39120
cggggctgga acgtcgagag cctctaccac cccgaccccg accaccccgg caccagctac   39180
acccgtgccg gaggcttcct gcacgacgcg gcggacttcg acccggagtt cttcgggatc   39240
tcaccgcgtg aggcactggc caccgacccc cagcagcgac tgctgctgga aaccagctgg   39300
gaagccatgg aacgggcggg aatcaacccc tccaccctga agggcacccc caccggcgtc   39360
ttcctcggcg tcatgtacaa cgactacggc actgccatgc agcaggcggc agaggtcttc   39420
gagggccata tggccagcgg tagcgcgggg agtgtggcgt cgggccgggt ctcgtacacg   39480
ttcggtctgg agggaccggc cgtcacggtg ataccgcgt gttcgtcgtc gctggtggcg   39540
ttgcatctgg ccgcgcaggc gttgcgcaac ggtgagtgca ctctggctct ggcgggcggt   39600
gttgcggtga tgtccactcc tgccacgttt gtcgagttca gccggcagcg ggggctggca   39660
gctgatgggc ggtgcaaagc cttcgcggac gctgccgacg gcaccggctg gggcgaaggc   39720
gtcggtgtgc tgctggtgga gcgtttgtcg gacgcgcgcc gcaacgggca tccggtgctg   39780
gcggtcgttt cgggcagtgc tgtcaaccag gacggggcca gcaatggtct gacggcgccc   39840
aatggtcctt cgcagcaacg ggtgatccaa caggcgctgg ccaatgcggg gttggcgggg   39900
gcggatgtcg atgccgtgga ggcgcacggc acgggaaccc ggctgggcga cccgatcgag   39960
gcgcaagcgt tgatcgccac ctacggacag gcccggtcgg cggaccggcc gttgtggctg   40020
ggttcgctga gtccaacat cggtcacacc caggccgccg cgggcgtcgc cggcgtcatc   40080
aaaatggtgc aggcgatgca gcacgggact ctgccgccca ccctgcacat cgaccagccc   40140
acgggccagg tcgactgggc tacggtgca gtggagctgc tgaccgaggc cgtgccctgg   40200
ccggacagtg accggccccg ccgggtggct gtctcctcgt tcggtgtcag cggtaccaac   40260
gcccacgtca tcatcgaaca caccccacac accccacaca ccaccccgcac ctgcccaatc   40320 ctcccaatcc ccccaggccc cgcagactgt gcaggcccat cggccggtgc gtggctgctg   40380
tcggcgaaga cctcgcaggc cctggccgcg caggcccggc gcctgtcagc tcacttgcga   40440
gccaaccccg atctgcgttc ggctgatgtg gcgcattccc tgctcaccac gcggtctgtc   40500
cacgccgagc gcgccgtctt catcgccggt gaccgggatg aggctcttgc cgccctggac   40560
gcactggcca acggcacccc tgcccctcac ctcgttcagg gccttgccga tgtgagtggc   40620
aagacggtgt tcgtcttccc cggtcagggt tcgcagtggg tgggtatggc cgttgagctg   40680
ctggacggct cggaggtttt cgccgagcat atggccgcct cgccagggc cctggaaccg   40740 ttgtgggact ggtccctgga ggacgtccta cgccagacgg acggtacgtg gccactggaa   40800
cgcgtcgaag tggtccagcc cgtgctgtgg cggtcatgg tctcgctcgc gggactgtgg   40860
caggcacatg gcgttgagcc tgctgcggtg ctgggccact cccaaggtga gatcgctgcg   40920
gcttgcgtgg cgggagccct gagtctggaa gacgagcccg cgttgtcgc gcttcgcagc   40980 caagccatcg ccgaaaccct cgcaggacac ggcggaatgc tctcaatcgc cgcccccgcc   41040
accgacatcg caccccctgat cgcccgctgg aacgagcgga tctccatcgc cacgtcaac   41100 ggaccgcatt cggtggtggt cgcaggagac cctgacgcgc tcgaggcact ccgcggcgaa   41160
ctggagaccc gtggtctccg caatcgtcgc atcccggtcg actacgcctc acacacccct   41220
cacgtcgagg cgatccgtga acggctcctg gccgacctgg cagtgatcca gccacgtgcc   41280
gcgagcattc ccgtgctgtc caccgtcacc ggcgcatggc tcgacaccac cgtgatggac   41340
gccgagtact ggtaccgcaa cctacgtcag accgtggagt tcgaagcagc cacccgcact   41400
```

```
ctcctcgacc aggaccaccg ctacttcgtc gagatcagcc cgcaccccgt actcaccatc   41460
ggtctacagc agaccatcga ggaaaccacc gctccggccc ggaccctctc caccctccga   41520
cgcaacgaag gcaccctccg gcacctgttc acttccctcg cccaggccca cgcccacggc   41580
ctgaccatcg actggacccc cgccttcacc cacaccgagc cccgcaccac cccctgccc    41640 acctacccct tccaacacga acgctactgg ctggacacgg cggagccgcc tgttgggcag   41700
ggagccggca ccgacaccgt cgagagcggt ttttggacg ccgtcgaggg cgaggagtgg    41760
cagacgttgg ccgacacgct cggcgttacc gccgacgcgc cgttcgactc cgtgatgtcc   41820
gccctgtcgt cctggcggct ccgacagcgt gagcagtcct tggtggacgg ctggcgttac   41880
cggatcgagt ggaagccgtt ccgcgccccc gtgtcggcac cggattccgt gtcgggcacc   41940
tggtgggtgg tcgttcccgc ccatgccggc gacgcggacc gggagagggc gcaagccgtg   42000
cggggcacgc tggagtcctc cggccgtgcg cggacgatcc tggtcgcggt ggacccggcc   42060
gccgacgacc gggggtcgct cgaactgaaa ctcaggacg ccgcgaccga ggcgggtccg    42120
ccggccgggg tgctgtccct gctggccacc gacgaacgtc ccctcccgg gcatgatgtg     42180 gtgcccgggg ggctggcagc caacctggct ctcgtccagg cactgggcga cgcgcagatc   42240
gatgccccgc tctgggtggg cacctgcggg gcggtctccg ccggccggtc cgaccggctg   42300
gcgaaccccg gcaggccgc ggtctggggg ctcggacggg tggtcgccct ggagcacccg     42360
gaacgctggg gcggtctgat cgatctgccc gtggtcctcg acccgcgcgc tgtggaacgg   42420
ctggtgacag tacttgccgc gtcgggcgag gaggaccagc tcgccgtacg ggcgtcgggg   42480
gtcctcgtgc gcaggctcgt gcgggtaccc gcacgccaag tgccggacgg cgtgcagtgg   42540
aagcccgagg ggacggtcct ggtgaccggt gggaccggag cgctgggcgc ggaggtcgcg   42600
cggtggctgg ctcatggcgg cgccgaacac ctggtgctga ccagccgtcg cggcggctcg   42660
gcgcccggtg cggccgagct gacggacgag ctgcttgccc tcgggacgga agtgacactg   42720
gccgcctgtg acatggcaga ccgggacgcg gtcgccgcgc tgctcgccga gcacgcgccg   42780
agctcggtgg tgcacaccgc cggcgtcctc gacgacggtg tactggacag cctggaccgc   42840
gggcggctgg agtcggttct gctgccgaag gtggccgccg ctcggcacct gcacgagttg   42900
acgaaggacg cgaacgtgtc ggcattcgtg ttgttctcgt ccgccgcagg cgtgctcggc   42960
agcgcaggcc agggcaacta cgcagccgcc aacgcctacc tggacgccct ggccgaacag   43020
cgcagggccg atggactggt cgcccattcg atcgcctggg gcgcgtggga cggcggtggg   43080
ctggccgtgg gcgacagcgt ggtcgaggaa cggctgcgcc acgaggagt ggtccccatg     43140 cgcccgcagc tggcgatcac ggcgctccag cagacgttgg accgggcgga gaccgcggtg   43200
gtcatcgctg acgttgactg gccgcgctac ctcaccgcgg tcacaccgcg cccatggctg   43260
gcggacctgc cggaggtcgc ccaggccctt aacgccgacg acgcggctgg tgccccttgc   43320
ggcacagccg gcagggctc gtccccgctg gccgagcgtc tctccgggcg cccggcaccc   43380
gagcagcggc gactggtgct cgacctggtc cgtacgaacg tggcggcggt gctcggccac   43440
gccggtgcga agtcgatcga gtccggccgg gccttccgcg agctgggctt cgactctctg   43500
accgccgtcg agctgcgcaa caggctggct gcggccaccg ggctgcggct gcccaccacc   43560
ctggtgttcg actacccgag cgctgccgtg ctcgccgatc acctgtacgc gcaggcgatc   43620
ggttcggacg aggggcccgt ggcggatctg tcctccggcg ccgatccggc ggccggaccg   43680
gacgacgagc ccatcgccat cgtgtcgatg agctgccgtt tccccggcgg tgtctcctcc   43740
ccggaggagc tgtggcagct gctgctggcc ggtgaggaca cgattaccgg gttcccggac   43800
```

```
gaccgggact gggatgtcga cgccctgtac gacccggacc cggaccaccc ggggaccacg    43860
tattcccgca gcggcgcgtt cctgtccgac gcggccggtt tcgacgcgac gctgttcggg    43920
atctcgccgc gtgaggcgct ggccatggac ccgcagcagc ggctgctgct ggagacggca    43980
tgggaggtgt tcgagcgggc gggcatcgat cccacctcgg tacgtggcag ccgggccggc    44040
gttttcgtcg ggaccaacgg ccaggactac gcccgccatg tgccccagga accgatcggc    44100
gtggaggggt atctgctggc gggcaatgcg ccagcgtca tctccggccg tctgtcgtac    44160
acgtttggtc tggaggggcc ggccgtcacg gtggacaccg cgtgttcgtc ctcgctggtc    44220
gccctgcacc tcgccgtcca ggccttgcgc aacggcgaat gctccatagc cctggcggga    44280
ggcgtgtcgg tgatgtccac cccggcggcg ttcgtggaat tcagccggca gcggggggctg    44340 gcggctgacg ggcggtgcaa ggcgttcgcg gacgcggcgg acggcaccgg ctggggcgag    44400
ggggttggcg tgctcctcgt ggagcgtctg tccgacgcgc gccgcaacgg tcacccggtg    44460
ctggccgtcg tacgcggcag cgccgttaac caggacggcg ccagcaacgg cctcacggcg    44520
cccaacggac cctcgcagca acgcgtcatc cgccaggcac tcgttgacgc cgcgctgacc    44580
ggtagcgaca tcgacgccgt cgaagcccac ggcaccggga cccggctggg tgacccgatc    44640
gaggcgcagg ccctgatcgc cacctacggt caggaccgcc cggcgaaccg gcccctgtgg    44700
ctgggctcgg tcaaatccaa catcgcacac acgcaggccg ccgcgggcgt cgccggcgtc    44760
atcaagatgg tccaggcgat ccgccatggc gtacttccca agaccctgca cgtggaccgg    44820
ccgaccagcc acgtcgactg ggaggcaggc gcggtggagt tgctgaccga ggccatgccc    44880
tggccggaga ccgaccggcc gcgtcgggcc ggcatctctt ccttcggcgt cagcggcacc    44940
aacgcacaca ccatcgtgga gcaggcacct gcggcggaag acgagccgga aacggggcca    45000
cccgccgatg ctccgcccac ggtggtgccc tgggtgctct ccgctgccac cgaggacgcg    45060
ctgcgagagc aggccgcacg cctcgccacg tacctgacg agcgccccga ccaagcccg    45120 gccgacatcg ggtcctccct ggtcaccacg cgtgcagccc ttgaccaccg ggcggtggtg    45180
ctcggtgagg accgcgacgc tctgcgggcc gggctggttc tgctggcgaa cgggaagtcc    45240
ggtcccgctg tcgtccgtgg cctcgccagg cccggacaga aggtggcgtt cctgttcacc    45300
gggcagggca gccagcgact gggcatgggc agggagctcc atcgccacct gccggtgttc    45360
cggcagttct tcgacgaggc gtgcgccgcg ctcgacgcac acctgccggt accgatagcg    45420
gccgcgctgt tcgcgcaggc ggatgggggcg gatgcggggc tgatcgatgg gacggaattc    45480
gcgcagccgc cgttgttcgc gctggagtg gcgttgtgcc ggacgttgga gttctgcggt    45540
gtcaggccgg tttacgttgc cgggcattcg gtcggtgaga tcgcggcggc ccatgtggcg    45600
ggggtgttct cgctggagga tgcggctcgt ctggtggtgg cgcgcggaca gttgatgcag    45660
gcgttgccgg ccggtggtgc gatggtcgcg ctccaggtgt ccgaagacga cctcctgcca    45720
tccttgactc cttggctgga gcaggaccgg ctgggtatcg cggcggtcaa cggcgcagca    45780
tccacagtgg tgtcgggcga tgaggaggcg gtcctggcgg ttgccgagca ctggcaggcg    45840
cggggccgca aggttcgtcg gctcactgtc agccatgcct tccactcacc tcgtatggac    45900
ccgatgctcg accagttccg tgtggtcgtg gagggtatcc gtttcgcgga gccggccatc    45960
ccggtcgtct ccagcgtcac cggtcgtctt gccgagcccg ggcagttgac cactgcggac    46020
tactgggtgc gccacgtccg tcaaacggtc cgcttccacg acgccctcca gaccctccag    46080
accgagaatg tgaccgcgtt tctggagatc ggtcccgacg gcaactctc ggcaatggcc    46140 caggagacgc tcaccgccca ggtccatacc atccccaccc tccgaaagaa ccggtctgag    46200
```

```
accaccggct tgctcaccgc actggcgcaa ctccacacca ccggcaccgt ccccgactgg    46260
accgcttacc tcaaccacca ccccacaccc tccacacccg tgcccaccta ccccttccaa    46320
caccaccact actggatgca cggcggtacc caggccaccg atgtcagctc cgccggcctg    46380
tcaggagcca accaccccgct gctggggcc gcggtcccgc tggccggtgg ggagggccac    46440
ctgttcaccg gccggctgtc ggtgcggacc caccgctggc tggccgacca ccaggtcggc    46500
agcaccgtcg tgttgccggg cactgccttc gtcgaactgg cggtacgggc cggtgaccag    46560
gtcggctgcg gccacgtgga ggagctgacg ctggaagcgc cgctcgtgct gcccgagagc    46620
ggcgccgtac agatacagct ccggctgcgc cgggcggacg aatccggacg gcgtgaactc    46680
gtcgtgtacg ggcggctcgc gacggaccgt gaggacctgt ggtccgagga ggaatggacc    46740
cggcacgcca gcggtgtcgt cgtcgcagca gcgccctcgg ccccgagcc cgtccaactg    46800 accgtatggc ccccggaagg cgccaccgag ctcatcgtga aggacctcta cgaacggatc    46860
gccggcacca gcttcggcta cggtcccgcc ttccaagggc tgcgcgccgc ctggcggctg    46920
gacgacgcgg tgttcgcgga ggtcgtgctg ccacaggatc agtacgccgt cgcgagccgg    46980
ttcggactcc accccgcgct gctcgacgcc gccctccacg gggtcgcgct ggggcagccg    47040
gcggctgaca ccgccgagcc gcacaccgac cggatgccct tctcctggag cggcgttacc    47100
ctctacgccg ccggtgccac cgcactgcgg gtgcggttgg acatcgcttc gcccgaggac    47160
gtgtcgctgc tcgtcgccga tggctcgggg gctccggtgg ccgcggtgaa ctcgctgaag    47220
ctgcgcccgg tcgcggccga cctggccagt gccggtgtcg ccgactcgct gttccggctg    47280
gagtggtcga aggcggtcga cgacgagccc ggccgggccg aaccggggca atgggccctg    47340
atcggaacgc cgcccggtgc cgacttcacg ccgggcgagg acggcgtcat catcggaagc    47400
tacccggaca tggccgcgtt gaccgacgcg ctcgacaagg gagtcgccgt cccgcagcgg    47460
gtgttgttgt ccgccccgtc ggaggaggag caggaccagg cgcacgatct cgcgagcgcg    47520
gtggacaagg ccacgaacgc gctgctcgca gtgctccagc agtggctgtc cgacgaccgg    47580
ttcgactcct ccaggctggc tgtgctgacc cgtcacgcgg tgtccacggc tgggcaggag    47640
gacgtgacgg accttgccca cgcctcgtgg tggggactcg ttcgctcggc gcagtccgaa    47700
catcccgacc ggttcgtgct ggccgacacc gacggcaccc agatcagtca cgctgccctt    47760
ctgcccgctt tgctgtccgg tgagccgcag gtcgcgctgc gtgacggaac ccggtatgtg    47820
ccgcggctgg ccagggccgt tgcgtccggg gacgggccgg tggcgcgggt ggacccggcg    47880
gggacggtgt tggtgaccgg tggtacgggg actctggggt cttcgctggc caggcatttg    47940
gtggttgagc acggggtgcg gcggttgttg ctggtgagcc gtcggggcgg ggagtcggag    48000
ggcgcggcgc agttggtggc tgagctgacc gggctcgggg cggatgtcac ggtggcggcg    48060
tgtgatgtgg gggaccgggg ggccgtggcg gagttgctgg cggggattcc ggccggtcat    48120
ccgttgacgg cggtggtgca tgcctcgggg gtcactgatg acgcggtgat cgaggcgttg    48180
actgcggagc aggtcggccg ggtgctgcgg tcgaaggtcg atgggcggt caatctgcat    48240 gagttgacgc ggggggctgga tctgtcgcg tttgtgttgt tctcttcggc ggccggtgtg    48300
ttcgggaatc cggggcaggg caactacgcg gcggccaatg cctttctgga tgcgttggcg    48360
gtgcggcgcc gggcggaggg cctggctgcg cggtcgctgg cctggggtct gtgggaggag    48420
gccagcgcga tgacgagccg gctggccggg gccgatctgg tccggatggg ccgtgcgggc    48480
ctgcttcccc tcaccaccgg gcaagggctc gccctcttcg acgccgccca ccggacagac    48540
gagcccctgg tactgccgat gaggctggac accacggccc tgcgctccac caccggacag    48600
```

```
ccgccggcgc tgctgcgcaa cctggtccgg gtccaggctc gccggacggc gggcgcggcc   48660 cccgaccgg acgcggccgc caccttccag cagcagctca tcagcctgtc cgtcgcggag    48720
cgcgggcggg tgctgctgga gaccgtacgc ggccacgcgg ccgccgtgct cgggcactcc   48780
ggcccggaag ccgtcgatgt cgacaagggc ttcatggaag cgggcttcga ctccttgagc   48840
gcggtggagt tccggaaccg gctgacgtcc accaccgggc tgcggatgcc ggccaccgtc   48900
acgttcgact acccgagccc ggccgcgctg ccgagcacc tgctgacgcg gttggttccc    48960
gaggtcgcca tgcccgcgga ggagcagcac ccgcacaccc ggcccgaaga cgggccggtg   49020
gacaggcccg gagacgaaca ggggggcgcg atcgacgaca tggacgtcga cagcctcgta   49080
gaactcgccc tcggcgaatg attcctgatg ccgcatcgat ccgggaggac agcatgagca   49140
agccccatga aaagtagtc gcggcgctcc gggcgtcgct gaaggccaac gaacgcctgc    49200
gggagctcaa cgacgagctc gcctcggcgt cccgcgaacc ggtcgccatc gtcggcatgg   49260
cgtgccggta tccggcggg gtgacgtccc ccgaggaact gtgggacctg gtcgccggcg    49320
gcaccgacgc ggtgtcggag ttccccgccg accgtggctg gaacgtcgag gagctctacc   49380 accggaccc ggaccactcg ggcacctcct acgtgaggga gggaggcttc ctgcatgagg    49440
cggcggagtt cgatccggtg ttcttcggca tgtccccacg ggaggcgctg gccacggatc   49500
cgcaacagcg gctgctcctg gaaacggcat gggaggcctt cgagcggggc ggtatcgacc   49560
cactccggct ccggggcagc cggaccggcg tattcgtcgg cgtcatgtac aacgactacc   49620 tcaccgcct ccagccggcc cccgcggact cgaggggca gctcggcaac ggcagcgcgg     49680
gcagcgtcgc caccggccgg ctggcctaca cgttcgggct ggaggggccg gcggtcacgg   49740
tggacacggc gtgttcgtcc tcactggtcg ctctgcacct cgccgccag gcgctgcgca    49800 acggcgaatg caccatggcg ctggcaggcg gggtcgccgt gatggccacc ccggggccct   49860
tcaccgagtt cagccggcag cgcggtctcg cggtggacgg ccggtgcaag ccgttcgccg   49920
cggcggcgga cggcaccggc tgggcagagg gcgtcggcct gctgctggtc gagcggctct   49980
cggacgcccg cgcaacgga cacccggtgc tggctgtcat acgcggaacg gcggtgaacc    50040
aggacggtgc cagcagcggc ctgaccgtgc ccaatggccc ctcgcagcag cgcgtcatcc   50100
ggcaggcact ggcgaacgcg ggcctgtcgg ccgccgacgt cgacgcggtg gaggcacacg   50160
gcacgggcac cccgctgggg gaccgatcg aggcccaggc cctgatcgcc acctacgggc    50220
aggaccgccc ggccggccgg ccgttgtggc ttggttcgct gaagtccaac atcggccaca   50280
cccaggccgc cgcgggcgcc gccggagtca tgaagatggt ccaggccatg cgccacggga   50340
ccctcccgaa gagcctgcac atcgacgccc ccacgcccca ggtcgactgg gaggccgggg   50400
cggtggaact gctcaccgag gccgtgccgt ggcacgagac cgaccggccc cgcagggcgg   50460
gcgtgtcctc cttcggggtc agtggcacca acgcccacgt gatcatcgag gaggctcccc   50520
cgaccgaagc tcccgagggc gtgacggcgc gggcgccgct caacgccgag accttgccgt   50580
gggtggtctc gggccgtggc gtagaggccg tccggcgca ggccgggcag ctgcgctcct    50640
atctgtcgga gcgtcaggac tcgtcactgg agggcatcgg actctctctg gccaccacgc   50700
ggtcggcgtt ccagcaccgg gccgtcgtac tggcggccga ccacgatggc ttcatggccg   50760
ggctggacgc gctggccacc ggggaaccgg cgaagggctt ggtcgatggg gaggccgtat   50820
cgggcggcgg agtcgccctg gtcttccccg gccagggctc ccaatgggcc ggaatggcgc   50880
tcgaactgct ggactcctca tccgtgttca gagaccggat ggaagcctgc gcgcaggcgc   50940 tgagcccta catcgactgg tcactgaccg aggtcctgcg ctcctgcgaa ggcgagctgg    51000
```

```
aacgggtgga cgtggtccag cccgcgctgt gggccgtgat ggtctcgctg ccgaactat    51060 ggcgttcctt cggagtccgg cccgccgcgg tcctgggcca ctcgcagggc gagatagcgg    51120
cggcctgtgt ggccggcgcg ctcagcttgg aggacgccgc gctggtggtc gcgctgcgca    51180
gccaggccat cgcgaccgag ctggccggcc ggggcgcaat gctgtccgtc gccctgccga    51240
aggcacgggc ccaggactgg atgacggggc gggcggaacg gctgtcggtc gcggcggtca    51300
acgggcccgg atcagttgtg gtctccgggg acgtggacgc ggtggaggag ctgcgggcgg    51360
agctggccgc cgagggggtg cgggtccgca ggcttccggt cgactacgcc tcgcacagct    51420
cgcatgtgga gcggatccgc acacgtctgc tggcggcgct cgccccggtc tccccgcgcc    51480
cttccgagat caccctgtac tcgtccgtga ccggtggtcc catcgacacc acgaccatgg    51540
acgccgagta ctggtaccgg aacctgcggc agaccgtgga gttcgagcgg gcggtccgca    51600
cctcgatgtc cgacggctac cggttcttca tcgagtccag cccgcacccg gtgctgacga    51660
cgggcatcga ggagaccgcg gaggacgctg accggttcgc ggcggcggtc ggttcgctgc    51720
gccgttcgga cggtggcccc gacaggttcc tgactgcgct cgcggaggct cacgtgcgcg    51780
gcgtgccggt ggagtgggcg gtgatgttcg ccggccggcc cgtgagtcag cccgatctcc    51840
cgacgtactc cttccagcgg cagcggtatt ggctggcccc cgacacgtcc cccggcgacg    51900
acggcggcgg cgacgaacgc tcggagacgc ggttctggga ggctgtcgag cgccaggacc    51960
tcggcgaact gagcgagacc ctgcggatcg gtgacgcgga ccggcaggcg tcgttgggtg    52020
agttgttgcc ggccctgtgg acgtggcgtg agcagaaccg gtccgccgcc gtcctggaca    52080
gctggcggta ccgggtctca tggcggcccg tctccccggc gtccgatcca gccttgccgg    52140
gcacctggct gatcgtggtc ccggcgggga cggcggacca gcagtgggcc gaagcgctct    52200
cccgagccgc cgagggcctg ggagaccagg ctgtccgggt cgaactgggc agggccgaag    52260
ccggccggga ggagtacgcg gccaggctcg ccgaggcggc ggccggcggt ccggtggccg    52320
gcgtgctttc cctgctcgcc ctggccgagg agccggcgga cgccgacccg gtgtggcgcc    52380
cgtatgtcac cagcacgctg gcacttatgc aggcgctggg cgacgcgggg atcggcgcgc    52440
cgctgtggct ggccacccgg ggcgcggtct cgatcgggcg gtccgacaag ccggtcccgt    52500
cgacagccgc acaggcccag ctgtggggcc tgggccgggt catgggactc gaacaccccg    52560
aacggtgggg tgggctcgtt gatctgccgg agacggccga cgctcgtgcg acggcgcggc    52620
tggccggcat cctggccggc ggtctcggcc ccgaggacca gtgcgcggtg cggtcctccg    52680
gcgtgtacgt acggcgtctg gtccgcgcac cgctcgaccg gcgagcgcgg aggccgtcct    52740
ggcacacgtc ccgtacggcc ctggtcaccg gtggcaccgg cggtctcggg gcgcacgtcg    52800
cccgatggct ggcgagcacc ggcgcggaac acctggtgct caccagcagg gcggccggg    52860 acgccctgg gacggacgag ctgtgcgccg aactgtccgc cctcggggtg cgggtgagcg    52920
tggtggcctg cgatgtgtcc gacgggacc aactggccgc cacattggca cgattgaccg    52980
ccgacggcca caccgtccgt acggtggtac atgccgccgg ggtcagtacg ccgggcgcgc    53040
tggccgacct cgggccgcc gagttcgccg aggccgtcgc gggcaaggcg gcgggcgccg    53100
cgcacctcga cgaactgctc ggcgacgcgg agctggacgc cttcgtgctc ttctcatcca    53160
acgccggcgt gtgggcggc ggcggccagg gcgcctatgc cgccgccaac gcctacctgg    53220
acgcgctggc caaacggcgc cggtcccgcg gccgcgtcgc gacctccgtc gcatgggggg    53280
cttgggccgg cggcggcatg gccgcggagc gtaccgccga cgagcagctg cgccgccgag    53340
gggtgcgggc gatggaccca gcgatggcga tctccgcact ccaggaggcg ctggagcacg    53400
```

```
aggagacgtt tctcgcggtg gccgacatgg actgggaccg tttcctcccg tccttcacca   53460
tggcccggcc ccgcccccctc ctcgacgacc tgccggaggt ccagcggcag cggctgagcg   53520
cggccccgtc atgggccacc gcggagaccg acgcccggc actcgcgcag cagctcgccg    53580
gggtctttga accggagcgc gggcggcgcc tgctcgacct ggtgcgcaag cacgcggcgg   53640
cggtgctcgg ctacgccggc ccgaacgagg tcgaggcgga acgggccttc cgggagctgg   53700
gcttcgactc cctcaccgcg gtggagatgc gcaaccgact ccagccggcg accgggctga   53760
cgctgcccgc caccctggtc ttcgaccacc cgacgccccg cgctctggcc gcgcatctgc   53820
gggatgagct gttcggtgtg caggacgaca cgccggaacc ggcgcggggcg tcggcaccgg   53880 acgacgaccc gatcgccatc gtgtcgatgg gctgccgttt ccccggtggt gtctcctccc   53940
cggaggggct gtgggagctg ctgctgtccg gccgtgacgc catgtcgtcg ttcccagtgg   54000
accgaggctg ggacctggac agccttgccg gtgacggccc cggacagatc ggcggcggtt   54060
acacccttga gggcggcttc ctcgatgacg cggccggttt cgacgcggcg ctgttcggga   54120
tctcgccgcg tgaggcgctg gccatggacc cacagcagcg gctgctgctg gaggcttcgt   54180
ggaggccctt cgaacgagcg ggcatcccct cggccgacct cgggtccagc cggaccgggg   54240
tgttcatcgg cgcttcctca cagggatacg cccaggtcgc cgcggagtcc gcggaaggag   54300
tcgagggaca tgtggtgacc ggtgacgcgg ccagcgtcat gtccggccgt ctgtcgtaca   54360
cgttcggtct ggagggaccg gccgtcacgg tggataccgc gtgttcgtcg tcgctggtgg   54420
cgttgcacct ggctgcgcag gcgttgcgca acgtgagtg cactctggct ctggcgggcg   54480
gggtcgcggt gatggtgacc ccggcggcgt tgtcgagtt cagccggcag cggggggctgg   54540 cagctgatgg gcggtgcaaa gccttcgcgg acgctgccga cggcaccggc tggggcgaag   54600
gcgtcggtgt gctgctggtg gagcgttgt cggacgcgcg ccgcaacggg catccggtgc   54660
tggcggtcgt ttcgggcagt gctgtcaacc aggacggggc cagcaatggt ctgacggcgc   54720
ccaatggtcc ttcgcagcaa cgggtgatcc aacaggcgct ggccaatgcg gggttggcgg   54780
gggcggatgt cgatgccgtg gaggcgcacg gcacgggaac ccggctgggc gaccgatcg    54840 aggcgcaggc gttgatcgcc acctacgac aggcccggtc ggcggaccgg ccgttgtggc    54900
tgggttcgct gaagtccaac atcggccaca cccaggccgc cgcgggcgtc gccggcgtca   54960
tcaagatgat ccaggccatg ggtcacggga cgctgccccg tacgctgcat gtcgaccggc   55020
cctcgtccca ggtggattgg gaagccggcg cggtggagct gctgaccgaa gccatgccct   55080
ggcccgaggc cgaccggccc cgccgggcag cagtctcctc gttcggtgtc agtggtacga   55140
acgcgcacgt catcatcgaa cacgccccgc aggtcactcc cgcctcccag gccccggaac   55200
cggtgaagtc cccggatgct gtggaggctg atcgaccggt cccgtggctg ctgtcggcgg   55260
gcagtgacgc ggcgttgggc gaggtggccg aacggctggc cgcctacgcc gaatcgcacc   55320
cggaggtcag tgcggccgag gtcgcgttct cgctcgcgac cacccggtcc ctgttgccgt   55380
gccgcgccgc cgtcgttggc gcggaccgcg acgagctggt ccagcgcatc cggtccgtgg   55440 gcggggcac caccgccccg ggcgtcttct cgggacggc gagttcggag tgcaccacgg    55500
cgttcctgtt ctccgggcag ggcagccagc gactgggcat ggggcatgag ctgtacgccg   55560
cgcacccgga ttcgccgag gcgctcgacg aggtctgcgg tcacctcgac gtgttcgggg    55620
accggccgtt gaaggaggtg ctgttcgcgc aggcggatgg ggcggatgcg gggctgatcg   55680
acggggcggg gttcgcgcag ccggcgttgt tcgcactgga ggtcgcgctg taccggaccc   55740
tggaagcatg gggcatcacc cccgactatc tggccgggca ctcccttggt gagatcgcgg   55800
```

```
cggctcatgt cgccggggtg ttcagcctgg aggacgccgc tcgcctggtc acggcgcggg    55860
ggcagctcat gcaggccctg cccggcgtgt gcgcgatggt ggccgtccag gcctccgagg    55920
acgagatcct ggccatctcg gcgccgtggc tggaggggga cggggtcggc atcgccgccg    55980
tcaacggtcc cgcctcggtc gtcgtctccg ggacgaggcc agccgtcctg cgatcgccg     56040 ggcactggcg ggcacagggc cgcaagaccc gtcggctcag cgtcagccac gccttccact    56100
caccccacat ggatcccatg ctcgacgggt tccgccgggt cgtcgacggc atgcaccttg    56160
tcgagccggt cattccggtc atctccaacc tcaccggtcg cctcgccgat cccgggcagc    56220
tgaccagcgc cgactactgg gtccggcacg tccgccaagc cgtccggttc cacgacggcc    56280
tacagaccct gcacgatcag ggcgtcacca cctacctgga aatcggccct gacgcccagc    56340
tcacggccat ggctcaggag gccctgagcc cccagtccca caccgtctcc accctgcgca    56400
ggaaccagcc cgaaaccacc agtctgctca ccacgctcgc gcgactccac accaccggta    56460 ccaccccga ctggatcacc tacctcaacc accgaccctc atccccgaca ccgctgccca     56520 cctaccccctt ccaacaccac cgctactggc cgcgcggcga tgctcaggcc gccgatgtca   56580
gctccgccgg cctgtccggt gcgaaccatc cactgctggg agccgcggtc ccgctggccg    56640
acggcgacgg ccatctgttc accgggcggc tgtcggcacg gacgcaccgc tggctggccg    56700
accaccaggt cggcggcaac gtcgtactgc cgggcaccgc cttcgtggaa ctggcggtac    56760
gggctggtga ccaggtcggc tgcagccagg ttgaagaact gacgctggaa gcgccgctgg    56820
tgctgcccga gagcggcgcg gtccaggtac agctccggct gggccgggcg gacgagtccg    56880
gccgacgtga cctcaccgtc tacgggcgac tggcggggggg cggcgaggac ctgtggctcg    56940
aggaggagtg gacccggcac gccagcgggg tcctctccag cgcctcggcc cccgaacccg    57000
tcgcactgac cgtatggccg ccgtccgccg ccgaggccgt gccggtggag ggcttctaca    57060
ccggtctggc cgagagcggg tacggctacg gccccgcctt ccagggcctg cgggccgcct    57120
ggcgtcaggg cgacacggtc ttcgccgagg tccaactccc tgaggtggta cgggaggagg    57180
ccgcctccta caccatccac ccggctctcc tggatgccgc cctccaagcc gtcggtttcg    57240
tcacggacgg gagcgacaac cccgtggtac ggatgccgtt cgcctggtcc ggcgtgtcca    57300
tgtacgcgtc cggcgcctcc gagctgcggg tgcggctcgc ccggacagga ccggagacgg    57360
tcaccttcgc cgtcaccgac cccaccggcc ggcccgtggc ctcggtcggc tgctcgtca     57420 tgcgcccggt cgccaccgga gtaccgcgcc tgacacgcaa cgggctccac gaggtggtct    57480
gggagcaact cctcgatgcg ccggccaccc ccgcgaccga gtgcgccgtc atcggggacg    57540
cggacgcggc ggcgctgctg ggcgcggagg cgcacccgga cctggcgtcg ttgggggaag    57600
cggtgccccc gctggtggtg gccgtggccg gcggcgacgg tacacgggcg gcactggagc    57660
gcgcccttgg ctgggtgcag ggatggatgg cggaggagcg gttcgccggt tcccggctcg    57720
ccgtcgtcac ccgtggtgcg gtgcggtcg gtgcgggcga ggtgctggcg gacgctgcgg    57780
gtgccgccgt gaccggcctg gtgaagtcgg cggagtcgga gaacccgggc cgcttcctgc    57840
tggtggatgt ggacggcacc accgagtcct ggcgggcgct gccgactctc ggcggcggc     57900 acgagccgca gatcgcgctc cgcgacgggc aggcgtacgt ccccgcctg gtgcgtgccg     57960 gtgaggacgg cggctcgctg ctgccccgg cggggcgga cgcctggcgc ctggagacag       58020
gcgaggccgg cagcctggac gggctccggc tcgcccctgc cgaggacgcg caggcggcgc    58080
tgctgccggg gcaggtgcgg atcgcggtcc gtgccgcagg cctcaacttc cgtgacgtcc    58140
tcggtgcgct cggcatgtac cccggcggac tcgacctcct cggcagcgag atcgccggcg    58200
```

```
aggtgctgga gaccggcgat ggggtgaccg gcctcgcggt gggcgaccgg gtcatgggcc    58260
tggtcgccgg cggcttcggt ccgatggccg tcgccgacag ctggcgggtc gtacggatac    58320
cgtccggctg gaccttcacc cgcgcggccg gtgttccggt cgccttcctc accgccctgt    58380
acggactgcg tgaactgggt gggctggcgg cgggccagcg ggtgcttgtg cacgcggccg    58440
ccggtggcgt gggtacggcg gcggtgcaac tcgcccggct attgggggct gaggtgtacg    58500
ccacggccag cgcccccaag caggagtatg tggcggatct gggcgtggac cgcgcccgta    58560
tcgcctcctc ccgcaccctg gacttcgctt ccagcttccc tgaggtcgac gtcgtgctga    58620
actccctggc cggggagtac gtggacgcct cgctggggtt gttgcgcgag ggcggccggt    58680
tcgtggagat gggcaagacc gatgttcggg atgctgccgc gtacgacggt gtgacgtacc    58740
ggacgttcga cctggggcag gccggtccgg agctgatcgc ccgaatgctg ggtgagttgg    58800
tggagtggtt cgaggccggg gaactcactc cggtccgcac agccgcctgg gatgtccggc    58860
gcgcggtggg cgcgttccgt tggatgagcc aggcccggca cacaggcaag atcgtcctga    58920
cggtgccgcg cgacctggac gccgacggca cggtcctgat caccggcggc accggcacgc    58980
tgggcggtct gctcgcccgg cacctggtca ccgaacacgg cgtacgacac ctgctgctgg    59040
tctcccgcac gggagaacgg gccgctctcc gtcgtgaact ggaggagctg ggcgccgagg    59100
tacggatcgc ggcctgcgac atggctgacc gcgcggcgt ggccgaactc ctcgacggca    59160
tcccgtcgga gcaccgctg accggtgtgt tccacgcggc gggtgtcctg gacgacggcg    59220
tggtcaccgg cctcgactcc gctcggctgg cacgggtgct ggctccgaag gtggacggcg    59280
ccctccacct gcacgaactg acggcggagc tggacctctc ggcgttcgtc ctgttctcct    59340
ctatgtcggg tctcctcggc gcctccggcc aggccgggta cgcggcggcg aacatgttcc    59400
tcgacgcgct cgcccagcag cggcgtgccc agggcctgcc cgcgctgtcg ctggcgtggg    59460
gtttgtggga gaccgcgagc gcgatgaccg cgcacctgag cgacaccgac ctgcgccgca    59520
tgggcgggat cggcatgctc gggctcaccc gcaacgaggg catggaactc ctcgacgcgg    59580
cctggcagag cggcgaggcg ctgctggtcc cggtccgctg gaccaccgg gtgctgcggg    59640 agcgggcctc ctcgggcgcc cggtgccct ccctgctgcg gaggctggtg cgggcgccga    59700
ggcgccgtac ggtgccggag agcgccaagg gcgcgggcgg cgggctgcgg gagcggctgg    59760
cgacgctgcc ggaggcggag cgccggggca tgctcatcga gctggtggcg gggcacgtgg    59820
ccgcggtgct gggccatgcg ggcaccgatg cggtgtcggt ggaccgcccg ttcaaggagc    59880
tcggcttcga ctcgctgacc tccgtggagt tccgcaaccg gctgaacgaa gcgaccgggc    59940
tgcggctgcc ttcgaccctg gtgttcgacc accccacacc taccacgctg gcggcccggc    60000
tcgacgccct gctgccgggg gcagagacgg cgacaacggt tgctgccccc acctcgcgc    60060 acgaggaact cgaccgactg gcaacggtgc tgctgtcacc cgcgttgaac atggcggatc    60120
gggacggcct cgccgcccgg ctccgagccc tggcttccca gcttggcgag ccgactggtc    60180
cggccgatgg cagcaccgtc gccgaccgga tccagtcggc caccgatgac gagctcttcg    60240
agttgctcga cgacaggttc gagaactcat gagccaacac gacgatgctt ctgacgcgct    60300
gaggacgggc gatgttccga tgacacagtt tccgacgaac gaggacaagc tccgcgacta    60360
tctgaagcgg gcggtcaccg acctgcacca caccgtgag cagctggccg cggccgagcc    60420
caagaaccgg gaaccgctgg cgatcgtgtc gatgagctgt cgcttccctg gcggagtcag    60480
gtcgcccgaa gccttgtggc agctggtgcg tgccggtgaa gacgtgatct cgtcgtttcc    60540
caccgaccgt ggatgggacc tcgacggcct ctacaacccg gatccgggga acagtggcac    60600
```

```
cacctacgtg cgagagggcg ggttcctgtc cgacgcgacg gagttcgacc ccgccgtgtt   60660
cgggatctcc ccgcgtgagg cgctgggaat ggacccgcag cagcggctga tgctggagac   60720
ctcgtgggag gccttcgagc gggccggcat cggtccggca tcggcacgcg gcagccggac   60780
cggtgtgttc atcggcgcct ccgcccaggg ctacagcttg ctgttccaga actcgcggga   60840
ggaggccgag ggcctcctgg ccaccggtga ctcggccagc gtgatctccg gccgggtctc   60900
ctacaccttc ggcctcgaag gacctgcggt cacactcgac accgcgtgct cctcgtccct   60960
ggtcgctctt cacctggccg tgcgctcggt tcggcagggc gagtgctcca tggcgttggt   61020
gggcggcgtc tcggtgatgt gcacgccggc gatcttcatc gagttcagcc gccagcgagg   61080
tctcgcggcg gacggccggt gcaagccgtt cgccgcggcg gcggacggca ccagctgggg   61140
ggaaggcgcc ggagtcgtcc tcatcgagcg gctggaggac gcccgacgca acgggcaccc   61200
ggtgctggcc gtcatccgcg gcagtgccat caaccaggac ggtgccagca acggcctgac   61260
tgccccgcac gggccgtcgc agcggcggct gatccagcag gcgctggcgg acgcccagct   61320
gtcgcccggc cagatcgaca tggtcgaggc acacggcacc ggcacctcgc tgggggatcc   61380
gatcgaggcg caggcactgc tggaaacgta cggtgccaac cgccccgcgg accgccgct   61440
ctggctcggt tccgtcaagt ccaacatcgg acacacccag gcggcggccg gtctcgcgtc   61500
cgtcatcaag accgtacagg cgctgcgaca cgcccacctg gccaggacac tgcacgtcga   61560
ccggccgacc ccgcgcgtgg actggtcgtc gggtggggtg gaactgctgg ccgacgacca   61620
gccgtggccc gagacggggc agccccgccg agccgccgtg tcctcgttcg gggtcagcgg   61680
caccaacgcg cacgtcgtcc tcgaacaggc gcccgcctcg gagaacccgc ccctccgccg   61740
tccgggaggg gaccgcgtcg cggcgcgccg ggtactcccg ctggtgatct ccggcaagac   61800
gccggaagcc ctgcgggctc aggcggggaa cctggtgtcc catgtgcgcg agcacccgga   61860
cctccggctg gaggacctcg ggtactcgct ggccaccacc aggtcggccc tcggacaccg   61920
ggccgtcgtc gtggcggaca cccccgacgg attcctccgt ggctgcgagg cggtggagcg   61980
cggcgagacc ccggcgtcgg tggaccgggg cgtggtccgg gggcgcggca cgaccgcgtt   62040
cctgttcacg gggcagggcg cccagcgggt cggcatgggc cggcagctct acgcggcgat   62100
ccccgcgttc gcgcggttcc tcgacgaggc ctgctcccat ctcgaccgct ttacgaagca   62160
gccccctgagg gacgtgctgt tcgctgccga gggcagcgcc gaggcagcgc tcctggaccg   62220
taccggattc gcccagccgg ccctgttcgc cctggaggtg gcgctgttcc gcaccctgga   62280
gtcctggggt gtgaccccgg actacctcgc cggacactcc atcggtgagc tcgctgccgc   62340
ccatgtggcc ggtgtgctct cgctgggaga cgccacccgg ctggtgaccg cgcgtggcaa   62400
cctcatggaa cagctccccg cgggggcgg catgctcgcc ctgcaagctt ccgaagccgg   62460
ggtgctcccg ctcctcgacg gcgccgatgg cctggtgtcc gtcgccgccg tcaacagccc   62520
ccgctccacc gtggttgccg gagacagcga cgccctcgcc ccctcgccg gccaggcccg   62580
ctctcagggc atcaaggccc gccacctcac tgtcagccac gccttccact cccgctgat   62640
ggacccccgtc ctcgacgcct accgcgagac cgccgagcag ctctcctacc accgccgcg   62700
tatcccgatc atctcgaccg tcaccggccg gtccgtcacc accgagatgt ccgaacccgg   62760
ctactgggtc cggcacgccc gcgaggccgt ccggttcacc gatgccgtgg ccacgctccg   62820
gcagcacggc accaccgcct acctggaact cggccccgac gccgtcctca ctgccatgac   62880
ccgcgaacac ctggcgggcg acggcacctc gggcaaggag tccaccttcg cggcggtgat   62940
gcgcaggaac cggccggagc cggaggtcct gaccagcgcc gtgtcccagc tgttcgcccg   63000
```

-continued

```
gggcacccgc gtcgactggc gggccgtgtt cgcggatgtg gatgggcagg tcgtccagct    63060
gccgacctac gccttccagc gcagccggta ctggccgcag gcatcactga cccggccggc    63120
cgggggcgcc tccgcgacgt cgctgttcca cctgcgctgg gtgccggtga cggcccagga    63180
cacggcgccg gcggacgact gggcgttgct cggcggggcc gacgcgctgc ccggccaggg    63240
cttcgccgac ctggcgtccc tgggggagac gatcgacggc ggatcggccg cacccgcac     63300
ggtgtgtgtg ccgttgctgc ctccggccga cggcgcccag gattccgccg ccacgcacga    63360
cgccgcccac cgggcgctgg cgctggctca ggcttggctc gccgacgatc gcttcacctc    63420
ctcccggctg gtgttcctca cccgtggtgc ggtggccgtg accgacgagg aatacccccga   63480
ggactccgtc gacgccttcg catacgcctc cgtgtgggt ctgctgcgtt cggcccagac     63540
ggagaacccg ggccggttcg gcctggtgga cctcgacccc gacgccgacc ggacgcggc     63600
cgggcagcgg tgcccggtcc cggccgccgc cctggacggc gacgaaccgc agctggcgat    63660
gcgccgaggc gtggtccacg ctccccggct cacccgggtc acggccgcgc caaggaccc     63720
ggaccgggca cccgccgggt tcgaccacgg cggaaccgtg ctgatcacgg cgccaccgg     63780
tggactcgga ccgctgctgg cccgccatct ggtcgtcgag cacggcgtac gccacctgct    63840
gctgacgagc cgtcgcggcg cggcggcgag cggcgcccag gcactgctgg acgagctcgc    63900
cgacctgggt gccgaggcca ccgtggtctc ctgcgacctg gctgaccggg aggcggtggc    63960
cggcctgctg gcccaggtgc cgcccgcgcg tccgctgacc gcggtggtgc acgccgcggg    64020
cgtcctggac gacggcgtga tcccgtccct gagcccggaa cgcgtcgacg ggtactgcg     64080
gccgaaggcg gacggggccc tgcacctgca tgagctgacc aaggatctgg acctggccca    64140
cttcatcctg ttctcctcga ccgccggtgt cctcggcagt gccggccagg caactacgc     64200
ggccgcgaac acgttcctgg acgcgctggc ccagcaccgg cgggcagcag ggctggccgc    64260
tgtctcgctc gcctggggaa cgtgggaacc gagcggcggc atgaccggcg ggctgacgcg    64320
cgcagacctg gagcgcatga cgaagggagg catgccaccg ttgtccccc gggacgggct     64380
ggcgctcttc gatgccgcca tcgcttcggg gcgggccctg gtggtgccgg ccgtgctcga    64440
tctcgacctg ctgcgttccc ggatcgggac gaacgtaccg cgcgctgctgc gcggcctcat   64500
cgagccccgg cccgtggagc cgtctgcccc aggggaggca gccgaggcac tcgccctgcg    64560
gatggcctcc tgctccgccg cggagcgcac gggcgtactc ctggacctgg tccgcgccga    64620
cgcggccacg gtgctgggac atgacggtcc gcacgccatc gacccggagc gtggactgct    64680
cgaagcgggc ttcgactccc tgacgacgct ggagctgcgc aaccggctgg ccgaggccac    64740
cggactggcc gtcccggccg gttacctcta cgagtacccc accccgaacc tgcttgccga    64800
acacctggcg gccgcgttgg ccgagtcgcc gcagtccggc gcggcgaccg gagccgacgg    64860
accggccgag ccgctgagcg tgctcttcca gcaggcgtat gacctcggca aggtcaccga    64920
gggcatgacc ctgctcagga gcgcgtccgc gctccgcccg acctacgaca ccccttcgga    64980
cctcagtgaa ctgccgcagc ccactcgcct ggcccgtggc cccgaacgtg ccacgctgct    65040
gtgcttctcc gccatcgtgg cactcgcggg ctcgcaccag tactcgcgct tcgcctcgtc    65100
cttccgcgag gaacgggacg tctcggtcct ctacgcgccg gggttcttcg ccggggagct    65160
cctgccgacc agcctcgaaa cggtcatcga cacccaggtg gaaaccgtgc ggcagcaggc    65220
cgcggacggt ccggtggtgc tcgtcggcgc gtcttccggc ggctggctcg cccatgccgc    65280
cgccgcccgg ctgaggcgc tgggaacacc accggcagcc gtggtcctgc tggacaccta    65340
cctgccggac gaccagttcc tcgcccgtga ccaggaccgt ttcatcggcg gagtcttcga    65400
```

-continued

```
ccggcaggac cggttctcca tccgggagga cgtcagcctg tccgcgatgg gctggtatct   65460
gcacctgttc gacggctgga agcccaccgc gatctccgtc ccggaactgc tggtccgggc   65520
gagtgagccg ctgcccagcc cttccggccg cccgccgagg ccgccgact  ggcggacctc   65580
atggcatgtg gcacagcaca gcgtcgaggt gcccggcgat cacttcacga tgctggagga   65640
attcaacgac gccacggccg acgccgtccg acgctggctt ctcgacattg actgaaaggc   65700
ctgtccatgg atctggaaac ccaacttctc tccccggcat acctacggaa cccgcacccg   65760
ctcaacgccg cattgcgttc cgccgaccct gttcaacgtg ccgtggcttc gggggggcctg   65820
tccgtctggg tggtgacccg ctacgaggac gtgcgcgcgc tgctcgccga ttccaggctg   65880
ggcaaaggcg tcacgcagct ccgcgaggcg gtactgctca acgcgggtga cgacgagcgg   65940
atcagccagt tcaccgactc cctcaccgag cacatgctca acagcgaccc acccgaccac   66000
acccggctgc gccgcctggt cggcaaggcg ttcaccgccg gccgcataga acagcttcgc   66060
cccaggatca cggagatcgt cgacaatcta ctggaccggc tgagtcccgg tcaggaggtc   66120
gacctcgtcc ctgtcttcgc cctgcccatg ccgaccactg tgatctgcga actgctcggc   66180
gtgccgtccg tcgaccggtc gtcgttcagc cactggtcca atgtgctggt gtcgaccgcg   66240
gaagtcggcg aactggccga ggccggcgga gcgatggtcg cctatctggc acagctcatc   66300
gcggacaaac gcgccaaccc ctgtgacgac ctgctcacca agctggtgca agccaccgac   66360
aacggcgacc agctctccga gacggaactc gtggcgacgg ccttcctgct gctgtccgcc   66420
gggcacgaga ccacggtgaa cctcattgcc gccggtacgc tcactctgct ccagaacccg   66480
gaccagctcg cccggttgcg ctccgacctc acgctgctgc ccggcgcgat cgaggagctc   66540
atacggtacg acgggcccgg cggcatggtg ctccggcaca ccctggagcc ggtcgaggtc   66600
ggcggtgtga ccatcccggc ccagcaggtc gtcctgctct cgctgtcctc ggcgggccgc   66660
gactccaccc ggttcagcga cgccgaccgg ctcgacatcg gccgtcccat cgggggcagc   66720
gtggggttcg ggcacggtat ccaccactgc atcggcgccc cgctcgccag gctggagggc   66780
gagatcgcgt tccgggccct gctcacccgc ttccccgacc tgcggctcgc ggtcccgccg   66840
gaggagctga actggcgcga cagtgtcttc atccgcggcc cggaatcgct gcccgtggtg   66900
ctgtgacgcg catggggaga ggggaccgac ccgtcagtgt cggtcccctc tccccatacc   66960
cggcggctac gccgacatga ggatccgacg ggtgctttcg actacctcgg cgatctgccg   67020
atgcccgaag cagctgggcg aatacgggac ttccagggcc agccggccct ccacggtgat   67080
cgccgacacc accagcggcc cccgcccctg ctccggcgac cagttctccg gtaccgggat   67140
ccaccgcaaa ccgcccagct cgagcccggg gggtgccacc aggtccgcga cacggcccag   67200
gttggtgagc acgagactgg ccgccagcag agcgggattc tcaaagaagt ggcgcaccgc   67260
gaggatctcg cgttcgggat cgccccgctc gacacccgcg cgaagccggt cgtagaccag   67320
ccggccgagc gtgcgcacat ccgccgcgcg ggagacttcg acaatgtcgt agaacgacgc   67380
ggcggccagc accagggtct cctctgccag cggtggagtg accggtgcc  ggaagtcgac   67440
gggggacgcc aaggccagcg aaaggggtgc gtcggtcgct tcgagggcgc ggcgcaccgc   67500
gatgagcagt gccgccgcca ccaggccctg taccgagatc ccggcggccc gggcggatcc   67560
ggcgagccgc gtcgtctcgt cggaagtgag ccggagggtc cttacgtgta tctcgccctg   67620
ctccggcgct tccacgcccg gtcccccag  ataggggcagc agcacggggg gaaggcgctt   67680
cgcctgctcg gccgcgcggg ccgcgtaggc gaggacatcc gcctccgggt gatggccgag   67740
acgggtctcg atgggcgccg ggtagctgtc ggccacgtgt gccgaggacg ccatcggccc   67800
```

```
ttcgcccagc gcggcgtacg tccgccacac cgccgacagc aaggcgacca cgctgcggcc   67860
gtcgcagatc cggtgatcga catggagtat gaaggtgtcc tccgccgcgc cgcgcagcag   67920
ggtggcgcgg accagcgggc cgcagcggtc cagccggctc cgcatctccc ggtcgaggtc   67980
ccaggagccg gcccggcgga cgacgagttc gggcggcccg tcgtccagcg ggtgcagcac   68040
caactcggta ccgtccggcg atatccggct ccgcaaggag gggtgcgcgg ccacggacga   68100
ggcgaaggcc cgttggagaa gctgttcgtt ggtatcgccc cgtaccgtgc acagcgccat   68160
gattctcgtg agacctggcc cggagagcat gagctctccc gtggacagct cacgtcgggt   68220
attcggttgc atgtttgctt gcgccttttcc gttgcccggg gccgagctac tggggcgagc   68280
cgacgatgga ttcccgttcc cgggaggtga gaggggccc ggtgagcggc ggccgggtag   68340
ggccgagaag ggtctcgaag acgatccggg gcgtcatcag ccgggtcagc ggggccgaca   68400
gggtgaacgt gtccgacacc gcggcggcca cccgggggcg gtcggctgcg gtcttggtca   68460
cccggttgac atagcgccgc tgcatccgcg cggccagccc cggccgccgg ccactcacat   68520
tcgggtagaa gatgtcctgt cctgtggcca tcgcccacgc attgttgacg gcgcccgcga   68580
cggcggcctg tgtggcgcgg ctcgtcccgg ccaccaaccc gtcgctccgc aggacgtcgc   68640
gcagcgccga agcgctcatg gcggccaccg acatgccgtg cccgtacacc gggttcaggg   68700
cggccgcggc gtcgccgagc accacgaagc ccttcggcca gtcggccagt tcctcgtagt   68760
agcggcggcg gttgaccgtg gtgcgactgc tgtggatcgg cccgatcggc tcggcgttcg   68820
cgatgaggtc cccgatcacc gaatgccgca gtctccgggc gaacgccacg aagccttccg   68880
gatcacgcgg cggctcgcac ccacgggtcc cggtcagcgt gacgatccac tgtccgtcct   68940
cgatcggcag cagcaccgcg ccctggcccg gctggtcgtc ctccgggtcc ggcagcacgt   69000
tcacgatggg aaagccgctc tccgcccggg ccggcgcgcg gtaccggcgg gtggcgtagg   69060
agagcccgat gtcgatcttc acctcgcgca cggcgggcag accgagcgcc tggagccagg   69120
tgttcgcgcc ggatccacgg ccggtggcgt ccaccacgaa gtccgcgtcc agccggagcg   69180
attccccgga cgcccggtcc tgggcctgga ccccggtcac ccgggtggca tcgccgtcga   69240
gccctggac gtcaacaccg ctccgcaggg tgatgcggtc gtcttccagg acgaggcgcc   69300
gcagcgtcca gtccagcagc ggacgaccac aggtgaccat gaactgggcg ccgggcatcc   69360
ttcgggccca ccctgccgt gagcaggaga cgagcccgct gggtacctcg gtccggtgcg   69420
caccggcggc cagcaggcgg tggaggctcc cgggcaccag cgagtcgatg gtccgtgcgc   69480
cgttcgacat caggatgtgc gagtggaggg tctgtgggt gcccttcctg acttccgggc   69540
cgtccggtac ctggtcccgg tccagcatca ctacctcgtc cacgaacttc gcgagcacgg   69600
atgccgtaag ggcaccagcc agaccgctgc cgagaactat tgcgcgattc accatatcca   69660
tcgtcctttc aacgtcgcag aacacgtaat taatacgccg aattcaagcc gtgatttctc   69720
cgacttagtg cgacgggat cgcgcctcaa tactcctggg ccccctcggt ctccccgtgc   69780
gtgcagagtg gatgggttta tatccgttgc cgttcgatga ggtcggcaag gaaaacaatg   69840
tggtttgcgc gacgctaccg gtgtttccct ctccggggtg atcgccttcg tcgtgccgtt   69900
gattggaggt tcccctgaag attcttttcg gtaatcgcta tggcgccgcg caggcctgcg   69960
gccggcatgt tcatgccgcc ggggcggccg tgcacccagg tcctgtccgg gtctcctcat   70020
gccgtctggg gcagggccag ctggagctcg agaggcaact cctcccggcg ggtgatgtcg   70080
agcttgcggt acacgcgggt caggtgctgc tccaccgtgc tcatcgtgat gaacaacttg   70140
gccgagattt cacggttggt cagacccttg gccgccagtg cggcaactcg gcgctcggac   70200
```

```
tcgctcagat tggcgccgac gtccgctccg cggaattcga gcgccgagga catgccaccc    70260 tcggggagg gacgatggct ggagccgatc ggctcggacg ggacctccgc actgcaatcg      70320
cctgcgatct gccgcgccat atggcggatg gcgtcggcac gcctgcccac gcccagttcc    70380
tcgtaggtgg acgccaggtc agcgaggacc ttggccagtt gcagccggtc cccggtctcc    70440
tgtaaccgct cggcagcctg gatgagcagt cgtgtccgtt cgcccggctc ggcgaacatc    70500
gcgcggacgc gcagcactgc accgtccgtc gccgcgccta tgccgccgt cgcgctgtcg     70560 tactcggcca gcatccgttc cgcctgctcc cgatcgttga gccggagcca ggcatgggcg    70620
gagtccacct gccagggcag ttctgccgac ggagccagac cccagcgctc cgcgagccgg    70680
ccgatgctga ggaagtcgga gagcgcgagg tggggccggt tgacggccag ggcgtagtgg    70740
ccgcgggcac ggagatacgg gagcccgtag acactccgga acagcgcctc gggaaccggg    70800
cggtccagca gatgagcgac gtccttgtaa cgtcccatct cggtgtagac agtcatcagg    70860
acggtcagcg ggccgccgtg cagccaggtg ctggacggtt cggcgaggcc gtccagggac    70920
atccatgcga acgtctcggc ctcggtcagc ttgccctgtc tcagcgcgat atcggctcgc    70980
acggcggcga acagccgttg ccagcccggg ataccccgca cggtcgcgtt cttcaggaaa    71040
acgtcgcacc acgtagccgc cagatccagc cggccgaccc gcgtgagcga gttcagctcg    71100
gtgaggatga ggctgagcgt catgtcggac agcggcgtgg tccgcagcag tttctccgag    71160
tcctggatat ccccgggctt gcgtcccagc tccttgatcc aagtggccag cgcccccagc    71220
gcgtcgctgc gggaggtgcc atcggcgcag tcctttccgg acagaccgtc cgccagagcg    71280
cgggatccgg cacaccaggc cgccggcatg ccggtcatcg gggggaagaa ccacagccac    71340
gtgttgccga cgaccgtcag gtccgttgta ctgcgaagac cgcgcagggt gggccgtacc    71400
tcccgcagca gttctcccgc ttcctccacg cggcccaggc tgaccagcag ttggatcagc    71460
agaacggcat cgacggggca gagctcgggt cccggtgccc gctccccgca gtagccgtcg    71520
agatggtggc gttcgacgga acaggggtcg acgcgccacc tgacgagtgc ccgcttcagg    71580
cggatgtggc cccgctccca ggagtcggtg gaggcgtcat gggccagttc gaggtacgcg    71640
ccggcctgtt cggcgtcgtc cgagtccaac gcctcctcgg cggcgtgccg cagggctccc    71700
acatgccagg gttccgtcgc cgagcccgct tcgagcaggt ggcgggcgat cgtacggctg    71760
ccgacgccgt gccgactcag cagttccgcg gcccggtggc gcagttcggc gcgctgcttg    71820
gggccgatga tgttcagggt cgcgcgctcg accaggggt gctggaaacg gtagccgtcg     71880
accagtccgg ccgaggccaa cgcaaggata ccgcgcgcga tctcggcggc gttcagcccg    71940
agcagctcct ccaacagttc cggcctggag tcctcgccca ggaccgcgat gccggtggcg    72000
agggacacca ccgcggggtc gttgccctgc acgcagttga ccgcgccctg cgcgaagagg    72060
ccgtcggcgg caggccacgg ggcggttttgg cctgcggcgt tgcggacccg tgttcttcc    72120 aacagcgccc gcacgagcag ggggttgccg ccgctcagcc ggaacacgtc gtccaggaag    72180
gtgtcctccg ccggccggcc ctccagggcg ccgaccaggt cgacgacatg gtcccgggtc    72240
attgggcgca gcgcgatccg gtggagattg ggctgccgca ggagctcgca gtggaactcc    72300
ggcccgagtg atgtgcggag tgcctgtacg acgatcagca tcagcctgct ggaccggagc    72360
ctggcccgtg tggcctccag cagccagcgc cagctcaggc tgtcgagatc ctgtaggtcg    72420
tcgaggcaga cgaccaccgg tgaccggtcg gccagggcct cgagtcggcc gcagaactcc    72480
acgaactcgg cggtttgtgc cgaactcatc gagctcatcc tgggaacatt gtcgaatcca    72540
aggtcgcggg cgttcaccac gaccgctccg gaggccttca catgctcgcc gaaatttacc    72600
```

```
agtaattcgc ttttcccgca gtaggcaccg ccctccaata ccacggtcac agccttgccg    72660
atctcgcatt cgacaagcaa ggatttcagt agatcaagtt ccgagtcccg cccgaagaga    72720
tgcatccgaa ttgaatcccc aatctccacc acgaaatgag tgccacgatc gactccggtt    72780
gcaaatcggg ccggccggcg ggttggttgc catacggttc gcctcgctcg tggccgaatc    72840
taagcgctgt cacgcggcga ttggggcact acaccgggca agtaagcggc aactcaggca    72900
ggtgacgtgc cgcccggctc gactggacgc ccggggttgca gaacaccgc cgaatgtggc     72960
cggaggactc gcttttccag aagacgccct ggtgtcggcc gagcccgcgg ttgagcgctt    73020
ccggccactt ctggccggcg cccgaatcgt cacgaccgaa accggtccgc accaggatcc    73080
atccgagacc caggcgcgct gcacgatcgg gcggagtgaa cgtctccgtc gactccaacc    73140
gcccgccgca ccgttcaagg caccgagtcc gtggggtcgg tcagccggtt gatcagcacc    73200
tcccgcacaa aggggacgt cacgcggacg gctcggttac tcctgctcgg ccgtcaggac      73260
ggacaggcag tgccggagtt ccccggcctc cgacggccgc catgggattc gacgacaagg    73320
agcgcccatc cccgcctcgc gggccgacgg tgacccggga ccagatctgg ctggagatca    73380
tccagagcgc actcgaccgt gcaccggctc ctacggcgcg gcgctgacac gctacgtgca    73440
caccgaaggc gtcacggtca tcgaggtcaa ccagccggac taggccaccc gccgccgacg    73500
cggcaagacc gacgctcgac gcggcgccgc cgcccaagcg gtgctgtccg gccgcgccac    73560
cgccaacgcc aagaccggcg gcagagacaa ccctgaacgg atggtcagcg aggcatcctt    73620
cgccgcactc ggcggcgtca gcccggtgga gtcatcctca gccaggaccc aacgccgcag    73680
gttcaaccgc ggcggcgacc gccaagccaa cggtgcgacg tcacatgtcg ggaacacccc    73740
gccgtcagcc acgtactggc ggagggtcag gggccgaagg cactggttct ggctcccgga    73800
aacgatgtga gcgtgccccg ggtcaggttc tggatccggg cacctgcgtt gtcacctgcg    73860
ggagttgtcg ggcactccca tcgcggcgaa caacgcgtcc gccgcaccac gtacatccga    73920
tgctcgcatc gcgccgagag cctgagcggc ctgggccata cacgccacgc actcgactgg    73980
gtgagctgca aggcgcgctc cgcgtcgtcc gtggcctccg tcggacggcc gagacggtga    74040
aggacgtcga ccgaacgtcg cgagggccag cgcgacgttg ccccggatcc cgcgtctcgt    74100
cgcacaactg ccgggccgta acccgctctt ggaccaccgc atggtagcgc cttgccgggc    74160
tccaggggag gagtggtcgg cacgcgctct tggattgccc cgcgatgctg attctggtgc    74220
ctcgacccaa ccttcgagcg gatccaggac gttgaacctc agctgctcct tcgtgtggtc    74280
cgctgtcaag cccctctgca cgtgacgtgc atgaaatctt ccgatgcagg gtgcgtttga    74340
ac                                                                   74342
```

<210> SEQ ID NO 2
<211> LENGTH: 6532
<212> TYPE: PRT
<213> ORGANISM: Streptomyces sp.

<400> SEQUENCE: 2

Val Leu Ser Ala Ala Asp Asp Ala Ile Ala Ile Ile Gly Met Ser Cys
1               5                   10                  15

Arg Leu Pro Arg Ala Val Asn Pro Gln Glu Phe Trp Glu Leu Leu Arg
            20                  25                  30

Asn Gly Glu Ser Gly Ile Thr Glu Val Pro Pro Gln Arg Trp Asp Ala
        35                  40                  45

Asn Ser Leu Phe Asp Ala Glu Arg Ser Thr Pro Gly Thr Met Asn Thr
    50                  55                  60

```
Arg Trp Gly Gly Phe Ile Asp Gly Val Asp Gln Phe Asp Pro Gly Phe
 65                  70                  75                  80

Phe Gly Ile Ser Ser Arg Glu Ala Val Ala Met Asp Pro Gln Gln Arg
             85                  90                  95

Leu Val Leu Glu Leu Ser Trp Glu Ala Leu Glu Asp Ala Arg Ile Val
            100                 105                 110

Pro Glu Arg Leu Arg His Thr Ala Thr Gly Val Phe Val Gly Ala Ile
        115                 120                 125

Trp Asp Asp Tyr Ala Ser Leu Met Ser Ala Arg Gly Arg Glu Ala Val
    130                 135                 140

Thr His His Thr Val Thr Gly Thr His Arg Ser Ile Ile Ala Asn Arg
145                 150                 155                 160

Val Ser Tyr Ala Leu Gly Leu Gln Gly Pro Ser Met Ala Val Asp Ser
                165                 170                 175

Gly Gln Ser Ser Ser Leu Val Ser Val His Leu Ala Cys Glu Ser Leu
            180                 185                 190

Arg Arg Gly Glu Ser Thr Leu Ala Leu Ala Gly Gly Val Asn Leu Asn
        195                 200                 205

Leu Val Pro Glu Ser Thr Ile Gly Met Ala Lys Phe Gly Gly Leu Ser
210                 215                 220

Pro Asp Gly Arg Cys Phe Thr Phe Asp Thr Arg Ala Asn Gly Tyr Val
225                 230                 235                 240

Arg Gly Glu Gly Gly Gly Val Val Leu Lys Pro Leu Ala Asp Ala
                245                 250                 255

Ile Ala Asp Gln Asp Pro Ile Tyr Cys Val Ile Arg Gly Ser Ala Val
                260                 265                 270

Asn Asn Asp Gly Ser Gly Glu Asn Leu Thr Thr Pro Asn Ser Gln Ala
            275                 280                 285

Gln Ala Ala Val Leu Arg Glu Ala Tyr Arg Arg Ala Gly Val Asp Pro
        290                 295                 300

Ala Gln Val Gln Tyr Val Glu Leu His Gly Thr Gly Thr Pro Val Gly
305                 310                 315                 320

Asp Pro Ile Glu Ala Glu Ala Leu Gly Ala Val Ile Gly Ala Ala Arg
                325                 330                 335

Pro Pro Gly Asp Pro Leu Trp Val Gly Ser Ala Lys Thr Asn Ile Gly
            340                 345                 350

His Leu Glu Ala Ala Ala Gly Ile Ala Gly Leu Leu Lys Val Val Leu
        355                 360                 365

Ser Ile Ser His Arg Glu Leu Pro Ala Ser Leu Asn Phe Ala Thr Ala
370                 375                 380

Asn Pro Arg Ile Pro Leu Asp Ser Leu Asn Leu Arg Val Gly Asp Glu
385                 390                 395                 400

Leu Thr Ser Trp Pro Ser Ala Gly Arg Pro Met Leu Ala Gly Val Ser
                405                 410                 415

Ala Phe Gly Met Gly Gly Thr Asn Ala His Ala Val Val Glu Gln Ser
            420                 425                 430

Pro Val Ala Ala Arg Gln Ile Pro Ala Pro Gly Gly Thr Pro Thr Asp
        435                 440                 445

Gln Gly Gly Pro Val Pro Trp Leu Leu Ser Gly Gly Ser Val Ala Ala
450                 455                 460

Val Arg Gly Gln Ala Ala Arg Leu Leu Ser His Leu Glu Gly Arg Ser
465                 470                 475                 480

Gly Leu Arg Ala Val Asp Val Gly Trp Ser Leu Ala Thr Thr Arg Ser
                485                 490                 495
```

```
Val Phe Pro His Arg Ala Val Val Ala Asp Asp Gly Gly Tyr Gly
            500                 505                 510
Gln Ser Leu Ala Ala Leu Ala Ala Gly Ser Val Asp Ala Gly Val Val
515                 520                 525
Glu Gly Leu Ala Asp Val Ser Gly Lys Thr Val Phe Val Phe Pro Gly
            530                 535                 540
Gln Gly Ser Gln Trp Val Gly Met Ala Val Glu Leu Leu Asp Gly Ser
545                 550                 555                 560
Glu Val Phe Ala Glu His Met Ala Ala Cys Ala Arg Ala Leu Glu Pro
                565                 570                 575
Phe Val Gly Trp Ser Leu Glu Asp Val Leu Arg Gln Val Asp Gly Thr
            580                 585                 590
Trp Ser Leu Asp Arg Val Asp Val Val Gln Pro Val Leu Trp Ala Val
            595                 600                 605
Met Val Ser Leu Ala Gly Leu Trp Gln Ala His Gly Val Glu Pro Ala
            610                 615                 620
Ala Val Leu Gly His Ser Gln Gly Glu Ile Ala Ala Ala Cys Val Ala
625                 630                 635                 640
Gly Ala Leu Ser Leu Glu Asp Gly Ala Arg Val Val Ala Leu Arg Ser
                645                 650                 655
Arg Ala Ile Ala Glu Ala Leu Ala Gly His Gly Gly Met Leu Ser Ile
                660                 665                 670
Ala Ala Pro Ala Thr Glu Val Thr Ala Leu Ile Thr Pro Trp Gly Arg
            675                 680                 685
Gln Ile Thr Ile Ala Thr Val Asn Gly Pro His Ser Val Val Val Ala
            690                 695                 700
Gly Asp Pro Asp Ala Leu Glu Ala Leu Arg Gly Glu Leu Glu Thr Arg
705                 710                 715                 720
Gly Leu Arg Asn Arg Arg Ile Pro Val Asp Tyr Ala Ser His Thr Pro
                725                 730                 735
His Val Glu Ala Ile Arg Glu Arg Leu Leu Ala Asp Leu Ala Val Ile
                740                 745                 750
Gln Pro Arg Ala Ala Ser Ile Pro Val Leu Ser Thr Val Thr Gly Ala
            755                 760                 765
Trp Leu Asp Thr Thr Val Met Asp Ala Glu Tyr Trp Tyr Arg Asn Leu
            770                 775                 780
Arg Gln Thr Val Glu Phe Glu Ala Ala Thr Arg Thr Leu Leu Asp Gln
785                 790                 795                 800
Asp His Arg Tyr Phe Val Glu Ile Ser Pro His Pro Val Leu Thr Thr
                805                 810                 815
Ala Ile Gln Glu Thr Leu Asp Val Thr Asp Thr Ala Ala Val Ala Thr
            820                 825                 830
Gly Thr Leu Arg Arg Asn Glu Gly Ser Leu Arg Arg Phe Gln Leu Ala
            835                 840                 845
Leu Ala Glu Leu Val Thr Arg Gly Leu Thr Pro His Trp Pro Ala Leu
850                 855                 860
Tyr Pro Asp Ala Arg His Thr Asp Leu Pro Thr Tyr Pro Phe Gln Arg
865                 870                 875                 880
Glu Arg Tyr Trp Val Gly Ser Ser Val Arg Asp Ala Ala Pro Ala
                885                 890                 895
Pro Gln Pro Asp Pro Ala Thr Gly Arg Ala Ala Gly Pro Ala Ser Gly
            900                 905                 910
Arg Ala Ala Val Asp Gly Gly Asp Gly Pro Ala Glu Leu Leu Ala Leu
```

915                 920                 925
Val Arg Ala His Val Ala Val Val Leu Gly Thr Thr Pro Asp Ser
    930                 935                 940
Val Asp Pro Lys Leu Thr Phe Lys Gln Leu Gly Phe Asp Ser Val Met
945                 950                 955                 960
Ser Val Glu Leu Arg Asn Arg Leu Ser Ser Ala Thr Gly Ser Ser Leu
                965                 970                 975
Pro Ser Thr Val Leu Phe Asn His Pro Thr Pro Asp Arg Leu Ala Arg
            980                 985                 990
His Leu Ser Ala Glu Ala Ser Ser Gln Val Glu Gly Ala His Asp Ala
            995                1000                1005
Ala Pro Thr Gly Ala Ala Asp Glu Pro Ile Ala Ile Val Gly Met
   1010                1015                1020
Gly Cys Arg Tyr Pro Gly Gly Val Ala Ser Pro Glu Asp Leu Trp
   1025                1030                1035
Arg Leu Val Thr Ser Gly Gly Asp Ala Ile Ser Gly Phe Pro Thr
   1040                1045                1050
Asp Arg Gly Trp Asp Leu Glu Val Met Tyr Asp Pro Asp His Arg
   1055                1060                1065
Arg Pro Gly Thr Ser Ser Thr Arg Glu Gly Gly Phe Leu Tyr Glu
   1070                1075                1080
Ala Gly Asp Phe Asp Ala Gly Phe Phe Gly Ile Ser Pro Arg Glu
   1085                1090                1095
Ala Ser Ala Met Asp Pro Gln Arg Leu Leu Leu Glu Thr Ser
   1100                1105                1110
Trp Glu Ala Val Glu Arg Ala Gly Ile Asp Pro Leu Ser Leu His
   1115                1120                1125
Gly Thr Arg Ala Gly Val Phe Val Gly Ala Met Ala Gln Glu Tyr
   1130                1135                1140
Gly Pro Arg Leu Asp Glu Gly Ala Asp Gly Tyr Glu Gly Phe Leu
   1145                1150                1155
Leu Thr Gly Gly Leu Thr Ser Val Leu Ser Gly Arg Leu Ala Tyr
   1160                1165                1170
Ser Leu Gly Leu Glu Gly Pro Ala Val Thr Val Asp Thr Ala Cys
   1175                1180                1185
Ser Ser Ser Leu Val Ala Val His Met Ala Ala Gln Ala Leu Arg
   1190                1195                1200
Gln Gly Gln Cys Ser Leu Ala Leu Ala Gly Gly Val Thr Val Met
   1205                1210                1215
Ser Gly Pro Gly Ile Phe Leu Glu Phe Ser Arg Gln Ser Gly Leu
   1220                1225                1230
Ala Pro Asp Gly Arg Cys Lys Ala Phe Ala Ala Gly Ala Asp Gly
   1235                1240                1245
Thr Gly Trp Ala Glu Gly Val Gly Val Leu Val Leu Glu Arg Leu
   1250                1255                1260
Ser Asp Ala Arg Arg Asn Gly His Pro Val Leu Ala Val Val Arg
   1265                1270                1275
Gly Ser Ala Ile Asn Gln Asp Gly Ala Ser Asn Gly Leu Thr Ala
   1280                1285                1290
Pro Asn Gly Leu Ala Gln Glu Arg Val Ile Arg Glu Ala Leu Thr
   1295                1300                1305
Asp Ala Gly Leu Ser Pro Ala Asp Val Asp Leu Val Glu Ala His
   1310                1315                1320

-continued

Gly Thr Gly Thr Thr Leu Gly Asp Pro Ile Glu Ala Gln Ala Leu
1325            1330                1335

Ile Ala Thr Tyr Gly Gln Gly Arg Pro Ala Asp Arg Pro Leu Arg
1340            1345                1350

Leu Gly Ser Leu Lys Ser Asn Ile Gly His Ala Gln Ala Ala Ala
1355            1360                1365

Gly Val Gly Gly Val Ile Lys Thr Val Met Ala Val Arg His Ala
1370            1375                1380

Thr Met Pro Gln Thr Leu His Val Asp Ala Pro Ser Pro His Val
1385            1390                1395

Asp Trp Ser Ser Gly Gln Val Arg Leu Leu Thr Glu Ala Val Pro
1400            1405                1410

Trp Pro Glu Ser Asp His Pro Arg Arg Ala Ala Val Ser Ser Phe
1415            1420                1425

Gly Ile Ser Gly Thr Asn Ala His Val Val Glu Gln Pro Pro
1430            1435                1440

Ala Glu Val Ser Ala Val Thr Gly Pro Ser Pro Met Ala Pro Asp
1445            1450                1455

Glu Ala Val Pro Ala Pro Gly Gln Pro Val Pro Trp Leu Leu Ser
1460            1465                1470

Gly Lys Ser Pro Glu Ala Val Arg Glu Gln Ala Ala Arg Leu Arg
1475            1480                1485

Ser Tyr Leu Ala Asp Arg Pro Gly Ala Gly Leu Ala Asp Ile Gly
1490            1495                1500

Trp Ser Leu Ala Ser Thr Arg Ser Ala Phe Glu His Arg Thr Val
1505            1510                1515

Val Val Ala Ala Asp His Gly Gln Phe Arg Glu Ala Leu Gly Ala
1520            1525                1530

Ala Ala Ala Gly Ser Ala Asp Ala Arg Val Val Glu Gly Val Ala
1535            1540                1545

Asp Ile Asp Gly Lys Thr Val Phe Val Phe Pro Gly Gln Gly Ala
1550            1555                1560

Gln Trp Ala Gly Met Ala Gly Glu Leu Leu Asp Ser Ser Glu Val
1565            1570                1575

Phe Ala Ala Arg Met Ala Asp Cys Ala Arg Ala Leu Ala Pro Phe
1580            1585                1590

Val Gly Trp Ser Leu Gln Asp Val Val Arg Gln Ala Glu Gly Ala
1595            1600                1605

Pro Pro Leu Asp Arg Val Asp Val Val Gln Pro Val Leu Trp Ala
1610            1615                1620

Val Met Val Ser Leu Ala Asp Leu Trp Arg Ala His Gly Val Glu
1625            1630                1635

Pro Ser Ala Val Val Gly His Ser Gln Gly Glu Ile Ala Ala Ala
1640            1645                1650

Cys Val Ala Gly Gly Leu Thr Leu Glu Asp Ala Ala Arg Val Val
1655            1660                1665

Ser Leu Arg Ser Arg Ala Ile Ala Glu Val Leu Ala Gly His Gly
1670            1675                1680

Gly Met Leu Ser Val Thr Ala Ala Arg Glu Gln Val Glu Glu Trp
1685            1690                1695

Leu Leu Pro Trp Glu Gly Arg Ile Ser Leu Ala Thr Ile Asn Gly
1700            1705                1710

Thr Glu Ser Val Val Val Ala Gly Asp Pro Asp Ala Leu Ala Glu
1715            1720                1725

```
Phe Arg Ala Trp Leu Gly Asn Arg Gln Ile Arg Ser Arg Thr Leu
    1730                1735                1740

Pro Val Asp Tyr Ala Ser His Ser Ala Gln Val Glu Ala Val His
    1745                1750                1755

Gln Arg Leu Leu Asp Asp Leu Ala Pro Ile Arg Pro Arg Thr Cys
    1760                1765                1770

Arg Thr Pro Leu Leu Ser Ser Val Thr Gly Gln Trp Leu Asp Thr
    1775                1780                1785

Ala Ser Met Asp Ala Glu Tyr Trp Tyr Gln Asn Leu Arg Arg Thr
    1790                1795                1800

Val Glu Phe Ala Ala Ala Thr Arg Thr Leu Ala Asp Gly Gly His
    1805                1810                1815

Arg Ile Phe Ile Glu Val Ser Ser His Pro Val Leu Val Gly Ala
    1820                1825                1830

Ile Arg Glu Thr Leu Glu Ala Val Glu Val Gln Ala Ala Val Ala
    1835                1840                1845

Gly Ser Leu Arg Arg Asp Asp Gly Gly Leu Arg Arg Phe Arg Leu
    1850                1855                1860

Ser Leu Ala Ala Leu Val Thr Arg Gly Leu Ala Pro Asp Trp Ser
    1865                1870                1875

Met Leu Cys Pro Gly Val Ser Arg Thr Asp Leu Pro Thr Tyr Pro
    1880                1885                1890

Phe Gln Arg Ser Arg Tyr Trp Ile Thr Ala Phe Ser Gly Ser Arg
    1895                1900                1905

Ser Ala Gly Glu Leu Asn Ala Ala Asp Ser Arg Phe Trp Glu Ala
    1910                1915                1920

Val Asp Ser Glu Asp Pro Gly Arg Leu Ala Glu Val Leu Ser Leu
    1925                1930                1935

Asp Asp Asp Ala Ser Leu Glu Pro Val Phe Leu Ala Leu Ser Ser
    1940                1945                1950

Trp Arg Arg Arg His Arg Val Arg Ser Thr Leu Asp Asp Trp Arg
    1955                1960                1965

Tyr Arg Val Thr Trp Gln Pro Leu Pro Gly Ala Ala Val Pro Leu
    1970                1975                1980

Thr Ala Ala Thr Leu Gly Gly Thr Trp Leu Val Ala Val Pro His
    1985                1990                1995

Glu Asp Ala Tyr Val Ser Gln Val Leu Arg Gly Leu Gly Asp Arg
    2000                2005                2010

Gly Ala Thr Val Ile Thr Leu Arg Ala Asp Asp Pro Arg His Gly
    2015                2020                2025

Pro Leu Ala Glu Arg Val Arg Glu Ala Leu Ala Gly Ala Gly Glu
    2030                2035                2040

Ile Thr Gly Val Leu Ser Leu Leu Ala Leu Asp Glu Arg Pro His
    2045                2050                2055

Pro Glu His Pro Val Leu Pro Met Gly Leu Ala Leu Asn Thr Ala
    2060                2065                2070

Leu Val Arg Ala Leu Val Asp Lys Asp Val Arg Ala Pro Leu Trp
    2075                2080                2085

Cys Ala Thr Arg Gly Ala Val Ser Val Gly Arg Ser Asp Arg Leu
    2090                2095                2100

Gly Ser Pro Ala Gln Ala Met Val Trp Gly Leu Gly Leu Val Ala
    2105                2110                2115

Ala Leu Glu His Pro Arg His Trp Gly Gly Leu Val Asp Leu Pro
```

```
                 2120                2125                2130

Glu Thr Val Asp Glu Arg Val Leu Asn Arg Leu Val Thr Val Ile
    2135                2140                2145

Ser Gly Gln Arg Val His Gly Gln Gly Ala Pro Gly Gln Asp Gly
    2150                2155                2160

Glu Asn Pro Gly Asp Glu Asp Gln Leu Ala Val Arg Ala Ser Gly
    2165                2170                2175

Val Phe Ala Arg Arg Leu Ser His Ala Pro Val Ser Gly Ser Arg
    2180                2185                2190

Asn Arg Glu Trp Thr Pro Arg Gly Thr Val Leu Val Thr Gly Gly
    2195                2200                2205

Thr Gly Gly Ala Gly Thr Gln Val Ala Arg Trp Leu Ala Arg Asn
    2210                2215                2220

Gly Ala Glu His Leu Leu Leu Thr Ser Arg Arg Gly Arg Asp Ala
    2225                2230                2235

Glu Gly Ala Ala Glu Leu Ala Ala Glu Leu Thr Glu Ala Gly Val
    2240                2245                2250

Arg Val Thr Val Ala Ala Cys Asp Val Ala Asp Arg Asp Ala Leu
    2255                2260                2265

Ala Arg Leu Leu Ala Gly Val Pro Asp Glu Leu Pro Leu Thr Ala
    2270                2275                2280

Val Ile His Ala Ala Gly Val Val Thr Thr Ala Pro Leu Asp Ser
    2285                2290                2295

Thr Gly Pro Glu Glu Leu Ala Glu Val Leu Ala Gly Lys Val Ala
    2300                2305                2310

Gly Ala Ala His Leu Asp Ala Leu Leu Gly Asp Arg Gln Leu Asp
    2315                2320                2325

Ala Phe Val Leu Phe Ser Ser Asn Ala Gly Val Trp Gly Ser Gly
    2330                2335                2340

Gly Gln Ala Ala Tyr Ala Ala Ala Asn Ala Tyr Leu Asp Ala Leu
    2345                2350                2355

Ala Gln Gln Arg Ser Ser Met Gly Gln Thr Ala Thr Ser Val Ala
    2360                2365                2370

Trp Gly Ala Trp Gly Gly Ala Gly Met Ala Ala Glu Glu Gly Phe
    2375                2380                2385

Lys Glu Arg Leu Arg Arg Gly Ile Ile Glu Met Asp Pro Glu
    2390                2395                2400

Leu Ala Val Thr Ala Leu Val Gln Ala Val Glu Ser Gly Glu Ala
    2405                2410                2415

Ser Ile Ala Val Ala Asp Val Asp Trp Ala Arg Phe Val Pro Gly
    2420                2425                2430

Phe Thr Ser Asn Arg Pro Ser Pro Leu Ile Gly Asp Leu Pro Glu
    2435                2440                2445

Val Arg Asp Ala Leu Arg Glu Ala Asp Ser Arg Pro Ala Val Asp
    2450                2455                2460

Gln Gly Gly Ser Ala Leu Ala Thr Arg Leu Ala Gly Leu Ser Val
    2465                2470                2475

Leu Glu Arg Glu Arg Val Leu Leu Asn Leu Val Arg Thr Glu Val
    2480                2485                2490

Ala Ser Val Leu Gly His Thr Thr Ala Asp Met Val Asp Ala Arg
    2495                2500                2505

Arg Pro Phe Arg Glu Leu Gly Phe Asp Ser Leu Ile Ala Val Glu
    2510                2515                2520
```

```
Phe Arg Gly Arg Leu Asn Ala Ala Thr Gly Leu Arg Leu Pro Thr
2525                2530                2535

Ser Val Ala Phe Asp His Pro Thr Pro Ala Glu Leu Ala Gly His
2540                2545                2550

Leu Arg Glu Leu Phe Ala Gly Ser Arg Gly Asp Thr Ala Met Pro
2555                2560                2565

Val Ser Val Thr Thr Ala Gly Asp Asp Glu Pro Ile Ala Ile Val
2570                2575                2580

Ala Met Ser Cys Arg Tyr Pro Gly Gly Val Arg Thr Pro Glu Asp
2585                2590                2595

Leu Trp Arg Leu Val Ala Glu Gly Arg Asp Ala Ile Thr Asp Phe
2600                2605                2610

Pro Thr Asp Arg Gly Trp Asp Ile Glu Ser Leu Tyr Asp Pro Asp
2615                2620                2625

Pro Gly Arg Ser Gly Thr Ser Tyr Thr Arg Arg Gly Gly Phe Leu
2630                2635                2640

Asp Asp Ala Ala Ala Phe Asp Pro Ala Phe Phe Arg Ile Ser Pro
2645                2650                2655

Arg Glu Ala Leu Ala Met Asp Pro Gln Gln Arg Leu Leu Leu Glu
2660                2665                2670

Met Thr Trp Glu Thr Leu Glu Arg Ala Leu Ile Asp Pro Thr Thr
2675                2680                2685

Leu Lys Gly Ser Gln Ala Gly Val Phe Ile Gly Thr Ala His Pro
2690                2695                2700

Gly Tyr Gly Glu Gly Ile His His Glu Ser Gln Gly Val Glu Gly
2705                2710                2715

Gln Gln Leu Phe Gly Gly Ser Ala Ala Val Ala Ala Gly Arg Ile
2720                2725                2730

Ala Tyr Thr Phe Gly Leu Glu Gly Pro Ala Met Thr Val Asp Thr
2735                2740                2745

Met Cys Ser Ser Ser Leu Val Ala Leu His Leu Ala Cys Gln Ser
2750                2755                2760

Leu Arg Thr Gly Glu Ser Ser Met Ala Leu Ala Gly Gly Val Thr
2765                2770                2775

Val Met Ala Arg Pro Thr Ala Phe Thr Glu Phe Ser Arg His Arg
2780                2785                2790

Gly Leu Ser Pro Asp Gly Arg Cys Lys Ser Phe Ser Asp Ala Ala
2795                2800                2805

Asp Gly Thr Gly Trp Ala Glu Gly Ala Gly Val Leu Leu Leu Glu
2810                2815                2820

Arg Leu Ser Asp Ala Arg Arg Asn Gly His Pro Val Leu Ala Val
2825                2830                2835

Ile Arg Gly Ser Ala Ile Asn Gln Asp Gly Ala Ser Asn Gly Leu
2840                2845                2850

Thr Ala Pro Asn Gly Pro Ser Gln Gln Arg Val Ile Gln Gln Ala
2855                2860                2865

Leu Ala Asn Ala Ser Leu Ser Pro Ala Asp Val Ala Ala Val Glu
2870                2875                2880

Ala His Gly Thr Gly Thr Thr Leu Gly Asp Pro Ile Glu Ala Gln
2885                2890                2895

Ala Leu Ile Ala Ala Tyr Gly Gln Asp Arg Pro Thr Asp Arg Pro
2900                2905                2910

Leu Arg Leu Gly Ser Leu Lys Ser Asn Ile Gly His Ala Gln Ser
2915                2920                2925
```

```
Ala Ala Ala Val Gly Gly Val Ile Lys Met Val Gln Ala Ile Arg
        2930                2935                2940

His Gly Leu Leu Pro Arg Thr Leu His Ala Glu Gln Pro Ser Arg
        2945                2950                2955

His Val Asp Trp Ser Ala Gly Ser Val Glu Leu Leu Thr Glu Ala
        2960                2965                2970

Met Pro Trp Pro Asp Asn Asp Gln Pro Arg Arg Ala Gly Val Ser
        2975                2980                2985

Ala Phe Gly Gly Ser Gly Thr Asn Ala His Met Ile Ile Glu Gln
        2990                2995                3000

Ala Pro Ala Pro Asp Glu Pro Glu His Thr Asp Gly Thr Ser Arg
        3005                3010                3015

Thr Ser Gly Glu Ser Gly Ala Glu Gln Ala Arg Pro Leu Pro Met
        3020                3025                3030

Val Pro Trp Val Leu Ser Ala Arg Ser Asp Thr Ala Leu Arg Ala
        3035                3040                3045

Gln Ala Arg Arg Leu Arg Ala Tyr Ala Ala Ala Glu Ala Gly
        3050                3055                3060

Ser Ile Cys Asp Ile Gly Trp Ala Leu Ala Thr Thr Arg Ala Thr
        3065                3070                3075

Leu Asp Asp Arg Ala Val Val Val Ala Ala Glu Arg Glu Gly Phe
        3080                3085                3090

Leu Thr Ala Leu Asp Ala Leu Ala Glu Asp Arg Thr Ala Pro Gly
        3095                3100                3105

Leu Val Arg Gly Ala Ala Gly Thr Gly Val Arg Ser Ala Phe Leu
        3110                3115                3120

Phe Ser Gly Gln Gly Ser Gln Arg Leu Gly Met Gly Arg Glu Leu
        3125                3130                3135

Tyr Asp Thr Ser Leu Val Phe Ala Glu Ala Leu Asp Glu Val Cys
        3140                3145                3150

Ala Gln Leu Asp Gly His Leu Asp Arg Pro Leu Leu Arg Val Leu
        3155                3160                3165

Phe Ala Ala Glu Gly Ser Asp Asp Ala Ser Met Leu Asp Gln Thr
        3170                3175                3180

Ala Phe Thr Gln Ala Ala Leu Phe Ala Val Glu Val Ala Leu Phe
        3185                3190                3195

Arg Leu Val Trp Ser Trp Gly Leu Arg Pro Asp Phe Leu Ile Gly
        3200                3205                3210

His Ser Val Gly Glu Val Ala Ala His Val Ser Gly Val Leu
        3215                3220                3225

Ser Leu Ala Asp Ala Ala Thr Leu Val Val Ala Arg Gly Arg Leu
        3230                3235                3240

Met Gln Ala Leu Pro Ser Gly Gly Ala Met Val Ala Leu Gln Ala
        3245                3250                3255

Gly Glu Glu Glu Val Arg Leu Ser Leu Ala Gly Leu Glu Asp Val
        3260                3265                3270

Val Gly Val Ala Ala Leu Asn Gly Pro Ala Ser Thr Val Ile Ser
        3275                3280                3285

Gly Asp Glu Glu Ala Val Leu Pro Val Ala Ala His Trp Arg Ala
        3290                3295                3300

Gln Gly Arg Lys Thr Arg Arg Leu Lys Val Ser His Ala Phe His
        3305                3310                3315

Ser Pro Arg Met Glu Pro Met Leu His Arg Phe His Ala Val Leu
```

```
                3320            3325            3330
Lys Thr Leu Ser Phe Ala Glu Pro Ala Ile Pro Val Val Ser Asn
            3335            3340            3345
Val Thr Gly Arg Pro Ala Glu Arg Thr Glu Leu Cys Ala Ala Asp
            3350            3355            3360
Tyr Trp Val Arg His Val Arg His Thr Val Arg Phe His Asp Gly
            3365            3370            3375
Ile Arg Ala Leu Glu Ala Glu Gly Val Ser Ala Phe Leu Glu Leu
            3380            3385            3390
Gly Pro Asp Gly Thr Leu Ser Ala Met Val Arg Asp Cys Leu Asp
            3395            3400            3405
Thr Ser Arg Pro Val Val Thr Ala Pro Val Leu Arg Arg Asp Arg
            3410            3415            3420
Thr Asp Val Ser Ala Ala Leu Thr Ala Leu Ala Glu Ala His Gly
            3425            3430            3435
His Gly Val Pro Val Asp Trp Ala Ser Leu Phe Ala Gly Ser Thr
            3440            3445            3450
Ala Arg Ala Val Glu Leu Pro Thr Tyr Pro Phe Gln Arg Glu His
            3455            3460            3465
Phe Trp Leu Asp Ser Val Thr Gly Ser Ser Asp Met Ser Thr Ala
            3470            3475            3480
Gly Leu Ala Ser Pro Asp His Pro Leu Leu Gly Ala Val Thr Thr
            3485            3490            3495
Val Ala Gly Glu Asp Gly Leu Leu Phe Thr Gly Asn Leu Ser Val
            3500            3505            3510
Arg Thr His Pro Trp Leu Ala Asp His Arg Ile Thr Gly Ser Val
            3515            3520            3525
Leu Leu Pro Gly Thr Ala Phe Leu Glu Leu Ala Val Gln Ala Gly
            3530            3535            3540
Asp Gln Ala Gly Cys Gly Arg Val Glu Asp Leu Thr Leu Leu Ala
            3545            3550            3555
Pro Leu Val Leu Pro Glu Glu Gly Ser Val Arg Val Gln Met Lys
            3560            3565            3570
Val Gly Glu Pro Asp Ala Thr Gly Arg Arg Thr Ile Glu Val Tyr
            3575            3580            3585
Ser Ser Asp Gln Gln Ala Pro Gly Arg Glu Arg Trp Val Leu Asn
            3590            3595            3600
Ala Ser Gly Met Leu Ala Gly Glu Pro Val Glu Ala Pro Pro Ser
            3605            3610            3615
Leu Thr Thr Trp Pro Pro Glu Gly Ala Val Pro Val Pro Leu Asp
            3620            3625            3630
Gly Phe His Asp Arg Leu Ala Ala Arg Gly Tyr Gly Tyr Gly Pro
            3635            3640            3645
Thr Phe Arg Gly Leu Ser Ala Ala Trp Ser Arg Gly Asp Glu Ile
            3650            3655            3660
Phe Ala Glu Ala Ala Leu Pro Ser Gly His Arg Gln Asp Ala Ala
            3665            3670            3675
Arg Tyr Gly Leu His Pro Ala Leu Leu Asp Ala Ala Leu His Ala
            3680            3685            3690
Met Glu Leu Arg Glu Pro Arg Pro Ala Gly Asp Gly Val Arg Leu
            3695            3700            3705
Pro Phe Ala Trp Asn Gly Phe Ser Leu His Ala Ser Gly Ala Glu
            3710            3715            3720
```

```
Ala Val Arg Leu Arg Leu Ala Pro Thr Gly Asp Ala Leu Ser
3725               3730                3735

Val Thr Leu Ala Asp Ala Ile Gly Arg Pro Val Ala Ser Ala Arg
3740               3745                3750

Ser Leu Ala Leu Arg Glu Leu Ser Ser Asp Leu Leu Arg Pro Ala
3755               3760                3765

Ser Val Ser Tyr Gly Asp Ser Leu Phe Arg Thr Ala Trp Ile Pro
3770               3775                3780

Ala Leu Val Gly Pro Glu Ala Glu Ser Gly Pro Val Arg Pro Ser
3785               3790                3795

Ala Gly Trp Ala Val Leu Gly Pro Asp Pro Leu Gly Ala Ala Asn
3800               3805                3810

Ala Leu Asn Leu Thr Gly Thr Ser Cys Ser Cys Tyr Pro Asp Leu
3815               3820                3825

Ala Ala Leu Ile Ala Ala Val Asp Gly Gly Ala Ala Val Pro Glu
3830               3835                3840

Ala Val Leu Ala Pro Tyr Ala Ala Glu Pro Ala Pro Asp Ala Gly
3845               3850                3855

Ser Pro Ala Asp Ala Val Arg Ala Ser Thr Gly Arg Ala Leu Gln
3860               3865                3870

Leu Leu Gln Ser Trp Leu Ser Glu Asp Arg Leu Glu Arg Ser Arg
3875               3880                3885

Leu Ile Val Leu Thr Arg Gly Ala Val Ala Val Gly Thr Asp Glu
3890               3895                3900

Gly Val Thr Asp Leu Val Ser Ala Ser Val Arg Gly Leu Val Arg
3905               3910                3915

Ser Ala Gln Ala Glu His Pro Gly Arg Phe Ser Leu Val Asp Ile
3920               3925                3930

Asp Asp Arg Glu Glu Ser Trp Ala Val Leu Ser Ala Ala Ala Val
3935               3940                3945

Ser Asp Glu Pro Gln Leu Ala Leu Arg Cys Gly Gln Met Lys Val
3950               3955                3960

Pro Arg Leu Gly Ser Val Asp Val Pro Thr Thr Gly Met Pro Glu
3965               3970                3975

Met Pro Asp Val Trp Gly Val Asp Gly Thr Val Leu Ile Thr Gly
3980               3985                3990

Gly Thr Gly Val Leu Gly Gly Leu Val Ala Arg His Leu Val Ala
3995               4000                4005

Gly His Gly Val Arg Arg Leu Leu Leu Cys Ser Arg Arg Gly Pro
4010               4015                4020

Asp Ala Pro Gly Ala Val Glu Leu Val Ala Glu Leu Thr Ala Leu
4025               4030                4035

Gly Ala Asp Val Thr Val Ala Ala Cys Asp Ala Ala Asp Arg Asp
4040               4045                4050

Ala Leu Ala Ala Leu Leu Asp Thr Val Pro Ala Thr His Pro Leu
4055               4060                4065

Thr Gly Val Val His Thr Ala Gly Val Ile Asp Asp Ala Thr Val
4070               4075                4080

Thr Thr Leu Thr Pro Glu Arg Ile Asp Ala Val Leu Arg Pro Lys
4085               4090                4095

Val Asp Ala Ala Leu Asn Leu His Gln Leu Thr Ala His Leu Gly
4100               4105                4110

Leu Thr Arg Phe Val Leu Phe Ser Ser Ala Ala Gly Leu Phe Gly
4115               4120                4125
```

-continued

Gly Ala Gly Gln Gly Asn Tyr Ala Ala Ala Asn Ala Phe Leu Asp
    4130            4135            4140

Ala Leu Ala Gln His Arg Arg Ala Asn Gly Leu Asn Ala Gln Ser
    4145            4150            4155

Leu Ala Trp Gly Leu Trp Ala Glu Ala Ser Gly Met Thr Gly His
    4160            4165            4170

Leu Asp Ala Ala Asp Leu Ala Arg Val Ala Arg Ser Gly Leu Thr
    4175            4180            4185

Ala Met Pro Thr Gly Asp Gly Leu Ala Leu Asp Thr Ala Gln
    4190            4195            4200

Arg Val Asp Glu Ala Thr Leu Val Thr Ala Ala Leu Asp Thr Arg
    4205            4210            4215

Ala Leu His Ala Arg Ala Ala Asp Gly Thr Leu Pro Ala Leu Phe
    4220            4225            4230

His Ala Leu Val Pro Val Pro Arg Arg Ser Ala Thr Ser Pro Ala
    4235            4240            4245

Ala Gln Ala Ala Gly Pro Asp Gly Leu Arg Gln Arg Leu Ser Gly
    4250            4255            4260

Leu Val Glu Gly Glu Arg Arg Ala Ala Leu Leu Asp Leu Val Cys
    4265            4270            4275

Gly His Val Ala Arg Val Leu Gly His Ala Asp Pro Ser Ser Ile
    4280            4285            4290

Glu Glu Thr Arg Pro Phe Lys Asp Thr Gly Phe Asp Ser Leu Thr
    4295            4300            4305

Ala Val Glu Leu Arg Asn Val Leu His Gly Ala Thr Gly Leu Arg
    4310            4315            4320

Leu Pro Ala Thr Leu Val Phe Asp Tyr Pro Thr Pro Ala Ala Leu
    4325            4330            4335

Thr Asp His Leu Tyr Asp Glu Leu Leu Gly Ser Arg Glu Asp Ala
    4340            4345            4350

Val Leu Ala Pro Ile Thr Arg Ala Ala Tyr Asp Glu Pro Ile Ala
    4355            4360            4365

Ile Val Gly Met Ala Cys Arg Tyr Pro Gly Gly Val Glu Ser Pro
    4370            4375            4380

Glu Asp Leu Trp Gln Leu Val Ala Asp Gly Arg Asp Ala Ile Ser
    4385            4390            4395

Asp Phe Pro Ala Asp Arg Gly Trp Asn Val Glu Ser Leu Tyr His
    4400            4405            4410

Pro Asp Pro Asp His Pro Gly Thr Ser Tyr Thr Arg Ala Gly Gly
    4415            4420            4425

Phe Leu His Asp Ala Ala Asp Phe Asp Pro Glu Phe Phe Gly Ile
    4430            4435            4440

Ser Pro Arg Glu Ala Leu Ala Thr Asp Pro Gln Gln Arg Leu Leu
    4445            4450            4455

Leu Glu Thr Thr Trp Glu Ala Phe Glu His Ala Gly Val Gly Pro
    4460            4465            4470

Ala Ser Leu Arg Gly Ser Arg Thr Gly Val Phe Val Gly Val Met
    4475            4480            4485

Tyr Asn Asp Tyr Ala Ser Arg Ile Arg His Ile Pro Glu Ser Val
    4490            4495            4500

Glu Gly Gly Leu Thr Thr Asn Ser Ala Gly Ser Val Ala Ser Gly
    4505            4510            4515

Arg Val Ser Tyr Thr Phe Gly Leu Glu Gly Pro Ala Val Thr Val

-continued

```
              4520             4525             4530

Asp Thr Ala Cys Ser Ser Leu Val Ala Leu His Leu Ala Ala
         4535             4540             4545

Gln Ala Leu Arg Asn Gly Glu Cys Thr Leu Ala Leu Ala Gly Gly
         4550             4555             4560

Val Ala Val Met Ser Thr Pro Ala Thr Phe Val Glu Phe Ser Arg
         4565             4570             4575

Gln Arg Gly Leu Ala Ala Asp Gly Arg Cys Lys Ala Phe Ala Asp
         4580             4585             4590

Ala Ala Asp Gly Thr Gly Trp Gly Glu Gly Val Gly Val Leu Leu
         4595             4600             4605

Val Glu Arg Leu Ser Asp Ala Arg Arg Asn Gly His Pro Val Leu
         4610             4615             4620

Ala Val Val Ser Gly Ser Ala Val Asn Gln Asp Gly Ala Ser Asn
         4625             4630             4635

Gly Leu Thr Ala Pro Asn Gly Pro Ser Gln Gln Arg Val Ile Gln
         4640             4645             4650

Gln Ala Leu Ala Asn Ala Gly Leu Ala Gly Ala Asp Val Asp Ala
         4655             4660             4665

Val Glu Ala His Gly Thr Gly Thr Arg Leu Gly Asp Pro Ile Glu
         4670             4675             4680

Ala Gln Ala Leu Ile Ala Thr Tyr Gly Gln Ala Arg Ser Ala Asp
         4685             4690             4695

Arg Pro Leu Trp Leu Gly Ser Leu Lys Ser Asn Ile Gly His Thr
         4700             4705             4710

Gln Ala Ala Ala Gly Val Ala Gly Val Ile Lys Met Val Gln Ala
         4715             4720             4725

Met Gln His Gly Thr Leu Pro Pro Thr Leu His Ile Asp Gln Pro
         4730             4735             4740

Thr Gly Gln Val Asp Trp Ala Thr Gly Ala Val Glu Leu Leu Thr
         4745             4750             4755

Glu Ala Val Pro Trp Pro Asp Ser Asp Arg Pro Arg Arg Val Ala
         4760             4765             4770

Val Ser Ser Phe Gly Val Ser Gly Thr Asn Ala His Val Ile Ile
         4775             4780             4785

Glu His Thr Pro His Thr Pro His Thr Thr Arg Thr Ser Gln Ser
         4790             4795             4800

Ser Gln Ser Pro Gln Ala Pro Gln Thr Val Gln Ala His Arg Pro
         4805             4810             4815

Val Pro Trp Leu Leu Ser Ala Lys Thr Ser Gln Ala Leu Ala Ala
         4820             4825             4830

Gln Ala Arg Arg Leu Ser Ala His Leu Arg Ala Asn Pro Asp Leu
         4835             4840             4845

Arg Ser Ala Asp Val Ala His Ser Leu Leu Thr Thr Arg Ser Val
         4850             4855             4860

His Ala Glu Arg Ala Val Phe Ile Ala Gly Asp Arg Asp Glu Ala
         4865             4870             4875

Leu Ala Ala Leu Asp Ala Leu Ala Asp Gly Thr Pro Ala Pro His
         4880             4885             4890

Leu Val Gln Gly Leu Ala Asp Val Ser Gly Lys Thr Val Phe Val
         4895             4900             4905

Phe Pro Gly Gln Gly Ser Gln Trp Val Gly Met Ala Val Glu Leu
         4910             4915             4920
```

-continued

```
Leu Asp Gly Ser Glu Val Phe Ala Glu His Met Ala Ala Cys Ala
4925                4930                4935

Arg Ala Leu Glu Pro Phe Val Asp Trp Ser Leu Glu Asp Val Leu
4940                4945                4950

Arg Gln Thr Asp Gly Thr Trp Pro Leu Glu Arg Val Glu Val Val
4955                4960                4965

Gln Pro Val Leu Trp Ala Val Met Val Ser Leu Ala Gly Leu Trp
4970                4975                4980

Gln Ala His Gly Val Glu Pro Ala Ala Val Leu Gly His Ser Gln
4985                4990                4995

Gly Glu Ile Ala Ala Ala Cys Val Ala Gly Ala Leu Ser Leu Glu
5000                5005                5010

Asp Gly Ala Arg Val Val Ala Leu Arg Ser Gln Ala Ile Ala Glu
5015                5020                5025

Thr Leu Ala Gly His Gly Gly Met Leu Ser Ile Ala Ala Pro Ala
5030                5035                5040

Thr Asp Ile Ala Pro Leu Ile Ala Arg Trp Asn Glu Arg Ile Ser
5045                5050                5055

Ile Ala Thr Val Asn Gly Pro His Ser Val Val Ala Gly Asp
5060                5065                5070

Pro Asp Ala Leu Glu Ala Leu Arg Gly Glu Leu Glu Thr Arg Gly
5075                5080                5085

Leu Arg Asn Arg Arg Ile Pro Val Asp Tyr Ala Ser His Thr Pro
5090                5095                5100

His Val Glu Ala Ile Arg Glu Arg Leu Leu Ala Asp Leu Ala Val
5105                5110                5115

Ile Gln Pro Arg Ala Ala Ser Ile Pro Val Leu Ser Thr Val Thr
5120                5125                5130

Gly Ala Trp Leu Asp Thr Thr Val Met Asp Ala Glu Tyr Trp Tyr
5135                5140                5145

Arg Asn Leu Arg Gln Thr Val Glu Phe Glu Ala Ala Thr Arg Thr
5150                5155                5160

Leu Leu Asp Gln Asp His Arg Tyr Phe Val Glu Ile Ser Pro His
5165                5170                5175

Pro Val Leu Thr Ile Gly Leu Gln Gln Thr Ile Glu Glu Thr Thr
5180                5185                5190

Ala Pro Ala Arg Thr Leu Ser Thr Leu Arg Arg Asn Glu Gly Thr
5195                5200                5205

Leu Arg His Leu Phe Thr Ser Leu Ala Gln Ala His Ala His Gly
5210                5215                5220

Leu Thr Ile Asp Trp Thr Pro Ala Phe Thr His Thr Glu Pro Arg
5225                5230                5235

Thr Thr Pro Leu Pro Thr Tyr Pro Phe Gln His Glu Arg Tyr Trp
5240                5245                5250

Leu Glu Asp Gly Ala Pro Lys Ser Gly Asp Val Ala Ser Ala Gly
5255                5260                5265

Leu Gly Ser Ala Asp His Pro Leu Leu Gly Ala Ala Val Pro Leu
5270                5275                5280

Pro Asp Ser Gly Gly Phe Leu Phe Thr Gly Gln Leu Ser Leu Arg
5285                5290                5295

Ser His Pro Trp Phe Ala Asp His Ala Val His Gly Thr Val Leu
5300                5305                5310

Leu Pro Gly Thr Ala Phe Val Glu Leu Ala Leu Gln Ala Gly Gly
5315                5320                5325
```

```
Arg Leu Gly Cys Gly Leu Leu Glu Glu Leu Thr Leu Glu Ala Pro
    5330            5335                    5340

Leu Val Leu Pro Glu Asn Ser Ser Val Gln Leu Gln Leu Val Val
    5345            5350                    5355

Asn Ala Pro Asp Ala Gln Asp Asp Ser Gly Gly Arg Thr Phe Ser
    5360            5365                    5370

Val Tyr Ser Arg Pro Gln Asp Arg Thr Ala Asp Ala Pro Trp Val
    5375            5380                    5385

Arg His Ala Thr Gly Val Val Arg Ser Gly Gly Ala Pro Glu Pro
    5390            5395                    5400

Glu Gly Leu Thr Val Trp Pro Pro Thr Gly Ala Val Ala Val Pro
    5405            5410                    5415

Val Glu Asp Phe Tyr Gln Val Leu Gly Asp Arg Gly Tyr Asp Tyr
    5420            5425                    5430

Gly Pro Ala Phe Arg Gly Val Arg Ala Ala Trp Arg His Gly Asp
    5435            5440                    5445

Val Val Tyr Ala Glu Ala Ala Leu Ala Glu Glu Gln Gln Ser Asp
    5450            5455                    5460

Ala Ala Leu Phe His Leu His Pro Ala Leu Leu Asp Ser Ala Leu
    5465            5470                    5475

His Gly Met Gly Leu Met Pro Ser Ala Ser Ala Glu Gln Thr Arg
    5480            5485                    5490

Leu Pro Phe Ala Trp Arg Gly Val Thr Leu His Ala Val Gly Ala
    5495            5500                    5505

Ser Ala Leu Arg Val Ser Leu Arg Pro Ala Gly Pro Asp Thr Val
    5510            5515                    5520

Glu Val Leu Leu Ala Asp Gly Ala Gly Arg Pro Val Ala Ser Ala
    5525            5530                    5535

Asp Ala Leu Val Val Arg Pro Leu Arg Gln Glu Glu Leu Ala Val
    5540            5545                    5550

Trp Gln Asp Ala Tyr Arg Asp Trp Leu Tyr Arg Val Asp Trp Pro
    5555            5560                    5565

Glu Leu Pro Glu Val Pro Leu Val Ala Pro Ala Gly Pro Trp Ala
    5570            5575                    5580

Val Leu Gly Gly Asn Ala Gly Gly Ile Leu Gly Thr Asp Gly Ser
    5585            5590                    5595

Ala Gly Leu Leu Ala Gly Val Pro Ile Asp Ala Tyr Arg Asp Leu
    5600            5605                    5610

Ala Glu Leu Arg Asp Arg Thr Gly Pro Ser Ser Ala Phe Pro Ala
    5615            5620                    5625

Val Val Val Ala Pro Val Ala Thr Gly Thr Gly Ala Ala Pro Asp
    5630            5635                    5640

Ala Val Arg Glu Val Thr Tyr Gln Val Leu Asp Met Ile Gln Ser
    5645            5650                    5655

Trp Leu Ala Asp Asp Arg Ser Ala Ser Ser Thr Leu Leu Leu Val
    5660            5665                    5670

Thr Arg Gly Ala Val Ser Thr Gly Phe Gly Asp Asp Leu Val Asp
    5675            5680                    5685

Leu Gly Gln Ala Ala Val Trp Gly Leu Val Arg Ala Ala Gln Ser
    5690            5695                    5700

Glu Asn Pro Asp Arg Phe Val Leu Leu Asp Leu Asp Gly Ser Glu
    5705            5710                    5715

Pro Val Gly Pro Leu Pro Thr Ala Ala Leu Leu Ser Gly Glu Pro
```

```
                   5720            5725            5730
Gln Leu Ala Phe Arg Glu Gly Lys Val Leu Thr Ala Arg Leu Asp
    5735            5740            5745
Arg Val Ser Ser Asp Ala Gly Thr Leu Leu Pro Pro Ala Gly Pro
    5750            5755            5760
Asp Pro Trp Arg Leu Asp Val Thr Ser Arg Gly Thr Leu Asp Asn
    5765            5770            5775
Leu Ala Leu Leu Ala Ala Pro Gln Val Ser Ala Pro Leu Ala Glu
    5780            5785            5790
Gly Gln Val Arg Val Ala Val His Ala Ala Gly Leu Asn Phe Arg
    5795            5800            5805
Asp Val Leu Val Ala Leu Gly Met Tyr Pro Gly Glu Gly Ser Met
    5810            5815            5820
Gly Ser Glu Gly Ala Gly Val Val Leu Glu Val Gly Pro Gly Val
    5825            5830            5835
Glu Arg Leu Ala Pro Gly Asp Arg Val Met Gly Met Leu Ala Gly
    5840            5845            5850
Gly Phe Phe Gly Pro Val Ala Val Thr Asp Gln Arg Met Val Thr
    5855            5860            5865
Lys Leu Pro Asp Gly Trp Ser Phe Thr Glu Gly Ala Ser Val Pro
    5870            5875            5880
Ile Val Phe Leu Thr Ala Tyr Tyr Gly Leu Val Asp Leu Gly Gly
    5885            5890            5895
Leu Arg Ala Gly Gln Ser Leu Leu Val His Ala Ala Thr Gly Gly
    5900            5905            5910
Val Gly Met Ala Ala Thr Gln Leu Ala Arg His Leu Gly Ala Glu
    5915            5920            5925
Val Phe Gly Thr Ala Ser Pro Gly Lys Trp Glu Ala Leu Arg Gly
    5930            5935            5940
Met Gly Leu Asp Glu Glu His Ile Ala Ser Ser Arg Asp Leu Asp
    5945            5950            5955
Phe Glu Lys Lys Phe Ser Ala Ala Thr Gly Gly Arg Gly Val Asp
    5960            5965            5970
Val Val Leu Asn Ser Leu Ala Arg Glu Phe Val Asp Ala Ser Leu
    5975            5980            5985
Arg Leu Leu Pro Arg Gly Gly Arg Phe Val Glu Met Gly Lys Thr
    5990            5995            6000
Asp Ile Arg Asp Ala Glu Ala Val Ala Ala Gly His Pro Gly Val
    6005            6010            6015
Val Tyr Arg Ala Phe Asp Leu Leu Asp Ala Ala Gly Pro Asp Arg
    6020            6025            6030
Ile Gln Glu Met Leu Ala Glu Leu Leu Ala Leu Phe Glu Ala Gly
    6035            6040            6045
Val Ile Glu Pro Leu Pro Leu Thr Thr Trp Asp Ile Arg Arg Ala
    6050            6055            6060
Pro Glu Ala Leu Arg His Leu Ser Gln Ala Arg His Ile Gly Lys
    6065            6070            6075
Met Val Phe Thr Leu Pro Pro Ala Pro Asp Pro Asp Gly Thr Phe
    6080            6085            6090
Leu Ile Thr Gly Val Pro Gly Ala Leu Gly Asn Leu Val Ala Arg
    6095            6100            6105
His Leu Val Thr Glu Gly Gly Ile Arg Asn Leu Leu Leu Val Ser
    6110            6115            6120
```

```
Arg Arg Gly Pro Ala Ala Pro Gly Ala Glu Gly Leu Ala Thr Glu
    6125                6130                6135

Leu Ala Gly Leu Gly Ala Thr Val Thr Leu Ala Ala Cys Asp Val
    6140                6145                6150

Ala Asp Arg Gln Ala Leu Ala Gly Leu Leu Ala Asp Ile Pro Ala
    6155                6160                6165

Glu His Pro Leu Thr Gly Val Val His Ala Ala Gly Val Leu Asp
    6170                6175                6180

Asp Gly Ile Val Ala Ser Leu Thr Arg Glu Arg Leu Asp Ala Val
    6185                6190                6195

Tyr Arg Pro Lys Val Asp Ala Ala Trp Asn Leu His Glu Leu Thr
    6200                6205                6210

Lys Asp Ser Gly Leu Ala Ala Phe Val Leu Phe Ser Ser Ala Ala
    6215                6220                6225

Ala Thr Leu Gly Ser Ala Gly Gln Gly Asn Tyr Ala Ala Ala Asn
    6230                6235                6240

Ala Phe Leu Asp Ala Leu Ala Gln Phe Arg Gln Ala Gln Gly Leu
    6245                6250                6255

Ala Ala Ser Ser Leu Gly Trp Gly Phe Trp Ala Glu Ser Gly Glu
    6260                6265                6270

Met Thr Gly His Leu Gly Ala Ser Asp Leu Ala Arg Met Ala Arg
    6275                6280                6285

Ser Gly Ile Ala Ala Leu Thr Val Glu Gln Gly Leu Ala Leu Phe
    6290                6295                6300

Asp Ser Ala Arg Ser Gly Val Cys Ala Ser Val Leu Pro Val Arg
    6305                6310                6315

Leu Glu Leu Thr Gly Pro Gly Ala Arg Ala Gly Ser Gly Thr Val
    6320                6325                6330

Pro Ala Leu Met Arg Gly Leu Val Arg Ala Pro Ala Arg Arg Val
    6335                6340                6345

Val Glu Thr Thr Thr Gly Gly Ala Val Thr Gly Leu Arg Gln Arg
    6350                6355                6360

Leu Ala Pro Leu Ser Gly Ala Asp Arg Asp Arg Ala Leu Gln Glu
    6365                6370                6375

Leu Val Cys Ser His Ala Ala Thr Val Leu Gly His Ser Arg Ser
    6380                6385                6390

Gly Ser Val Pro Ala Gln Arg Ala Phe Lys Glu Leu Gly Phe Asp
    6395                6400                6405

Ser Leu Thr Ala Val Glu Leu Arg Asn Arg Leu Asn Val Ala Thr
    6410                6415                6420

Gly Leu Arg Leu Pro Ala Thr Leu Val Phe Asp His Pro Thr Pro
    6425                6430                6435

Leu Ala Met Ala Glu Gln Leu Arg Lys Glu Leu Phe Ala Asp Glu
    6440                6445                6450

Ile Pro Val Ala Pro Gln Val Leu Glu Glu Leu Asp Arg Leu Glu
    6455                6460                6465

Ala Ala Phe Ala Val Ser Ser Ala Gly Asp Leu Gln Gln Ser Gly
    6470                6475                6480

Ala Ala Ala Arg Leu Arg Ala Leu Leu Arg Arg Ile Gly Thr Val
    6485                6490                6495

Thr Pro Ala Gly Gly Asp Ala Ala Asp Gly Leu Ala Val Glu Leu
    6500                6505                6510

Glu Thr Ala Thr His Asp Glu Ile Phe Ala Leu Ile Asp Glu Glu
    6515                6520                6525
```

Val Gly Asp Val
    65  30

<210> SEQ ID NO 3
<211> LENGTH: 7026
<212> TYPE: PRT
<213> ORGANISM: Streptomyces sp.

<400> SEQUENCE: 3

Val Pro Lys Thr Glu Thr Thr Glu Glu Lys Leu Phe Ser Tyr Leu Lys
1               5                   10                  15

Lys Ala Thr Ser Glu Leu Gln Gln Ser Arg Arg Arg Val Ala Glu Leu
            20                  25                  30

Glu Ala Ala Glu Ala Glu Pro Ile Ala Ile Val Gly Thr Ala Cys Arg
        35                  40                  45

Tyr Pro Gly Gly Val Arg Ser Pro Glu Asp Leu Trp Arg Leu Val Ala
    50                  55                  60

Glu Gly Gln His Ala Ile Ser Ser Phe Pro Thr Asp Arg Gly Trp Asp
65                  70                  75                  80

Leu Glu Asp Leu Tyr Asp Pro Asp Pro Asp Arg Pro Gly Lys Ser Tyr
                85                  90                  95

Ala Arg Asp Gly Gly Phe Leu Asp Gly Ala Ala Gln Phe Asp Ala Ala
            100                 105                 110

Phe Phe Gly Ile Ser Pro Arg Glu Ala Leu Ala Met Asp Pro Gln Gln
        115                 120                 125

Arg Leu Leu Leu Glu Thr Thr Trp Glu Val Phe Glu Arg Ala Gly Ile
    130                 135                 140

Asp Pro Thr Ser Leu Arg Gly Ser Arg Thr Gly Val Phe Ala Gly Ile
145                 150                 155                 160

Ser His Gln Asp Tyr Ala Ala Gly Gln Arg Pro Ser Ala Glu Val Ser
                165                 170                 175

Glu Gly His Leu Met Thr Gly Thr Ala Val Ser Val Val Ser Gly Arg
            180                 185                 190

Val Ala Tyr Ala Phe Gly Leu Glu Gly Pro Ala Met Thr Val Asp Thr
        195                 200                 205

Ala Cys Ser Ser Ser Leu Val Ala Leu His Leu Ala Ala Gln Ala Leu
    210                 215                 220

Arg Asn Gly Glu Cys Thr Leu Ala Val Ala Gly Gly Val Thr Val Met
225                 230                 235                 240

Ala Thr Pro Gly Ala Phe Thr Arg Phe Ser Arg Glu Arg Gly Leu Ala
                245                 250                 255

Pro Asp Gly Arg Cys Lys Ala Phe Ser Ser Asp Ala Asp Gly Thr Gly
            260                 265                 270

Phe Ser Glu Gly Val Gly Val Leu Leu Val Glu Arg Leu Ser Asp Ala
        275                 280                 285

Arg Arg Asn Gly His Pro Val Leu Ala Val Val Ser Gly Ser Ala Val
    290                 295                 300

Asn Gln Asp Gly Ala Ser Asn Gly Leu Thr Ala Pro Asn Gly Pro Ser
305                 310                 315                 320

Gln Gln Arg Val Ile Gln Gln Ala Leu Ala Asn Ala Gly Leu Ala Gly
                325                 330                 335

Ala Asp Val Asp Ala Val Glu Ala His Gly Thr Gly Thr Arg Leu Gly
            340                 345                 350

Asp Pro Ile Glu Ala Gln Ala Leu Ile Ala Thr Tyr Gly Gln Ala Arg
        355                 360                 365

-continued

Ser Ala Asp Arg Pro Leu Trp Leu Gly Ser Leu Lys Ser Asn Ile Gly
     370                 375                 380

His Thr Gln Ala Ala Ala Gly Val Ala Gly Val Ile Lys Met Ile Gln
385                 390                 395                 400

Ala Met Gly His Gly Thr Leu Pro Arg Thr Leu His Val Asn Gln Pro
                405                 410                 415

Ser Pro Gln Val Asp Trp Ala Ala Gly Ala Val Glu Leu Leu Thr Glu
             420                 425                 430

Ala Met Pro Trp Pro Glu Gly Asp Arg Pro Arg Arg Ala Gly Ile Ser
         435                 440                 445

Ser Phe Gly Ile Ser Gly Thr Asn Ala His Val Ile Ile Glu Gln Gly
     450                 455                 460

Ala Pro Pro Arg Thr Ala Ser Asp Pro Gly Glu Ser Arg Ala Asp Glu
465                 470                 475                 480

Pro Gly Val Arg Gly Gly Ala Pro Val Pro Ala Thr Thr Glu Ser Ala
                485                 490                 495

Thr Glu Pro Gln Pro Val Pro Trp Leu Leu Ser Gly His Ser Ala Thr
             500                 505                 510

Ala Leu Arg Ala Gln Ala Asp Arg Leu Lys Ser Tyr Ala Ala Asn Asn
         515                 520                 525

Thr Gly Ile Arg Pro Ala Asp Ile Gly Phe Ser Leu Val Thr Thr Arg
     530                 535                 540

Ala Ala Leu Glu His Arg Ala Val Val Ala Ala Asp His Ala Gly
545                 550                 555                 560

Phe Thr Ala Gly Leu Asp Ala Leu Ala Glu Gly Arg Thr Ala Pro Gly
                565                 570                 575

Val Val Ser Gly Thr Val Ala Gly Ala Arg Ser Ala Phe Leu Phe
             580                 585                 590

Ser Gly Gln Gly Ser Gln Arg Val Gly Met Gly Arg Glu Leu Gln Gln
         595                 600                 605

Ala Phe Pro Val Phe Ala Glu Ala Phe Glu Ala Val Cys Ala Gln Val
     610                 615                 620

Asp Pro Tyr Leu Glu His Pro Leu Leu Asp Val Val Leu Ala Ala Pro
625                 630                 635                 640

Asp Ser Asp Phe Gly Ala Leu Leu His Gln Thr Ala Tyr Thr Gln Pro
                645                 650                 655

Ala Leu Phe Ala Leu Glu Val Ala Leu Phe Arg Leu Val Glu Ser Trp
             660                 665                 670

Gly Val Arg Pro Asp Tyr Val Ala Gly His Ser Val Gly Glu Ile Ala
         675                 680                 685

Ala Ala His Val Ala Gly Val Phe Ser Leu Glu Asp Ala Ala Arg Leu
     690                 695                 700

Val Val Ala Arg Gly Gln Leu Met Gln Ala Leu Pro Ala Glu Gly Ala
705                 710                 715                 720

Met Val Ala Leu Gln Val Ser Glu Asp Glu Val Leu Pro Ser Leu Thr
                725                 730                 735

Pro Trp Leu Glu Gln Asp Arg Val Asp Val Ala Ala Val Asn Gly Ala
             740                 745                 750

Ala Ser Thr Val Val Ser Gly Asp Glu Glu Ala Val Leu Ala Val Ala
         755                 760                 765

Glu His Trp Gln Ala Arg Gly Arg Lys Val Arg Arg Leu Thr Val Ser
     770                 775                 780

His Ala Phe His Ser Pro Arg Met Asp Pro Met Leu Asp Gln Phe Arg

```
                785                 790                 795                 800
Val Val Val Glu Gly Ile Arg Phe Ala Glu Pro Ala Ile Pro Val Val
                    805                 810                 815
Ser Ser Val Thr Gly Arg Leu Ala Glu Pro Gly Gln Leu Thr Thr Ala
                    820                 825                 830
Asp Tyr Trp Val Arg His Val Arg Gln Thr Val Arg Phe His Asp Ala
                    835                 840                 845
Leu Gln Thr Leu Gln Thr Glu Asn Val Thr Ala Phe Leu Glu Ile Gly
    850                 855                 860
Pro Asp Gly Gln Leu Ser Ala Met Thr Arg Asp Phe Leu Thr Asp Thr
865                 870                 875                 880
Gly Ala His Ala Ala Val Ala Pro Leu Leu Arg Arg Glu Arg Pro Glu
                    885                 890                 895
Ala Pro Ser Ala Leu Thr Ala Ile Ala Gly Leu His Thr His Gly Val
                    900                 905                 910
Ser Ile Asp Trp Arg Thr Tyr Phe Thr Ser Thr Ser Ser Thr Ser Ser
                915                 920                 925
Thr Ser Thr Gly Thr Gly Thr Gly Thr Gly Gln Ala Thr Ala Asp Thr
    930                 935                 940
Pro Val Gln Leu Pro Thr Tyr Ala Phe Gln His Gln Ser Phe Trp Leu
945                 950                 955                 960
Gly Pro Thr Ala Pro Val Gly Asp Val Ser Thr Ala Gly Leu Thr Ser
                    965                 970                 975
Pro Asp His Pro Leu Leu Ser Ala Ala Thr Thr Thr Ala Val Asp Gly
                    980                 985                 990
Ser Leu Leu Leu Thr Gly Arg Leu Ser Gln Arg Ser Pro Ala Trp Ile
                995                1000                1005
Gly Asp His Arg Ile Gly Gly Val Val Leu Leu Pro Gly Thr Ala
    1010                1015                1020
Leu Val Glu Leu Val Val Arg Ala Gly Asp Gln Ala Gly Cys Ser
    1025                1030                1035
Arg Ile Asp Glu Leu Ile Met Leu Thr Pro Leu Thr Leu Pro Glu
    1040                1045                1050
His Gly Ala Val Arg Ile Gln Val Ala Val Gly Pro Ala His
    1055                1060                1065
Asp Gly Arg Arg Pro Val His Ile His Ser Ser Thr Ser Asp Thr
    1070                1075                1080
Thr Gly Asp Glu Gln Trp Thr Leu Asn Ala Ser Gly Leu Leu Thr
    1085                1090                1095
Val Glu Met Thr Asp Pro Pro Ala Asp Leu Thr Pro Trp Pro Pro
    1100                1105                1110
Gln His Ala Thr Arg Ile Pro Leu Asp Gly Leu Tyr Glu Arg Leu
    1115                1120                1125
Ala Glu Ser Gly Tyr Gly Tyr Gly Pro Val Phe Gln Gly Leu Arg
    1130                1135                1140
Ala Ala Trp Thr Leu Gly Asp Asp Thr Tyr Ala Glu Val Glu Ile
    1145                1150                1155
Pro Ala Gly Asp Gln Thr Thr Asp Arg Tyr Glu Leu His Pro
    1160                1165                1170
Ala Leu Leu Asp Ala Ala Leu His Ala Ser Ser Leu Gln Gly Asp
    1175                1180                1185
Glu Ala Gly Ala Gly Gln Leu Leu Pro Phe Ala Trp Thr Gly Val
    1190                1195                1200
```

-continued

| | | | | | | | | | | |
|---|---|---|---|---|---|---|---|---|---|---|
| Ser | Leu | Tyr | Ala | Ala | Gly | Ala | Ser | Ala | Leu | Leu | Val | Lys | Val | Ser |
| | 1205 | | | | 1210 | | | | 1215 | | | | | |
| Arg | Thr | Gly | Pro | Asp | Thr | Met | Ala | Leu | Leu | Val | Ala | Asp | Thr | Glu |
| | 1220 | | | | 1225 | | | | 1230 | | | | | |
| Gly | His | Pro | Val | Ala | Thr | Val | Asp | Ser | Leu | Thr | Val | Arg | Pro | Met |
| | 1235 | | | | 1240 | | | | 1245 | | | | | |
| Ala | Ile | Asp | Gln | Thr | Ala | Arg | Ser | Thr | Ser | His | Pro | Asp | Ala | Leu |
| | 1250 | | | | 1255 | | | | 1260 | | | | | |
| Phe | Thr | Val | Gly | Leu | Glu | Trp | Ala | Gln | Ala | Arg | Glu | Gly | Asn | Arg |
| | 1265 | | | | 1270 | | | | 1275 | | | | | |
| Thr | Ile | Pro | Leu | Ser | Asp | Cys | Ala | Met | Leu | Ala | Pro | Asp | Glu | Pro |
| | 1280 | | | | 1285 | | | | 1290 | | | | | |
| Asp | Leu | Thr | Ser | Ala | Pro | Ala | Trp | Pro | Gly | Ser | Ser | Ala | Gln | Arg |
| | 1295 | | | | 1300 | | | | 1305 | | | | | |
| Tyr | Ala | Gly | Leu | Ala | Ala | Leu | Ala | Glu | Ile | Cys | Gly | Thr | Asp | Gly |
| | 1310 | | | | 1315 | | | | 1320 | | | | | |
| Pro | Val | Pro | Ala | Val | Val | Leu | Ala | Pro | Phe | Leu | Pro | Gly | Asp | Ala |
| | 1325 | | | | 1330 | | | | 1335 | | | | | |
| Ala | Pro | Ala | Asp | Thr | Ala | Ala | Ala | Thr | His | Ala | Thr | Thr | Arg | Arg |
| | 1340 | | | | 1345 | | | | 1350 | | | | | |
| Ala | Ala | Ala | Leu | Ile | Lys | Gly | Trp | Leu | Gly | Asp | Asp | Arg | Phe | Thr |
| | 1355 | | | | 1360 | | | | 1365 | | | | | |
| Asp | Ser | Arg | Leu | Val | Phe | Val | Thr | Arg | Gly | Ala | Val | Ala | Thr | Ser |
| | 1370 | | | | 1375 | | | | 1380 | | | | | |
| Gly | Arg | Asp | Glu | Leu | His | Asp | Leu | Glu | His | Ser | Thr | Val | Trp | Gly |
| | 1385 | | | | 1390 | | | | 1395 | | | | | |
| Leu | Val | Arg | Ser | Ala | Gln | Thr | Glu | Asn | Pro | Gly | Arg | Phe | Ala | Leu |
| | 1400 | | | | 1405 | | | | 1410 | | | | | |
| Leu | Asp | Leu | Asp | Asp | Pro | Asp | Thr | Val | Thr | Glu | Leu | Pro | Glu | Ala |
| | 1415 | | | | 1420 | | | | 1425 | | | | | |
| Ile | Leu | Ala | Asp | Gln | Ala | Gln | Leu | Val | Leu | Arg | Asp | Gly | Arg | Leu |
| | 1430 | | | | 1435 | | | | 1440 | | | | | |
| Gly | Asn | Leu | Arg | Leu | Ala | Lys | Gly | Ala | Ala | Ile | Gln | Asp | Pro | Asp |
| | 1445 | | | | 1450 | | | | 1455 | | | | | |
| Pro | Gly | Trp | Gly | Val | Asp | Gly | Thr | Val | Leu | Ile | Thr | Gly | Gly | Thr |
| | 1460 | | | | 1465 | | | | 1470 | | | | | |
| Gly | Val | Leu | Gly | Gly | Leu | Val | Ala | Arg | His | Leu | Val | Ala | Gly | His |
| | 1475 | | | | 1480 | | | | 1485 | | | | | |
| Gly | Val | Arg | Arg | Leu | Leu | Leu | Cys | Ser | Arg | Arg | Gly | Pro | Asp | Ala |
| | 1490 | | | | 1495 | | | | 1500 | | | | | |
| Pro | Gly | Ala | Val | Glu | Leu | Val | Ala | Glu | Leu | Thr | Ala | Leu | Gly | Ala |
| | 1505 | | | | 1510 | | | | 1515 | | | | | |
| Asp | Val | Thr | Val | Ala | Ala | Cys | Asp | Ala | Ala | Asp | Arg | Asp | Ala | Leu |
| | 1520 | | | | 1525 | | | | 1530 | | | | | |
| Ala | Ala | Leu | Leu | Asp | Thr | Val | Pro | Ala | Thr | His | Pro | Leu | Thr | Gly |
| | 1535 | | | | 1540 | | | | 1545 | | | | | |
| Val | Val | His | Thr | Ala | Gly | Val | Ile | Asp | Asp | Ala | Thr | Val | Thr | Thr |
| | 1550 | | | | 1555 | | | | 1560 | | | | | |
| Leu | Thr | Pro | Glu | Arg | Ile | Asp | Ala | Val | Leu | Arg | Pro | Lys | Val | Asp |
| | 1565 | | | | 1570 | | | | 1575 | | | | | |
| Ala | Ala | Leu | Asn | Leu | His | Gln | Leu | Thr | Ala | His | Leu | Gly | Leu | Thr |
| | 1580 | | | | 1585 | | | | 1590 | | | | | |
| Arg | Phe | Val | Leu | Phe | Ser | Ser | Ala | Ala | Gly | Leu | Phe | Gly | Gly | Ala |
| | 1595 | | | | 1600 | | | | 1605 | | | | | |

Gly Gln Gly Asn Tyr Ala Ala Ala Asn Ala Phe Leu Asp Ala Leu
        1610            1615                1620

Ala Gln Leu Arg Lys Arg Gln Gly Leu Pro Gly Val Ser Leu Ala
        1625            1630                1635

Trp Gly Ala Trp Val Gln Asp Gly Gly Met Thr Ala Thr Leu Asp
        1640            1645                1650

Ala Gly Asp Val Glu Arg Met Ala Arg Gly Gly Val Leu Pro Leu
        1655            1660                1665

Ser His Glu Gln Gly Leu Asn Leu Phe Asp Leu Ala Val Ala Gly
        1670            1675                1680

Ser Glu Pro Leu Val Ala Pro Met Arg Leu Asp Thr Thr Ala Leu
        1685            1690                1695

Arg Glu Ser Gly Ala Thr Val Pro Glu Met Leu Arg Gly Leu Val
        1700            1705                1710

Arg Glu Arg Ser Arg Arg Val Gly Pro Ser His Thr Thr Ser
        1715            1720                1725

Ala Ala Met Ala Leu Glu Gln Arg Leu Ser Gly Leu Val Glu Gly
        1730            1735                1740

Glu Arg Arg Ala Ala Leu Leu Asp Leu Val Cys Gly His Val Ala
        1745            1750                1755

Arg Val Leu Gly His Ala Asp Pro Ser Ser Ile Glu Glu Thr Arg
        1760            1765                1770

Pro Phe Lys Asp Thr Gly Phe Asp Ser Leu Thr Ala Val Glu Leu
        1775            1780                1785

Arg Asn Val Leu His Gly Ala Thr Gly Leu Arg Leu Pro Ala Thr
        1790            1795                1800

Leu Val Phe Asp Tyr Pro Thr Pro Ala Ala Leu Thr Asp His Leu
        1805            1810                1815

Tyr Asp Glu Leu Leu Gly Ser Arg Glu Asp Ala Val Leu Ala Pro
        1820            1825                1830

Ile Thr Arg Ala Ala Tyr Asp Glu Pro Ile Ala Ile Val Ala Met
        1835            1840                1845

Ser Cys Arg Tyr Pro Gly Gly Val Cys Thr Pro Glu Asp Leu Trp
        1850            1855                1860

Arg Leu Val Ala Glu Gly Arg Asp Thr Ile Thr Asp Phe Pro Asp
        1865            1870                1875

Asp Arg Gly Trp Asp Ile Asp Ala Leu Tyr Asp Pro Asp Pro Gly
        1880            1885                1890

His Pro Gly Thr Ser Tyr Thr Arg Arg Gly Gly Phe Leu Ser Asp
        1895            1900                1905

Ala Ala Gly Phe Asp Pro Ala Phe Phe Arg Ile Ser Pro Arg Glu
        1910            1915                1920

Ala Leu Ala Met Asp Pro Gln Gln Arg Leu Leu Leu Glu Met Thr
        1925            1930                1935

Trp Glu Met Phe Glu Arg Ala Leu Ile Asp Pro Thr Thr Leu Lys
        1940            1945                1950

Gly Ser Gln Ala Gly Val Phe Ile Gly Thr Ala Gly Pro Gly Tyr
        1955            1960                1965

Gly Gly Arg Ile His His Glu Ser Gln Gly Val Glu Gly Gln Gln
        1970            1975                1980

Leu Phe Gly Gly Ser Ala Ala Val Thr Ser Gly Arg Ile Ser Tyr
        1985            1990                1995

Thr Phe Gly Leu Glu Gly Pro Ala Met Thr Val Asp Thr Met Cys

```
                    2000            2005             2010
Ser  Ser  Ser  Leu  Val  Ala  Leu  His  Leu  Ala  Val  Gln  Ser  Leu  Arg
     2015                 2020                 2025

Asn  Gly  Glu  Ser  Ser  Met  Ala  Leu  Ala  Gly  Gly  Val  Thr  Val  Met
     2030                 2035                 2040

Ser  Arg  Pro  Ala  Ala  Phe  Thr  Glu  Phe  Ser  Arg  Gln  Arg  Gly  Leu
     2045                 2050                 2055

Ser  Pro  Asp  Gly  Arg  Cys  Lys  Ser  Phe  Ala  Asp  Ala  Ala  Asp  Gly
     2060                 2065                 2070

Thr  Gly  Trp  Gly  Glu  Gly  Ala  Gly  Val  Leu  Leu  Leu  Glu  Arg  Leu
     2075                 2080                 2085

Ser  Asp  Ala  Arg  Arg  Asn  Gly  His  Pro  Val  Leu  Ala  Val  Ile  Arg
     2090                 2095                 2100

Gly  Ser  Ala  Val  Asn  Gln  Asp  Gly  Ala  Ser  Asn  Gly  Leu  Thr  Ala
     2105                 2110                 2115

Pro  Asn  Gly  Pro  Ser  Gln  Gln  Arg  Val  Ile  Arg  Gln  Ala  Leu  Ala
     2120                 2125                 2130

Asn  Ala  Ser  Leu  Ser  Pro  Ala  Asp  Val  Asp  Ala  Val  Glu  Ala  His
     2135                 2140                 2145

Gly  Thr  Gly  Thr  Pro  Leu  Gly  Asp  Pro  Ile  Glu  Ala  Gln  Ala  Leu
     2150                 2155                 2160

Ile  Ala  Thr  Tyr  Gly  Gln  Asp  Arg  Pro  Ala  Asp  Arg  Pro  Leu  Arg
     2165                 2170                 2175

Leu  Gly  Ser  Val  Lys  Ser  Asn  Ile  Ala  His  Ala  Gln  Ala  Ala  Ala
     2180                 2185                 2190

Ala  Val  Gly  Gly  Val  Ile  Lys  Met  Val  Gln  Ala  Ile  Arg  His  Gly
     2195                 2200                 2205

Leu  Leu  Pro  Lys  Thr  Leu  His  Val  Glu  Gln  Pro  Ser  Arg  His  Val
     2210                 2215                 2220

Asp  Trp  Ser  Ala  Gly  Ser  Val  Glu  Leu  Leu  Thr  Glu  Ala  Met  Pro
     2225                 2230                 2235

Trp  Pro  Glu  Thr  Asp  Gln  Pro  Arg  Arg  Ala  Gly  Val  Ser  Ala  Phe
     2240                 2245                 2250

Gly  Gly  Ser  Gly  Thr  Asn  Ala  His  Met  Ile  Ile  Glu  Gln  Ala  Pro
     2255                 2260                 2265

Ala  Pro  Asp  Glu  Glu  His  Thr  Asp  Gly  Thr  Ser  Arg  Thr  Ser  Gly
     2270                 2275                 2280

Glu  Ser  Gly  Ala  Glu  Gln  Ala  Arg  Pro  Leu  Pro  Met  Val  Pro  Trp
     2285                 2290                 2295

Leu  Leu  Ser  Ala  Lys  Thr  Ser  Gln  Ala  Leu  Ala  Ala  Gln  Ala  Arg
     2300                 2305                 2310

Arg  Leu  Ser  Ala  His  Leu  Arg  Ala  Asn  Pro  Asp  Leu  Arg  Ser  Ala
     2315                 2320                 2325

Asp  Val  Ala  His  Ser  Leu  Leu  Thr  Thr  Arg  Ser  Val  His  Ala  Glu
     2330                 2335                 2340

Arg  Ala  Val  Phe  Ile  Ala  Gly  Asp  Arg  Asp  Glu  Ala  Leu  Ala  Ala
     2345                 2350                 2355

Leu  Asp  Ala  Leu  Ala  Asp  Gly  Thr  Pro  Ala  Pro  His  Leu  Val  Gln
     2360                 2365                 2370

Gly  Leu  Ala  Asp  Val  Ser  Gly  Lys  Thr  Val  Phe  Val  Phe  Pro  Gly
     2375                 2380                 2385

Gln  Gly  Ser  Gln  Trp  Val  Gly  Met  Ala  Val  Glu  Leu  Leu  Asp  Gly
     2390                 2395                 2400
```

```
Ser Glu Val Phe Ala Glu His Met Ala Ala Cys Ala Arg Ala Leu
2405                2410                2415

Glu Pro Phe Val Asp Trp Ser Leu Glu Asp Val Leu Arg Gln Thr
2420                2425                2430

Asp Gly Thr Trp Pro Leu Glu Arg Val Glu Val Gln Pro Val
2435                2440                2445

Leu Trp Ala Val Met Val Ser Leu Ala Gly Leu Trp Gln Ala His
2450                2455                2460

Gly Val Glu Pro Ala Ala Val Leu Gly His Ser Gln Gly Glu Ile
2465                2470                2475

Ala Ala Ala Cys Val Ala Gly Ala Leu Ser Leu Glu Asp Gly Ala
2480                2485                2490

Arg Val Val Ala Leu Arg Ser Gln Ala Ile Ala Glu Thr Leu Ala
2495                2500                2505

Gly His Gly Gly Met Leu Ser Ile Ala Ala Pro Ala Thr Asp Ile
2510                2515                2520

Ala Pro Leu Ile Ala Arg Trp Asn Glu Arg Ile Ser Ile Ala Thr
2525                2530                2535

Val Asn Gly Pro His Ser Val Val Ala Gly Asp Pro Asp Ala
2540                2545                2550

Leu Glu Ala Leu Arg Gly Glu Leu Glu Thr Arg Gly Leu Arg Asn
2555                2560                2565

Arg Arg Ile Pro Val Asp Tyr Ala Ser His Thr Pro His Val Glu
2570                2575                2580

Ala Ile Arg Glu Arg Leu Leu Ala Asp Leu Ala Val Ile Gln Pro
2585                2590                2595

Arg Ala Ala Ser Ile Pro Val Leu Ser Thr Val Thr Gly Ala Trp
2600                2605                2610

Leu Asp Thr Thr Val Met Asp Ala Glu Tyr Trp Tyr Arg Asn Leu
2615                2620                2625

Arg Gln Thr Val Glu Phe Glu Ala Ala Thr Arg Thr Leu Leu Asp
2630                2635                2640

Gln Asp His Arg Tyr Phe Val Glu Ile Ser Pro His Pro Val Leu
2645                2650                2655

Ser Ala Met Val Arg Asp Cys Leu Asp Thr Ser Arg Pro Val Val
2660                2665                2670

Thr Ala Pro Thr Leu Arg Arg Asp Arg Thr Asp Ala Thr Ala Ala
2675                2680                2685

Leu Thr Ala Leu Ala Glu Ala His Gly His Gly Val Pro Val Asp
2690                2695                2700

Trp Ala Ser Leu Phe Ala Gly Ser Thr Ala Arg Ala Val His Leu
2705                2710                2715

Pro Thr Tyr Pro Phe Gln Arg Gln His Tyr Trp Leu Asp Ser Gly
2720                2725                2730

Thr Gly Ser Ser Asp Met Ser Thr Ala Gly Leu Ala Ser Pro Asp
2735                2740                2745

His Pro Leu Leu Gly Ala Val Thr Thr Val Ala Gly Glu Asp Gly
2750                2755                2760

His Leu Phe Thr Gly Arg Leu Ser Val Arg Thr His Pro Trp Leu
2765                2770                2775

Ala Asp His Gln Ile Thr Gly Ser Val Leu Leu Pro Gly Thr Ala
2780                2785                2790

Phe Val Glu Leu Ala Val Arg Ala Gly Asp Gln Ala Gly Cys Gly
2795                2800                2805
```

Arg Val Glu Glu Leu Thr Leu Leu Ala Pro Val Leu Pro Glu
2810            2815                2820

Glu Gly Ser Val Arg Val Gln Met Lys Val Gly Glu Pro Asp Ala
2825            2830                2835

Thr Gly Arg Arg Thr Ile Glu Val Tyr Ser Ser Asp Gln Gln Ala
2840            2845                2850

Pro Gly Arg Glu Arg Trp Val Leu Asn Ala Ser Gly Met Leu Ala
2855            2860                2865

Gly Glu Pro Val Glu Ala Pro Pro Ser Leu Thr Thr Trp Pro Pro
2870            2875                2880

Glu Gly Ala Val Pro Val Pro Leu Asp Gly Phe His Asp Arg Leu
2885            2890                2895

Ala Ala Arg Gly Phe Gly Tyr Gly Pro Thr Phe Arg Gly Leu Ser
2900            2905                2910

Ala Ala Trp Ser Arg Gly Asp Glu Ile Phe Ala Glu Ala Ala Leu
2915            2920                2925

Pro Ser Gly His Arg Gln Asp Ala Ala Arg Phe Gly Leu His Pro
2930            2935                2940

Ala Leu Leu Asp Ala Ala Leu His Ala Met Glu Leu Arg Glu Pro
2945            2950                2955

Arg Pro Ala Gly Asp Gly Val Arg Leu Pro Phe Ala Trp Asn Gly
2960            2965                2970

Phe Ser Leu His Ala Ser Gly Ala Glu Ala Val Arg Leu Arg Leu
2975            2980                2985

Ala Pro Thr Gly Ala Asp Ala Leu Ser Val Thr Leu Ala Asp Ala
2990            2995                3000

Ile Gly Arg Pro Val Ala Ser Ala Arg Ser Leu Ala Leu Arg Glu
3005            3010                3015

Leu Ser Ser Asp Leu Leu Arg Pro Ala Ser Val Ser Tyr Gly Asp
3020            3025                3030

Ser Leu Phe Arg Thr Ala Trp Ile Pro Ala Leu Val Gly Pro Glu
3035            3040                3045

Ala Glu Ser Gly Pro Gly Arg Pro Ser Ala Gly Trp Ala Val Leu
3050            3055                3060

Gly Pro Asp Pro Leu Gly Ala Ala Asn Ala Leu Asn Leu Thr Gly
3065            3070                3075

Thr Ser Cys Ser Cys Tyr Pro Asp Leu Ala Ala Leu Ile Ala Ala
3080            3085                3090

Val Asp Gly Gly Ala Ala Val Pro Glu Ala Val Leu Ala Pro Tyr
3095            3100                3105

Ala Ala Glu Pro Ala Pro Asp Ala Gly Ser Pro Ala Asp Ala Val
3110            3115                3120

Arg Ala Ser Thr Gly Arg Ala Leu Gln Leu Leu Gln Ser Trp Leu
3125            3130                3135

Ser Glu Asp Arg Leu Glu Arg Ser Arg Leu Ile Val Leu Thr Arg
3140            3145                3150

Gly Ala Val Ala Val Gly Thr Asp Glu Gly Val Thr Asp Leu Val
3155            3160                3165

Ser Ala Ser Val Arg Gly Leu Val Arg Ser Ala Gln Ala Glu His
3170            3175                3180

Pro Gly Arg Phe Ser Leu Val Asp Ile Asp Asp Arg Glu Glu Ser
3185            3190                3195

Trp Ala Val Leu Ser Ala Ala Ala Val Ser Gly Glu Pro Gln Val

```
                       3200                3205                   3210

Ala Leu Arg Cys Gly Gln Met Lys Val Pro Arg Leu Gly Ser Val
        3215                3220                   3225

Asp Val Pro Thr Thr Gly Met Pro Glu Met Pro Asp Val Trp Gly
        3230                3235                   3240

Val Asp Gly Thr Val Leu Ile Thr Gly Thr Gly Val Leu Gly
        3245                3250                   3255

Gly Leu Val Ala Arg His Leu Ala Gly His Gly Val Arg Arg
        3260                3265                   3270

Leu Leu Leu Cys Ser Arg Arg Gly Pro Asp Ala Pro Gly Ala Val
        3275                3280                   3285

Glu Leu Val Ala Glu Leu Thr Ala Leu Gly Ala Asp Val Thr Val
        3290                3295                   3300

Ala Ala Cys Asp Ala Ala Asp Arg Asp Ala Leu Ala Ala Leu Leu
        3305                3310                   3315

Asp Thr Val Pro Ala Thr His Pro Leu Thr Gly Val Val His Thr
        3320                3325                   3330

Ala Gly Val Ile Asp Asp Ala Thr Val Thr Thr Leu Thr Pro Glu
        3335                3340                   3345

Arg Ile Asp Ala Val Leu Arg Pro Lys Val Asp Ala Ala Leu Asn
        3350                3355                   3360

Leu His Gln Leu Thr Ala His Leu Gly Leu Thr Arg Phe Val Leu
        3365                3370                   3375

Phe Ser Ser Ala Ala Gly Leu Phe Gly Gly Ala Gly Gln Gly Asn
        3380                3385                   3390

Tyr Ala Ala Ala Asn Ala Phe Leu Asp Ala Leu Ala Gln His Arg
        3395                3400                   3405

Arg Ala Asn Gly Leu Asn Ala Gln Ser Leu Ala Trp Gly Leu Trp
        3410                3415                   3420

Ala Glu Ala Ser Gly Met Thr Gly His Leu Asp Ala Ala Asp Leu
        3425                3430                   3435

Ala Arg Met Gly Arg Ser Gly Leu Thr Ala Met Pro Thr Gly Asp
        3440                3445                   3450

Gly Leu Ala Leu Leu Asp Thr Ala Gln Arg Val Asp Glu Ala Thr
        3455                3460                   3465

Leu Val Thr Ala Ala Leu Asp Thr Arg Ala Leu His Ala Arg Ala
        3470                3475                   3480

Ala Asp Gly Thr Leu Pro Ala Leu Phe His Ala Leu Val Pro Val
        3485                3490                   3495

Pro Arg Arg Ser Ala Thr Ser Pro Ala Ala Gln Ala Ala Gly Pro
        3500                3505                   3510

Asp Gly Leu Arg Gln Arg Leu Ser Gly Leu Val Gly Glu Arg
        3515                3520                   3525

Arg Ala Ala Leu Leu Asp Leu Val Cys Gly His Val Ala Arg Val
        3530                3535                   3540

Leu Gly His Ala Asp Pro Ser Ser Ile Glu Glu Asn Lys Gly Phe
        3545                3550                   3555

Lys Asp Thr Gly Phe Asp Ser Leu Ser Ala Val Glu Phe Arg Asn
        3560                3565                   3570

Arg Leu His Gly Ala Thr Gly Leu Arg Leu Pro Ala Thr Leu Val
        3575                3580                   3585

Phe Asp Tyr Pro Thr Pro Ala Ala Leu Thr Asp His Leu Tyr Asp
        3590                3595                   3600
```

-continued

| | | | | | | | | | | |
|---|---|---|---|---|---|---|---|---|---|---|
| Glu | Leu | Leu | Gly | Ser | Arg | Glu | Asp | Ala | Val | Leu | Ala | Pro | Ile | Thr |
| | | | 3605 | | | | 3610 | | | 3615 |
| Arg | Ala | Ala | Tyr | Asp | Pro | Val | Asp | Phe | Asp | Tyr | Pro | Thr | Pro | Ala |
| 3620 | | | | | 3625 | | | | | 3630 |
| Ala | Leu | Thr | Asp | His | Leu | Tyr | Asp | Glu | Leu | Leu | Gly | Ser | Arg | Glu |
| 3635 | | | | | 3640 | | | | | 3645 |
| Asp | Ala | Val | Leu | Ala | Pro | Ile | Thr | Arg | Ala | Ala | Tyr | Asp | Glu | Pro |
| 3650 | | | | | 3655 | | | | | 3660 |
| Ile | Ala | Ile | Val | Gly | Met | Ala | Cys | Arg | Tyr | Pro | Gly | Gly | Val | Glu |
| 3665 | | | | | 3670 | | | | | 3675 |
| Ser | Pro | Glu | Asp | Leu | Trp | Gln | Leu | Val | Ala | Asp | Gly | Arg | Asp | Ala |
| 3680 | | | | | 3685 | | | | | 3690 |
| Ile | Ser | Asp | Phe | Pro | Ala | Asp | Arg | Gly | Trp | Asn | Val | Glu | Ser | Leu |
| 3695 | | | | | 3700 | | | | | 3705 |
| Tyr | His | Pro | Asp | Pro | Asp | His | Pro | Gly | Thr | Ser | Tyr | Thr | Arg | Ala |
| 3710 | | | | | 3715 | | | | | 3720 |
| Gly | Gly | Phe | Leu | His | Asp | Ala | Ala | Asp | Phe | Asp | Pro | Glu | Phe | Phe |
| 3725 | | | | | 3730 | | | | | 3735 |
| Gly | Ile | Ser | Pro | Arg | Glu | Ala | Leu | Ala | Thr | Asp | Pro | Gln | Gln | Arg |
| 3740 | | | | | 3745 | | | | | 3750 |
| Leu | Leu | Leu | Glu | Thr | Ser | Trp | Glu | Ala | Met | Glu | Arg | Ala | Gly | Ile |
| 3755 | | | | | 3760 | | | | | 3765 |
| Asn | Pro | Ser | Thr | Leu | Lys | Gly | Thr | Pro | Thr | Gly | Val | Phe | Leu | Gly |
| 3770 | | | | | 3775 | | | | | 3780 |
| Val | Met | Tyr | Asn | Asp | Tyr | Gly | Thr | Ala | Met | Gln | Gln | Ala | Ala | Glu |
| 3785 | | | | | 3790 | | | | | 3795 |
| Val | Phe | Glu | Gly | His | Met | Ala | Ser | Gly | Ser | Ala | Gly | Ser | Val | Ala |
| 3800 | | | | | 3805 | | | | | 3810 |
| Ser | Gly | Arg | Val | Ser | Tyr | Thr | Phe | Gly | Leu | Glu | Gly | Pro | Ala | Val |
| 3815 | | | | | 3820 | | | | | 3825 |
| Thr | Val | Asp | Thr | Ala | Cys | Ser | Ser | Ser | Leu | Val | Ala | Leu | His | Leu |
| 3830 | | | | | 3835 | | | | | 3840 |
| Ala | Ala | Gln | Ala | Leu | Arg | Asn | Gly | Glu | Cys | Thr | Leu | Ala | Leu | Ala |
| 3845 | | | | | 3850 | | | | | 3855 |
| Gly | Gly | Val | Ala | Val | Met | Ser | Thr | Pro | Ala | Thr | Phe | Val | Glu | Phe |
| 3860 | | | | | 3865 | | | | | 3870 |
| Ser | Arg | Gln | Arg | Gly | Leu | Ala | Ala | Asp | Gly | Arg | Cys | Lys | Ala | Phe |
| 3875 | | | | | 3880 | | | | | 3885 |
| Ala | Asp | Ala | Ala | Asp | Gly | Thr | Gly | Trp | Gly | Glu | Gly | Val | Gly | Val |
| 3890 | | | | | 3895 | | | | | 3900 |
| Leu | Leu | Val | Glu | Arg | Leu | Ser | Asp | Ala | Arg | Arg | Asn | Gly | His | Pro |
| 3905 | | | | | 3910 | | | | | 3915 |
| Val | Leu | Ala | Val | Val | Ser | Gly | Ser | Ala | Val | Asn | Gln | Asp | Gly | Ala |
| 3920 | | | | | 3925 | | | | | 3930 |
| Ser | Asn | Gly | Leu | Thr | Ala | Pro | Asn | Gly | Pro | Ser | Gln | Gln | Arg | Val |
| 3935 | | | | | 3940 | | | | | 3945 |
| Ile | Gln | Gln | Ala | Leu | Ala | Asn | Ala | Gly | Leu | Ala | Gly | Ala | Asp | Val |
| 3950 | | | | | 3955 | | | | | 3960 |
| Asp | Ala | Val | Glu | Ala | His | Gly | Thr | Gly | Thr | Arg | Leu | Gly | Asp | Pro |
| 3965 | | | | | 3970 | | | | | 3975 |
| Ile | Glu | Ala | Gln | Ala | Leu | Ile | Ala | Thr | Tyr | Gly | Gln | Ala | Arg | Ser |
| 3980 | | | | | 3985 | | | | | 3990 |
| Ala | Asp | Arg | Pro | Leu | Trp | Leu | Gly | Ser | Leu | Lys | Ser | Asn | Ile | Gly |
| 3995 | | | | | 4000 | | | | | 4005 |

His Thr Gln Ala Ala Gly Val Ala Gly Val Ile Lys Met Val
4010                4015                4020

Gln Ala Met Gln His Gly Thr Leu Pro Pro Thr Leu His Ile Asp
    4025                4030                4035

Gln Pro Thr Gly Gln Val Asp Trp Ala Thr Gly Ala Val Glu Leu
4040                4045                4050

Leu Thr Glu Ala Val Pro Trp Pro Asp Ser Asp Arg Pro Arg Arg
    4055                4060                4065

Val Ala Val Ser Ser Phe Gly Val Ser Gly Thr Asn Ala His Val
4070                4075                4080

Ile Ile Glu His Thr Pro His Thr Pro His Thr Thr Arg Thr Cys
    4085                4090                4095

Pro Ile Leu Pro Ile Pro Pro Gly Pro Ala Asp Cys Ala Gly Pro
4100                4105                4110

Ser Ala Gly Ala Trp Leu Leu Ser Ala Lys Thr Ser Gln Ala Leu
    4115                4120                4125

Ala Ala Gln Ala Arg Arg Leu Ser Ala His Leu Arg Ala Asn Pro
4130                4135                4140

Asp Leu Arg Ser Ala Asp Val Ala His Ser Leu Leu Thr Thr Arg
    4145                4150                4155

Ser Val His Ala Glu Arg Ala Val Phe Ile Ala Gly Asp Arg Asp
4160                4165                4170

Glu Ala Leu Ala Ala Leu Asp Ala Leu Ala Asp Gly Thr Pro Ala
    4175                4180                4185

Pro His Leu Val Gln Gly Leu Ala Asp Val Ser Gly Lys Thr Val
4190                4195                4200

Phe Val Phe Pro Gly Gln Gly Ser Gln Trp Val Gly Met Ala Val
    4205                4210                4215

Glu Leu Leu Asp Gly Ser Glu Val Phe Ala Glu His Met Ala Ala
4220                4225                4230

Cys Ala Arg Ala Leu Glu Pro Phe Val Asp Trp Ser Leu Glu Asp
    4235                4240                4245

Val Leu Arg Gln Thr Asp Gly Thr Trp Pro Leu Glu Arg Val Glu
4250                4255                4260

Val Val Gln Pro Val Leu Trp Ala Val Met Val Ser Leu Ala Gly
    4265                4270                4275

Leu Trp Gln Ala His Gly Val Glu Pro Ala Ala Val Leu Gly His
4280                4285                4290

Ser Gln Gly Glu Ile Ala Ala Cys Val Ala Gly Ala Leu Ser
    4295                4300                4305

Leu Glu Asp Gly Ala Arg Val Val Ala Leu Arg Ser Gln Ala Ile
4310                4315                4320

Ala Glu Thr Leu Ala Gly His Gly Gly Met Leu Ser Ile Ala Ala
    4325                4330                4335

Pro Ala Thr Asp Ile Ala Pro Leu Ile Ala Arg Trp Asn Glu Arg
4340                4345                4350

Ile Ser Ile Ala Thr Val Asn Gly Pro His Ser Val Val Val Ala
    4355                4360                4365

Gly Asp Pro Asp Ala Leu Glu Ala Leu Arg Gly Glu Leu Glu Thr
4370                4375                4380

Arg Gly Leu Arg Asn Arg Arg Ile Pro Val Asp Tyr Ala Ser His
    4385                4390                4395

Thr Pro His Val Glu Ala Ile Arg Glu Arg Leu Leu Ala Asp Leu

-continued

```
                4400            4405            4410
Ala Val Ile Gln Pro Arg Ala Ser Ile Pro Val Leu Ser Thr
        4415            4420            4425
Val Thr Gly Ala Trp Leu Asp Thr Thr Val Met Asp Ala Glu Tyr
        4430            4435            4440
Trp Tyr Arg Asn Leu Arg Gln Thr Val Glu Phe Glu Ala Ala Thr
        4445            4450            4455
Arg Thr Leu Leu Asp Gln Asp His Arg Tyr Phe Val Glu Ile Ser
        4460            4465            4470
Pro His Pro Val Leu Thr Ile Gly Leu Gln Gln Thr Ile Glu Glu
        4475            4480            4485
Thr Thr Ala Pro Ala Arg Thr Leu Ser Thr Leu Arg Arg Asn Glu
        4490            4495            4500
Gly Thr Leu Arg His Leu Phe Thr Ser Leu Ala Gln Ala His Ala
        4505            4510            4515
His Gly Leu Thr Ile Asp Trp Thr Pro Ala Phe Thr His Thr Glu
        4520            4525            4530
Pro Arg Thr Thr Pro Leu Pro Thr Tyr Pro Phe Gln His Glu Arg
        4535            4540            4545
Tyr Trp Leu Asp Thr Ala Glu Pro Pro Val Gly Gln Gly Ala Gly
        4550            4555            4560
Thr Asp Thr Val Glu Ser Gly Phe Trp Asp Ala Val Glu Gly Glu
        4565            4570            4575
Glu Trp Gln Thr Leu Ala Asp Thr Leu Gly Val Thr Ala Asp Ala
        4580            4585            4590
Pro Phe Asp Ser Val Met Ser Ala Leu Ser Ser Trp Arg Leu Arg
        4595            4600            4605
Gln Arg Glu Gln Ser Leu Val Asp Gly Trp Arg Tyr Arg Ile Glu
        4610            4615            4620
Trp Lys Pro Phe Arg Ala Pro Val Ser Ala Pro Asp Ser Val Ser
        4625            4630            4635
Gly Thr Trp Trp Val Val Pro Ala His Ala Gly Asp Ala Asp
        4640            4645            4650
Arg Glu Arg Ala Gln Ala Val Arg Gly Thr Leu Glu Ser Ser Gly
        4655            4660            4665
Arg Ala Arg Thr Ile Leu Val Ala Val Asp Pro Ala Ala Asp Asp
        4670            4675            4680
Arg Gly Ser Leu Glu Leu Lys Leu Arg Asp Ala Ala Thr Glu Ala
        4685            4690            4695
Gly Pro Pro Ala Gly Val Leu Ser Leu Leu Ala Thr Asp Glu Arg
        4700            4705            4710
Pro Leu Pro Gly His Asp Val Val Pro Gly Gly Leu Ala Ala Asn
        4715            4720            4725
Leu Ala Leu Val Gln Ala Leu Gly Asp Ala Gln Ile Asp Ala Pro
        4730            4735            4740
Leu Trp Val Gly Thr Cys Gly Ala Val Ser Ala Gly Arg Ser Asp
        4745            4750            4755
Arg Leu Ala Asn Pro Gly Gln Ala Ala Val Trp Gly Leu Gly Arg
        4760            4765            4770
Val Val Ala Leu Glu His Pro Glu Arg Trp Gly Gly Leu Ile Asp
        4775            4780            4785
Leu Pro Val Val Leu Asp Pro Arg Ala Val Glu Arg Leu Val Thr
        4790            4795            4800
```

```
Val Leu Ala Ala Ser Gly Glu Glu Asp Gln Leu Ala Val Arg Ala
4805                 4810                4815

Ser Gly Val Leu Val Arg Arg Leu Val Arg Val Pro Ala Arg Gln
4820                 4825                4830

Val Pro Asp Gly Val Gln Trp Lys Pro Glu Gly Thr Val Leu Val
4835                 4840                4845

Thr Gly Gly Thr Gly Ala Leu Gly Ala Glu Val Ala Arg Trp Leu
4850                 4855                4860

Ala His Gly Gly Ala Glu His Leu Val Leu Thr Ser Arg Arg Gly
4865                 4870                4875

Gly Ser Ala Pro Gly Ala Ala Glu Leu Thr Asp Glu Leu Leu Ala
4880                 4885                4890

Leu Gly Thr Glu Val Thr Leu Ala Ala Cys Asp Met Ala Asp Arg
4895                 4900                4905

Asp Ala Val Ala Ala Leu Leu Ala Glu His Ala Pro Ser Ser Val
4910                 4915                4920

Val His Thr Ala Gly Val Leu Asp Asp Gly Val Leu Asp Ser Leu
4925                 4930                4935

Asp Arg Gly Arg Leu Glu Ser Val Leu Leu Pro Lys Val Ala Ala
4940                 4945                4950

Ala Arg His Leu His Glu Leu Thr Lys Asp Ala Asn Val Ser Ala
4955                 4960                4965

Phe Val Leu Phe Ser Ser Ala Ala Gly Val Leu Gly Ser Ala Gly
4970                 4975                4980

Gln Gly Asn Tyr Ala Ala Ala Asn Ala Tyr Leu Asp Ala Leu Ala
4985                 4990                4995

Glu Gln Arg Arg Ala Asp Gly Leu Val Ala His Ser Ile Ala Trp
5000                 5005                5010

Gly Ala Trp Asp Gly Gly Gly Leu Ala Val Gly Asp Ser Val Val
5015                 5020                5025

Glu Glu Arg Leu Arg His Gly Gly Val Val Pro Met Arg Pro Gln
5030                 5035                5040

Leu Ala Ile Thr Ala Leu Gln Gln Thr Leu Asp Arg Ala Glu Thr
5045                 5050                5055

Ala Val Val Ile Ala Asp Val Asp Trp Pro Arg Tyr Leu Thr Ala
5060                 5065                5070

Val Thr Pro Arg Pro Trp Leu Ala Asp Leu Pro Glu Val Ala Gln
5075                 5080                5085

Ala Leu Asn Ala Asp Asp Ala Ala Gly Ala Pro Cys Gly Thr Ala
5090                 5095                5100

Gly Gln Gly Ser Ser Pro Leu Ala Glu Arg Leu Ser Gly Arg Pro
5105                 5110                5115

Ala Pro Glu Gln Arg Arg Leu Val Leu Asp Leu Val Arg Thr Asn
5120                 5125                5130

Val Ala Ala Val Leu Gly His Ala Gly Ala Glu Ser Ile Glu Ser
5135                 5140                5145

Gly Arg Ala Phe Arg Glu Leu Gly Phe Asp Ser Leu Thr Ala Val
5150                 5155                5160

Glu Leu Arg Asn Arg Leu Ala Ala Ala Thr Gly Leu Arg Leu Pro
5165                 5170                5175

Thr Thr Leu Val Phe Asp Tyr Pro Ser Ala Ala Val Leu Ala Asp
5180                 5185                5190

His Leu Tyr Ala Gln Ala Ile Gly Ser Asp Glu Gly Pro Val Ala
5195                 5200                5205
```

```
Asp Leu Ser Ser Gly Ala Asp Pro Ala Ala Gly Pro Asp Asp Glu
    5210            5215                5220

Pro Ile Ala Ile Val Ser Met Ser Cys Arg Phe Pro Gly Gly Val
    5225            5230                5235

Ser Ser Pro Glu Glu Leu Trp Gln Leu Leu Leu Ala Gly Glu Asp
    5240            5245                5250

Thr Ile Thr Gly Phe Pro Asp Arg Asp Trp Asp Val Asp Ala
    5255            5260                5265

Leu Tyr Asp Pro Asp Pro Asp His Pro Gly Thr Thr Tyr Ser Arg
    5270            5275                5280

Ser Gly Ala Phe Leu Ser Asp Ala Ala Gly Phe Asp Ala Thr Leu
    5285            5290                5295

Phe Gly Ile Ser Pro Arg Glu Ala Leu Ala Met Asp Pro Gln Gln
    5300            5305                5310

Arg Leu Leu Leu Glu Thr Ala Trp Glu Val Phe Glu Arg Ala Gly
    5315            5320                5325

Ile Asp Pro Thr Ser Val Arg Gly Ser Arg Ala Gly Val Phe Val
    5330            5335                5340

Gly Thr Asn Gly Gln Asp Tyr Ala Arg His Val Pro Gln Glu Pro
    5345            5350                5355

Ile Gly Val Glu Gly Tyr Leu Leu Ala Gly Asn Ala Ala Ser Val
    5360            5365                5370

Ile Ser Gly Arg Leu Ser Tyr Thr Phe Gly Leu Glu Gly Pro Ala
    5375            5380                5385

Val Thr Val Asp Thr Ala Cys Ser Ser Ser Leu Val Ala Leu His
    5390            5395                5400

Leu Ala Val Gln Ala Leu Arg Asn Gly Glu Cys Ser Ile Ala Leu
    5405            5410                5415

Ala Gly Gly Val Ser Val Met Ser Thr Pro Ala Ala Phe Val Glu
    5420            5425                5430

Phe Ser Arg Gln Arg Gly Leu Ala Ala Asp Gly Arg Cys Lys Ala
    5435            5440                5445

Phe Ala Asp Ala Ala Asp Gly Thr Gly Trp Gly Glu Gly Val Gly
    5450            5455                5460

Val Leu Leu Val Glu Arg Leu Ser Asp Ala Arg Arg Asn Gly His
    5465            5470                5475

Pro Val Leu Ala Val Val Arg Gly Ser Ala Val Asn Gln Asp Gly
    5480            5485                5490

Ala Ser Asn Gly Leu Thr Ala Pro Asn Gly Pro Ser Gln Gln Arg
    5495            5500                5505

Val Ile Arg Gln Ala Leu Val Asp Ala Ala Leu Thr Gly Ser Asp
    5510            5515                5520

Ile Asp Ala Val Glu Ala His Gly Thr Gly Thr Arg Leu Gly Asp
    5525            5530                5535

Pro Ile Glu Ala Gln Ala Leu Ile Ala Thr Tyr Gly Gln Asp Arg
    5540            5545                5550

Pro Ala Asn Arg Pro Leu Trp Leu Gly Ser Val Lys Ser Asn Ile
    5555            5560                5565

Ala His Thr Gln Ala Ala Ala Gly Val Ala Gly Val Ile Lys Met
    5570            5575                5580

Val Gln Ala Ile Arg His Gly Val Leu Pro Lys Thr Leu His Val
    5585            5590                5595

Asp Arg Pro Thr Ser His Val Asp Trp Glu Ala Gly Ala Val Glu
```

-continued

```
                      5600              5605              5610

Leu Leu Thr Glu Ala Met Pro Trp Pro Glu Thr Asp Arg Pro Arg
            5615              5620              5625

Arg Ala Gly Ile Ser Ser Phe Gly Val Ser Gly Thr Asn Ala His
            5630              5635              5640

Thr Ile Val Glu Gln Ala Pro Ala Ala Glu Asp Glu Pro Glu Thr
            5645              5650              5655

Gly Pro Pro Ala Asp Ala Pro Pro Thr Val Val Pro Trp Val Leu
            5660              5665              5670

Ser Ala Ala Thr Glu Asp Ala Leu Arg Glu Gln Ala Ala Arg Leu
            5675              5680              5685

Ala Thr Tyr Leu Asp Glu Arg Pro Glu Pro Ser Pro Ala Asp Ile
            5690              5695              5700

Gly Ser Ser Leu Val Thr Thr Arg Ala Ala Leu Asp His Arg Ala
            5705              5710              5715

Val Val Leu Gly Glu Asp Arg Asp Ala Leu Arg Ala Gly Leu Val
            5720              5725              5730

Leu Leu Ala Asn Gly Lys Ser Gly Pro Ala Val Val Arg Gly Leu
            5735              5740              5745

Ala Arg Pro Gly Gln Lys Val Ala Phe Leu Phe Thr Gly Gln Gly
            5750              5755              5760

Ser Gln Arg Leu Gly Met Gly Arg Glu Leu His Arg His Leu Pro
            5765              5770              5775

Val Phe Arg Gln Phe Phe Asp Glu Ala Cys Ala Ala Leu Asp Ala
            5780              5785              5790

His Leu Pro Val Pro Ile Ala Ala Ala Leu Phe Ala Gln Ala Asp
            5795              5800              5805

Gly Ala Asp Ala Gly Leu Ile Asp Gly Thr Glu Phe Ala Gln Pro
            5810              5815              5820

Ala Leu Phe Ala Leu Glu Val Ala Leu Cys Arg Thr Leu Glu Phe
            5825              5830              5835

Cys Gly Val Arg Pro Val Tyr Val Ala Gly His Ser Val Gly Glu
            5840              5845              5850

Ile Ala Ala Ala His Val Ala Gly Val Phe Ser Leu Glu Asp Ala
            5855              5860              5865

Ala Arg Leu Val Val Ala Arg Gly Gln Leu Met Gln Ala Leu Pro
            5870              5875              5880

Ala Gly Gly Ala Met Val Ala Leu Gln Val Ser Glu Asp Asp Leu
            5885              5890              5895

Leu Pro Ser Leu Thr Pro Trp Leu Glu Gln Asp Arg Leu Gly Ile
            5900              5905              5910

Ala Ala Val Asn Gly Ala Ala Ser Thr Val Val Ser Gly Asp Glu
            5915              5920              5925

Glu Ala Val Leu Ala Val Ala Glu His Trp Gln Ala Arg Gly Arg
            5930              5935              5940

Lys Val Arg Arg Leu Thr Val Ser His Ala Phe His Ser Pro Arg
            5945              5950              5955

Met Asp Pro Met Leu Asp Gln Phe Arg Val Val Val Glu Gly Ile
            5960              5965              5970

Arg Phe Ala Glu Pro Ala Ile Pro Val Val Ser Val Thr Gly
            5975              5980              5985

Arg Leu Ala Glu Pro Gly Gln Leu Thr Thr Ala Asp Tyr Trp Val
            5990              5995              6000
```

```
Arg His Val Arg Gln Thr Val  Arg Phe His Asp Ala  Leu Gln Thr
6005               6010                6015

Leu Gln Thr Glu Asn Val Thr  Ala Phe Leu Glu Ile  Gly Pro Asp
6020               6025                6030

Gly Gln Leu Ser Ala Met Ala  Gln Glu Thr Leu Thr  Ala Gln Val
6035               6040                6045

His Thr Ile Pro Thr Leu Arg  Lys Asn Arg Ser Glu  Thr Thr Gly
6050               6055                6060

Leu Leu Thr Ala Leu Ala Gln  Leu His Thr Thr Gly  Thr Val Pro
6065               6070                6075

Asp Trp Thr Ala Tyr Leu Asn  His His Pro Thr Pro  Ser Thr Pro
6080               6085                6090

Val Pro Thr Tyr Pro Phe Gln  His His His Tyr Trp  Met His Gly
6095               6100                6105

Gly Thr Gln Ala Thr Asp Val  Ser Ser Ala Gly Leu  Ser Gly Ala
6110               6115                6120

Asn His Pro Leu Leu Gly Ala  Ala Val Pro Leu Ala  Gly Gly Glu
6125               6130                6135

Gly His Leu Phe Thr Gly Arg  Leu Ser Val Arg Thr  His Arg Trp
6140               6145                6150

Leu Ala Asp His Gln Val Gly  Ser Thr Val Val Leu  Pro Gly Thr
6155               6160                6165

Ala Phe Val Glu Leu Ala Val  Arg Ala Gly Asp Gln  Val Gly Cys
6170               6175                6180

Gly His Val Glu Glu Leu Thr  Leu Glu Ala Pro Leu  Val Leu Pro
6185               6190                6195

Glu Ser Gly Ala Val Gln Ile  Gln Leu Arg Leu Arg  Arg Ala Asp
6200               6205                6210

Glu Ser Gly Arg Arg Glu Leu  Val Val Tyr Gly Arg  Leu Ala Thr
6215               6220                6225

Asp Arg Glu Asp Leu Trp Ser  Glu Glu Glu Trp Thr  Arg His Ala
6230               6235                6240

Ser Gly Val Val Val Ala Ala  Ala Pro Ser Ala Pro  Glu Pro Val
6245               6250                6255

Gln Leu Thr Val Trp Pro Pro  Glu Gly Ala Thr Glu  Leu Ile Val
6260               6265                6270

Lys Asp Leu Tyr Glu Arg Ile  Ala Gly Thr Ser Phe  Gly Tyr Gly
6275               6280                6285

Pro Ala Phe Gln Gly Leu Arg  Ala Ala Trp Arg Leu  Asp Asp Ala
6290               6295                6300

Val Phe Ala Glu Val Val Leu  Pro Gln Asp Gln Tyr  Ala Val Ala
6305               6310                6315

Ser Arg Phe Gly Leu His Pro  Ala Leu Leu Asp Ala  Ala Leu His
6320               6325                6330

Gly Val Ala Leu Gly Gln Pro  Ala Ala Asp Thr Ala  Glu Pro His
6335               6340                6345

Thr Asp Arg Met Pro Phe Ser  Trp Ser Gly Val Thr  Leu Tyr Ala
6350               6355                6360

Ala Gly Ala Thr Ala Leu Arg  Val Arg Leu Asp Ile  Ala Ser Pro
6365               6370                6375

Glu Asp Val Ser Leu Leu Val  Ala Asp Gly Ser Gly  Ala Pro Val
6380               6385                6390

Ala Ala Val Asn Ser Leu Lys  Leu Arg Pro Val Ala  Ala Asp Leu
6395               6400                6405
```

```
Ala Ser Ala Gly Val Ala Asp Ser Leu Phe Arg Leu Glu Trp Ser
6410                6415                6420

Lys Ala Val Asp Asp Glu Pro Gly Arg Ala Glu Pro Gly Gln Trp
6425                6430                6435

Ala Leu Ile Gly Thr Pro Pro Gly Ala Asp Phe Thr Pro Gly Glu
6440                6445                6450

Asp Gly Val Ile Ile Gly Ser Tyr Pro Asp Met Ala Ala Leu Thr
6455                6460                6465

Asp Ala Leu Asp Lys Gly Val Ala Val Pro Gln Arg Val Leu Leu
6470                6475                6480

Ser Ala Pro Ser Glu Glu Glu Gln Asp Gln Ala His Asp Leu Ala
6485                6490                6495

Ser Ala Val Asp Lys Ala Thr Asn Ala Leu Leu Ala Val Leu Gln
6500                6505                6510

Gln Trp Leu Ser Asp Asp Arg Phe Asp Ser Ser Arg Leu Ala Val
6515                6520                6525

Leu Thr Arg His Ala Val Ser Thr Ala Gly Gln Glu Asp Val Thr
6530                6535                6540

Asp Leu Ala His Ala Ser Trp Trp Gly Leu Val Arg Ser Ala Gln
6545                6550                6555

Ser Glu His Pro Asp Arg Phe Val Leu Ala Asp Thr Asp Gly Thr
6560                6565                6570

Gln Ile Ser His Ala Ala Leu Leu Pro Ala Leu Leu Ser Gly Glu
6575                6580                6585

Pro Gln Val Ala Leu Arg Asp Gly Thr Arg Tyr Val Pro Arg Leu
6590                6595                6600

Ala Arg Ala Val Ala Ser Gly Asp Gly Pro Val Ala Arg Val Asp
6605                6610                6615

Pro Ala Gly Thr Val Leu Val Thr Gly Gly Thr Gly Thr Leu Gly
6620                6625                6630

Ser Ser Leu Ala Arg His Leu Val Val Glu His Gly Val Arg Arg
6635                6640                6645

Leu Leu Leu Val Ser Arg Arg Gly Gly Glu Ser Glu Gly Ala Ala
6650                6655                6660

Glu Leu Val Ala Glu Leu Thr Gly Leu Gly Ala Asp Val Thr Val
6665                6670                6675

Ala Ala Cys Asp Val Gly Asp Arg Gly Ala Val Ala Glu Leu Leu
6680                6685                6690

Ala Gly Ile Pro Ala Gly His Pro Leu Thr Ala Val Val His Ala
6695                6700                6705

Ser Gly Val Thr Asp Asp Ala Val Ile Glu Ala Leu Thr Ala Glu
6710                6715                6720

Gln Val Gly Arg Val Leu Arg Ser Lys Val Asp Gly Ala Val Asn
6725                6730                6735

Leu His Glu Leu Thr Arg Gly Leu Asp Leu Ser Ala Phe Val Leu
6740                6745                6750

Phe Ser Ser Ala Ala Gly Val Phe Gly Asn Pro Gly Gln Gly Asn
6755                6760                6765

Tyr Ala Ala Ala Asn Ala Phe Leu Asp Ala Leu Ala Val Arg Arg
6770                6775                6780

Arg Ala Glu Gly Leu Ala Ala Arg Ser Leu Ala Trp Gly Leu Trp
6785                6790                6795

Glu Glu Ala Ser Ala Met Thr Ser Arg Leu Ala Gly Ala Asp Leu
```

-continued

```
            6800                6805                6810

Val Arg Met Gly Arg Ala Gly Leu Leu Pro Leu Thr Thr Gly Gln
    6815                6820                6825

Gly Leu Ala Leu Phe Asp Ala Ala His Arg Thr Asp Glu Pro Leu
    6830                6835                6840

Val Leu Pro Met Arg Leu Asp Thr Thr Ala Leu Arg Ser Thr Thr
    6845                6850                6855

Gly Gln Pro Pro Ala Leu Leu Arg Asn Leu Val Arg Val Gln Ala
    6860                6865                6870

Arg Arg Thr Ala Gly Ala Ala Pro Gly Pro Asp Ala Ala Ala Thr
    6875                6880                6885

Phe Gln Gln Gln Leu Ile Ser Leu Ser Val Ala Glu Arg Gly Arg
    6890                6895                6900

Val Leu Leu Glu Thr Val Arg Gly His Ala Ala Ala Val Leu Gly
    6905                6910                6915

His Ser Gly Pro Glu Ala Val Asp Val Asp Lys Gly Phe Met Glu
    6920                6925                6930

Ala Gly Phe Asp Ser Leu Ser Ala Val Glu Phe Arg Asn Arg Leu
    6935                6940                6945

Thr Ser Thr Thr Gly Leu Arg Met Pro Ala Thr Val Thr Phe Asp
    6950                6955                6960

Tyr Pro Ser Pro Ala Ala Leu Ala Glu His Leu Leu Thr Arg Leu
    6965                6970                6975

Val Pro Glu Val Ala Met Pro Ala Glu Glu Gln His Pro His Thr
    6980                6985                6990

Arg Pro Glu Asp Gly Pro Val Asp Arg Pro Gly Asp Glu Gln Gly
    6995                7000                7005

Gly Ala Ile Asp Asp Met Asp Val Asp Ser Leu Val Glu Leu Ala
    7010                7015                7020

Leu Gly Glu
    7025

<210> SEQ ID NO 4
<211> LENGTH: 3712
<212> TYPE: PRT
<213> ORGANISM: Streptomyces sp.

<400> SEQUENCE: 4

Met Ser Lys Pro His Glu Lys Val Val Ala Ala Leu Arg Ala Ser Leu
1               5                   10                  15

Lys Ala Asn Glu Arg Leu Arg Glu Leu Asn Asp Glu Leu Ala Ser Ala
                20                  25                  30

Ser Arg Glu Pro Val Ala Ile Val Gly Met Ala Cys Arg Tyr Pro Gly
            35                  40                  45

Gly Val Thr Ser Pro Glu Glu Leu Trp Asp Leu Val Ala Gly Gly Thr
        50                  55                  60

Asp Ala Val Ser Glu Phe Pro Ala Asp Arg Gly Trp Asn Val Glu Glu
65                  70                  75                  80

Leu Tyr His Pro Asp Pro Asp His Ser Gly Thr Ser Tyr Val Arg Glu
                85                  90                  95

Gly Gly Phe Leu His Glu Ala Glu Phe Asp Pro Val Phe Phe Gly
            100                 105                 110

Met Ser Pro Arg Glu Ala Leu Ala Thr Asp Pro Gln Gln Arg Leu Leu
        115                 120                 125

Leu Glu Thr Ala Trp Glu Ala Phe Glu Arg Gly Gly Ile Asp Pro Leu
```

```
          130                 135                 140
Arg Leu Arg Gly Ser Arg Thr Gly Val Phe Val Gly Val Met Tyr Asn
145                 150                 155                 160

Asp Tyr Leu Thr Arg Leu Gln Pro Ala Pro Ala Asp Phe Glu Gly Gln
                165                 170                 175

Leu Gly Asn Gly Ser Ala Gly Ser Val Ala Thr Gly Arg Leu Ala Tyr
                180                 185                 190

Thr Phe Gly Leu Glu Gly Pro Ala Val Thr Val Asp Thr Ala Cys Ser
                195                 200                 205

Ser Ser Leu Val Ala Leu His Leu Ala Ala Gln Ala Leu Arg Asn Gly
                210                 215                 220

Glu Cys Thr Met Ala Leu Ala Gly Gly Val Ala Val Met Ala Thr Pro
225                 230                 235                 240

Gly Pro Phe Thr Glu Phe Ser Arg Gln Arg Gly Leu Ala Val Asp Gly
                245                 250                 255

Arg Cys Lys Pro Phe Ala Ala Ala Asp Gly Thr Gly Trp Ala Glu
                260                 265                 270

Gly Val Gly Leu Leu Leu Val Glu Arg Leu Ser Asp Ala Arg Arg Asn
                275                 280                 285

Gly His Pro Val Leu Ala Val Ile Arg Gly Thr Ala Val Asn Gln Asp
                290                 295                 300

Gly Ala Ser Ser Gly Leu Thr Val Pro Asn Gly Pro Ser Gln Gln Arg
305                 310                 315                 320

Val Ile Arg Gln Ala Leu Ala Asn Ala Gly Leu Ser Ala Ala Asp Val
                325                 330                 335

Asp Ala Val Glu Ala His Gly Thr Gly Thr Pro Leu Gly Asp Pro Ile
                340                 345                 350

Glu Ala Gln Ala Leu Ile Ala Thr Tyr Gly Gln Asp Arg Pro Ala Gly
                355                 360                 365

Arg Pro Leu Trp Leu Gly Ser Leu Lys Ser Asn Ile Gly His Thr Gln
                370                 375                 380

Ala Ala Ala Gly Ala Ala Gly Val Met Lys Met Val Gln Ala Met Arg
385                 390                 395                 400

His Gly Thr Leu Pro Lys Ser Leu His Ile Asp Ala Pro Thr Pro Gln
                405                 410                 415

Val Asp Trp Glu Ala Gly Ala Val Glu Leu Leu Thr Glu Ala Val Pro
                420                 425                 430

Trp His Glu Thr Asp Arg Pro Arg Arg Ala Gly Val Ser Ser Phe Gly
                435                 440                 445

Val Ser Gly Thr Asn Ala His Val Ile Ile Glu Glu Ala Pro Pro Thr
450                 455                 460

Glu Ala Pro Glu Gly Val Thr Ala Arg Ala Pro Leu Asn Ala Glu Thr
465                 470                 475                 480

Leu Pro Trp Val Val Ser Gly Arg Gly Val Ala Val Arg Ala Gln
                485                 490                 495

Ala Gly Gln Leu Arg Ser Tyr Leu Ser Glu Arg Gln Asp Ser Ser Leu
                500                 505                 510

Glu Gly Ile Gly Leu Ser Leu Ala Thr Thr Arg Ser Ala Phe Gln His
                515                 520                 525

Arg Ala Val Val Leu Ala Ala Asp His Asp Gly Phe Met Ala Gly Leu
                530                 535                 540

Asp Ala Leu Ala Thr Gly Glu Pro Ala Lys Gly Leu Val Asp Gly Glu
545                 550                 555                 560
```

```
Ala Val Ser Gly Gly Val Ala Leu Val Phe Pro Gly Gln Gly Ser
            565                 570                 575

Gln Trp Ala Gly Met Ala Leu Glu Leu Leu Asp Ser Ser Val Phe
            580                 585                 590

Arg Asp Arg Met Glu Ala Cys Ala Gln Ala Leu Ser Pro Tyr Ile Asp
            595                 600                 605

Trp Ser Leu Thr Glu Val Leu Arg Ser Cys Glu Gly Glu Leu Glu Arg
            610                 615                 620

Val Asp Val Val Gln Pro Ala Leu Trp Ala Val Met Val Ser Leu Ala
625                 630                 635                 640

Glu Leu Trp Arg Ser Phe Gly Val Arg Pro Ala Ala Val Leu Gly His
                645                 650                 655

Ser Gln Gly Glu Ile Ala Ala Ala Cys Val Ala Gly Ala Leu Ser Leu
                660                 665                 670

Glu Asp Ala Ala Leu Val Val Ala Leu Arg Ser Gln Ala Ile Ala Thr
            675                 680                 685

Glu Leu Ala Gly Arg Gly Ala Met Leu Ser Val Ala Leu Pro Lys Ala
            690                 695                 700

Arg Ala Gln Asp Trp Met Thr Gly Arg Ala Glu Arg Leu Ser Val Ala
705                 710                 715                 720

Ala Val Asn Gly Pro Gly Ser Val Val Ser Gly Asp Val Asp Ala
                725                 730                 735

Val Glu Glu Leu Arg Ala Glu Leu Ala Ala Glu Gly Val Arg Val Arg
                740                 745                 750

Arg Leu Pro Val Asp Tyr Ala Ser His Ser Ser His Val Glu Arg Ile
                755                 760                 765

Arg Thr Arg Leu Leu Ala Ala Leu Ala Pro Val Ser Pro Arg Pro Ser
770                 775                 780

Glu Ile Thr Leu Tyr Ser Ser Val Thr Gly Gly Pro Ile Asp Thr Thr
785                 790                 795                 800

Thr Met Asp Ala Glu Tyr Trp Tyr Arg Asn Leu Arg Gln Thr Val Glu
                805                 810                 815

Phe Glu Arg Ala Val Arg Thr Ser Met Ser Asp Gly Tyr Arg Phe Phe
            820                 825                 830

Ile Glu Ser Ser Pro His Pro Val Leu Thr Thr Gly Ile Glu Glu Thr
            835                 840                 845

Ala Glu Asp Ala Asp Arg Phe Ala Ala Val Gly Ser Leu Arg Arg
850                 855                 860

Ser Asp Gly Gly Pro Asp Arg Phe Leu Thr Ala Leu Ala Glu Ala His
865                 870                 875                 880

Val Arg Gly Val Pro Val Glu Trp Ala Val Met Phe Ala Gly Arg Pro
                885                 890                 895

Val Ser Gln Pro Asp Leu Pro Thr Tyr Ser Phe Gln Arg Gln Arg Tyr
                900                 905                 910

Trp Leu Ala Pro Asp Thr Ser Pro Gly Asp Asp Gly Gly Asp Glu
            915                 920                 925

Arg Ser Glu Thr Arg Phe Trp Glu Ala Val Glu Arg Gln Asp Leu Gly
            930                 935                 940

Glu Leu Ser Glu Thr Leu Arg Ile Gly Asp Ala Asp Arg Gln Ala Ser
945                 950                 955                 960

Leu Gly Glu Leu Leu Pro Ala Leu Trp Thr Trp Arg Glu Gln Asn Arg
                965                 970                 975

Ser Ala Ala Val Leu Asp Ser Trp Arg Tyr Arg Val Ser Trp Arg Pro
                980                 985                 990
```

```
Val Ser Pro Ala Ser Asp Pro Ala  Leu Pro Gly Thr Trp  Leu Ile Val
        995              1000              1005

Val Pro Ala Gly Thr Ala Asp  Gln Gln Trp Ala Glu  Ala Leu Ser
    1010            1015              1020

Arg Ala Ala Glu Gly Leu Gly  Asp Gln Ala Val Arg  Val Glu Leu
    1025            1030              1035

Gly Arg Ala Glu Ala Gly Arg  Glu Glu Tyr Ala Ala  Arg Leu Ala
    1040            1045              1050

Glu Ala Ala Ala Gly Gly Pro  Val Ala Gly Val Leu  Ser Leu Leu
    1055            1060              1065

Ala Leu Ala Glu Glu Pro Ala  Asp Ala Asp Pro Val  Trp Arg Pro
    1070            1075              1080

Tyr Val Thr Ser Thr Leu Ala  Leu Met Gln Ala Leu  Gly Asp Ala
    1085            1090              1095

Gly Ile Gly Ala Pro Leu Trp  Leu Ala Thr Arg Gly  Ala Val Ser
    1100            1105              1110

Ile Gly Arg Ser Asp Lys Pro  Val Pro Ser Thr Ala  Ala Gln Ala
    1115            1120              1125

Gln Leu Trp Gly Leu Gly Arg  Val Met Gly Leu Glu  His Pro Glu
    1130            1135              1140

Arg Trp Gly Gly Leu Val Asp  Leu Pro Glu Thr Ala  Asp Ala Arg
    1145            1150              1155

Ala Thr Ala Arg Leu Ala Gly  Ile Leu Ala Gly Gly  Leu Gly Pro
    1160            1165              1170

Glu Asp Gln Cys Ala Val Arg  Ser Ser Gly Val Tyr  Val Arg Arg
    1175            1180              1185

Leu Val Arg Ala Pro Leu Asp  Arg Arg Ala Arg Arg  Pro Ser Trp
    1190            1195              1200

His Thr Ser Arg Thr Ala Leu  Val Thr Gly Gly Thr  Gly Gly Leu
    1205            1210              1215

Gly Ala His Val Ala Arg Trp  Leu Ala Ser Thr Gly  Ala Glu His
    1220            1225              1230

Leu Val Leu Thr Ser Arg Arg  Gly Pro Asp Ala Pro  Gly Thr Asp
    1235            1240              1245

Glu Leu Cys Ala Glu Leu Ser  Ala Leu Gly Val Arg  Val Ser Val
    1250            1255              1260

Val Ala Cys Asp Val Ser Asp  Arg Asp Gln Leu Ala  Ala Thr Leu
    1265            1270              1275

Ala Arg Leu Thr Ala Asp Gly  His Thr Val Arg Thr  Val Val His
    1280            1285              1290

Ala Ala Gly Val Ser Thr Pro  Gly Ala Leu Ala Asp  Leu Gly Pro
    1295            1300              1305

Ala Glu Phe Ala Glu Ala Val  Ala Gly Lys Ala Ala  Gly Ala Ala
    1310            1315              1320

His Leu Asp Glu Leu Leu Gly  Asp Ala Glu Leu Asp  Ala Phe Val
    1325            1330              1335

Leu Phe Ser Ser Asn Ala Gly  Val Trp Gly Gly Gly  Gly Gln Gly
    1340            1345              1350

Ala Tyr Ala Ala Ala Asn Ala  Tyr Leu Asp Ala Leu  Ala Lys Arg
    1355            1360              1365

Arg Arg Ser Arg Gly Arg Val  Ala Thr Ser Val Ala  Trp Gly Ala
    1370            1375              1380

Trp Ala Gly Gly Gly Met Ala  Ala Glu Arg Thr Ala  Asp Glu Gln
```

```
                1385                1390                1395

Leu Arg Arg Arg Gly Val Arg Ala Met Asp Pro Ala Met Ala Ile
    1400                1405                1410

Ser Ala Leu Gln Glu Ala Leu Glu His Glu Thr Phe Leu Ala
    1415                1420                1425

Val Ala Asp Met Asp Trp Asp Arg Phe Leu Pro Ser Phe Thr Met
    1430                1435                1440

Ala Arg Pro Arg Pro Leu Leu Asp Asp Leu Pro Glu Val Gln Arg
    1445                1450                1455

Gln Arg Leu Ser Ala Ala Pro Ser Trp Ala Thr Ala Glu Thr Asp
    1460                1465                1470

Gly Pro Ala Leu Ala Gln Gln Leu Ala Gly Val Phe Glu Pro Glu
    1475                1480                1485

Arg Gly Arg Arg Leu Leu Asp Leu Val Arg Lys His Ala Ala Ala
    1490                1495                1500

Val Leu Gly Tyr Ala Gly Pro Asn Glu Val Glu Ala Glu Arg Ala
    1505                1510                1515

Phe Arg Glu Leu Gly Phe Asp Ser Leu Thr Ala Val Glu Met Arg
    1520                1525                1530

Asn Arg Leu Gln Pro Ala Thr Gly Leu Thr Leu Pro Ala Thr Leu
    1535                1540                1545

Val Phe Asp His Pro Thr Pro Arg Ala Leu Ala Ala His Leu Arg
    1550                1555                1560

Asp Glu Leu Phe Gly Val Gln Asp Asp Thr Pro Glu Pro Ala Arg
    1565                1570                1575

Ala Ser Ala Pro Asp Asp Asp Pro Ile Ala Ile Val Ser Met Gly
    1580                1585                1590

Cys Arg Phe Pro Gly Gly Val Ser Ser Pro Glu Gly Leu Trp Glu
    1595                1600                1605

Leu Leu Leu Ser Gly Arg Asp Ala Met Ser Ser Phe Pro Val Asp
    1610                1615                1620

Arg Gly Trp Asp Leu Asp Ser Leu Ala Gly Asp Gly Pro Gly Gln
    1625                1630                1635

Ile Gly Gly Gly Tyr Thr Leu Glu Gly Gly Phe Leu Asp Asp Ala
    1640                1645                1650

Ala Gly Phe Asp Ala Ala Leu Phe Gly Ile Ser Pro Arg Glu Ala
    1655                1660                1665

Leu Ala Met Asp Pro Gln Gln Arg Leu Leu Leu Glu Ala Ser Trp
    1670                1675                1680

Glu Ala Phe Glu Arg Ala Gly Ile Pro Ser Ala Asp Leu Arg Ser
    1685                1690                1695

Ser Arg Thr Gly Val Phe Ile Gly Ala Ser Ser Gln Gly Tyr Ala
    1700                1705                1710

Gln Val Ala Ala Glu Ser Ala Glu Gly Val Glu Gly His Val Val
    1715                1720                1725

Thr Gly Asp Ala Ala Ser Val Met Ser Gly Arg Leu Ser Tyr Thr
    1730                1735                1740

Phe Gly Leu Glu Gly Pro Ala Val Thr Val Asp Thr Ala Cys Ser
    1745                1750                1755

Ser Ser Leu Val Ala Leu His Leu Ala Ala Gln Ala Leu Arg Asn
    1760                1765                1770

Gly Glu Cys Thr Leu Ala Leu Ala Gly Gly Val Ala Val Met Val
    1775                1780                1785
```

```
Thr Pro Ala Ala Phe Val Glu Phe Ser Arg Gln Arg Gly Leu Ala
    1790            1795                1800

Ala Asp Gly Arg Cys Lys Ala Phe Ala Asp Ala Ala Asp Gly Thr
    1805            1810                1815

Gly Trp Gly Glu Gly Val Gly Val Leu Leu Val Glu Arg Leu Ser
    1820            1825                1830

Asp Ala Arg Arg Asn Gly His Pro Val Leu Ala Val Val Ser Gly
    1835            1840                1845

Ser Ala Val Asn Gln Asp Gly Ala Ser Asn Gly Leu Thr Ala Pro
    1850            1855                1860

Asn Gly Pro Ser Gln Gln Arg Val Ile Gln Gln Ala Leu Ala Asn
    1865            1870                1875

Ala Gly Leu Ala Gly Ala Asp Val Asp Ala Val Glu Ala His Gly
    1880            1885                1890

Thr Gly Thr Arg Leu Gly Asp Pro Ile Glu Ala Gln Ala Leu Ile
    1895            1900                1905

Ala Thr Tyr Gly Gln Ala Arg Ser Ala Asp Arg Pro Leu Trp Leu
    1910            1915                1920

Gly Ser Leu Lys Ser Asn Ile Gly His Thr Gln Ala Ala Ala Gly
    1925            1930                1935

Val Ala Gly Val Ile Lys Met Ile Gln Ala Met Gly His Gly Thr
    1940            1945                1950

Leu Pro Arg Thr Leu His Val Asp Arg Pro Ser Ser Gln Val Asp
    1955            1960                1965

Trp Glu Ala Gly Ala Val Glu Leu Leu Thr Glu Ala Met Pro Trp
    1970            1975                1980

Pro Glu Ala Asp Arg Pro Arg Arg Ala Ala Val Ser Ser Phe Gly
    1985            1990                1995

Val Ser Gly Thr Asn Ala His Val Ile Ile Glu His Ala Pro Gln
    2000            2005                2010

Val Thr Pro Ala Ser Gln Ala Pro Glu Pro Val Lys Ser Pro Asp
    2015            2020                2025

Ala Val Glu Ala Asp Arg Pro Val Pro Trp Leu Leu Ser Ala Gly
    2030            2035                2040

Ser Asp Ala Ala Leu Gly Glu Val Ala Glu Arg Leu Ala Ala Tyr
    2045            2050                2055

Ala Glu Ser His Pro Glu Val Ser Ala Ala Glu Val Ala Phe Ser
    2060            2065                2070

Leu Ala Thr Thr Arg Ser Leu Leu Pro Cys Arg Ala Ala Val Val
    2075            2080                2085

Gly Ala Asp Arg Asp Glu Leu Val Gln Arg Ile Arg Ser Val Gly
    2090            2095                2100

Gly Gly Thr Thr Ala Pro Gly Val Phe Cys Gly Thr Ala Ser Ser
    2105            2110                2115

Glu Cys Thr Thr Ala Phe Leu Phe Ser Gly Gln Gly Ser Gln Arg
    2120            2125                2130

Leu Gly Met Gly His Glu Leu Tyr Ala Ala His Pro Glu Phe Ala
    2135            2140                2145

Glu Ala Leu Asp Glu Val Cys Gly His Leu Asp Val Phe Gly Asp
    2150            2155                2160

Arg Pro Leu Lys Glu Val Leu Phe Ala Gln Ala Asp Gly Ala Asp
    2165            2170                2175

Ala Gly Leu Ile Asp Gly Ala Gly Phe Ala Gln Pro Ala Leu Phe
    2180            2185                2190
```

```
Ala Leu Glu Val Ala Leu Tyr Arg Thr Leu Glu Ala Trp Gly Ile
    2195                2200                2205

Thr Pro Asp Tyr Leu Ala Gly His Ser Leu Gly Glu Ile Ala Ala
    2210                2215                2220

Ala His Val Ala Gly Val Phe Ser Leu Glu Asp Ala Ala Arg Leu
    2225                2230                2235

Val Thr Ala Arg Gly Gln Leu Met Gln Ala Leu Pro Gly Gly Gly
    2240                2245                2250

Ala Met Val Ala Val Gln Ala Ser Glu Asp Glu Ile Leu Ala Ile
    2255                2260                2265

Ser Ala Pro Trp Leu Glu Gly Asp Gly Val Gly Ile Ala Ala Val
    2270                2275                2280

Asn Gly Pro Ala Ser Val Val Val Ser Gly Asp Glu Glu Ala Val
    2285                2290                2295

Leu Ala Ile Ala Gly His Trp Arg Ala Gln Gly Arg Lys Thr Arg
    2300                2305                2310

Arg Leu Ser Val Ser His Ala Phe His Ser Pro His Met Asp Pro
    2315                2320                2325

Met Leu Asp Gly Phe Arg Arg Val Val Asp Gly Met His Leu Val
    2330                2335                2340

Glu Pro Val Ile Pro Val Ile Ser Asn Leu Thr Gly Arg Leu Ala
    2345                2350                2355

Asp Pro Gly Gln Leu Thr Ser Ala Asp Tyr Trp Val Arg His Val
    2360                2365                2370

Arg Gln Ala Val Arg Phe His Asp Gly Leu Gln Thr Leu His Asp
    2375                2380                2385

Gln Gly Val Thr Thr Tyr Leu Glu Ile Gly Pro Asp Ala Gln Leu
    2390                2395                2400

Thr Ala Met Ala Gln Glu Ala Leu Ser Pro Gln Ser His Thr Val
    2405                2410                2415

Ser Thr Leu Arg Arg Asn Gln Pro Glu Thr Thr Ser Leu Leu Thr
    2420                2425                2430

Thr Leu Ala Arg Leu His Thr Thr Gly Thr Thr Pro Asp Trp Ile
    2435                2440                2445

Thr Tyr Leu Asn His Arg Pro Ser Ser Pro Thr Pro Leu Pro Thr
    2450                2455                2460

Tyr Pro Phe Gln His His Arg Tyr Trp Pro Arg Gly Asp Ala Gln
    2465                2470                2475

Ala Ala Asp Val Ser Ser Ala Gly Leu Ser Gly Ala Asn His Pro
    2480                2485                2490

Leu Leu Gly Ala Ala Val Pro Leu Ala Asp Gly Asp Gly His Leu
    2495                2500                2505

Phe Thr Gly Arg Leu Ser Ala Arg Thr His Arg Trp Leu Ala Asp
    2510                2515                2520

His Gln Val Gly Gly Asn Val Val Leu Pro Gly Thr Ala Phe Val
    2525                2530                2535

Glu Leu Ala Val Arg Ala Gly Asp Gln Val Gly Cys Ser Gln Val
    2540                2545                2550

Glu Glu Leu Thr Leu Glu Ala Pro Leu Val Leu Pro Glu Ser Gly
    2555                2560                2565

Ala Val Gln Val Gln Leu Arg Leu Gly Arg Ala Asp Glu Ser Gly
    2570                2575                2580

Arg Arg Asp Leu Thr Val Tyr Gly Arg Leu Ala Gly Gly Gly Glu
```

2585                2590                2595

Asp Leu Trp Leu Glu Glu Glu Trp Thr Arg His Ala Ser Gly Val
    2600                2605                2610

Leu Ser Ser Ala Ser Ala Pro Glu Pro Val Ala Leu Thr Val Trp
    2615                2620                2625

Pro Pro Ser Ala Ala Glu Ala Val Pro Val Glu Gly Phe Tyr Thr
    2630                2635                2640

Gly Leu Ala Glu Ser Gly Tyr Gly Tyr Gly Pro Ala Phe Gln Gly
    2645                2650                2655

Leu Arg Ala Ala Trp Arg Gln Gly Asp Thr Val Phe Ala Glu Val
    2660                2665                2670

Gln Leu Pro Glu Val Val Arg Glu Glu Ala Ala Ser Tyr Thr Ile
    2675                2680                2685

His Pro Ala Leu Leu Asp Ala Ala Leu Gln Ala Val Gly Phe Val
    2690                2695                2700

Thr Asp Gly Ser Asp Asn Pro Val Val Arg Met Pro Phe Ala Trp
    2705                2710                2715

Ser Gly Val Ser Met Tyr Ala Ser Gly Ala Ser Glu Leu Arg Val
    2720                2725                2730

Arg Leu Ala Arg Thr Gly Pro Glu Thr Val Thr Phe Ala Val Thr
    2735                2740                2745

Asp Pro Thr Gly Arg Pro Val Ala Ser Val Gly Ser Leu Val Met
    2750                2755                2760

Arg Pro Val Ala Thr Gly Val Pro Arg Leu Thr Arg Asn Gly Leu
    2765                2770                2775

His Glu Val Val Trp Glu Gln Leu Leu Asp Ala Pro Ala Thr Pro
    2780                2785                2790

Ala Thr Glu Cys Ala Val Ile Gly Asp Ala Asp Ala Ala Ala Leu
    2795                2800                2805

Leu Gly Ala Glu Ala His Pro Asp Leu Ala Ser Leu Gly Glu Ala
    2810                2815                2820

Val Pro Pro Leu Val Val Ala Val Ala Gly Gly Asp Gly Thr Arg
    2825                2830                2835

Ala Ala Leu Glu Arg Ala Leu Gly Trp Val Gln Gly Trp Met Ala
    2840                2845                2850

Glu Glu Arg Phe Ala Gly Ser Arg Leu Ala Val Val Thr Arg Gly
    2855                2860                2865

Ala Val Ala Val Gly Ala Gly Glu Val Leu Ala Asp Ala Ala Gly
    2870                2875                2880

Ala Ala Val Thr Gly Leu Val Lys Ser Ala Glu Ser Glu Asn Pro
    2885                2890                2895

Gly Arg Phe Leu Leu Val Asp Val Asp Gly Thr Thr Glu Ser Trp
    2900                2905                2910

Arg Ala Leu Pro Thr Leu Gly Gly Gly Asp Glu Pro Gln Ile Ala
    2915                2920                2925

Leu Arg Asp Gly Gln Ala Tyr Val Pro Arg Leu Val Arg Ala Gly
    2930                2935                2940

Glu Asp Gly Gly Ser Leu Leu Pro Pro Ala Gly Ala Asp Ala Trp
    2945                2950                2955

Arg Leu Glu Thr Gly Glu Ala Gly Ser Leu Asp Gly Leu Arg Leu
    2960                2965                2970

Ala Pro Ala Glu Asp Ala Gln Ala Ala Leu Leu Pro Gly Gln Val
    2975                2980                2985

-continued

```
Arg Ile Ala Val Arg Ala Ala Gly Leu Asn Phe Arg Asp Val Leu
    2990                2995                3000

Gly Ala Leu Gly Met Tyr Pro Gly Gly Leu Asp Leu Leu Gly Ser
    3005                3010                3015

Glu Ile Ala Gly Glu Val Leu Glu Thr Gly Asp Gly Val Thr Gly
    3020                3025                3030

Leu Ala Val Gly Asp Arg Val Met Gly Leu Val Ala Gly Gly Phe
    3035                3040                3045

Gly Pro Met Ala Val Ala Asp Ser Trp Arg Val Arg Ile Pro
    3050                3055                3060

Ser Gly Trp Thr Phe Thr Arg Ala Ala Gly Val Pro Val Ala Phe
    3065                3070                3075

Leu Thr Ala Leu Tyr Gly Leu Arg Glu Leu Gly Gly Leu Ala Ala
    3080                3085                3090

Gly Gln Arg Val Leu Val His Ala Ala Ala Gly Gly Val Gly Thr
    3095                3100                3105

Ala Ala Val Gln Leu Ala Arg Leu Leu Gly Ala Glu Val Tyr Ala
    3110                3115                3120

Thr Ala Ser Ala Pro Lys Gln Glu Tyr Val Ala Asp Leu Gly Val
    3125                3130                3135

Asp Arg Ala Arg Ile Ala Ser Ser Arg Thr Leu Asp Phe Ala Ser
    3140                3145                3150

Ser Phe Pro Glu Val Asp Val Val Leu Asn Ser Leu Ala Gly Glu
    3155                3160                3165

Tyr Val Asp Ala Ser Leu Gly Leu Leu Arg Glu Gly Gly Arg Phe
    3170                3175                3180

Val Glu Met Gly Lys Thr Asp Val Arg Asp Ala Ala Ala Tyr Asp
    3185                3190                3195

Gly Val Thr Tyr Arg Thr Phe Asp Leu Gly Gln Ala Gly Pro Glu
    3200                3205                3210

Leu Ile Ala Arg Met Leu Gly Glu Leu Val Glu Trp Phe Glu Ala
    3215                3220                3225

Gly Glu Leu Thr Pro Val Arg Thr Ala Ala Trp Asp Val Arg Arg
    3230                3235                3240

Ala Val Gly Ala Phe Arg Trp Met Ser Gln Ala Arg His Thr Gly
    3245                3250                3255

Lys Ile Val Leu Thr Val Pro Arg Asp Leu Asp Ala Asp Gly Thr
    3260                3265                3270

Val Leu Ile Thr Gly Gly Thr Gly Thr Leu Gly Gly Leu Leu Ala
    3275                3280                3285

Arg His Leu Val Thr Glu His Gly Val Arg His Leu Leu Leu Val
    3290                3295                3300

Ser Arg Thr Gly Glu Arg Ala Ala Leu Arg Arg Glu Leu Glu Glu
    3305                3310                3315

Leu Gly Ala Glu Val Arg Ile Ala Ala Cys Asp Met Ala Asp Arg
    3320                3325                3330

Ala Ala Val Ala Glu Leu Leu Asp Gly Ile Pro Ser Glu His Pro
    3335                3340                3345

Leu Thr Gly Val Phe His Ala Ala Gly Val Leu Asp Asp Gly Val
    3350                3355                3360

Val Thr Gly Leu Asp Ser Ala Arg Leu Ala Arg Val Leu Ala Pro
    3365                3370                3375

Lys Val Asp Gly Ala Leu His Leu His Glu Leu Thr Ala Glu Leu
    3380                3385                3390
```

```
Asp Leu Ser Ala Phe Val Leu Phe Ser Ser Met Ser Gly Leu Leu
    3395                3400                3405

Gly Ala Ser Gly Gln Ala Gly Tyr Ala Ala Asn Met Phe Leu
    3410                3415                3420

Asp Ala Leu Ala Gln Gln Arg Arg Ala Gln Gly Leu Pro Ala Leu
    3425                3430                3435

Ser Leu Ala Trp Gly Leu Trp Glu Thr Ala Ser Ala Met Thr Ala
    3440                3445                3450

His Leu Ser Asp Thr Asp Leu Arg Arg Met Gly Gly Ile Gly Met
    3455                3460                3465

Leu Gly Leu Thr Arg Asn Glu Gly Met Glu Leu Leu Asp Ala Ala
    3470                3475                3480

Trp Gln Ser Gly Glu Ala Leu Leu Val Pro Val Arg Trp Asp His
    3485                3490                3495

Arg Val Leu Arg Glu Arg Ala Ser Ser Gly Ala Arg Val Pro Ser
    3500                3505                3510

Leu Leu Arg Arg Leu Val Arg Ala Pro Arg Arg Thr Val Pro
    3515                3520                3525

Glu Ser Ala Lys Gly Ala Gly Gly Gly Leu Arg Glu Arg Leu Ala
    3530                3535                3540

Thr Leu Pro Glu Ala Glu Arg Arg Gly Met Leu Ile Glu Leu Val
    3545                3550                3555

Ala Gly His Val Ala Ala Val Leu Gly His Ala Gly Thr Asp Ala
    3560                3565                3570

Val Ser Val Asp Arg Pro Phe Lys Glu Leu Gly Phe Asp Ser Leu
    3575                3580                3585

Thr Ser Val Glu Phe Arg Asn Arg Leu Asn Glu Ala Thr Gly Leu
    3590                3595                3600

Arg Leu Pro Ser Thr Leu Val Phe Asp His Pro Thr Pro Thr Thr
    3605                3610                3615

Leu Ala Ala Arg Leu Asp Ala Leu Leu Pro Gly Ala Glu Thr Ala
    3620                3625                3630

Thr Thr Val Ala Ala Pro Thr Ser Pro His Glu Glu Leu Asp Arg
    3635                3640                3645

Leu Ala Thr Val Leu Leu Ser Pro Ala Leu Asn Met Ala Asp Arg
    3650                3655                3660

Asp Gly Leu Ala Ala Arg Leu Arg Ala Leu Ala Ser Gln Leu Gly
    3665                3670                3675

Glu Pro Thr Gly Pro Ala Asp Gly Ser Thr Val Ala Asp Arg Ile
    3680                3685                3690

Gln Ser Ala Thr Asp Asp Glu Leu Phe Glu Leu Leu Asp Asp Arg
    3695                3700                3705

Phe Glu Asn Ser
    3710

<210> SEQ ID NO 5
<211> LENGTH: 1808
<212> TYPE: PRT
<213> ORGANISM: Streptomyces sp.

<400> SEQUENCE: 5

Met Ser Gln His Asp Asp Ala Ser Asp Ala Leu Arg Thr Gly Asp Val
1               5                   10                  15

Pro Met Thr Gln Phe Pro Thr Asn Glu Asp Lys Leu Arg Asp Tyr Leu
            20                  25                  30
```

```
Lys Arg Ala Val Thr Asp Leu His His Thr Arg Glu Gln Leu Ala Ala
             35                  40                  45

Ala Glu Ala Lys Asn Arg Glu Pro Leu Ala Ile Val Ser Met Ser Cys
 50                  55                  60

Arg Phe Pro Gly Gly Val Arg Ser Pro Glu Ala Leu Trp Gln Leu Val
 65                  70                  75                  80

Arg Ala Gly Glu Asp Val Ile Ser Ser Phe Pro Thr Asp Arg Gly Trp
                 85                  90                  95

Asp Leu Asp Gly Leu Tyr Asn Pro Asp Pro Gly Asn Ser Gly Thr Thr
                100                 105                 110

Tyr Val Arg Glu Gly Gly Phe Leu Ser Asp Ala Thr Glu Phe Asp Pro
                115                 120                 125

Ala Val Phe Gly Ile Ser Pro Arg Glu Ala Leu Gly Met Asp Pro Gln
            130                 135                 140

Gln Arg Leu Met Leu Glu Thr Ser Trp Glu Ala Phe Glu Arg Ala Gly
145                 150                 155                 160

Ile Gly Pro Ala Ser Ala Arg Gly Ser Arg Thr Gly Val Phe Ile Gly
                165                 170                 175

Ala Ser Ala Gln Gly Tyr Ser Leu Leu Phe Gln Asn Ser Arg Glu Glu
            180                 185                 190

Ala Glu Gly Leu Leu Ala Thr Gly Asp Ser Ala Ser Val Ile Ser Gly
                195                 200                 205

Arg Val Ser Tyr Thr Phe Gly Leu Glu Gly Pro Ala Val Thr Leu Asp
            210                 215                 220

Thr Ala Cys Ser Ser Ser Leu Val Ala Leu His Leu Ala Val Arg Ser
225                 230                 235                 240

Val Arg Gln Gly Glu Cys Ser Met Ala Leu Val Gly Gly Val Ser Val
                245                 250                 255

Met Cys Thr Pro Ala Ile Phe Ile Glu Phe Ser Arg Gln Arg Gly Leu
            260                 265                 270

Ala Ala Asp Gly Arg Cys Lys Pro Phe Ala Ala Ala Asp Gly Thr
            275                 280                 285

Ser Trp Gly Glu Gly Ala Gly Val Val Leu Ile Glu Arg Leu Glu Asp
            290                 295                 300

Ala Arg Arg Asn Gly His Pro Val Leu Ala Val Ile Arg Gly Ser Ala
305                 310                 315                 320

Ile Asn Gln Asp Gly Ala Ser Asn Gly Leu Thr Ala Pro His Gly Pro
                325                 330                 335

Ser Gln Arg Arg Leu Ile Gln Gln Ala Leu Ala Asp Ala Gln Leu Ser
            340                 345                 350

Pro Gly Gln Ile Asp Met Val Glu Ala His Gly Thr Gly Thr Ser Leu
            355                 360                 365

Gly Asp Pro Ile Glu Ala Gln Ala Leu Leu Glu Thr Tyr Gly Ala Asn
        370                 375                 380

Arg Pro Ala Asp Arg Pro Leu Trp Leu Gly Ser Val Lys Ser Asn Ile
385                 390                 395                 400

Gly His Thr Gln Ala Ala Ala Gly Leu Ala Ser Val Ile Lys Thr Val
                405                 410                 415

Gln Ala Leu Arg His Ala His Leu Ala Arg Thr Leu His Val Asp Arg
            420                 425                 430

Pro Thr Pro Arg Val Asp Trp Ser Ser Gly Gly Val Glu Leu Leu Ala
            435                 440                 445

Asp Asp Gln Pro Trp Pro Glu Thr Gly Gln Pro Arg Arg Ala Ala Val
```

```
              450                 455                 460
Ser Ser Phe Gly Val Ser Gly Thr Asn Ala His Val Val Leu Glu Gln
465                 470                 475                 480

Ala Pro Ala Ser Glu Asn Pro Pro Leu Arg Arg Pro Gly Gly Asp Arg
                485                 490                 495

Val Ala Ala Arg Arg Val Leu Pro Leu Val Ile Ser Gly Lys Thr Pro
                500                 505                 510

Glu Ala Leu Arg Ala Gln Ala Gly Asn Leu Val Ser His Val Arg Glu
                515                 520                 525

His Pro Asp Leu Arg Leu Glu Asp Leu Gly Tyr Ser Leu Ala Thr Thr
                530                 535                 540

Arg Ser Ala Leu Gly His Arg Ala Val Val Ala Asp Thr Pro Asp
545                 550                 555                 560

Gly Phe Leu Arg Gly Cys Glu Ala Val Glu Arg Gly Glu Thr Pro Ala
                565                 570                 575

Ser Val Asp Arg Gly Val Val Arg Gly Arg Gly Thr Thr Ala Phe Leu
                580                 585                 590

Phe Thr Gly Gln Gly Ala Gln Arg Val Gly Met Gly Arg Gln Leu Tyr
                595                 600                 605

Ala Ala Ile Pro Ala Phe Ala Arg Phe Leu Asp Glu Ala Cys Ser His
                610                 615                 620

Leu Asp Arg Phe Thr Lys Gln Pro Leu Arg Asp Val Leu Phe Ala Ala
625                 630                 635                 640

Glu Gly Ser Ala Glu Ala Ala Leu Leu Asp Arg Thr Gly Phe Ala Gln
                645                 650                 655

Pro Ala Leu Phe Ala Leu Glu Val Ala Leu Phe Arg Thr Leu Glu Ser
                660                 665                 670

Trp Gly Val Thr Pro Asp Tyr Leu Ala Gly His Ser Ile Gly Glu Leu
                675                 680                 685

Ala Ala Ala His Val Ala Gly Val Leu Ser Leu Gly Asp Ala Thr Arg
                690                 695                 700

Leu Val Thr Ala Arg Gly Asn Leu Met Glu Gln Leu Pro Ala Gly Gly
705                 710                 715                 720

Gly Met Leu Ala Leu Gln Ala Ser Glu Ala Gly Val Leu Pro Leu Leu
                725                 730                 735

Asp Gly Ala Asp Gly Leu Val Ser Val Ala Ala Val Asn Ser Pro Arg
                740                 745                 750

Ser Thr Val Val Ala Gly Asp Ser Asp Ala Leu Ala Ala Leu Ala Gly
                755                 760                 765

Gln Ala Arg Ser Gln Gly Ile Lys Ala Arg His Leu Thr Val Ser His
                770                 775                 780

Ala Phe His Ser Pro Leu Met Asp Pro Val Leu Asp Ala Tyr Arg Glu
785                 790                 795                 800

Thr Ala Glu Gln Leu Ser Tyr His Pro Pro Arg Ile Pro Ile Ile Ser
                805                 810                 815

Thr Val Thr Gly Arg Ser Val Thr Thr Glu Met Ser Glu Pro Gly Tyr
                820                 825                 830

Trp Val Arg His Ala Arg Glu Ala Val Arg Phe Thr Asp Ala Val Ala
                835                 840                 845

Thr Leu Arg Gln His Gly Thr Thr Ala Tyr Leu Glu Leu Gly Pro Asp
                850                 855                 860

Ala Val Leu Thr Ala Met Thr Arg Glu His Leu Ala Gly Asp Gly Thr
865                 870                 875                 880
```

```
Ser Gly Lys Glu Ser Thr Phe Ala Ala Val Met Arg Arg Asn Arg Pro
            885                 890                 895

Glu Pro Glu Val Leu Thr Ser Ala Val Ser Gln Leu Phe Ala Arg Gly
            900                 905                 910

Thr Arg Val Asp Trp Arg Ala Val Phe Ala Asp Val Asp Gly Gln Val
            915                 920                 925

Val Gln Leu Pro Thr Tyr Ala Phe Gln Arg Ser Arg Tyr Trp Pro Gln
        930                 935                 940

Ala Ser Leu Thr Arg Pro Ala Gly Ala Ser Ala Thr Ser Leu Phe
945                 950                 955                 960

His Leu Arg Trp Val Pro Val Thr Ala Gln Asp Thr Ala Pro Ala Asp
            965                 970                 975

Asp Trp Ala Leu Leu Gly Gly Ala Asp Ala Leu Pro Gly Gln Gly Phe
        980                 985                 990

Ala Asp Leu Ala Ser Leu Gly Glu Thr Ile Asp Gly Gly Ser Ala Ala
        995                 1000                1005

Pro Arg Thr Val Cys Val Pro Leu Leu Pro Ala Asp Gly Ala
        1010            1015                1020

Gln Asp Ser Ala Ala Thr His Asp Ala His Arg Ala Leu Ala
        1025            1030                1035

Leu Ala Gln Ala Trp Leu Ala Asp Asp Arg Phe Thr Ser Ser Arg
        1040            1045                1050

Leu Val Phe Leu Thr Arg Gly Ala Val Ala Val Thr Asp Glu Glu
        1055            1060                1065

Tyr Pro Glu Asp Ser Val Asp Ala Phe Ala Tyr Ala Ser Val Trp
        1070            1075                1080

Gly Leu Leu Arg Ser Ala Gln Thr Glu Asn Pro Gly Arg Phe Gly
        1085            1090                1095

Leu Val Asp Leu Asp Pro Ala Asp Pro Asp Ala Ala Gly Gln
        1100            1105                1110

Arg Cys Pro Val Pro Ala Ala Ala Leu Asp Gly Asp Glu Pro Gln
        1115            1120                1125

Leu Ala Met Arg Arg Gly Val Val His Ala Pro Arg Leu Thr Arg
        1130            1135                1140

Val Thr Ala Ala Pro Lys Asp Pro Asp Arg Ala Pro Ala Gly Phe
        1145            1150                1155

Asp His Gly Gly Thr Val Leu Ile Thr Gly Ala Thr Gly Gly Leu
        1160            1165                1170

Gly Pro Leu Leu Ala Arg His Leu Val Val Glu His Gly Val Arg
        1175            1180                1185

His Leu Leu Leu Thr Ser Arg Arg Gly Ala Ala Ala Ser Gly Ala
        1190            1195                1200

Gln Ala Leu Leu Asp Glu Leu Ala Asp Leu Gly Ala Glu Ala Thr
        1205            1210                1215

Val Val Ser Cys Asp Leu Ala Asp Arg Glu Ala Val Ala Gly Leu
        1220            1225                1230

Leu Ala Gln Val Pro Pro Ala Arg Pro Leu Thr Ala Val Val His
        1235            1240                1245

Ala Ala Gly Val Leu Asp Asp Gly Val Ile Pro Ser Leu Ser Pro
        1250            1255                1260

Glu Arg Val Asp Gly Val Leu Arg Pro Lys Ala Asp Gly Ala Leu
        1265            1270                1275

His Leu His Glu Leu Thr Lys Asp Leu Asp Leu Ala His Phe Ile
        1280            1285                1290
```

-continued

```
Leu Phe Ser Ser Thr Ala Gly Val Leu Gly Ser Ala Gly Gln Gly
    1295                1300                1305

Asn Tyr Ala Ala Ala Asn Thr Phe Leu Asp Ala Leu Ala Gln His
    1310                1315                1320

Arg Arg Ala Ala Gly Leu Ala Ala Val Ser Leu Ala Trp Gly Thr
    1325                1330                1335

Trp Glu Pro Ser Gly Gly Met Thr Gly Gly Leu Thr Arg Ala Asp
    1340                1345                1350

Leu Glu Arg Met Thr Lys Gly Gly Met Pro Pro Leu Ser Pro Arg
    1355                1360                1365

Asp Gly Leu Ala Leu Phe Asp Ala Ala Ile Ala Ser Gly Arg Ala
    1370                1375                1380

Leu Val Val Pro Ala Val Leu Asp Leu Asp Leu Leu Arg Ser Arg
    1385                1390                1395

Ile Gly Thr Asn Val Pro Ala Leu Leu Arg Gly Leu Ile Glu Pro
    1400                1405                1410

Arg Pro Val Glu Pro Ser Ala Pro Gly Glu Ala Ala Glu Ala Leu
    1415                1420                1425

Ala Leu Arg Met Ala Ser Cys Ser Ala Ala Glu Arg Thr Gly Val
    1430                1435                1440

Leu Leu Asp Leu Val Arg Ala Asp Ala Ala Thr Val Leu Gly His
    1445                1450                1455

Asp Gly Pro His Ala Ile Asp Pro Glu Arg Gly Leu Leu Glu Ala
    1460                1465                1470

Gly Phe Asp Ser Leu Thr Thr Leu Glu Leu Arg Asn Arg Leu Ala
    1475                1480                1485

Glu Ala Thr Gly Leu Ala Val Pro Ala Gly Tyr Leu Tyr Glu Tyr
    1490                1495                1500

Pro Thr Pro Asn Leu Leu Ala Glu His Leu Ala Ala Ala Leu Ala
    1505                1510                1515

Glu Ser Pro Gln Ser Gly Ala Ala Thr Gly Ala Asp Gly Pro Ala
    1520                1525                1530

Glu Pro Leu Ser Val Leu Phe Gln Gln Ala Tyr Asp Leu Gly Lys
    1535                1540                1545

Val Thr Glu Gly Met Thr Leu Leu Arg Ser Ala Ser Ala Leu Arg
    1550                1555                1560

Pro Thr Tyr Asp Thr Pro Ser Asp Leu Ser Glu Leu Pro Gln Pro
    1565                1570                1575

Thr Arg Leu Ala Arg Gly Pro Glu Arg Ala Thr Leu Leu Cys Phe
    1580                1585                1590

Ser Ala Ile Val Ala Leu Ala Gly Ser His Gln Tyr Ser Arg Phe
    1595                1600                1605

Ala Ser Ser Phe Arg Glu Glu Arg Asp Val Ser Val Leu Tyr Ala
    1610                1615                1620

Pro Gly Phe Phe Ala Gly Glu Leu Leu Pro Thr Ser Leu Glu Thr
    1625                1630                1635

Val Ile Asp Thr Gln Val Glu Thr Val Arg Gln Gln Ala Ala Asp
    1640                1645                1650

Gly Pro Val Val Leu Val Gly Ala Ser Ser Gly Gly Trp Leu Ala
    1655                1660                1665

His Ala Ala Ala Ala Arg Leu Glu Ala Leu Gly Thr Pro Pro Ala
    1670                1675                1680

Ala Val Val Leu Leu Asp Thr Tyr Leu Pro Asp Asp Gln Phe Leu
```

```
                   1685                1690                1695

Ala Arg Asp Gln Asp Arg Phe Ile Gly Gly Val Phe Asp Arg Gln
    1700                1705                1710

Asp Arg Phe Ser Ile Arg Glu Asp Val Ser Leu Ser Ala Met Gly
    1715                1720                1725

Trp Tyr Leu His Leu Phe Asp Gly Trp Lys Pro Thr Ala Ile Ser
    1730                1735                1740

Val Pro Glu Leu Leu Val Arg Ala Ser Glu Pro Leu Pro Ser Pro
    1745                1750                1755

Ser Gly Arg Pro Pro Arg Ala Ala Asp Trp Arg Thr Ser Trp His
    1760                1765                1770

Val Ala Gln His Ser Val Glu Val Pro Gly Asp His Phe Thr Met
    1775                1780                1785

Leu Glu Glu Phe Asn Asp Ala Thr Ala Asp Ala Val Arg Arg Trp
    1790                1795                1800

Leu Leu Asp Ile Asp
    1805

<210> SEQ ID NO 6
<211> LENGTH: 399
<212> TYPE: PRT
<213> ORGANISM: Streptomyces sp.

<400> SEQUENCE: 6

Met Asp Leu Glu Thr Gln Leu Leu Ser Pro Ala Tyr Leu Arg Asn Pro
1               5                   10                  15

His Pro Leu Asn Ala Ala Leu Arg Ser Ala Asp Pro Val Gln Arg Ala
            20                  25                  30

Val Ala Ser Gly Gly Leu Ser Val Trp Val Val Thr Arg Tyr Glu Asp
        35                  40                  45

Val Arg Ala Leu Leu Ala Asp Ser Arg Leu Gly Lys Gly Val Thr Gln
    50                  55                  60

Leu Arg Glu Ala Val Leu Leu Asn Ala Gly Asp Asp Glu Arg Ile Ser
65                  70                  75                  80

Gln Phe Thr Asp Ser Leu Thr Glu His Met Leu Asn Ser Asp Pro Pro
                85                  90                  95

Asp His Thr Arg Leu Arg Arg Leu Val Gly Lys Ala Phe Thr Ala Gly
            100                 105                 110

Arg Ile Glu Gln Leu Arg Pro Arg Ile Thr Glu Ile Val Asp Asn Leu
        115                 120                 125

Leu Asp Arg Leu Ser Pro Gly Gln Glu Val Asp Leu Val Pro Val Phe
    130                 135                 140

Ala Leu Pro Met Pro Thr Thr Val Ile Cys Glu Leu Leu Gly Val Pro
145                 150                 155                 160

Ser Val Asp Arg Ser Ser Phe Ser His Trp Ser Asn Val Leu Val Ser
                165                 170                 175

Thr Ala Glu Val Gly Glu Leu Ala Glu Ala Gly Gly Ala Met Val Ala
            180                 185                 190

Tyr Leu Ala Gln Leu Ile Ala Asp Lys Arg Ala Asn Pro Cys Asp Asp
        195                 200                 205

Leu Leu Thr Lys Leu Val Gln Ala Thr Asp Asn Gly Asp Gln Leu Ser
    210                 215                 220

Glu Thr Glu Leu Val Ala Thr Ala Phe Leu Leu Leu Ser Ala Gly His
225                 230                 235                 240

Glu Thr Thr Val Asn Leu Ile Ala Ala Gly Thr Leu Thr Leu Leu Gln
```

```
                        245                 250                 255
Asn Pro Asp Gln Leu Ala Arg Leu Arg Ser Asp Leu Thr Leu Leu Pro
            260                 265                 270

Gly Ala Ile Glu Glu Leu Ile Arg Tyr Asp Gly Pro Gly Gly Met Val
            275                 280                 285

Leu Arg His Thr Leu Glu Pro Val Glu Val Gly Val Thr Ile Pro
            290                 295                 300

Ala Gln Gln Val Val Leu Leu Ser Leu Ser Ala Gly Arg Asp Ser
305                 310                 315                 320

Thr Arg Phe Ser Asp Ala Asp Arg Leu Asp Ile Gly Arg Pro Ile Gly
                325                 330                 335

Gly Ser Val Gly Phe Gly His Gly Ile His His Cys Ile Gly Ala Pro
            340                 345                 350

Leu Ala Arg Leu Glu Gly Glu Ile Ala Phe Arg Ala Leu Leu Thr Arg
            355                 360                 365

Phe Pro Asp Leu Arg Leu Ala Val Pro Pro Glu Glu Leu Asn Trp Arg
            370                 375                 380

Asp Ser Val Phe Ile Arg Gly Pro Glu Ser Leu Pro Val Val Leu
385                 390                 395

<210> SEQ ID NO 7
<211> LENGTH: 397
<212> TYPE: PRT
<213> ORGANISM: Streptomyces sp.

<400> SEQUENCE: 7

Met Ala Leu Cys Thr Val Arg Gly Asp Thr Asn Glu Gln Leu Leu Gln
1               5                   10                  15

Arg Ala Phe Ala Ser Ser Val Ala His Pro Ser Leu Arg Ser Arg
            20                  25                  30

Ile Ser Pro Asp Gly Thr Glu Leu Val His Pro Leu Asp Asp Gly
            35                  40                  45

Pro Pro Glu Leu Val Val Arg Arg Ala Gly Ser Trp Asp Leu Asp Arg
50                  55                  60

Glu Met Arg Ser Arg Leu Asp Arg Cys Gly Pro Leu Val Arg Ala Thr
65                  70                  75                  80

Leu Leu Arg Gly Ala Ala Glu Asp Thr Phe Ile Leu His Val Asp His
                85                  90                  95

Arg Ile Cys Asp Gly Arg Ser Val Val Ala Leu Leu Ser Ala Val Trp
            100                 105                 110

Arg Thr Tyr Ala Ala Leu Gly Glu Gly Pro Met Ala Ser Ser Ala His
            115                 120                 125

Val Ala Asp Ser Tyr Pro Ala Pro Ile Glu Thr Arg Leu Gly His His
    130                 135                 140

Pro Glu Ala Asp Val Leu Ala Tyr Ala Ala Arg Arg Ala Glu Gln Ala
145                 150                 155                 160

Lys Arg Leu Pro Pro Val Leu Pro Tyr Leu Gly Asp Pro Gly Val
                165                 170                 175

Glu Ala Pro Glu Gln Gly Glu Ile His Val Arg Thr Leu Arg Leu Thr
            180                 185                 190

Ser Asp Glu Thr Thr Arg Leu Ala Gly Ser Ala Arg Ala Ala Gly Ile
            195                 200                 205

Ser Val Gln Gly Leu Val Ala Ala Leu Leu Ile Ala Val Arg Arg
    210                 215                 220

Ala Leu Glu Ala Thr Asp Ala Pro Leu Ser Leu Ala Leu Ala Ser Pro
```

```
                225                 230                 235                 240
Val Asp Phe Arg His Arg Val Thr Pro Pro Leu Ala Glu Glu Thr Leu
                    245                 250                 255

Val Leu Ala Ala Ala Ser Phe Tyr Asp Ile Val Glu Val Ser Pro Arg
                    260                 265                 270

Ala Asp Val Arg Thr Leu Gly Arg Leu Val Tyr Asp Arg Leu Arg Ala
                    275                 280                 285

Gly Val Glu Arg Gly Asp Pro Glu Arg Glu Ile Leu Ala Val Arg His
                    290                 295                 300

Phe Phe Glu Asn Pro Ala Leu Leu Ala Ala Ser Leu Val Leu Thr Asn
305                 310                 315                 320

Leu Gly Arg Val Ala Asp Leu Val Ala Pro Pro Gly Leu Glu Leu Gly
                    325                 330                 335

Gly Leu Arg Trp Ile Pro Val Pro Glu Asn Trp Ser Pro Glu Gln Gly
                    340                 345                 350

Arg Gly Pro Leu Val Val Ser Ala Ile Thr Val Glu Gly Arg Leu Ala
                    355                 360                 365

Leu Glu Val Pro Tyr Ser Pro Ser Cys Phe Gly His Arg Gln Ile Ala
                    370                 375                 380

Glu Val Val Glu Ser Thr Arg Arg Ile Leu Met Ser Ala
385                 390                 395

<210> SEQ ID NO 8
<211> LENGTH: 433
<212> TYPE: PRT
<213> ORGANISM: Streptomyces sp.

<400> SEQUENCE: 8

Met Leu Asp Arg Asp Gln Val Pro Asp Gly Pro Glu Val Arg Lys Gly
1               5                   10                  15

Thr Pro Gln Thr Leu His Ser His Ile Leu Met Ser Asn Gly Ala Arg
                20                  25                  30

Thr Ile Asp Ser Leu Val Pro Gly Ser Leu His Arg Leu Leu Ala Ala
                35                  40                  45

Gly Ala His Arg Thr Glu Val Pro Ser Gly Leu Val Ser Cys Ser Arg
            50                  55                  60

Gln Gly Trp Ala Arg Arg Met Pro Gly Ala Gln Phe Met Val Thr Cys
65              70                  75                  80

Gly Arg Pro Leu Leu Asp Trp Thr Leu Arg Arg Leu Val Leu Glu Asp
                85                  90                  95

Asp Arg Ile Thr Leu Arg Ser Gly Val Asp Val Gln Gly Leu Asp Gly
                100                 105                 110

Asp Ala Thr Arg Val Thr Gly Val Gln Ala Gln Asp Arg Ala Ser Gly
                115                 120                 125

Glu Ser Leu Arg Leu Asp Ala Asp Phe Val Val Asp Ala Thr Gly Arg
                130                 135                 140

Gly Ser Gly Ala Asn Thr Trp Leu Gln Ala Leu Gly Leu Pro Ala Val
145                 150                 155                 160

Arg Glu Val Lys Ile Asp Ile Gly Leu Ser Tyr Ala Thr Arg Arg Tyr
                165                 170                 175

Arg Ala Pro Ala Gly Ala Glu Ser Gly Phe Pro Ile Val Asn Val Leu
                180                 185                 190

Pro Asp Pro Glu Asp Asp Gln Pro Gly Gln Gly Ala Val Leu Leu Pro
                195                 200                 205

Ile Glu Asp Gly Gln Trp Ile Val Thr Leu Thr Gly Thr Arg Gly Cys
```

```
                    210                 215                 220
Glu Pro Pro Arg Asp Pro Glu Gly Phe Val Ala Phe Ala Arg Arg Leu
225                 230                 235                 240

Arg His Ser Val Ile Gly Asp Leu Ile Ala Asn Ala Glu Pro Ile Gly
                245                 250                 255

Pro Ile His Ser Ser Arg Thr Thr Val Asn Arg Arg Tyr Tyr Glu
            260                 265                 270

Glu Leu Ala Asp Trp Pro Lys Gly Phe Val Val Leu Gly Asp Ala Ala
            275                 280                 285

Ala Ala Leu Asn Pro Val Tyr Gly His Gly Met Ser Val Ala Ala Met
290                 295                 300

Ser Ala Ser Ala Leu Arg Asp Val Leu Arg Ser Asp Gly Leu Val Ala
305                 310                 315                 320

Gly Thr Ser Arg Ala Thr Gln Ala Ala Val Ala Gly Ala Val Asn Asn
                325                 330                 335

Ala Trp Ala Met Ala Thr Gly Gln Asp Ile Phe Tyr Pro Asn Val Ser
                340                 345                 350

Gly Arg Arg Pro Gly Leu Ala Ala Arg Met Gln Arg Arg Tyr Val Asn
            355                 360                 365

Arg Val Thr Lys Thr Ala Ala Asp Arg Pro Arg Val Ala Ala Val
370                 375                 380

Ser Asp Thr Phe Thr Leu Ser Ala Pro Leu Thr Arg Leu Met Thr Pro
385                 390                 395                 400

Arg Ile Val Phe Glu Thr Leu Leu Gly Pro Thr Arg Pro Leu Thr
                405                 410                 415

Gly Pro Pro Leu Thr Ser Arg Glu Arg Glu Ser Ile Val Gly Ser Pro
                420                 425                 430

Gln

<210> SEQ ID NO 9
<211> LENGTH: 902
<212> TYPE: PRT
<213> ORGANISM: Streptomyces sp.

<400> SEQUENCE: 9

Met His Leu Phe Gly Arg Asp Ser Glu Leu Asp Leu Leu Lys Ser Leu
1               5                   10                  15

Leu Val Glu Cys Glu Ile Gly Lys Ala Val Thr Val Leu Glu Gly
            20                  25                  30

Gly Ala Tyr Cys Gly Lys Ser Glu Leu Leu Val Asn Phe Gly Glu His
            35                  40                  45

Val Lys Ala Ser Gly Ala Val Val Asn Ala Arg Asp Leu Gly Phe
        50                  55                  60

Asp Asn Val Pro Arg Met Ser Ser Met Ser Ser Ala Gln Thr Ala Glu
65                  70                  75                  80

Phe Val Glu Phe Cys Gly Arg Leu Glu Ala Leu Ala Asp Arg Ser Pro
                85                  90                  95

Val Val Val Cys Leu Asp Asp Leu Gln Asp Leu Asp Ser Leu Ser Trp
            100                 105                 110

Arg Trp Leu Leu Glu Ala Thr Arg Ala Arg Leu Arg Ser Ser Arg Leu
        115                 120                 125

Met Leu Ile Val Val Gln Ala Leu Arg Thr Ser Leu Gly Pro Glu Phe
130                 135                 140

His Cys Glu Leu Leu Arg Gln Pro Asn Leu His Arg Ile Ala Leu Arg
145                 150                 155                 160
```

```
Pro Met Thr Arg Asp His Val Asp Leu Val Gly Ala Leu Glu Gly
                165                 170                 175

Arg Pro Ala Glu Asp Thr Phe Leu Asp Asp Val Phe Arg Leu Ser Gly
            180                 185                 190

Gly Asn Pro Leu Leu Val Arg Ala Leu Leu Glu Glu His Arg Val Arg
        195                 200                 205

Asn Ala Ala Gly Gln Thr Ala Pro Trp Pro Ala Ala Asp Gly Leu Phe
    210                 215                 220

Ala Gln Ala Ala Val Asn Cys Val Gln Gly Asn Asp Pro Ala Val Val
225                 230                 235                 240

Ser Leu Ala Thr Gly Ile Ala Val Leu Gly Glu Asp Ser Arg Pro Glu
                245                 250                 255

Leu Leu Glu Glu Leu Leu Gly Leu Asn Ala Ala Glu Ile Ala Arg Gly
            260                 265                 270

Ile Leu Ala Leu Ala Ser Ala Gly Leu Val Asp Gly Tyr Arg Phe Gln
        275                 280                 285

His Pro Leu Val Glu Arg Ala Thr Leu Asn Ile Ile Gly Pro Lys Gln
    290                 295                 300

Arg Ala Glu Leu Arg His Arg Ala Glu Leu Leu Ser Arg His Gly
305                 310                 315                 320

Val Gly Ser Arg Thr Ile Ala Arg His Leu Leu Glu Ala Gly Ser Ala
                325                 330                 335

Thr Glu Pro Trp His Val Gly Ala Leu Arg His Ala Ala Glu Glu Ala
            340                 345                 350

Leu Asp Ser Asp Ala Glu Gln Ala Gly Ala Tyr Leu Glu Leu Ala
        355                 360                 365

His Asp Ala Ser Thr Asp Ser Trp Glu Arg Gly His Ile Arg Leu Lys
    370                 375                 380

Arg Ala Leu Val Arg Trp Arg Val Asp Pro Cys Ser Val Glu Arg His
385                 390                 395                 400

His Leu Asp Gly Tyr Cys Gly Glu Arg Ala Pro Gly Pro Glu Leu Cys
                405                 410                 415

Pro Val Asp Ala Val Leu Leu Ile Gln Leu Leu Val Ser Leu Gly Arg
            420                 425                 430

Val Glu Glu Ala Gly Glu Leu Leu Arg Glu Val Arg Pro Thr Leu Arg
        435                 440                 445

Gly Leu Arg Ser Thr Thr Asp Leu Thr Val Val Gly Asn Thr Trp Leu
    450                 455                 460

Trp Phe Phe Pro Pro Met Thr Gly Met Pro Ala Ala Trp Cys Ala Gly
465                 470                 475                 480

Ser Arg Ala Leu Ala Asp Gly Leu Ser Gly Lys Asp Cys Ala Asp Gly
                485                 490                 495

Thr Ser Arg Ser Asp Ala Leu Gly Ala Leu Ala Thr Trp Ile Lys Glu
            500                 505                 510

Leu Gly Arg Lys Pro Gly Asp Ile Gln Asp Ser Glu Lys Leu Leu Arg
        515                 520                 525

Thr Thr Pro Leu Ser Asp Met Thr Leu Ser Leu Ile Leu Thr Glu Leu
    530                 535                 540

Asn Ser Leu Thr Arg Val Gly Arg Leu Asp Leu Ala Ala Thr Trp Cys
545                 550                 555                 560

Asp Val Phe Leu Lys Asn Ala Thr Val Arg Gly Ile Pro Gly Trp Gln
                565                 570                 575

Arg Leu Phe Ala Ala Val Arg Ala Asp Ile Ala Leu Arg Gln Gly Lys
```

-continued

```
                580                 585                 590
Leu Thr Glu Ala Glu Thr Phe Ala Trp Met Ser Leu Asp Gly Leu Ala
            595                 600                 605

Glu Pro Ser Ser Thr Trp Leu His Gly Gly Pro Leu Thr Val Leu Met
        610                 615                 620

Thr Val Tyr Thr Glu Met Gly Arg Tyr Lys Asp Val Ala His Leu Leu
625                 630                 635                 640

Asp Arg Pro Val Pro Glu Ala Leu Phe Arg Ser Val Tyr Gly Leu Pro
                645                 650                 655

Tyr Leu Arg Ala Arg Gly His Tyr Ala Leu Ala Val Asn Arg Pro His
            660                 665                 670

Leu Ala Leu Ser Asp Phe Leu Ser Ile Gly Arg Leu Ala Glu Arg Trp
        675                 680                 685

Gly Leu Ala Pro Ser Ala Glu Leu Pro Trp Gln Val Asp Ser Ala His
        690                 695                 700

Ala Trp Leu Arg Leu Asn Asp Arg Glu Gln Ala Glu Arg Met Leu Ala
705                 710                 715                 720

Glu Tyr Asp Ser Ala Thr Ala Gly Ile Gly Ala Thr Asp Gly Ala
                725                 730                 735

Val Leu Arg Val Arg Ala Met Phe Ala Glu Pro Gly Glu Arg Thr Arg
            740                 745                 750

Leu Leu Ile Gln Ala Ala Glu Arg Leu Gln Glu Thr Gly Asp Arg Leu
        755                 760                 765

Gln Leu Ala Lys Val Leu Ala Asp Leu Ala Ser Thr Tyr Glu Glu Leu
        770                 775                 780

Gly Val Gly Arg Arg Ala Asp Ala Ile Arg His Met Ala Arg Gln Ile
785                 790                 795                 800

Ala Gly Asp Cys Ser Ala Glu Val Pro Ser Glu Pro Ile Gly Ser Ser
                805                 810                 815

His Arg Pro Ser Pro Glu Gly Gly Met Ser Ser Ala Leu Glu Phe Arg
            820                 825                 830

Gly Ala Asp Val Gly Ala Asn Leu Ser Glu Ser Glu Arg Arg Val Ala
        835                 840                 845

Ala Leu Ala Ala Lys Gly Leu Thr Asn Arg Glu Ile Ser Ala Lys Leu
850                 855                 860

Phe Ile Thr Met Ser Thr Val Glu Gln His Leu Thr Arg Val Tyr Arg
865                 870                 875                 880

Lys Leu Asp Ile Thr Arg Arg Glu Glu Leu Pro Leu Glu Leu Gln Leu
                885                 890                 895

Ala Leu Pro Gln Thr Ala
            900

<210> SEQ ID NO 10
<211> LENGTH: 23
<212> TYPE: DNA
<213> ORGANISM: Artificial Sequence
<220> FEATURE:
<223> OTHER INFORMATION: KS-3F synthetic primer

<400> SEQUENCE: 10
gaccgcggct gggacgtgga ggg                                            23

<210> SEQ ID NO 11
<211> LENGTH: 24
<212> TYPE: DNA
<213> ORGANISM: Artificial Sequence
<220> FEATURE:
```

<223> OTHER INFORMATION: KS-4R synthetic primer

<400> SEQUENCE: 11
gtgcccgatg ttggacttca acga                                              24

<210> SEQ ID NO 12
<211> LENGTH: 27
<212> TYPE: DNA
<213> ORGANISM: Artificial Sequence
<220> FEATURE:
<223> OTHER INFORMATION: CB-1F synthetic primer

<400> SEQUENCE: 12
atgacagctt tgaatctgat ggatccc                                           27

<210> SEQ ID NO 13
<211> LENGTH: 30
<212> TYPE: DNA
<213> ORGANISM: Artificial Sequence
<220> FEATURE:
<223> OTHER INFORMATION: CB-2R synthetic primer

<400> SEQUENCE: 13
tcagagacgg accggcagac tcttcagacg                                        30

<210> SEQ ID NO 14
<211> LENGTH: 27
<212> TYPE: DNA
<213> ORGANISM: Artificial Sequence
<220> FEATURE:
<223> OTHER INFORMATION: PKC-1F synthetic primer

<400> SEQUENCE: 14
gtgcgccgta cccagcaggg aacgacc                                           27

<210> SEQ ID NO 15
<211> LENGTH: 27
<212> TYPE: DNA
<213> ORGANISM: Artificial Sequence
<220> FEATURE:
<223> OTHER INFORMATION: PKC-2R synthetic primer

<400> SEQUENCE: 15
tcacgcgctc tccgcccgcc ccctgcc                                           27

<210> SEQ ID NO 16
<211> LENGTH: 33
<212> TYPE: DNA
<213> ORGANISM: Artificial Sequence
<220> FEATURE:
<223> OTHER INFORMATION: PDL58-1F synthetic primer

<400> SEQUENCE: 16
gccccgcata tggatctgga aacccaactt ctc                                    33

<210> SEQ ID NO 17
<211> LENGTH: 31
<212> TYPE: DNA
<213> ORGANISM: Artificial Sequence
<220> FEATURE:
<223> OTHER INFORMATION: PDL58-2R synthetic primer

<400> SEQUENCE: 17
gcactagtca gccgcgctcg acgaggaggt g                                      31

<210> SEQ ID NO 18

```
<211> LENGTH: 33
<212> TYPE: DNA
<213> ORGANISM: Artificial Sequence
<220> FEATURE:
<223> OTHER INFORMATION: pldB-L-Bgl2F synthetic primer

<400> SEQUENCE: 18
gggagatcta gaggccggtt acctctacga gta                                33

<210> SEQ ID NO 19
<211> LENGTH: 30
<212> TYPE: DNA
<213> ORGANISM: Artificial Sequence
<220> FEATURE:
<223> OTHER INFORMATION: pldB-L-Hind3R synthetic primer

<400> SEQUENCE: 19
gggaagcttg cgatgagctg tgccagatag                                    30

<210> SEQ ID NO 20
<211> LENGTH: 30
<212> TYPE: DNA
<213> ORGANISM: Artificial Sequence
<220> FEATURE:
<223> OTHER INFORMATION: pldB-R-Hind3F synthetic primer

<400> SEQUENCE: 20
gggaagcttg aactggcgcg acagtgtctt                                    30

<210> SEQ ID NO 21
<211> LENGTH: 34
<212> TYPE: DNA
<213> ORGANISM: Artificial Sequence
<220> FEATURE:
<223> OTHER INFORMATION: pldB-R-Bgl2R synthetic primer

<400> SEQUENCE: 21
gggagatctg cagcggatcg tcttcgagac cctt                               34

<210> SEQ ID NO 22
<211> LENGTH: 28
<212> TYPE: DNA
<213> ORGANISM: Artificial Sequence
<220> FEATURE:
<223> OTHER INFORMATION: pldC-L-Hind3R synthetic primer

<400> SEQUENCE: 22
gggaagcttc cagtctcgtg ctcaccaa                                      28

<210> SEQ ID NO 23
<211> LENGTH: 30
<212> TYPE: DNA
<213> ORGANISM: Artificial Sequence
<220> FEATURE:
<223> OTHER INFORMATION: pldC-R-Hind3F synthetic primer

<400> SEQUENCE: 23
gggaagctta ggcccgttgg agaagctgtt                                    30

<210> SEQ ID NO 24
<211> LENGTH: 34
<212> TYPE: DNA
<213> ORGANISM: Artificial Sequence
<220> FEATURE:
<223> OTHER INFORMATION: pldC-R-Bgl2R synthetic primer

<400> SEQUENCE: 24
```

-continued

```
gggagatctg cagcctcatc ctcaccgagc tgaa                    34
```

<210> SEQ ID NO 25
<211> LENGTH: 33
<212> TYPE: DNA
<213> ORGANISM: Artificial Sequence
<220> FEATURE:
<223> OTHER INFORMATION: pldD-L-Bgl2F synthetic primer

<400> SEQUENCE: 25

```
gggagatcta gacctgtcca tggatctgga aac                     33
```

<210> SEQ ID NO 26
<211> LENGTH: 30
<212> TYPE: DNA
<213> ORGANISM: Artificial Sequence
<220> FEATURE:
<223> OTHER INFORMATION: pldD-L-Hind3R synthetic primer

<400> SEQUENCE: 26

```
gggaagcttc ggatcgtctt cgagaccctt                         30
```

<210> SEQ ID NO 27
<211> LENGTH: 30
<212> TYPE: DNA
<213> ORGANISM: Artificial Sequence
<220> FEATURE:
<223> OTHER INFORMATION: pldD-R-Hind3F synthetic primer

<400> SEQUENCE: 27

```
gggaagcttg tggggtgccc tttctgactt                         30
```

<210> SEQ ID NO 28
<211> LENGTH: 33
<212> TYPE: DNA
<213> ORGANISM: Artificial Sequence
<220> FEATURE:
<223> OTHER INFORMATION: pldD-R-Bgl2R synthetic primer

<400> SEQUENCE: 28

```
gggagatctg caggaggagc tgctcgggct gaa                     33
```